(12) United States Patent
Gregory et al.

(10) Patent No.: US 9,504,728 B2
(45) Date of Patent: Nov. 29, 2016

(54) DOSAGE FORM

(71) Applicant: NeuroVive Pharmaceutical AB, Lund (SE)

(72) Inventors: Matthew Alan Gregory, Cambridge (GB); Steven James Moss, Cambridge (GB)

(73) Assignee: NeuroVive Pharmaceutical AB, Lund (SE)

( * ) Notice: Subject to any disclaimer, the term of this patent is extended or adjusted under 35 U.S.C. 154(b) by 128 days.

(21) Appl. No.: 14/348,859

(22) PCT Filed: Oct. 24, 2012

(86) PCT No.: PCT/GB2012/052633
§ 371 (c)(1),
(2) Date: Mar. 31, 2014

(87) PCT Pub. No.: WO2013/061052
PCT Pub. Date: May 2, 2013

(65) Prior Publication Data
US 2014/0234414 A1    Aug. 21, 2014

(30) Foreign Application Priority Data

Oct. 24, 2011    (GB) .................................. 1118334.0

(51) Int. Cl.
| | | |
|---|---|---|
| A61K 38/12 | (2006.01) | |
| A61K 9/48 | (2006.01) | |
| A61K 9/00 | (2006.01) | |
| A61K 47/02 | (2006.01) | |
| A61K 47/10 | (2006.01) | |
| A61K 9/08 | (2006.01) | |
| A61K 47/44 | (2006.01) | |
| A61K 9/28 | (2006.01) | |
| A61K 31/5025 | (2006.01) | |

(52) U.S. Cl.
CPC ............. *A61K 38/12* (2013.01); *A61K 9/0019* (2013.01); *A61K 9/08* (2013.01); *A61K 9/2866* (2013.01); *A61K 9/4891* (2013.01); *A61K 31/5025* (2013.01); *A61K 47/02* (2013.01); *A61K 47/10* (2013.01); *A61K 47/44* (2013.01)

(58) Field of Classification Search
CPC .. A61K 38/12; A61K 47/02; A61K 31/5025; A61K 9/08; A61K 47/44; A61K 9/2866; A61K 47/10
See application file for complete search history.

(56) References Cited

U.S. PATENT DOCUMENTS 5,356,625 A * 10/1994 Ying ..................... A23K 1/005
                                                              424/438

FOREIGN PATENT DOCUMENTS

| WO | 2006/138507 | 12/2006 | | |
|---|---|---|---|---|
| WO | 2011/098808 | 8/2011 | | |
| WO | WO2011098809 | * | 8/2011 | ......... A61K 31/5025 |

OTHER PUBLICATIONS

Gregory, M.A., et al., "Preclinical Characterization of Naturally Occurring Polyketide Cyclophilin Inhibitors from the Sanglifehrin Family", Antimicrob. Agents Chemother., 2011, 55:1975-1981.
Moss, S.J., et al., "Sangamides, a New Class of Cyclophilin-Inhibiting Host-Targeted Antivirals for Treatment of HCV Infection", Med. Chem. Commun., 2012, 3:944-949.
Sanglier, J.J., et al., "Sanglifehrins A, B, C, and D, Novel Cyclophilin-Binding Compounds Isolated from *Streptomyces* sp. A92-308110", J. Antibiotics, 1999, 52:466-473.
Sedrani, R., et al., "Sanglifehrin-Cyclophilin Interaction: Degradation Work, Synthetic Macrocyclic Analogues, X-ray Crystal Structure, and Binding Data", J. Am. Chem. Soc., 2003, 125:3849-3859.

* cited by examiner

*Primary Examiner* — Suzanne Ziska
*Assistant Examiner* — Thurman Wheeler
(74) *Attorney, Agent, or Firm* — Robert C. Netter, Jr.; Dann, Dorfman, Herrell & Skillman

(57) ABSTRACT

There is provided inter alia a pharmaceutical dosage form for oral administration comprising a sanglifehrin as active ingredient in which the sanglifehrin active ingredient is protected from acid degradation in the stomach environment following oral administration.

7 Claims, 3 Drawing Sheets

SEQUENCE LISTING

```
<160> NUMBER OF SEQ ID NOS: 3

<210> SEQ ID NO 1
<211> LENGTH: 77
<212> TYPE: DNA
<213> ORGANISM: Artificial
<220> FEATURE:
<223> OTHER INFORMATION: Primer

<400> SEQUENCE: 1
cgctctgtgg cgcctggttt ccaagcggct cgcggaccgg caccggcaca tgcataatta      60
accctcacta aagggcg                                                     77

<210> SEQ ID NO 2
<211> LENGTH: 78
<212> TYPE: DNA
<213> ORGANISM: Artificial
<220> FEATURE:
<223> OTHER INFORMATION: Primer

<400> SEQUENCE: 2
tggatgtatc gtcgcaggac gcccagaatt cacctgcgac gtcctccaga tgcattaata      60
cgactcacta tagggctc                                                    78

<210> SEQ ID NO 3
<211> LENGTH: 46596
<212> TYPE: DNA
<213> ORGANISM: Artificial
<220> FEATURE:
<223> OTHER INFORMATION: Cosmid

<400> SEQUENCE: 3
acaccggcca caccggcggc ggcctgcgtg tgcccgatgt tggacttcac cgaaccgagc      60
cacagcggct cgtcccgctc ctgcccgtag gtggcgagca gcgcctgcgc ctcgatcggg     120
tcgcccagcc gcgtgcccgt accgtgcgcc tccaccgcgt ccacgtccgc gggcgtgagc     180
ccggcaccgg agagcgcctg acggatcacc cgctgctgcg aaggaccgtt cggggccgtc     240
agaccgttcg acgcgccgtc ctggttgatc gcggtgccgc gtacgacggc cagtacctgg     300
tggccgtggc ggcgggcgtc ggagagccgt tccacgagga gcatgccggc gccctcggac     360
cagccggtgc cgtcggccgc ggcggcgaag gacttgcagc ggccgtccac ggccaggccg     420
cgctggcggg agaagtcgac gaagacgtcg ggggcggaca tgacggtgac accgccggcc     480
agcgccatcg agcactcgcc gctgcgcagc gcctggatcg cccagtgcag ggcgaccagc     540
gacgccgagc acgcggtgtc cacggtgacc gcagggcctt ccaggccgag gacgtaggcg     600
atgcggcccg acagcacgct ggcggagttg ccgatgccga cgtagccctc cgcgctctcg     660
```

```
acggtcctgc gcacgagctg ggcatagtcc tggccgttgg tgccgaggta gacgccgacg    720
tccgcgccgc gcagggactt cgggtcgatg ccggcgcgtt cgacggcctc ccaggcggtc    780
tccagggcca gccgctgctg cgggtccatc gccagcgcct cgcgcggcga gatcccgaag    840
aagtccgcgt cgaacccggc gacgtccgcg aggaagccgc cctcccgcac gtacgacgtg    900
cccgcgtgct ccggatccgg gtggaagagg cccgcgaggt cccagccccg gtcgtcgggg    960 aacgggtga gcgcgtcgcg ctcgtcgcg agcagccgcc acaggtcctc gggcgaggtc    1020
acgccgccgg ggtaccggca cgccatgccg acgatcgcga tgggatcgtc gtcggcgggg   1080
cgggcgacgg cgggcaccgg cgccgtctcc tcggcgcgtt cgccgaggag ttcggccagc   1140
aggtggccgg ccagggagcg cgggttgggg tggtcgaaca cgagggtcgc gggcaggcgc   1200
agcccggtgg cggcggacag ccggttgcgg agttcgacgg cggtcagcga gtcgaagccc   1260
agttccttga acgcccggcc gggggtcacg gcggtgtcgt cggtgtggcc gaggaccacg   1320
gcggcgtgcg agcggacgag cgtgagcagg gtccgttcgc gttccgcggc ggtgagtccg   1380
gtgagctttc cggccagggt gtccggtccg gcgcccgcgg tggcggcgcg ccggacgggg   1440
ccacggacca gccggcgcat cagcgcgggt acggcggtga cgccggtggc gaacgaggtg   1500
aggtccagcc aggcggggac gacgacgggg gcggagccgg cggtggcgcg gtcgaacagg   1560
gcgagcgcgt cgggcgtcgg cagcggcacc acgccgtcgc gggccgcgcg ccgcaggtcg   1620
gcgccgccca ggtggccggt catgccgctg gcgtgcgccc acaggcccca cacctgggag   1680
gtggcgggca ggccctgggc cggcggtgt gccgcgagcg cgtccacgaa ggcgttgccc   1740
gccgcgtagt tgccctgtcc gggcgccccg aagaggccgg aggtggagga gaacagcacg   1800
aagacggccg gccggtgcgg ggcggtgagt tcgtgcaggt tccaggcggc gtcgaccttg   1860
gggcggagca ccttggcgag ccgctcgggg gtctgggagg cgatgacgcc gtcgtccagg   1920
acgccggcgg cgtggacgac tccggtcagg gggtgctcgg cggtgatccg gtcgagcagg   1980
gcggccagtt cggtgcggtc ggcggcgtcg caggcggcga cggtcacctc ggcgccgagg   2040
gcgcgcagtt cgccggcgag ggtcacggcg tcggggccg cgtcgccgcg ccgtccggcc   2100
aggaccagcc ggcgtacgcc gtgctcggtg accaggtggc gggcgcagag ggcgccgagc   2160
gtgccggtgc cgccggtgac gaggacgacg ccgtcggacg gccacagggc cgcctggctc   2220
gtgggctcgt cggtgcgcgg ggcgcggacc agccggggtg cgaggacccg gccggagcgc   2280
acggcgatct cggggttcgcc ggtggcgagg acagcgggca gctgttgcag tgcgtcgggg   2340
ccgtcgatgt cgaccagcac cagcctgccg gggtgttcgg cgcgggcgga gcggatcagg   2400
ccccacacgg gcgcgtgggc gaggtcggtg acgtcctcgt gctcgaccgg gaccgcgccg   2460
tgggtgagga cggccagacg ggtgccggcc agtcgctcgt cggcgagcca ctcctgaaga   2520
gcggtcagca cgcgccgggc gccggcgtgg gccgcgccgg cggtgtcgtc ggccgactgc   2580
tgccgacacg gcagcacgag ggtgccggcc acggtgtcca gggcggcgac ggcggcgagg   2640
tcggggcagg agggggtatcc gggcagcgga aggccgccga gcacggcgat gccgtcgacg   2700
tcggccgcgg gcagcggcac gggcgtccac tcgacccggt acagctcgtg gtcgcggccg   2760 gggcggccg tggccggcgg gcgcagggtc accgcgtcga cggtgagcac ggcggctccg   2820
ctgtcgtcgg tggcgtgcag ggtgaccgtg tgctcgcccg cggggtgcag gcgtacccgc   2880
agccgggtgg cgcccacggc gtgcagggtg acgccgtgcc aggcgccggg gaccaggccg   2940
gggtgtacgg ccgcgagggc gtcggtgagc agggcggggt gtacgcccca gccgccggcg   3000
gtctcgtcgg tcagctcaac ggtcacgtcg gtcagctcga cggtcacgtc ggtgtccggg   3060
```

```
tccccctggcg cggcggccgg ggcggtgccg gtgtgcggga ggaggacgcc ggtcgcgtgc   3120
cgggtccagg gctggtcgtc gtcggcgtcg gcggggcggg agtggacggc gaccgggcgg   3180
gcgccgtcct cgttctccgc gcccaggggtg acctggaggc ggcgggcttc gccgacggtg   3240
tcgagcggtg cctcctcggt cagttcgccg agcgtcctgc cgtcggccgc gtgcagggcc   3300
aggtcgagta cggcgccggc cggcagctcg gtgccggccg gcacgcgccc ggtgaacacc   3360
tgtccgccgc atccggcgag cggggtgacg gcgccgagca gcgggtgccc ggcgccggtc   3420
aggcccaggc cggcggcgtc ggaggcgacc gggccgctgg gccagaagcg gcggcgctgg   3480
aaggcgtagg tggcaggtc gacgtggcgt ccgtcggggc agcccaccgt ccagtcgacg   3540
gacacgccgt ggacggcggc ctcggcgagc gaggtgagga ggcggcgcgg gccgtcctcg   3600
tcgcggcgga gggtgccgac gacgacgcg gtccgctcgg tggcctccgc cgtctcctgc   3660
acggcggccg tcagcaccgg gtgcgggctg atctccacga acacggcgtg gccggagtcg   3720
agcaggccgc gcaccacggg ctcgaaccgt acgggctccc gcaggttgcg gtaccagtag   3780
ccggcgtcga gccgtgtctc gccgaggggg ccgcccagca gggtggagtg gaaggcgatg   3840
ccggcctcac cgggccgcag ttcggcgagc gcggcgcgca actcggcttc gagggactcg   3900
acatgggccg agtgggaggc gtagtcgacc gcgatgcggc gcagtcgtac cccgtcggcc   3960
gaccaggcgg ccatcacctc gtccagcgca tcggggtcgc cgctgaggac caccgacgac   4020
gggccgttga gggcggcgac gcaaacgcgt ccggaccacg gtgcgagccg ccgtgtgacg   4080
gtggcctcgg gcagggcgac ggagaccatg ccgccgcgcc cggccagccg ctcggcgatg   4140
agccgcgacc gcagggcgac gatccgggcg ccgtccgcca gcgacagcac acccgccaca   4200
caagcagccg cgatctcccc ctgcgaatga ccgaccacag ccgacggcac gacaccgtac   4260
gaacgccaca cctccgccaa cgacaccatc accgcccaca acaccggctg aacgacatcc   4320
accgctccca acgccaccgg atcacccagc acaccacgca acgaccagcc cacgaacggc   4380
tccaacgcca ccgcacactc agccatccgc cccgcgaaca ccggcgacga atccagcaga   4440
tccaccgcca tcccaccca ctgcgccccc tgacccggga acacgaacac cacccggccc   4500
tcacccggca acccggcaac acccgacacc acaccctcca ccggctcccc cgcggccaac   4560
gccgccagag aagcccgcgc accggccaca tcagcggcca ccaccaccgc acgatgcggc   4620
aacaacgccc gcgacgcggc aagggaccag gagaggtcca ccgggtccag gccggggtgg   4680
gtgtcgaggt gggcggcgag ccgggtggcc tgctcggcga gggcggcctg ggagcgggcg   4740
gagagcagcc acggcaccca gcgcggcgcg gcgccgcgcg cgggcgcggc cggttccgcc   4800
ggggcctcct ccaggatgag gtgggcgttg gtgccgctgg cgccgaacga cgacacgccc   4860
gcgcggcgcg gccggtcggt cggggccag acggcggcgc cggtgacgag ttcgacggag   4920
ccggaggccc agtcgatgtg cggtgagggg gcgtccacgt gcagggtgcg gggcacttcg   4980
ccggcgcgca gcgcgagcac cgtcttgatc acgccggcca cgcccgccgc ggggccggtg   5040
tggccgatgt tggacttcag cgagcccagc cgcagcggct gtgcgcggtc ctggccgtag   5100
gtggccagca gggcgttggc ctcgatgggg tcgccgaggg tggtgccggt gccgtgtgcc   5160
tccacgacgt cgacgtcggc ggcggtgagg ccggcggcg ccagcgcgga gcggatgacc   5220
cgctgctggg cggagccgtt gggggcggtg agcccggagg aggcgccgtc ctggttgatc   5280
gccgagccgc ggaccacggc cagcacgggg tggccgttgc ggcgggcgtc ggacagccgc   5340
tccagcacga ccacgcccgc gccctcggac cagccgatgc cgtccgcggc ggcggcgaac   5400
```

```
gccttgcagc ggccgtcggg ggcgaggccg cgctgccggg agaactccac gaaggcacgc   5460
ggggtcgaca tgaccatcac gccgccggcg agggccagcg agcattcgcc gctgcgcagg   5520
gactggccgg ccaggtgcag ggcgacgagc gaggacgagc aggcggtgtc cacgctgacg   5580
gccgggcctt ccaggccgag ggtgtaggcc acccggccgg agagcacgct ggcgtagttc   5640
ccggtgccga gcagcccctc gtccacgccg gcgaccgcgc cgtgccgtga gtcgtagcgc   5700
tggtcggtga cgcccgcgaa gacgccggtg gcgctgccgc gcaggccgtg cggatcgacg   5760
ccggcgtgct cgaacgcctc ccaggcgact tcgaggaaca gccgctgctg cgggtccatc   5820
gccagcgcct cgcgcgggct gatgccgaag aagtcggcgt cgaagccggc ggcgtcgttc   5880
aggaagccgc cctggcgcag gtaggtgtgt ccggcccggt ccgggtcggg gtcgtagagg   5940
ccgtcgaggt cccagccgcg gtcggcgggg aagtcgccga tgacgtcacg gccttcggcg   6000
aggagctgcc acaggtcgtc gggcgaggcc actccgccgg ggaagcggca ggccatgccg   6060
accacgccca gcggctcgtc ggccggggtg gcgcggacgg cggggcgggc cgggacgggc   6120
gcgccgtcga gccgggtgag cagatggtcg gtgagggcgg ccgggttcgg gtggtcgaag   6180
acgacgctgc tggccagcgt caggccggtc gcctcggtca gcgcggtgcg cagccgcagg   6240
gaggcgaggg agtcgaagcc gagggcggcg aaaccgcggt gcggttcgat cgcggcgggg   6300
tcggcgtggc cgagcacggc ggcggtccgc agccgtacca ggtccatgac gcggtgccgg   6360
cgttcggcgg gggtcagccc ggccagctcg tcgcgcaggg gcgtgccctc gtcggcggtc   6420
cgctgcgcgg ggagcgcgac gggggtggcg gccggggggca gcggggcgggc cgctgcgtcc   6480 acgggcggcc agtaccggtc gcgctggaag gcgtacgtcg gcaggtcggc cgggtgggct   6540
ccggtgcccc ggaagaaggc ggtccagtcg atgcgcacgc cgtgcgtgtg cgcctcggcc   6600
aggttggtca gcagggtcgg caggccggcc cgtcgcgct ggagggtgcc gacgaccgcg   6660
gctccggtct ccgtgcgctc gacggtctcc tgggtgccga cggtcagtac ggggtgcgga   6720
ctgacctcga tgaagccccg gtggccctgg gcgagcaggg cggcgacggc gtcggcgtag   6780
cggacgggtt cgcgcaggtt gcggtaccag tagccggcgt ccagcgccgt gccgtccgcc   6840
cactcccccg tcacggtgga gaacagcgga accgtgccct cacccggccg cacgccctcc   6900
agatcagcca gcagagcctc acgcaccggc tccaccagca ccgaatgcga ggcatagtcg   6960
acagcgatac gccgggcccg cacccccga ccccgcaat gagccaggaa ctcctccagc   7020
gccaccccct cacccgcgac gacgaccgac tcaggaccgt tgaccgcagc caccgccaac   7080
cggcccgccc agcccaccaa cagctcctcg acaccggacg gccggcagc gaccgacacc   7140 atccccccac tgcccgccag cgccgtcaaa gccctgctgc gcagggcgac gacccgggcg   7200
ccgtccgcca gcgacaacac acccgccaca caagcagccg cgatctcccc ctgcgaatga   7260
ccgaccacag ccgacggcac gacaccgtac gaacgccaca cctccgccaa cgacaccatc   7320
accgccacac acaccggctg aacgacatcc acccgctcca acgccaccgg atcccccagc   7380
acaccacgca acgaccagcc cacgaacggc tccaacgcca ccgcacactc agccatccgc   7440
cccgcgaaca ccggcgacga atccagcaga tccaccgcca tccccaccca ctgcgccccc   7500
tgacccggga acacgaagac ggcgcggccg tcgccgacgg cgcggccgcg caccacgtcg   7560
gccgactcgg cgccttccgc cacggcggtc aggccggcga gcaggtgtc gtggtccgcg   7620 ccgaggacga ccacgcggtg ttcgaaggcc gtacgggtgg tggcgagggc gagggccacg   7680
tcgtgggggg cggcgtcgtg cgcgggccgg tgggcgagga ggcgttcggc ctgggcgcgc   7740
agtccggccg ccgtccggga ggacagcgtc cacgggacga ccggcagggt gcggtccgtg   7800
```

```
gcctcgtcgg tgggctcggg ccgggcgggt gcctgctcca ggatggcgtg ggcgttggtg   7860
ccggacacgc cgaacgacga cacgcccgcg cggcgcggct gctccccgcc cggccagtcc   7920
cgctcctcgg tgagcagttc cacggcgccg gcggtccagt cgacgtgcgg tgacgcctcg   7980
tccacgtgga gcgtgcgcgg cagcgtgccg tggcgcatgg cctgcaccat cttgatcaca   8040
ccggccacac cggcggcggc ctgcgtgtgc ccgatgttgg acttcaccga accgagccac   8100
agcggctcgt cccgctcctg gccgtaggtg gcgaggaggg cctgcgcctc gatcgggtcg   8160
cccagccggg tgcccgtacc gtgcgcctcc acggcgtcga cctggctcgc ggccaggcgg   8220
gcgtcggcca gcgcctggcg gatcacgcgc tgctgggcga gtccgttggg ggcggtgagt   8280
ccgctgctcg cgccgtcctg gttgatggcg gtgccgcgga ccacggccag cacggggtgg   8340
ccgttgcggc gggcgtccga gagccgttcc aggacgagca tgcccgcgcc ctcggcgaag   8400
ccgaacccgt cggccgccgc ggcgaacgcc ttgcagcggc cgtcggccgc gagggcccgc   8460
tgccggctgt actcggtgaa cacgccgggc gtggacagca cggtcgcccc gccggtgagc   8520
gccagcgtgc actccccggc gcgcagcgag cggaccgcga ggtgcagggc gaccagggac   8580
gaggagcagg cggtgtccac ggagagggcg gggccctcca ggccgagggt gtaggcgacc   8640
cggccggaga gcacgctggg cgaggtgccg gtgacgacgt acccctccag ctcggtggcc   8700
accgggccgg tgatgtcgga gtagtcctcg ctgctgaagc cgacgaacac gccggtggcg   8760
gtggagcgca ggccggccgg gtcgatgcca gcccgctcca gggcctccca tgaggtctcc   8820
agcaccagcc gctgctgcgg gtccatggcc agcgcctcgc gcgggctgat gccgaagaag   8880
ccggcgtcga agtccgcggc gccgtcgagg aatccgcctt cgcgggcgta ggaggttccg   8940
ggccggtcgg ggtccgggtc gtagaccgag gccatgtccc agccgcggtc ggcggggaac   9000
gccgagaccg cgtcggtccc atcggtcacc agccgccaca ggtcctcggg cgaggtcacg   9060
ccgccggggt agcggcaggc catgcccacg atcgcgatcg gttcgcggtc gcgggcctcg   9120
gcctcgcgca gccggcgccg ggcgacctgg agatcgcccg tgacctgctt gaggtagtcg   9180
agcagtttgg cctcgtcagc catcggtgca ccccgtgcg gttcgttcgg cgcgggtcac    9240
gagacgcccc ggtcgatcag gtcgaagagt tcgtcggcgg tgacgccgtc cagagcggcc   9300
cgctcgggtg tgccgtcggt cgtgccggcg tcccagcggg ccgcgaggtc ccgcaggtgc   9360
gccgccaccc gggcgcggtc ggtgccgtcg gccggcagtg cgccgagcgc gctctccacg   9420
cgggccagtt cggcgatgat ccggtcggcg ctcgcctcgc cggactcgct cggcaggagc   9480
gcgtcgagga ggtggtcggc gagcgcggcc gggttcgggt ggtcgaacac gatggtggtg   9540
ggcagtcgca ggccggtggc ggtgccgagg cggttgcgca gttccacggc ggtcagcgag   9600
tcgaagccca gttccttgaa gccgcggtcg ggtgccaccg cgtcgcgtcc ccggtgtccc   9660
aggacgtcgg cgacctggcc gcggacgacg tcgagcaggg cggggcgcg ctcgggcgcg    9720 ggcagcccgg tgatccgcgc caccaggcc gccgcaccgg gcaccgggcg gcggcggcc      9780 gggccggccg gggtggcgac caggccgcgc agcagcggcg gggtgggcgc ggcggaggcg   9840
gtggcgaggt ccaggcgcgc ggtgacggtc acggcgtcgc cggtggcggt ggccgtgtcg   9900
aacagggcca gtccttcggc ggcggccatc ggcacgatgc ggttgcgcc ggcgcggcg      9960 acgtcggcgg cgtccaggtg ccgggtgagg ccggtggcgt cggcccacag gccccaggcc  10020
gcggcggtgc cggcaggcc ggcggcgcgg cgccgttcgg cgagcgcgtc gaggaaggcg   10080
ttggcggcgg cgtagttggc ctgcgcgggg gtgccgaggg tggccgccgc ggaggagaac  10140
```

```
agcacgaagg cggacaggtc cttgtcctcg gtgagttcgt gcaggtgcca ggcggcgtcg   10200
gccttcgggc gcagtacgcc cggcagccgg ccggcgccga gttcggtcag cacgccgtcg   10260
tcgagggcgc ccgcggtgtg caccaccgcg gtcagcgggg cctcggcggt cagcttggcg   10320
agcagcgcgt cgagggcggc gcggtcggtg acgtcgcagg tctcgaagcg gacggtggcg   10380
cccgccgcgg ccagttcggc gaccaggtcc gcgctgccgg gggcggcggc gccgcgccgg   10440
ctggccagca ccaggtcacg ggcgccgtgt tcggacacca gatgccgggc gagcatgccg   10500
ccgagcacgc cggcgccggt gatcaggacg gtgccgtcgg cgtacggggc gacggtgagc   10560
acgatcttgc cggtgtgccg ggcctgggcc atgaaccgga acgcggtgcg cgcgtcggcg   10620
aggggccagg tccgggtggg cagcccggtc agctcgcccg cctcggcgtg ggcgacgacc   10680
tcggtcagca ggctctggac gcggtcgggg ccggcgtcca gcagcaggtc gaacgggagg   10740
tagtcgacac cgggcaggcc ggcggggtcg cggcggtcgg tcttgccgag ttccacgaac   10800
cgtccgccgg gacggagcag tcgcagcgac gcgtccacga actcacccgt gagggagttc   10860
agcacgacgt ccatctccgg gaaccgctgc gcgaactccg tatcccgcga cgacgccaca   10920
cgcgcctcgt ccagaccggc cgcccgcagc acctcgtgct tgccgggact cgccgtcgca   10980
tacacctcgg cgcccagcag ccgcgccacc cgcaccgcgg ccatgcccac accaccggcc   11040
gccgcgtgca ccagcacccg ctcccccgcc cgcaccccgg ccacatcgcg cagcgcgaac   11100
caggcggtgg cgaacacgga cggcagggcc gcggcgcgga cccaggacca gccggcggga   11160
acgggcacca cgagccgccg gtccaccacg gcgagggtgc cgaagccgcc cggcaccatg   11220
ccgaggactc ggtcgccgac ggcgaggtcg gtgacgtccg gggcgaccgc gaccacggtg   11280
cccgcggcct cggagccgat cgcgtcgacc tcgtccgggt acatgtcgag cgcgcacagc   11340
acgtcgcgga agttcaggcc cgccgcgcgg acggcgatgc ggacctggcc gggtgccagg   11400
ggggcggtgg cgtcgggagc ggcgacggcg tcgacgccgt cgatgctgcc gggccggacc   11460
acgtcgacgc gccaggcgtc ggcgccgacg ggcgggcgca gcgcggtctc agcggcccgg   11520
gtgagccggg cgacgaggcg ttcgccgtcg cggagcgcgg tctgcggctc gtcgccgacg   11580
gccggcacag cgtccaggga ggcggtgtgt ccgtcggtgt cgacgagcag gaaccggtcg   11640
gggtgctcgg tctgcgcgga gcgcaccagg ccccagaccg cggcggcggc cgggtcgggt   11700
tcctcgccgg gccgggcggc gacggcgtgc cgggtgacga tcgcgagccg ggcctgcccg   11760
aaccggtcgt cggcgagcca ctcgtgcagc agttccagca cctgggcggt ggcccggtgg   11820
gcggcggcga ccacatcggc tcctgtgctg acggagcga ggacgaggtc caccgcgccg   11880
gcgtcgatgt cggcgagggc ggtgctcagg ggcgcggcga ggccttccgg tccgtcgccc   11940
aggacgcgc agcgcgcggc ggcgggtgtc tcggcgtcgg gggtctgcca ggtcacgcgg   12000
aacagcgcgt cgcgcgtgcc ggcggcggcc acggcgcgga gctgcccggc cgacgcgggc   12060
cgcagccgca gcgcggccag ctccacgacg ggcggccct cgcggtcggt cgcggtgagg   12120
ctcagcgtgt cggcgctctc ccgggcgcg cgcacccgca ggaccgggc cgggccgggg   12180
tgcacggtca cgccggtcca ggtgaacggc agcagcagcg gcgcgtcctc gggctcggcg   12240
gcggcacgg cctgggtgac ggcgtcgagc agcgccgggt gcacgagatg gccggcgtg   12300
tcgacggtgt cggggagttc gacctcggcg tagacctcgg tgtcccggcg ccacagggcg   12360
cgcaggccct ggaaggcggg cccgtagccg tagccgcggg cggcgaaacg gtcgtacacg   12420
ccgtccaccg gaccggctc agcgcccgcc ggggccacg cgccggtctc gggctccgcc   12480
ggctcggccg gctcggccgg tgccaggacg cccgtggcgt gccgggtcca gccgtcgccg   12540
```

```
gagtgggagt ggacggcgac cgtgcggcgg ccggacccgt cggcgccgtg cacggtgacg    12600
cgcagggtca ggccgtcggc ggggacgccg atgggcgcgg ccagggtcag ctcctcgatc    12660
tgggcgcggt cgagccggtg gccggcgtgg gccaccatct ccaggacggc ggtgccgggc    12720
agcagggcgg tgcccagcac ggtgtgctcg gtcagccagg ggtgcgtctc ggggctgatc    12780
cggccggtga ggagcaggcc gtcctcgtcg gggagttcgg cctcggcggc gagcagcgga    12840
tgccctccgg cggtgaggcc gacggcggtc aggtcgccgg cggcggcctg ggggtgagc     12900 cagtagcgct cgcgctggaa ggggtaggcg ggcagttcga ccgggcgggc gccggtggcg    12960
tcgaacaggg ggcgccagtc gaccggcacg ccgtcggcgg ccacctcggc cagtgcggtg    13020
gtcaggcgca gccggtcgct ctcgtcgcgg cgcagggtgg cggcgacccg cagttcggtg    13080
cccgccgcct cggcggtctg ctgcatggcg accgtgagca cggggtgcgg gctgatctcc    13140
acgaagccgt ggtggccggc ggcgagcaga tcgctgatcg cgttctggaa gagcacgggc    13200
tcgcgcaggt tgcggtacca gtagcgggcg cccagttcgc tgccgtcgat ccagtcggcg    13260
gtgacggtgg agtagagggg cacgtcgccg tcccgggggc ggatgccctt gaggtcggcg    13320
agcagccgct gccgtacggc ctccacctgc ggggagtgcg aggcgtagtc ggcggcgacg    13380
cggccggcgc gcagcccctc gtcgtcgcag aggtcgagca gctcctccag ggcatcgcgg    13440
tcgcccgcga cgaccagcga gcggggggctg ttggcagcgg cgatgccgag ccggccgggc    13500
cagcgctcca gcatccgctc gacgttcgcc gcggggggcgg cgacgaaggc catgccgcag    13560
cggccgggca ggtcggcgac ggccttggcg cgcagcgcga cggtcttcgc ggcgtcgtcc    13620
agggtgaggg cgccggcgac gcaggcggcg gcgatctcgc cctgggagtg gccgaccacg    13680
gccgccggca cgacgccgtg ggagcgccac accgcggcca gcgagaccat gagcgcgaac    13740
agcaccggct gcaccacgtc gacgcggctg agcggcggcg cgtcctcggc tccgcgcagc    13800
acgtccacga ccgaccagtc caggtagggg gcgagggcgc gctcgcactc ggccatgcgc    13860
gcggcgaaca ccgggtgggt gtcgagcagt tccacgccca tgccgagcca ctgtccgccc    13920
tggccggcga agacgaagac gacgctgccg tcggctccgg cggtgccgcg gacgacggcc    13980
gggtcggcgc cgcccgcggc gagcacgtcg agcgcggcga gcagttcggc gcggtcccgg    14040
cccacgacgg cggcgcggtg ctcgaacgcg gtgcggcggg tggccagggt gaacccgacg    14100
gaggcgggct cgaggccggg gtcggcggcg acgaactcgc gcagccgggc ggcctgttcg    14160
agcagcgcgg cctcggtgcg cgcggacagc tgccagggca cggggagcgc accggccggc    14220
ggcgccgtcc cttcctcggg ttcgggcgcc tccgccacga tcacatgggc gttggtgccg    14280
ctgacgccga acgaggacac gccggcccgg cggggacgct cgccccgggg ccacgggcgg    14340
gcctcggtca gcagccgtac gtcgccggac acccagtcca cgtgcggggt gggctcgtcg    14400
acgtgcagcg tcttcgggag cagtccgtgc cggagcgcga gcaccgtctt gatcactccg    14460
ccgacgccgg cggcggcctg ggcgtggccg aggttggact tcagcgagcc cagccacagc    14520
ggccggtcgc ggtcctggcc gtaggaggag aggagtgcct gggcctcgat ggggtcgccc    14580
agggcggtgc cggtgccgtg gccctccacg gcgtccacgt cggcgggacg cagtccggcg    14640
tcggccagtg cctgccggac cacgcgctgc tgggcggcgc cgctcggcgc ggtgaggccg    14700
ttggaggcgc cgtcctggtt gacggcggtg ccgggcagca gggcgagcac cgggtggccg    14760
tttcgccggg cgtcggagag ccgctccagc aggagcatgc cgacgccctc ggaccagccg    14820
agtccgtcgg cggccttggc gtacgagcgg cagcgaccgt cctcggacag gccgccctgc    14880
```

```
ttggtgaagt cgacgaacag ctccggcgtc ggcatgacgg tcacaccgcc ggccagcgcg   14940
agggtgctct cgcccgagcg cagcgaccgc accgcctggt gcagggcgac gagggaggac   15000
gagcaggcgg tgtccaccgt gaaggcgggg ccttccaggc cgaggacgta ggagatgcgg   15060
ccggccacca cgctggccag gcggccggtc agggcgtgcc cgtcgccgcc ttccgggatg   15120
ccggcgagca gcgaggagta ggactgggcg ttggcgccga cgaacacgcc gacgcgtccg   15180
ccccgccacg agccgggtgc gacgccggcc cgctccagcg cctcccagct ggtctccagc   15240
agcagccgct gctgggggtc catcagctgg gcctcgcgcg ggctgatgcc gaagaagccg   15300
gcgtcgaaca gggcgacgtc gtcgaggaat ccgccgtgcc gggtgcggct ggccgagggg   15360
ccgtccgggt cggcgagggc ggcgaggtcc cagccgcggt cggcggggaa cggcgtgatg   15420
gcgtcgcgct cctccagcac gagccgccac agctcgtcgg gggtggtcac accgcccggg   15480
aagcggcagg ccatgccgac cacggcgacc gggtcgtcgt cggccgcgcg ctgtacgggc   15540
tcgtcgtcct cggcgagccg gacgtgccgg ccggaggcgg cgtcgaccag gacgtccgcc   15600
agggcgcggg cggtgggggtg gtcgtagatg gcggtggtgg gcagcttcac gccggtgccg   15660
cggctgagcc gcagcagcag ttgtacggcg gtcagcgagc gcagtccgag ttccgggatc   15720
gcccggtccg gcggtacgtc ggcggcggtg ccgaggtcga gcacctccgc gacctgtgtc   15780
cggaccaggt ccaggacgac gcgccggcgc tcgggttcgg gcagaccggc gagccggtgc   15840
gcgagcgcgg cggctgagc agccttcggg tcggtcagcg gctcagtcat gggtggtccc   15900
ctccagcggg tccggtgcgt gcagtgcgga gacgggcagg ccgggttcgg cgagtgcggc   15960
ctgtagcagc gcggcggtgc cggccagcag gccgtccacg acgcgtcggc cgagggcggc   16020
ggcgcggtgt acgacgtgtc cggtgaggcc gccgtcgggg tcctcgacca ggtgcacctc   16080
gaggtgccag cgggcgtacg cctgttggcc cgtgaactgc tcgacgcggg cgccaggcag   16140
gccgagttcg ccgagttcga cgttgacgag ctggaacacg acgtcgacca gcggctgttc   16200
ggggtccagg ccgaggcctt cgacgacgcg ttcccagggc agggcctggt gggcgtaggc   16260
gtcgagggcg gtgtcccgga cccgctccag caggccggcg aaggacgggt cgccgctgag   16320
gtcgacgcgc aggggcacga agttggcgaa gaagccgatc agcccctcga cctcggcccg   16380
ggtgcggccc gccaccgggg agccgacggc gaggtcgtcc gtgcccgccc agcgggcgag   16440
cgtggccgtg aacgcggcca gcagggtcat gtagaggggtg gcgtcgtgct cggcgccgac   16500
ccggcgggcg gtggcgacca ggccggcggg cagccgccac tcggtcagca cgccggtggc   16560
gtcgtgggcc gcgtcggccg ggacgcccgg cagggcgagg ggccgcaggc cgtccagccg   16620
gcggcgccag tggccgagct gggcgtcgag cgcggctccg gtcagccagg accgctgcca   16680
gaaggcgaag tcgccgtact ggacgggcag ttcgggcagc tcggccggac ggttctctcg   16740
tagtgccgcg taggcgccgg acagttcggt ccagagcacg ccctgggacc agccgtcggt   16800
ggcgatgtgg tgcaccgtca gcagcaggac gtggtcgtcg ggggcgatcc gcagcagtgc   16860
gggccgcagc accggtcccc ggacgaggtc gaacggccgg gccgctgcct cgtcggccag   16920
ggcgcgggcg gcggtctcgt cggccacgtc caccgggtcc agcacgatgt ccgtggcggg   16980
caggatcacc gacgccggct cgtcgccggg cacgaagacc gtgcgcagcg cctcgtccgg   17040
gcgcacgacc tcggtcaggg cgcggcccag caggtccgcg tccagttcgc cggtgatccg   17100
cacggccagc gggatcgtcc agaccgggtc gccggggtcg gcctcgtgca gccgccacag   17160
ccgcagctgg cccagcgaca gcggcagggg ctcctgccgg acaccggca ccaggggcgg   17220 tacggccgtg cgcggggcca cggcgacgac ctcggcgagg gcgcgcgggg tgcggtgctg   17280
```

```
gaacagctcc cgcagggaca cctcggcgcc cagcgcctcg cggatccggg cgaccgtgcg   17340
ggccgcgacc agcgagtgcc cgccgagcgc gaagaagtcg tcgtcgatgc cgaccccgcc   17400
ggtctccagc acctcggcga acacctcgca cagcgtctgc tccgcaccgg tacggggtgc   17460
ggtgaagccg tgtcgagcg tggtgcgcag gtccggggcg ggcagcgcgg cccggtcgat   17520
cttgccggtg gtggtcagcg ggaacgcgtc cagcgcgacg agcgccgacg gcaccatgta   17580
gtccggtacg gcgtcggcca ggtgggcgcg cagccgggcc ggcagccctc cgtcggtacc   17640
ggggacgggc acgacgtagc cgacgagccg cttgacgccg ggggcgtcct cgcgggcgac   17700
gatgacggcg cgggtgacct cggggtggcg cagcaggacg gcctcgacct cgcccagctc   17760
cacccggaag ccccggatct tgacctggtg gtcgagccgg cccaggtatt ccaggctgcc   17820
gtcgggccgc cagcggccca ggtccccggt gcggtagagg cggagccggc gcgggccgaa   17880
cgggtcgggc acgaacttct gcgccgtcag ttccggcttg ccgacgtagc cgcgggcgag   17940
tccggggccg gcgaagcaga gttgccggc cacgcccacg ggaccggcc gcagccggtc   18000 gtccaggacg taggcgcggg agttgtcgac cggctcgccc aggtgtgcgg tccggggcca   18060
gtcggcgacg tcagcgggca gggtgaagga ggtgacgacc tggatctcgg tggagccgta   18120
gtggttgtgc agacgcagac ggggccgggc ggcgcagaac tcgcgcagca cggtgtccag   18180
cgacagcggc tcgcccgcct gggagatgtg ccgcagcgag gtgagccggg cccggccggc   18240
gccggcctcc tcggcgagcg cgcggatcat caggttgggc acgaatatct gctcgacggc   18300
ccgttcgtcg agccagcggg cgaagcgggc cgggtcgcgg cgggtctcct cggtggggat   18360
gaccagcgtc tcgccgtaca ggagcgcgga gagcacctcc tgcacatgca cgtcgaaggt   18420
gagggcggtg aactgggcgg tgcgcgtgcc gggtccgccc ggtaccgtct tcttctgcca   18480
ggcgagcatg ttgaccacac accgggcggg catggcgatg cccttgggca cgccggtgga   18540 gccgaggtg tagacgacgt aggcgaggga gtcggggccg ggtcgtccgg cggccgttgc   18600
cgcgggcggc tcctgcccgg ccggggcgtc cacgaggacg agggcggtgc cctcggcgaa   18660
gacgtccgcg tgagcccggt cggtgacggc gacggtcatc cgggcgtcgt cgacgatgag   18720
ccggatccgg tccgggggt ggctcgggtc gatcggcaca taggcggcgc cggccttgag   18780
gatgccgatc agagcggcca tctgcacggt gccgcgctcc aggcagaggc cgacgaggtc   18840
gtccggcccc acgccctggg cccgcagccc ggcggcgatc cgctcggcct cgtggtccag   18900
cgcggcgtag gtgaggacgt cgtcctcgca ctccacggcg cgggcgccgg gggtgcgggc   18960
gacctgctcg gcgaacagct ccacgagcgg gacgtcccgg tacgggaggg cggtgtcgtt   19020
ccaccgctcc agcagcaggc gccggtcgtc gtcgtccagc agcgagagcg cggacagcgg   19080
cgcgtccggg tcggcgaggg cggcgcgcag cagcaccgtg tggtgatgca gcaggcggcg   19140
gaccgtgtcc gcctcgaaca gcgcggtgga gtgcagcacg gtgccgcgca cccggtcgcc   19200
gtcctcggtg aggtgcactt cgaggtcgac gcggtgaag gcgtgctcgt ccagcagcgg   19260
ttccaggcgg gcggcgccga ggcggtcgcc cttgtcccg ggcgcccgca tcagctggaa   19320
gaccacctgg accagcgggt tgcgggacag gtcccgctcg ggtgccaggg tctccaccag   19380
gtgctcgaag gcaggtcct ggtggtccat ggcgcccacc accgtctcgc gcacccgcc   19440 cagcaggtcg cggaaggtcg ggtcgccgga gacgtcggtg cgcagcacca gcatgttgac   19500
gaagaagccg atcagccgct ccacctcggg gcgggtacgg cctgccacgg gggcgccgac   19560
ggcgacgtcc tcggtgccgg cgaaccgtgc caggaccacg gtgaaggcgg tcagcagcgt   19620
```

```
catgtagagg gtggcgccct cggtgtcgcc gaacgcgcgc gcggcccgga ccaggtcctc  19680
gggcagttcc cacggctggg aggcgcccgc cgagccggcg accgcgggc ggggccggtc   19740
caggggaagt tccagggggc gcagcccggc gagccgcgcc cgccagtagg tgaggtaccg   19800
ctccagttcg cgccggtga gccggccctg ctgccagacg cgcaagtcgc cgtactggac    19860
aggcagttcg ggcagttcgg cggggtcgcc ggacagttcg gcgcggtagg cctcggccag    19920
ctcgccccag aacacggcgt gcgaccagcc gtccgtgacc gcgtggtgcg cggtgatcag    19980
gacggcgtgg tcctcggccg cgaggcgcag cacgcgggcg cgcagcagcg gtccccgggc   20040
caggtcgaag gggcgcgcgg cgtccgcctc ggccagggcg cgtacctcgg cctcgtcggc   20100
gacgtccgtg acctccaggc ggagcggggt cgcgggccgt acgacggcca taggctcgcc   20160
ggcgtcggcg gcgaagacgg tgcgcagcgc ctcgtggcgg gagaccacca gggacagtgc   20220
ccggccgagg gcgtcgacgt cgagcgggcc gtgggcgcgt acgcccatcg ccacgttcca   20280
gaagccgctg tccggggtga gccggtccag gaaccacagg cgccgctggg aggacgacag   20340
cggaagcgcg gcgccgtccc ggcgggccgg ccggatgacg tccgtggccg tgccgggctc   20400
gccgagggtc tcggccagcc ggcgcgggga cgccgttcg aacaccgcct ggagcggcac   20460
gtcgggccca agcgggcgc ggatccgggc gatggcgcgg gtggccagca gcgagtgccc    20520
gcccaggggcg aagaagtcgt cgtcggcgcc caccgggtgg acgtccagca cctcggcgaa   20580
gatctcgcac agcacccgct ccgcctcggt cgcgggcggg acgtacccgc tctcggcgac    20640
cgagcgggtg tcgggcgcgg gcagggcccg gcggtcgatc ttgccggtgg tggacagcgg   20700
gaacgcgtcg agcgcgacga acgccgacgg caccatgtag tcgggtacgg agcccgcggc   20760
gtgggcgcgc agggcgggca gcacgctcgc gccggcctcc ggctccagca ccacataggc   20820
gaccaggcgc ttgtcgcccg ggatgtcctc gcgcacggcg acggtgacct gcgagaccgc   20880
cgggtgccgc agcagcgcgg cctcgacctc gccgggctcc acccggaagc cgcggatctt   20940
gacctggacg tcgcgcgcc cgaggaactc cagcgcgccg ccgggcagcc accgtacgac   21000
gtcgcccgta cggtacatcc gctcgcccgg cccgcccac gggtccggca cgaacttctc    21060
ggcggtcagg tcgggccggc ccaggtagcc gcgcgccacc cggggcccgc cgatgaccag   21120
ttcgcccgcc acgcccagcg gcgccgggcg gagggtgtcg tcgaggacgt acacccgggt   21180
gttgtcgatc ggcgcgccga tgggcacccg ggagccggcg agccggaagc cgggttccat   21240
cgggaacagc gtggtgaacg cggtcgcctc ggtcgggccg taggcgtcgg ccacggtcag   21300
gtgcgggtgg gcgccatca cctgggcgac ggtctcgccg acacggcct cgccgccggt    21360
gagcacctcg cgcagcccgc cgaagcactc catgcactcc tcggccagga ggctgaacag   21420
gggtgcgggc aggcacatcg cggtgacgcc gtgctcgcgg atgagccggt cgaaggtgtg   21480
cggttcgacg tgctcgtcgg tggcgacgac gatctgcttg ccggtcagca ggaacggcca   21540
cagctcgtag gtggagatgt cggtggccag cggatagtgc agcagcaccc gttcgtggtt   21600
gccgttgctc cagcggcgt cggcggccag cacgacgacg ttgcggtggg tcacggccac   21660
gcccttgggc tcgccgctgg acccggaggt gtagatgacg tacgccgtgg tgtcggggtg   21720
cgggtcgata ccggggtcgg tgtcgggccc ggggcccggg tcggtgacgt cgaggacggt   21780
gatgccgtcg gtgccgggca ccgggcggtc ggcgatgacg acgcgcagcc cgaggtggc    21840
cacgatcgcg tcggtgcggc ccggggggtt gcgcgggtcg agcggcacgt aggcggcgcc   21900
cgccttgagc acgccgagca cggcggccac catgccggtg gagcgtccgg tggcgacgcc   21960
gaccggttcg tcggcgccga cgccgtgggc cagcaggagg tgggcgaagc ggttggcccg   22020
```

```
ccggtccagt tcggcgtagg tgacccgctc gtcgccgcag atcagggcga cggcgtcggg    22080
ggtgcgggcg gcctgctcgg cgtagagccg gggcacgcag ccgtccggca gcggtgcggc    22140
cgtgtcgttc caggcgacca gggtgcggtg ccggtcggtc tcgtcgagca tggtcgccgc    22200
ggagaccggc cggtcggggt cggcgagcac ctcgccgagg accaccgaca cgtggtgcat    22260
cagctggcgg acggtgtcgg cgtcgaacag gtcggccgcg tacaggacgg tcgcgccgac    22320
ctcgtcgccg gtctcgacgg cgtgcacctc caggtccatc cgggtgtacg cgtggtcgat    22380
gtcgaacggc tcggcccggg cgccctgcca ccagggccgc cggggcgcgt cggcgagcag    22440
ctggaacgcc acctgcacga gcgggttgcg ggacaggtcg cgctcggggc gcagccgttc    22500
caccaggtgc tcgaagggga cgtcctggtg ctcgacggcg ccgaccaccg actcccgtac    22560
ccggcccagg agttcccgga aggtcgggtc gccggacagg tcggtgcgga cggcgacgac    22620
gttgacgaag aagccgatca gcgcctcggt tcggcgcgg gtccggccgg ccgtcggcga    22680
gcccacggcg atgtcctcgg tgcgggcgta ccgggacagg acgagggtga acgcggccag    22740
gagcaccatg tagagcgtgg ctccctcgcg ggcggcgacg gcccgggcgt cccggatcag    22800
ctcggcgggc agctgccagg gcagggtgcc cgcccgcccg gtggcgacgg cgggccgggc    22860
cttgtccagc ggcagttcca gcggggcgag gccggccagc cggccggtcc agtagccggc    22920
ccggcgctcc agcacctcgc cggtcagcca ggaccgctgc catacggcgt ggtcgccgta    22980
ctggacgggc agttcgggca gcggggcgcc gtcgtacgcg gcggcgatct cggcccacag    23040
cagggcctgg gaccagccgt cggtcgcgat gtggtgcacg gcgacgacga ggacgtggtc    23100
gtcggggggcg agccggagca gcgtggcgcg cagcagcggg cccgcgtca ggtcgaaccc    23160
ggtggacagc tcggcggagg ccgcggcgcg tgccgcgtcg gcgtcgggta cgtcgacgat    23220
ccgcggggcg accggggcgg cggcgccgat gaccgcggcg ggcacgccgt cggcgaccgt    23280
gaaggtggtg cgcagggtct cgtgccgggc gacgaccgcc gacagggcgc cggccagccg    23340
ctcggggtcc agcggtccgc gcacgcgcag ggctccgccg gaggtgtacg aggcgctgcc    23400
gggggcgagc tggtccagga accacatccg ctgctgggcg aaggacagcg gcagcagccg    23460
gtcgcggtcc gcgggcacca gcggcggcgc cgggtcggcc gggagcgcgg cgccggcgac    23520
caccgaggcc agggctcgcg gggtgcggtg ctcgaacacc tcgcgcagcg ggacctcggt    23580
gccgaaggcg cgggcgattc gggcgacgag gcgggtggcg agcagcgagt ggccgccgcg    23640
tacgaagaag tcgtcctcgg cgccgaacgc gtcggcgtcg agcagctcgg cgaagatctc    23700
gcacagcgcc cgctcggcgt cggtgcgcgg ggcggccagg ccggcgtccg ccgtctccgc    23760
cggggcgggc agcgcggcgc ggtcgaccct gccggtggcg gtcagcggca gcgcgtcggc    23820
gaggacgaag gccgagggca ccaggtagtc gggcagggcc gccgcggcgt gggcgcgcag    23880
ggcggcggtg tcggtggtgc ggccggcgcg cgggacgacg tgggcgacga gccgcttgcc    23940
ggccgggccg tcaccgcgca ccacgacggc ggcgtgcgcg acggcggggt gggcggccag    24000
gacggcctcg acctcgccgg gctcgacccg gaggccgcgc agcttcgcct ggtcgtcggc    24060
gcggccgagg aactccagga cgccgtcggg gcggcggcgc accacgtcgc cggtgcggta    24120
catgcggctg cccgccggtc cggacgggtc gggcaggaag cgctcggcgg tggccgccgg    24180
ccggccggcg tagccgcggg ccaggcgcgg gccgccgacg tacagttcgc cgggcacgcc    24240
gaacgggacg ggccgcagcc ggtcgtcgag gacgtgggcg cgggtgttgt ccaggggggct    24300
gccgatgggc acccggccgc cggggggccgg gtcggccggc gcgatcgggt ggagggtggc    24360
```

```
gaaggtggtg gtctcggtgg ggccgtagcc gttgacgacc gtcaggtccg ggtgggcgcc    24420
gcgcacgcgg gccacggtcg ccggggacac ggtgtcgccg ccgacgacga gttcgcggac    24480
gccggccagg caggtgacgt cctcctcgac cacgaggtcg aagaggccgg aggtcagcca    24540
cagcgcggtg acgccctggt cggcgacgac acgggcgagg gcggcgggtc cgagggcgcc    24600
gggcggggcc accacgacgc ggcggccgga cagcagcggg gaccacagtt cgtaggtgga    24660
ggcgtcgaac gcctgcgggg agtgcagcag gacccgttcg tgggcgccgc cggaccagcg    24720
ccggtggagg gcgagggcgg ccacggcgcg gtgggtcgtg gcgacggcct tgggcgtgcc    24780
ggtggaaccg gaggtggaca tcacgtacgc gaggccgtcc gggccgacgg tgttcggcaa    24840
agccgtgtcg ggggctgtgc cggggacggc gcgcaggtct acggccggca ggtgctcggt    24900
gccggcgggt gcgggaccgc cgtcggtcag cagcagcgcg gcaccggtgt cggcgaggac    24960
ggcgcgggtc cgggcggccg ggttgcgggc gtcgagcggc aggtaggcgc cgccggcctt    25020
gaggaccgcg agcacggcga cgaccaggtg ggcggaacgt tccgtcgcca gcgcgacgac    25080
gctctcgggt ccggctccgt ggccggccag gacatgggcg agccggttgg cggcgcggtc    25140
cagctgggcg taggtgaggt gttccgtccc gtcggccacg gcgacggcgt ccggggtgcg    25200
ggcggcctgg gcgcgaaca gctcgggcag cgaggcctcg gcagcggta cgccggtgcc    25260 ccgggcggcc cggtccaggg ccgcgtcctc gcccgcgtcg gtcatcgtca gccgggacag    25320
cggccggtcg ggctcggcgc aggcggcgcg cagcagggcc gtcaggtggc gggccagccg    25380
ctcgacggtc tcccggtcga acagggcgcg gctgtagttg atcagtccct cgacgccgcc    25440
ctcggcgtcc tcgccgaggt agacctccag gtccatgcgg gtgaaggcgc ggtcgcccgc    25500
gaagggttcg gcgtggtgc cggggaacgg cgcggggcgc gcggcgggcc ggggcacgta    25560
ctggaagacg acctgggcga gcgggttgcg ggacaggtcg cgctcgggga ccagccgctc    25620
caccaggtac tcgaacggca cgtcctggtg cgccatctcg tccaccgagg cggcgcggac    25680
gcgttcgacg agttccgcga aggtgggggtc gccgccgagg tcggtgcggg tgacgacggt    25740
gttgacgaag aatccgatga gttgctcgac ctcggccagg ggccggccgg cgaccggctg    25800
ggcgacggcg acgtcctcgg tgcggcgtg ccgcccgagg accgcgctga acgcggccag    25860
cagggtcatg tgcagggtcg cgccctgccg tgcggcgacg gcccgggcgg cggcgacggc    25920
gtccgccggc agccgccagg tgacgacgcc gccctcggcg gaggcgacgg ccgggcgggg    25980
ccggtcgagc ggcaggtcca gcgggggcag gccggccagc cggtcctgcc agtacgccag    26040
ccgccgctcc agcacggcgg gcgacagggt acggcgctgc caggcggcga agtcggcgta    26100
ctgcaccggc agttccggca gcgcgggctg ccggccgtcg gccagggcgg tgtaggccgc    26160
ggtcagctcg gcccacagca ggccgtgcga ccagccgtcg gtggcgatgt gatgcaccgt    26220
cagcagcagg acgtggtcgt cgtcggcgag ccgcagcagg cgggcgcgga gcaggggcc    26280 cttggtgagg tcgaagggc gcgcggcctc ctcgccggcc agccgctcgg cgtcggcctc    26340
gtccacggcg tcggtcacgg gaacgggcac cggctccggc ggcaggacga cggcgccggc    26400
cacgccctcg tggtcggcga agacggtgcg caggtctcg tgccgggcga cgacacagct    26460
cagcgcccgg gccagcaggc cggcgccgag cgggccgcgg acgcgcacgg cggtgccgaa    26520
gttgtagaag gcgctgtccg gcatcagccg gtcgaggaac cacagccgct gctgggcgaa    26580
cgacagctcc agcggccggt cgcggggac ccggctgatg cccgcgggtg tcgtgccggt    26640
cctcgccgtg cgctcccgga gccggttgag tgccgagtcc agtccggcc gtcgcgagct    26700 cccctgcgtc atccggctgt ctcccgctcc tcgtcggctt cggtgagtcc gcggtcgcgc    26760
```

```
atcacgctgg ccagggcgcg gtgggtgccg gactcgcttg cttcgaactg ctcgaccacg   26820
cgccgccgca tcggggcggg cttctcctgg ctgagcttga acatcgtctg cacggaatcg   26880
acccgcaggg tgaaggcgcc cacgccgggc gcgatctggc ggaagtagtc gagggaggac   26940
tcctggtccc agccgcgccc gaagccgac tccagccgcc gggcggtgtc ggagacgatg    27000
tccagcacgg cggcggggtc ggcggtgggc tccactgtgc cgttcacgtg gacggcgatg   27060
aagtcccagg tgggggccgc gggcgtgacc ccgtagaccg tcggcgagac atagccgtgc   27120
gggccctgga agacgatgag cgcccggtcg ccggagcgca tccggcgcca ctgcgggttc   27180
tcgacgttca tgtggccgat cagggtggag ccggcgagcg ggacggtgcc cgcggcgacg   27240
gcctcggcgt cggcgccgtc gggtccgtgc cggaacagca ccggcgcgtg ggtggccacc   27300
gggacgtcgt cgtgcgaggt gacgaccatt gccagtgggt tgtgtcgcag aaacgccagg   27360
acgacgccgt cgcaatcctc ccggtacagc ggacgttcgt acacttcagc ccctgttccc   27420
cgctgctgcc ttgcttccgg tggagcggtc cgggtcgcac cggccgccgg tgatcgaccg   27480
ggcgatctcg cccgcgcgga ccgccaccat ggacagcagg gtggaggcga tgccgtgggt   27540
cgcctcggtg gcgccctgga cgtagatgcc gcaccggaaa tccccggtgg tgccgagccg   27600
gtagtcgcgg ccgatcagca actcccccgc ctcgtcccgg cggagggcgc cggagacgcc   27660
gccgagcagt tcggccgggt cggtggagtc gtacccggtg gcgtacacga ccaggtcggc   27720
gtccaggtcg gtgtgttcgc ccgtgggcag gaactccacg cgtacggcgg cggattcctg   27780
gcgcggttcg acggacacca ggcgggaggc gttcatcacc cgcagccgcg gggcgccgga   27840
caccttctgc tcgtactggc ggcggtagag gccctggagg acgtcctcgt cgacgacggc   27900
gtagttggtg ccgccgtggt agcgcatgat ggcctgcttg acctcgggcg gggcgaagta   27960
gaagtcgtcc acgcggccg gtcgaagac gcggttggcg aacgggctgg agtcggcgac     28020
gctgtagccg tagcgggcga acaccgcgca cacctcggcc tgcgggtagc ggtccatgag   28080
gtgcgcggcg acctcggccg cgctctggcc ggcgccgacc acgacggccc ggcggggcgg   28140
gcgttcgtcg aacgcgggca gccggtgcag caactgggag ctgtgccaga cgcgttcgcc   28200
ggtctccgcg ccctcgggca gccggggggcg caggccggag gcgaggacga ggtttctggt    28260
ccgggcgacc acccggtccc cggcgagcac gtcgagcgcg acgacctcac cggcttcggt   28320
caccggccgc acaccggtgg cctccacgcc gtactcgacc aggtggttca gccggtcggc   28380
ggcccactgg aggtagtcgt ggtactcgat ccgggagggc agcagggtgt gctggttgat   28440
gaagtcgacc agccggtcct tctcctggag ataggacagg aatccgaaat cactggtggg   28500
attgcgcatc gtggcgatgt ccttgagaaa ggacacctgg agcgaggagc cccccaggag   28560
catcccccga tgccagccga attccttctg cttctccagg aaaagggcct tcccggcggc   28620
ttcggattca tggagcgcca ccgccagggc gagattcgcg gcaccgaatc cgattccggt   28680
gacgtccagt acttctgatt ccgggctctg ctgcgcagtg gatgattgct ctgcgagccg   28740
ggtcatatat caaccgccat tagtttttca atggatgtat cgtcgcagga cgcccagaat   28800
tcacctgcga cgtcctccag atgcgtgagg gaacgcgcgc tgtaaaaggt ggtctggtac   28860
tgggttatgt cgtagtcgac gtgggccatg tcggcgatgt ccagcggccg gatctccgcg   28920
gaacggaagt gctccagctc gccgtaggag gagacgacgc tggcgccgta ggcccggggc   28980
ccgtcggcgg cgtccagcag gccgcattcg agcgtgaacc agaaggtctt ggcgacgaac   29040
tggacggcgt cctcggactc caccctgcgc acggcctcgc cggccaggcg gtacaggttg   29100
```

```
gcgaaccggt cgtcggccag ggcgctgccg tgcccgatga cctcgtgcag gatgtccggt   29160
tccgtcgagt agaagggtgt cgcgctgtcg cggaggtact gggtggagtg gaagtacccg   29220
tcggccagag agccgcagaa cagggcgaag ggaaccacgc cggacgcggg gcgtaggcgg   29280
aatccggtca gctggtcgag ccggtcggac acttcacgca actgcgggac gccgtcgccg   29340
cccacctcga gccgctccgc cgcctcgacg aactccggcg ccgccatgtg ccggtgccgg   29400
tccgcgagcc gcttggaaac caggcgccac agagcgtgct cggcgtccgt gtactcgacc   29460
tctggaatgg gctcgccggg cacataggcg gcagcgcttg cggcgatttg gtcacgccgc   29520
tgctgataca ccgacgacgc ggttaattcg ggcgcgcccg agccgatttc cacgaacttc   29580
cccctacttc catcgacaga aggcagcagt tgctgtccga agctattttg gttcggacgc   29640
ccgcatcaac cttcccttgt ccagccgatt cattaggacc ctacaagcca cccgcagcac   29700
tcgcaagagt tttctatgcg cccgctatgt accctttggg gcagactcac cggaaattat   29760
cgtcatccgc accgccggaa ccggagtcaa cgttggctc ggcagggcgg cttcaagttc   29820
ccgataggag cgggccctag gcgattcctc agatccggcc ggcgcgttcg ggtgtgtccc   29880
aaatcactgg cctaaatcct tcatgaggac ccgtcagctt gccgacggac gctctttcgc   29940
ttgtggtgcc gggcgtttcg gtgtccgggc aggccgcgcg ggagcgcccc aactgccgcg   30000
tcgggctgtc gcgtcgggtg ggcgccgggt tccacggctc cgggagtcct tcgacagggc   30060
ccggcgaata tctccaggac caagccgtgg gcggtgaggt ggtcggcgag ggcggtgagt   30120
tcggcggcgt tgcgaccgag ccgcttccgc tcgtacaccg tgaagatgac acggcagtgt   30180
ggggcgtgcg ccttgacctc ccgcgccgcc ctcagcgcct cctcccggaa cttcgggctg   30240
ccccgcgccc gggtgctgat cttctcgccg aagatgtagt cgcgcgagat gccgtgtttg   30300
gcgagcgcgt cgagctggga gtcacttcgc ctgcatccgc ccgcgcgcgg agtggtgcgg   30360
catcgtggca gcgcgcgtca gatgcgcggc gtcgcccca ggtgaactcc gtccgccctg   30420
gggcagggtg ggcggagttc accgcgtcgt gcggttcaac gggtccaatg gaggtcgcga   30480
tacggtccgc ccggcgcgcg ggccgcgatc atcattccgg cggggcggag ccgtcagtgc   30540
ttgacggtga acgtggcgcc ttggggcgcg aaggtcgtgt cgtggtcctt ggcggtggcc   30600
agcacggata cgtgccagac gcccttgggc aacgcggcgg cttccttggc cgagctcttc   30660
acggtgtagg tgcacaccga ggccgtcgcg gaagtcgcct tgcacgtggc ttcctcgaca   30720
tcccgcatct cgcccgccgt gggcgcaagg cccgaactcg ccggccaggc gagcacccgc   30780
aggctcttga ttccggagtt gtcggccacg gtggcgctga aggtgagcga ggcgctccca   30840
ccggccgtac tggtgtagtg ggcggtggcc tttgagatct ccggcttggc cggcacagcg   30900
gcgtcggccg aggagacgaa caccacggtg ccggcaacga cggctgcggc cacggcgagc   30960
gacgagacga caaggcgctt ggacatgaag tatcccctca tagatgaccg ctactggtct   31020
cttcgccgag cgctctgcgc accgcggcgt tgtgtacaca gcctgtctcg acggccctgc   31080
ccctcacatg ggcagaacta ctcaaccgaa gtactcagac gccctgagct tgtcgttcaa   31140
cctcgtctcc gttgggggcg ggtattgagc aggcgctttt cgaatgtggc gtccagcacc   31200 gccgtccagat atgtgcagcc ggtctgcaag cttcgtcgcg atcaggacct tcagcagatc   31260
cagcgcgtcg tccaccgccc gcgacgtgag gtacaccgcc gcggccagca gcgttgtgag   31320
gctgcgagag tccgagtgcc ggccggcaa cgacaccttg tcgtccgccc cgtaccgcga   31380
ccactctgcg ccgccccgtc acccgtaccg gtccgcggcg cagccggtcc agctccacca   31440
ggcggcccga cgagcagaga atccagcacc gcccgctgca cgacgcgcgg catcccgcac   31500
```

```
aaggcgtccc aaaacgccga ttcgccgcct cccacaccga tcccacagga caggccggac    31560
agctcgcccc cagcagcagc ggctactgtc acccgttcgg cggcgggcgc gacagagccc    31620
gtgacaacca gattgtgacg ttcggtgatc gtgacaccaa ttcggagctg gcccgctgac    31680
ctgtgacagc ggactggcct cgaaggtgga ccgaatgcag ttcttgacag caaagacgga    31740
ccgccgcagc tcagggcgc agtgcccgcc cgcagcacag tcggttcagg gctcgacgcc     31800
ggctacggac agacgtggat cgccggtcgc ggtcagcgcg aacgctgtcc ggtgaagagg    31860
cggtacagca ggagcacgat caccgagccg acgaccgcgg cgatccatgt cgagaggtgg    31920
aagaagccgt tgatggagtg cacgccgaag atcaccttgc cgagccagcc gccgagcaga    31980
ccgccgacga tgccgatgag catcgtgacg aggcagccgc ccgggtcctt gccgggcatg    32040
agtgccttgg cgatggcgcc cgcgatgagg ccgatgagaa tccaggcgat gatgcccacg    32100
gtgtgcgtcc tttgctgtag gtggtgccga ggaaggcccg acgaggctcc gccggggctg    32160
cccgccggtc gctccgcgcg gacgaccggc gacatacgga tatccgctcc ggaacactcc    32220
acacgggtca aggtcccgt ttcctccgac cgacccaccc ggcatccgat ccgtcggccg      32280
atccggtcga cggcggattc ggtgactggt caaccttcga tggcgctcga tcaaggttcg    32340
ctgtcacagg tcatccgccc tcagtccctc aggtcgcccc tcggaaggcg tccaccagag    32400
gtcaggcggg tccattcctc cggatcccca gctgcctcac agggtgctgg ggacccgggg    32460
acggccctcg gtgttatgga taagccgaag ctcaggacgt tctcacggcg acgccggatg    32520
agctggcgag gagggcgtgc cgaggcagtt cggttgtcac cgaggaggca tcccacttct    32580
cacgcgtgct cattcggcgg acttcctgtc accggcgccg acgagccgga gttcccgggc    32640
tccccggctg ggcccggctg agggctgagc ccttccacgg cgaggcggaa gaggcggtcg    32700
gcctgggtgt cggggtctgt gtggtgctcg gtggccaggg cgatgccgac ggcgagggtc    32760
agcaggtcgt gaaaggtgac gtgccggtgca accgccttgt cgcggatggc ccgctggagc    32820
aagggagttg cggctgcttc gattacgccc ccgcagctct tcggggaggg ttcttcggtg     32880
ggcggctcgt agctgaggat atgggcgaat ccgcgggctg agacggcgta gcggacgaag    32940
gcgtggaacc actccagcag tgcggtgcgg ccgtcctcgg acgcactcag ccgatgggcg    33000
cgctcgcaca ggcccgcaat gcgctcctgg aagacggctt cgaggagcgc ccggcgggtg    33060
gggaagtgac ggcgcacggt cgccgaaccg acgcctgcga tgcgggcgat ctgctcctgg    33120
gatgcctcgg cgccgtgcgc ggcgacttcg gcttcggcga cggcgaggat gcgctgatag    33180
ttgcgtcggg cgtccgagcg ctggccagtc atggtctcct cgttgctaag tggcgggccc    33240
cgccatatct tagcggcaca cgaaacggcg ggccccgccg ttttgtctct ccggcccttg    33300
aggagcagca ccatgcccag cagcagcgat accgtcctgg tcaccggcgc caccggccag    33360
caaggcgggg ccacggctcg cgcgcttttg gccgccaagg tgcccgtacg tgcgctcgta    33420
cgcgatccct cgtcgaagtc cgccggggcg atcgaggcgc tgggcgcgga actggtacgc    33480
gcggatcttt ccgaccgggc ctccctcgac ccggcggtcg aggggtccg cgcggtgttc      33540 tcggtgcaga tgccgcccat gaccgagacc agcgtggact tcgcgagcga actcgcccag    33600
gccaccaacc tggtggacgc ggcgaagata ggggagtac ggcagttcgt acagtcctcg      33660
accagtggag tcggtgaaca caccgggtc gccggctggg ccgagggccg ctgggcggcg       33720
atggcggagt acttccacac caagcaggcg atcatggagg cggtgcgtgg tgcgggtttc    33780
gcccgctgga cggtgatcaa gcccgccttc ttcatggaga acctgcccct gctggcaccc    33840
```

```
aaggggcccc gcggcggact gctgacggta ctgaagccgg acaccgaact ggccttggtg   33900
gccgtgcggg acatcggcac ggccgcggca cacgccctcc gagacccga ccggttccac    33960 caggtggaac tggaactggc tggtgacctt cgcacgatgg agcagatcgc gcagaccttg   34020
tccgccgcct gggcgtgcc cgtgaccgcg ccctccctga gcgtggaaga ggcccttgcc    34080
gcgggcatgc cgaagtgggg agccggacac gagtggaaca acgtggtcct ccagcccgcc   34140
cggcccacat cgcccggaa gttgggcatc ccgctcacca ccttcgccga gtgggcggat    34200
gagcagttga cacatgtgtc tgattagggg tgtggcggca agggcgcgcc attgacccct   34260
acggggagcg cggcggttgc ccgcagaggg cattgcggtc gggggcatc ggtgccggtc    34320 ccctggacgg gctgcaatga gcaggacagc gcagaggggt ggacacgaga tccctggagt   34380
gcacgacgtg gccatcaggg ggtcgggcgg tacgggatgg ggatgatgta gcgcgggtgt   34440
ggaggcatcg gcccagtgcg ctgcttccgc tgttcgcgcg ggtgccggca gcctgttcgt   34500
tggagtcgtc gtggcttcgg agcccgtccg ggaagtacac gccgtgggcg ctggcccatg   34560
ctgcccgggt gtcgctcgcg tggggaacg agtaccgcaa ggacgcgggc gatgcggctt    34620
cggcggcctc cctcgggtcc tcgccctctt cctcgtcgct ctcgttccag tcgagagcgc   34680
ggccgggtcc cgcccatccg cacgagcaca ccgcgcgcaa cgctgccgcc gcggtccgc    34740 catgaggccg gccgtcgtag acgctccgct ccgatagcca cctggcctcc gctccggaag   34800
agctgaggaa gagcacagga tccgggacgg tgccatcggc cagcaacacc ccgaccgcac   34860
ccacgtggga cgacccgaac tcctccgtcg tccacgtctc cctctcacct tcacccatcg   34920
tctcgcccct ctcctcatcg ccgcatccgc acccggccga acgcacggat acagacgatt   34980
ccggagtcca aggttccgca cagcgagatc ctcgaaaagg tgacctcgca cctccaccgt   35040
gcaccaggcc tcaaagccca cgacgagccg accgagcgca gaccaccgaa gacgaagcgc   35100
atcgccgctt cccagtgcgc tggttgatga ggttcaggaa agcggggtca cttctctaca   35160
tcggacagct accgcagctt gccgcgcccg ccgcccggag cggcggttgc tcggcgcccg   35220
cgtgcgggtc ggaagcggag gctcggccgg cgaggttcgc cgtcgatgcc ggcggcacga   35280
cgggccagct ctccgatctt ctcctcgggc agtccggaca tcctgacggc ctggcgcact   35340
gcggcccggc agtcgggccg tgagcagtgc gccgacgata ccggccgtcc gaccgtcgga   35400
tgctcgggcg gcaggtagat cgctgcgcag ccgacgcaca gatagattga tcgcaaggcg   35460 cttcccttc gtcagctgag gccgctgccg tggcaggtat tgcaggagcc ggtccagcta    35520
cgggcgacgg gcttctggtt cccgtcctta tcgacttcga cagagtgctc ggtgtgctca   35580
gtgactccgg atccgctgca agcggagcaa ggcacgtcag acattttccc aggatgcccg   35640
attctgtggg gccgtgtcag tcgtcccgcg acactcgcgc gctaccggac cgggcgggcc   35700
catcccgaga atctcccgcc tgcatcacgg cggcgccaac ggcgagcccg aacctctggg   35760
ccacgcggtc gctcgccggc ccggtgggcg acctcgtgcc gccacgttcc cactgcgcgc   35820
tgttccgcca ctccccgcc ccccagggcg agtcctcgct cgcgtcgcag tactgccgca    35880
cgagcaggtc gcccgctccc ggagaggccc cagcatcacg gcccgtcaag gtgctccgga   35940
tcggtggtgg ccgttgtgaa ccgccacgcg ccgcccggct cgtcggcctg gccatcgccc   36000
ggcctggtcc cgctcaggat gccggggcgg tcaggacggc cttggcagcc agccggaaat   36060
tcctgatcat cggattcggg tcgcccttgc ggctgaccag gacgaccggg ctgggggggag  36120 cgccctcgac cgggacggtg acgaggtcgg gacgcagtga gctgcgccga tcgccgaccg   36180
gtagcacggc gatggccctg ccgctcgcga cgagttcgag cttgtcctcg tagctctcga   36240
```

```
tcggcggcac gccggtcccg aggaactggt aggaagccca gcctgcggtc tcgaacgcac   36300
acggcgccgc ctcttcgccg gccagttctt ccgcggtcac cgacgcgcgg tcggccgag   36360 gatggccgcg cgggaccacg agcatccggg gctcctcgta cagcggggtg gtgaacacgt   36420
cgtcggcgac gagcggcagc ggggcccgcg cgatcagggc gtcgacgcgc ctgtcggaca   36480
gtgccccgac gtcgcggcag tgcagatgcc gggtggcgat ctcggcgtcg gggtaacggc   36540
ggcgcagttc ccgcacggcg gcagtgatca ccaggtcttc gacgtagccg atggcgattc   36600
gttcggtccg ggcttgttca cgcacggcca gctcggcctg gcgggcggcc cgcagcaggg   36660
cctgggcccg ggggaggaac gtccggccgg ccggagtgag ccgggtgccc tgggggggtgc   36720 ggtccagcag tcgtgtgccg agatatttct cgagccgttg gatctgacgg ctcagcgccg   36780
gctgggctac gtgcaggtcg gcggcggccc ggccgaagtg ctggtgcgcc gccaccacgg   36840
tgaagtagcg caccagccgc agttccaggt cctgcccgag atcgttcacc ctcgcagggt   36900
acgcgtcatg ccgtttcgga atggtcagat tgccgaaccg gtcttggacg gccatgccgt   36960
cccgggcttt gactgaagga gcaacgtttc cccgagaaag cgacaggcgc gatgaaggcg   37020
atccagatcc acgaagcggg tgggccggaa gttctgcggt acgacgaggt gccggctccc   37080
gagatcggcc cgggcgaggt gctcgtccgg gtgcacgcgg cgggcatcaa cccgccggac   37140
tggtacctgc gtgaagggat gaaggtcatg ccggccggga tgaggccggc gctggagttc   37200
cctctgatcc ccggaacgga catgtcgggc gtggtccagg cggtcgctcc ggacgtgccg   37260
gggttcggcg tcgcgacga ggtcttcggc atgctgcggt tccccggatt cgacggccgg   37320
acgtacgccc agtacgtggc cgcgccggct tctgacctgg ctcacaagcc ggccggtatc   37380
gaccacgtgc aggcggccgg ggcgccgatg gccgtgctca cggcctggca gtacctggtc   37440
gacctcggcc acgaggtgcc gtctcctttc accggccagg tgcaccagcc ggtgccgatc   37500 acgccggga tgaccgtgct ggtcaacggg gccgccggtg gagtgggcca tttcgcggtg   37560
caattggcga aatggaaggg ggcacacgtc atcgcggtgg cctcaagtcg gcacgagcgg   37620
ttcctgcgcg agctcggtgc cgatgagttc atcgactaca ccacgacgca ggccgcggac   37680
gtggtcagcg gtgtcgacct ggtgatcgac accgtcggcg gccggacgg ctcacgcttc   37740 ctgaccgtac tcaagcgcgg cggcacccctg ctcccggtgt tcttcgccga gtacgacccg   37800
gaagagacgg cgagtctgga catcaccgtc tcgaacattc aggtacgttc ccacggcccc   37860
cagctcgccg agatcgggcg cctgttcgac gagggcacac tccgggtcgg ggtggacagc   37920
acctacccgc tgtccgaagc ggtcagcgca cacacgcgag ccgcgcaggg ccacatccaa   37980
ggcaagatcg tgctgacggt ggcctcgtga tcgccgaaac tccagcaggc ggtggcgaac   38040
tacgcccacg ccttggacga gttgcatata cccgagctgg aaacggtcct ggccgaagac   38100
accacctgga ccgtcacgat gcccggacag gggatgctcg gccccgtcgc cggacgcgcg   38160 gccgcggcg tgctcgactt catcttcatc ccccgtgtca gctcggtgag cggtgtccca   38220
gaccggcccg ggacctcagc agttgcccag ccgacccgat gagcgcgggc gccgagttgc   38280
ccgcgagcag ccgcggcgcc atcttgacgg gcaggcccag tcgcgctgcc gcgtcggatt   38340
cacgccggtt tcctcgggtc gctgtcgcc aagtcagcgg tcattgtgcc acccgtccca   38400
cttcggaaga cgctgaccgc cgctccccg atcctggatg cggcggcttt cacggcacgc   38460
tgctccgctg ccgtgccgac gaggtctccg gacggctgag ccgtgctgcg catgccgcgc   38520
cgcctcggcg accgatcgcc gcgcagcgtc agatgcgccg gactttcgcc acggcaaggg   38580
```

```
cgtccgcgac ctcccggacg acacgcttcg cgtcgtcggg gctgttcacc acgtcggtgc   38640
ggttcatgtc gatcacgagg acatcgctgg cggaatagtg ctcgtgcacc cagtcgtcgt   38700
acccggccca aagcgtccgg tagtactcga cgagactttg gtcctgctcg aagtcacgcc   38760
cccgcagtcc gatgcggcgc agcaccgtct cgaagtccgc tctgagatac accatgagat   38820
cgggtgcctt gcgatagggc aggccgtcga tctcacgcat catctccgcg agcaacccct   38880
cgtacacctg catctccagg gaactgatcc tgccgaggtc gtgattgact ttggcgaagt   38940
accagtcctc gtagatcgac cggtcgagga cgttgtcgtc ctgtttgtac gcctccttga   39000
tcgcggcgaa tcgcgtctgc aagaagtaga gctggagaag gaagggatag cgcttcgccg   39060
ctatctcctc aggaccggcg gtgtagaaga gcggcaggat cgggttgtcc tccacgctct   39120
cgtagaagac catgctcccc agctctttgg cgatcagctc ggccacgctt gtcttcccga   39180
tcccgatcat gccgccgacg cagatcactg ccatacctcg cttctttccc gggacaccgt   39240
ccgcgggcgc gattcccgcg caccggctct ccacggcac acgcaccgcc gcggagcgca   39300
gtcgtggaag cgccccaggc gcaggtgacg agcctggcct ccgtcggacg accgaagcgg   39360
catcatatcg gcacggaggg gtgttcgaat ctacgtgctc gtgccctgga tggaagacgc   39420
tggtgcaccg ggtagcggga tcatcggagg tgatcatgta gcgggtgggc ggaacgacgc   39480
ggaacgacgg agtggtggga caggggccac tgacgcacgt atccgcagcc gcgctggagt   39540
cgccgacctc cacaggttca ctctcaccgg tgaccaagga aagatcgccc gcatgccagg   39600
ctcgcccgct cctccccgga acagcgcgta caccgatcag gagaacgacg ccgcgacccc   39660
gagcgagcag ccgagcctgt gtggacgccg aacgtgtcgg ttaccactcg acgaccagcc   39720
ttgacacacc gcgcgtcgcg aggccctccc gccatacgag ggcctcgtcc cccggtgcga   39780
gtcgcaggcc ggggaagcgc tgccacaagc gggtcagcgc gatcttcatc tggagaagaa   39840
ccagtggcgc gcccatgcac cggtgggcgc cgtgtccgaa tgtgaggtgt gcaggccggc   39900
gggcgctgct cttcgcaccc gatgtgcaaa atacttcggc gtcatgattg ccgtgcagca   39960
acgagacgat gacggcctct ccttggcgca ccgtcgtccc gcccaggaca aggtcctcga   40020
tggccactcg gggaaaactg ataggtgtgg acggcgtctt gcggagcagc tcctcaacca   40080
gatcctccac ggattgcccg tcgagcgcgt caccggtgag cagttcgagt atggcaaggc   40140
tcaattgatg ggcggtggtc tcgtaaccgg ccatgagaag tgccagtccg aggttgatca   40200
actcgatgcg ggatatctca cccgactgct caacccgcac cagcgcgctc aggagatcct   40260
gcccgggcgc atccctcttt ctttcgatca gtgaggacat gtacttgata agagtcagga   40320
tatggcggcc tcttctgcgg gttccctgag gcgtcatgtc gaacagcgca gtcacggcgg   40380
cgtcgaaaac gggccgctcc gccgccggca cgccgagcag tgagctcaac gcgaccatgg   40440
gaaggggcga agcataaccg ctgaccaggt cggcgcctgg ccccgcaacc tgtagccgat   40500
ccagcagtgc gtcggcggcc tcctcgatca ccgctgcctg tgcggtgact cgggcgctgg   40560
tgaacgctgc tccggcgacc cggcgcagcc gggcgtggtc cgcaccgtcc agactcatga   40620
tcgagttggg tgagaggtcg acggatcccc atttcggagc atcggggtgg gtggccgcag   40680
ctctgctgag acgtgtgtcg gcgagcgcgg cgcgccccac ggcgtagtcg gtgaccagcc   40740
acatgtgatc accagtgggc atccgcaccc gtttgacggc ctcacttgat ggcgctgcca   40800
ggaagggcgg caggggccgg accctgtggt gatcgaaagt gccggacatg gtcgattact   40860
cctgttcggt cggaaacgcc gcggggtgtc tgtctcccct gccgccgacg gccgtgggag   40920
acgacccatc gggtggcggc cgggtcgggc gagcgggctt tttccaccgc ccggaaggcg   40980
```

```
gcccgctgtt cggtctgcac gctgttcggg ctgcccggct tcggcggaca gaccggcttt    41040
ggcggacaga ccggctgccg gatgttcgtc acgtagcgcg cacggtgtgt tccctgcctc    41100
tcagcgcatc ccgccgtcgc ggcctgacgc gttggacgcc tgtggtctca gccgagcgtg    41160
ggcaccgaac tgcgtcggcc cgtcgacctg cgctctgcgg gacaggacga ggtcccggag    41220
tcgctgtggc agggcgtcgt caaagcggag gtggtccggc accgtgacgc cggcgttgcg    41280
cagcggcgtc gcgatctcgc ggcaggtggt gctgagccag ttgaggaccg cgggatctcc    41340
cgagcggccc gcgaccggcg tccaggtggc cacttccggc tgccggaggc cggcgtcgag    41400
gaacgtccgg gtgaggcggg ggccgaagtc ggggacggcg ccggccgcca ggaaggggcc    41460
gggccacagc gcgtagtact cgtcccactc cggcagcggc ggacgtgacg gcgacgtgtt    41520
ggtgaagtcc atctcgtgca tgacgacgat cccgtccggt ttcagcaggg acgtcagacg    41580
gcgcagtgcg gatgcgggat cgggcaggta catcaggatg tacctgccga ccaggacgtc    41640
gaacttcatc ggccaggtga agtcggccag gtccgcggct tcgtaccgca ccgagtccgc    41700
gagccccgcc tcctgtgcca ggatccgcgc cttgtggacg gttccggggt cgcgctcgat    41760
tcccacgacg tgtccgccgg gcccgaccag ttgggcggcc agcagagaga cgtatcccag    41820
tccggcaccg atgtcgagga cgctcatccc cggacgtact ccggccgacc gcagggtgcg    41880
ttcggtgaac ggcgagatcg cctcgttctg aagggtcagc ctttggtgct cgctatcgga    41940
gtaaccgagc aggtatgcgt cgtgcgccat gcgaggcctc cagggccggt cgtgcgggga    42000
gttccccacg gcaggtggcc aggggggctcc gcggtgtctg gagcactgag tgccctgtag    42060
cggccgtgcg gtgtggtccg gtgttccggg tatgtcacgc accggagcgg gacatgtacg    42120
tgtccgaagg cggcgggcgg cgcagagcct tgccgctgga ggtgcgtgcg atcccgccgc    42180
gccgcacgaa ctcgatcgtg tcgggtgtga tgcccagctc ggccaccaca cgtgcgcgga    42240
tgtgttgcgt cgtggcacga cggctcgcct cgtcgtgccg cgtcgtctcg acgacgagcc    42300
cgaggcggcc tccctcgtcg ctccagatct gctcggccag gacgccgtgg acgaggaggc    42360
cgggtgtgtc ccgcacgacc gcctcgatgt cgctcgccca gtggttcgcg ccgaagacga    42420
tgatcacctc tttcgtgcgg cccacgatgt acagctcgcc gtcgtgccac aggcccaggt    42480
caccggtcgc caaccagccg cccggaagga ggacgcgacg gctctcttcg gggtggcggt    42540
cgtacccggt gctcgtgacg gacgccccc ggacctcgac ggcgccgacc gtgccgggca    42600
cggccggtgc gccgctcgcg gtggtgagcc ggacctcggt acgccgcacc ggcgttccca    42660
cactgaccag ttcgcgacac ggcccggcgc cggacggcac cggtacgtaa cggccccggt    42720
tcagttcgtc ccggtcggca cgcagcacct tggccgggcg gccgagggga gggaaggcga    42780 ccgcagggt cgcctccgcc agtccgtagg ccggcaggaa gacgttctcg gacagtccgg    42840
cgggcgcgaa acgctcggcg aaggcgtcct gaagccgccg gtcgaccggc tcggcgccgt    42900
tcaccgcgat gcgccagcgg gagagatcga ggccggccgg cggcgccgcg tcgcgcctca    42960
ggacgtagcg gtagccggag tcaggagcca tggtgaaggt cgcccccagc cgcccatgg    43020 cccggatcca gtcacccgga ctgcgcaggt agtcctccgg tgtcagcaga tggatgtcga    43080
cgtcgtgcag cagcggtgtc aagaaggaac cgatcaggcc catgtcgtgg aagagggca    43140 gccaggtgca gccgacgtcg gtcctggcga gccgtgtgcc atgggcgatg gccgccaccc    43200
cggccgccac gttgccgtgg ctgagcacga cgccccgcgg ttcgctgctc gtgcccgacg    43260
tgtactgaac gacggccggg tccgacgccg cccgcgcgac gtgggccgcg gacggctcgg    43320
```

```
ccacctccgg caccaggagt acgtcgaccg ggcgggcgcc gtcggacagt ccaggaccga   43380
gcagcgggcg catggccgga gccgtcagca cggtccgtac ccgagagcgg cgcagggccg   43440
cggaggtgcg ccggagatag gcgtcggacg acccgaaggg cgcgggaccg ggcagcggca   43500
ccgcgaccgc gcccgccgcc agcacgccga agaaggcgcg cgccgaagtcc accgacgtcg   43560 gcaggacgag ggcgacccgc tcgccgggtc gcaccccgcg cgacagcagc cccgcggcca   43620
cccgcccggc ctcggcgaag aggtcgctgt aggacagcgc gtcgccgtcc tggcccggc    43680 gcagcacgtg catgcccgt ccggagcctt gtgcggcgac gcggccgagc gcggcgaaca    43740
gggtcacgac agcggttccg tgccggcctc cgcgatcacc ttggtgatcg cggccgcgaa   43800
ctcccgcacg gtgctcgtct cgaagacgat gcggtcctcc acctcgatgt cgtagtgctg   43860
ctcgatctcc agcacgatct ggagcgcgtg gatcgagtcg aagcgcggca aggagcgcag   43920
atcggtgtcc acgcccacct cctcgacacc gatgcgcagt tgctcggcga cggatcggcg   43980
gacggtctgt tcgatgtcgg tgacactcgc ctgtgacatg gcgtggtgtt gtcctgttct   44040
gtgaggccgc cgcgtcgggg cgcggcggga ggcggacgcc gggactgacg gtcagcgagc   44100
gccgggccgg cgggccaggg cgcgcagctt ggctttgatg tcccgcgggg tctccaacga   44160
gtcgtcgtcc gccaggagcc ggacgatcga catcaccttg gcgtccgcgg cgtccaccga   44220
gtcgtgctgg atggtctcga tacggcggat gccggccgtg gatgtggaat gcgggtagaa   44280
catgcccgcc gggtgcttga cgccgttgct acggtccgcg agccagatgt aggccatgcg   44340
cagcgcggcg gcctgatggg ccggatcgct gtcgcacagt tcccgcatga agacggagaa   44400
cgcacggcag tgccgggcct cgtcgcgggc caggagccgc cagattctgc ggatcaccgg   44460
ctccgacaca tgggcggcga gcgccttgta gagggcggac gcgcgtgact ccgagatcac   44520
gttcatcatg agggtggcgg agcgcacgtc gccctgcgga tacggctctc gtttgtagag   44580
cgcgtgcttc gaacggagtg agaccccgat ccggtccagg tagcgggcct ggaccagtga   44640
gtgccgggat tcctccgcac cccattgcag tgcccaggag gagaagctga cctcgtcctg   44700
ccattcccgc aggaagttgt gagcgccggg tagggtgccg aactcgatga cggccgcctc   44760
ggtgaggaag tccacggtcc gttcgtcgag catgccgtgc tcgatgcggt ccaggtccac   44820
ctcggtccag tcccagcgcg tcgtctcgaa ccagtcgaag atcttgttga aggtcatgtc   44880
gaggtagtag tcggtgtaga ggtcgtccgt catcagcgcg cggtgcgccc gcagggccag   44940
ttcgaccgag gtggtgaacc cttcgggcgc caccgcggcg ggccggacga tgtcctcgac   45000
gtccagtgct tccgcccagc cgggaaccgg gcccgccgta tcgggcccga cgacgtacac   45060
ccgggtccgg ttgaacttcg agtgcgaccg cagcgcccgg acggcgggca gcggctcggc   45120
gtccgccccg atccacaccg ccgcgagctc ggatgacggt tcgaactcgt gcaggtagcg   45180
gtgccagtcg gcgtgtgccg gccggtccac ggtgacgtcg ccgaaggcgg ggacggtgag   45240
cctttcggcg ggggagactg cggtggtggg tgccagcagg gcgatggtgt gcggggcac    45300 ggagggcgtc ctctctgtcg gtctgcgcag gccgtcggcg agcaccttgc cgcgcgttgt   45360
gtggggctcg gctccgtaac acgtgcgtgc cgcgacgtca gagccgcccg tactccgcgg   45420
cagggccgag gagtacgggc agcgcctcga tgctgttgct gacgaacgag ggcacgggcc   45480
gcacggtcca cgtgtcggac ggggccagcc gcacgtcggg gaaccgggtg aagaatccgg   45540
ccagtgccgt ctccagctgg agacgggcca ggtgtgtccc gatacagaag tgcgggccgt   45600
gcccgaagcc gaggtggccg gcctgccgcc ggcggacgtc gaagaggtcc gcgtccggcc   45660
cgtggtgcgc cgggtcccgg cccgccgagc cgaaggacgc gaggatggct tctccccggt   45720
```

```
ggatcgtctg gccggcgatg acgacgtcct cggtcgggta gcgcatcggg aactggttca   45780
ccgcgccgtt ccagcgcatc gtctcctcga ccaccgcact ccacgggacc tccccggcgc   45840
gggcggaggc cagttgctcg gggtgggtga gcagcgcgtg gcaggcgttg acgagtacgt   45900
tgatgacgct ctggtggccg gcgaagaaca tcagcaggat catgccgtgc agttcgctgt   45960
cggtgagccg gtcgtctccg tcctggcgtg ccgtgagcag gacgctgatg aggtcgtccc   46020
gggggacgtc gcgacgttcg gcgacgatct cccggagcag cgcttcgatc cgtccgtcga   46080
tctcctggac ctgttcgggg gagttgttcg tacgggtctg catgccggtg agcacgtgca   46140
gcagacgccg cttgcgctgc gggatcccca gcaggtccga gatgacggtg gtggggatgg   46200
ggtaggcgaa agccttgcgg agatccaccg gccggtcttc cggccgtgtg gcgagctggt   46260
cgaggagccc gtcgacgagg cgttccaccc ccgggcgcat ggcctccacc cgttccgggg   46320
tcagtgcctg gtcgaccagt ccgcgcagcc gccggtgatc cgcgccgtgc gaattgatga   46380
cgctgtcggt cgcgacgaag cccatcaacg gccaccgtc cggcacttcg ccgcgggccg   46440
ctgcctccca gtgcgtgatt cccttggcga ccctgggatc cgtcagcact cggcgcaggt   46500
cctcgtggtg cggaatcgcc cacgcccgca caccgccggg gagttggacc ggaacggctc   46560
tccccgccgc ccgcaggcgg gcgttctccg cgtgct                             46596
```

DOSAGE FORM

Figure 1A:
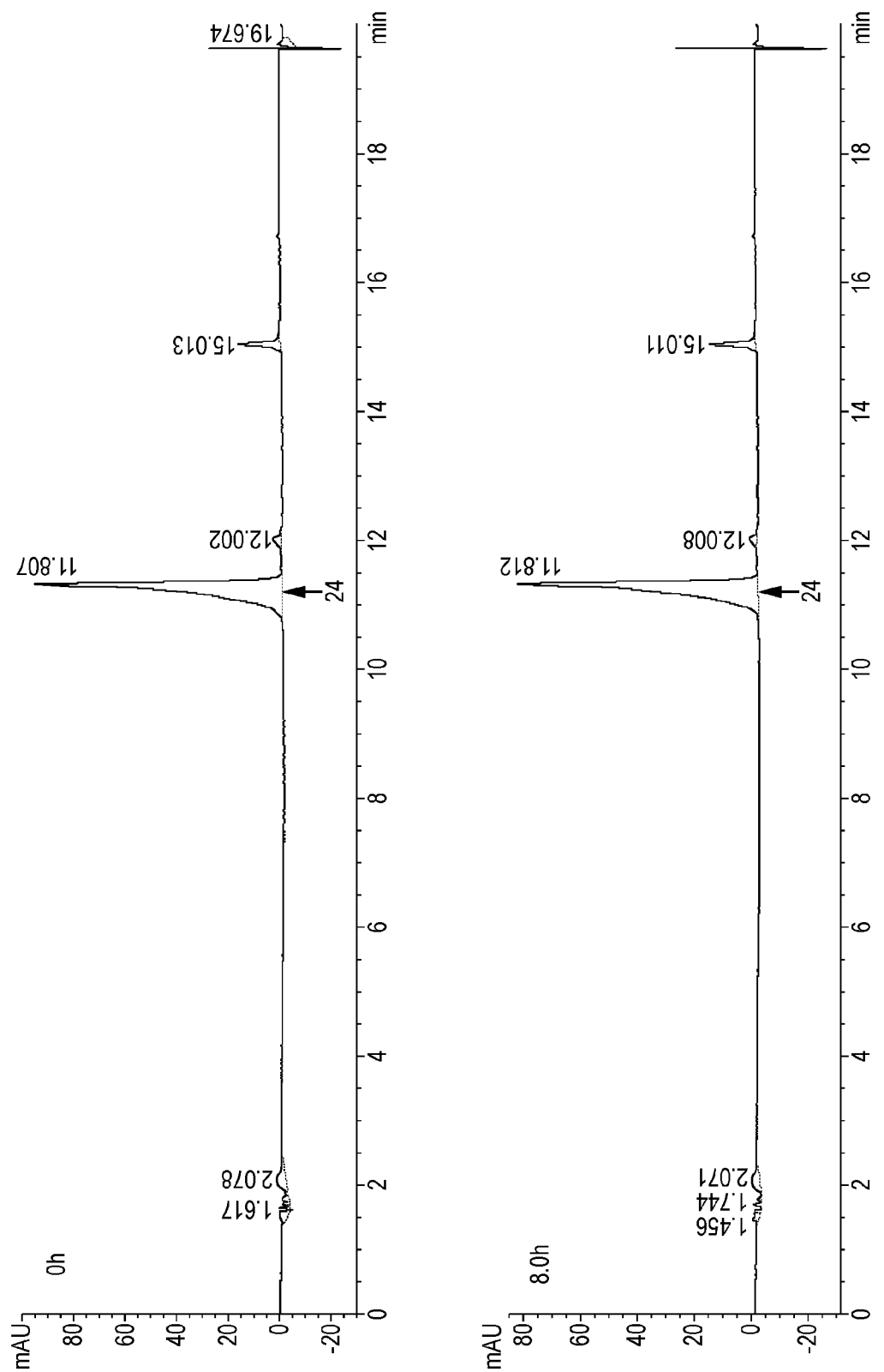

This application is a §371 application of PCT/GB2012/052633, filed Oct. 24, 2012, which in turn claims priority to GB Application 1118334.0, filed Oct. 24, 2011. The entire disclosure of each of the foregoing applications is incorporated by reference herein.

Incorporated herein by reference in its entirety is the Sequence Listing being concurrently submitted via EFS-Web as an ASCII text file named SequenceListing.txt, created Mar. 27, 2014, and having a size of 59,900 bytes.

The present invention relates to formulations for increasing the oral bioavailability of sanglifehrins, including natural sanglifehrins (such as sanglifehrin A, B, C and D) and non-natural sanglifehrins, such as sangamides, by protecting the drug substance. e.g. by enteric coating to reduce acid degradation in the stomach. This is anticipated to increase oral bioavailability by releasing material directly into the intestinal compartment of the subject, where sanglifehrins are less prone to degradation.

BACKGROUND OF THE INVENTION

Sanglifehrins

Sanglifehrin A (SfA), 5 and its natural congeners belong to a class of mixed non-ribosomal peptide/polyketides, produced by *Streptomyces* sp. A92-308110 (also known as DSM 9954) (see WO 97/02285 and WO 98/07743), which were originally discovered on the basis of their high affinity to cyclophilin A (CypA). SfA is the most abundant component in fermentation broths and exhibits approximately 20-fold higher affinity for CyPA compared to Cyclosporine A (CsA), 1. This has led to the suggestion that sanglifehrins could be useful for the treatment of HCV (WO2006/138507). Sanglifehrins have also been shown to exhibit a novel mechanism of immunosuppressive activity as compared to CsA (Sanglier et al., 1999; Fehr et al., 1999). SfA binds with high affinity to the CsA binding site of CyPA (Kallen et al., 2005).

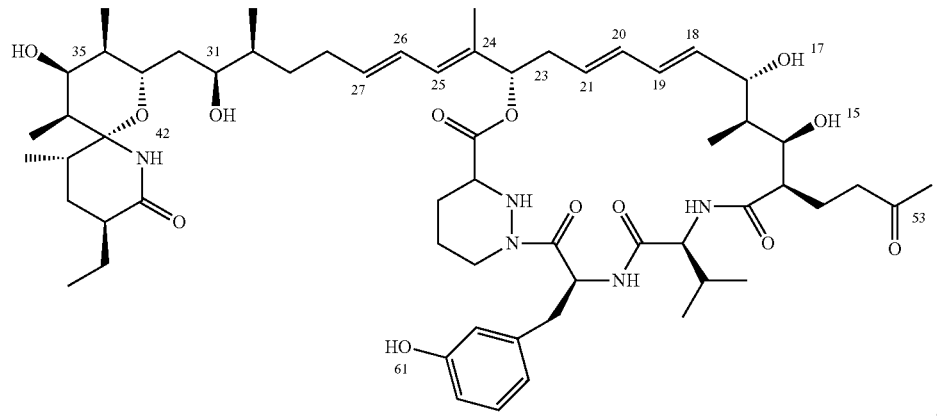

sanglifehrin A

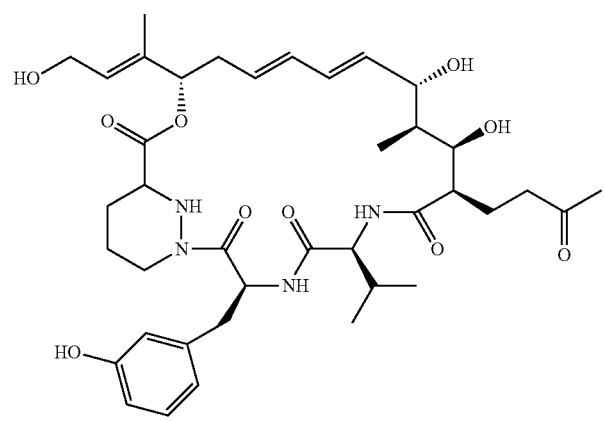

hydroxymacrocycle

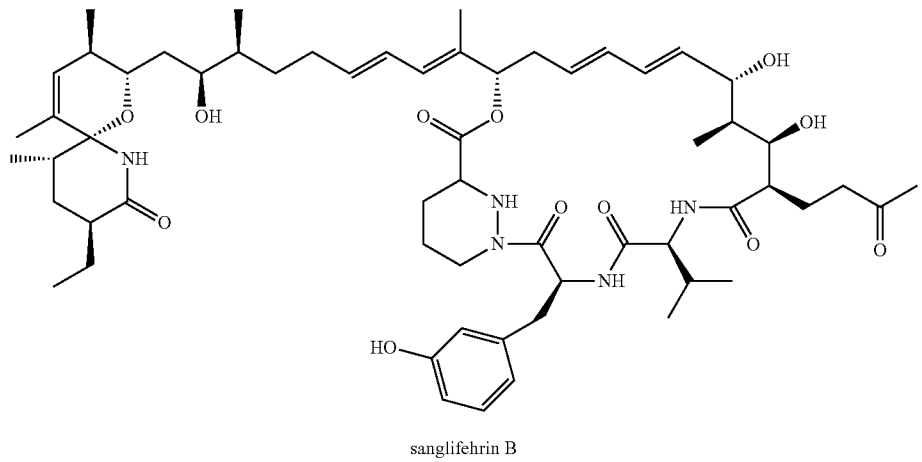

sanglifehrin B

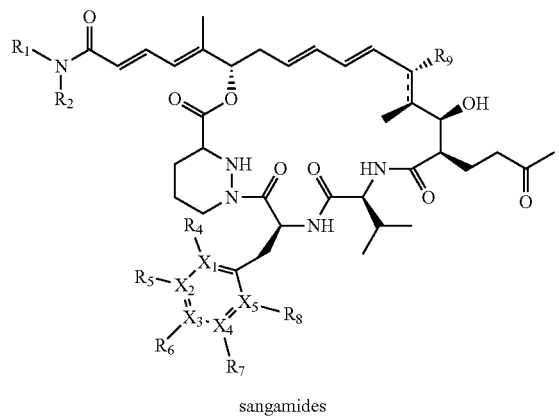

sangamides

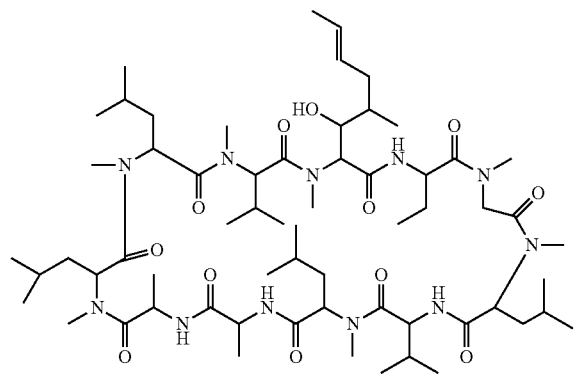

cyclosporine A

Biosynthesis of Sanglifehrins

Sanglifehrins are biosynthesised by a mixed polyketide synthase (PKS)/Non-ribosomal peptide synthetase (NRPS) (see WO2010/034243). The 22-membered macrolide backbone consists of a polyketide carbon chain and a tripeptide chain. The peptide chain consists of one natural amino acid, valine, and two non-natural amino acids: (S)-meta-tyrosine and (S)-piperazic acid, linked by an amide bond. Hydroxylation of phenylalanine (either in situ on the NRPS or prior to biosynthesis) to generate (S)-meta-tyrosine is thought to occur via the gene product of sfaA.

Semisynthetic Sanglifehrins

Examples of the generation of semisynthetic derivatives of natural sanglifehrins have been described in the literature. These include sangamides (Moss et al., 2011, WO2011/098809), ester macrocyclic analogues of sanglifehrin (WO2011/098805) and ketone macrocyclic analogues of sanglifehrin (WO2011/098808). One of the cited reasons for generation of analogues has been to improve oral bioavailability. Other analogues have also been described in the literature (e.g. Sedrani et al., 2003, WO 2006/138507, Gaither et al., 2010).

Uses of Sanglifehrins

Immunosuppressive Action of Sanglifehrins

The immunosuppressive mechanism of action of SfA is different to that of other known immunophilin-binding immunosuppressive drugs such as CsA, FK506 and rapamycin. SfA does not inhibit the phosphatase activity of calcineurin, the target of CsA (Zenke et al. 2001), instead its immunosuppressive activity has been attributed to the inhibition of interleukin-6 (Hartel et al., 2005), interleukin-12 (Steinschulte et al., 2003) and inhibition of interleukin-2-dependent T cell proliferation (Zhang & Liu, 2001). However, the molecular target and mechanism through which SfA exerts its immunosuppressive effect is hitherto unknown.

The molecular structure of SfA is complex and its interaction with CyPA is thought to be mediated largely by the macrocyclic portion of the molecule. In fact, a macrocyclic compound (hydroxymacrocycle, 6) derived from oxidative cleavage of SfA has shown strong affinity for CyPA (Sedrani et al., 2003). X-ray crystal structure data has shown that the hydroxymacrocycle binds to the same active site of CyPA as CsA. Analogues based on the macrocycle moiety of SfA have also previously been shown to be devoid of immunosuppressive properties (Sedrani et al., 2003), providing opportunity for design of non-immunosuppressive CyP inhibitors for potential use in HCV and HIV therapy.

Converse to this, there is also an opportunity to develop immunosuppressive agents with low toxicity for use in such areas as prophylaxis of transplant rejection, autoimmune, inflammatory and respiratory disorders, including, but not limited to, Crohn's disease, Behcet syndrome, uveitis, psoriasis, atopic dermatitis, rheumatoid arthritis, nephritic syndrome, aplastic anaemia, biliary cirrhosis, asthma, pulmonary fibrosis, chronic obstructive pulmonary disease (COPD) and celiac disease. Sanglifehrins have been shown to have a novel mechanism of immunosuppressive activity (Zenke et al., 2001), potentially acting through dendritic cell chemokines (Immecke et al., 2011), and there is therefore an opportunity to develop agents with a mechanism of action different to current clinical agents, such as cyclosporine A, rapamycin and FK506.

Human Immunodeficiency Virus (HIV)

Cyclophilin inhibitors, such as CsA and DEBIO-025 have also shown potential utility in inhibition of HIV replication. The cyclophilin inhibitors are thought to interfere with function of CyPA during progression/completion of HIV reverse transcription (Ptak et al., 2008). However, when tested clinically, DEBIO-025 only reduced HIV-1 RNA levels ≥0.5 and >1 log 10 copies/mL in nine and two patients respectively, whilst 27 of the treated patients showed no reduction in HIV-1 RNA levels (Steyn et al., 2006). Following this, DEBIO-025 was trialled in HCV/HIV coinfected patients, and showed better efficacy against HCV, and the HIV clinical trials were discontinued (see Watashi et al., 2010).

Hepatitis B Virus

Hepatitis B is a DNA virus of the family hepadnaviridae, and is the causative agent of Hepatitis B. As opposed to the cases with HCV and HIV, there have been very few published accounts of activity of cyclophilin inhibitors against Hepatitis B virus. Ptak et al. 2008 have described weak activity of DEBIO-025 against HBV (IC50 of 4.1 µM), whilst Xie et al., 2007 described some activity of CsA against HBV (IC50>1.3 µg/mL). This is in contrast to HIV and HCV, where there are numerous reports of nanomolar antiviral activity of cyclophilin inhibitors.

Inhibition of the Mitochondrial Permeability Transition Pore (mPTP)

Opening of the high conductance permeability transition pores in mitochondria initiates onset of the mitochondrial permeability transition (MPT). This is a causative event, leading to necrosis and apoptosis in hepatocytes after oxidative stress, $Ca^{2+}$ toxicity, and ischaemia/reperfusion. Inhibition of Cyclophilin D (also known as Cyclophilin F) by cyclophilin inhibitors has been shown to block opening of permeability transition pores and protects cell death after these stresses. Cyclophilin D inhibitors may therefore be useful in indications where the mPTP opening has been implicated, such as muscular dystrophy, in particular Ullrich congenital muscular dystrophy and Bethlem myopathy (Millay et al., 2008, WO2008/084368, Palma et al., 2009), multiple sclerosis (Forte et al., 2009), diabetes (Fujimoto et al., 2010), amyotrophic lateral sclerosis (Martin 2009), bipolar disorder (Kubota et al., 2010), Alzheimer's disease (Du and Yan, 2010), Huntington's disease (Perry et al., 2010), recovery after myocardial infarction (Gomez et al., 2007) and chronic alcohol consumption (King et al., 2010).

Further Therapeutic Uses

Cyclophilin inhibitors have potential activity against and therefore in the treatment of infections of other viruses, such as Varicella-zoster virus (Ptak et al., 2008), Influenza A virus (Liu et al., 2009), Severe acute respiratory syndrome coronavirus and other human and feline coronaviruses (Chen et al., 2005, Ptak et al., 2008), Dengue virus (Kaul et al., 2009), Yellow fever virus (Qing et al., 2009), West Nile virus (Qing et al., 2009), Western equine encephalitis virus (Qing et al., 2009), Cytomegalovirus (Kawasaki et al., 2007) and Vaccinia virus (Castro et al., 2003).

There are also reports of utility of cyclophilin inhibitors and cyclophilin inhibition in other therapeutic areas, such as in cancer (Han et al., 2009).

Oral Bioavailability of Sanglifehrins

One of the issues in drug development of natural and non-natural sanglifehrins is low oral bioavailability (e.g. see Gregory et al., 2011). This can lead to higher cost of goods, increased chance of food effect and higher interpatient variability. Whilst one route to improve this is to generate novel analogues, another route is to use formulations.

Therefore there remains a need to identify novel formulations for oral dosage of sanglifehrins, which can increase the oral bioavailability of this potentially important class of drug. Sanglifehrins may have utility in the treatment of HCV infection, but also in the treatment of other disease areas where inhibition of cyclophilins may be useful, such as HIV infection, muscular dystrophy or aiding recovery after myocardial infarction or where immunosuppression or anti-inflammatory effect is useful.

SUMMARY OF THE INVENTION

The present inventors have unexpectedly discovered that whereas sanglifehrins are stable metabolically, and are stable at neutral pH, they are rapidly degraded in acidic conditions, such as simulated gut fluid (SGF) or the stomach.

Thus the invention provides oral dosage forms of sanglifehrins in which the sanglifehrin compound is protected from acid degradation in the stomach (most preferably by enteric coating of the material) such that it is released directly into the higher pH environment of the small intestine from where it may be absorbed into the system. Such dosage forms are expected to have greatly improved bioavailability relative to forms in which the sanglifehrins are not protected from acid degradation in the stomach.

These dosage forms can be used for natural sanglifehrins such as sanglifehrins A, B, C and D, and for non-natural sanglifehrins such as sangamides.

Hence, according to a first aspect of the invention, there is provided a pharmaceutical dosage form for oral administration comprising a sanglifehrin as active ingredient in which the sanglifehrin active ingredient is protected from acid degradation in the stomach environment following oral administration.

DEFINITIONS

The articles "a" and "an" are used herein to refer to one or to more than one (i.e. at least one) of the grammatical objects of the article. By way of example "an analogue" means one analogue or more than one analogue.

As used herein the term "analogue(s)" refers to chemical compounds that are structurally similar to another but which differ slightly in composition (as in the replacement of one atom by another or in the presence or absence of a particular functional group).

As used herein the term "sanglifehrin(s)" refers to chemical compounds such as sanglifehrin A and those compounds that are structurally similar to sanglifehrin A but which differ slightly in chemical composition (such as in the replacement of one or more atom by another or in the presence or absence of a particular functional group), in particular those generated by fermentation of *Streptomyces* sp. A92-308110. Examples include the sanglifehrin-like compounds discussed in WO97/02285 and WO98/07743, such as sanglifehrin B. Other examples include compounds of formula (X) or (I) to (VII). The term "sanglifehrin(s)" includes compounds known as "sangamides" (see Moss et al., 2011, WO2011/098809).

As used herein the term "mutasynthetic sanglifehrin(s)" refers to chemical compounds that are structurally similar to sanglifehrin A, B, C or D but which differ slightly in composition (as in the replacement of one or more atom by another or in the presence or absence of a particular functional group) due to incorporation of a non-natural precursor, in particular, those generated by fermentation of *Streptomyces* sp. A92-308110 or a mutant thereof, where the culture is fed with a meta-tyrosine analogue.

As used herein the term "biosynthetically altered sanglifehrin(s)" refers to chemical compounds that are biosynthesized by the sanglifehrin gene cluster (see WO2010/034243), and are structurally similar to sanglifehrin A, B, C or D but which differ slightly in composition (as in the replacement of one or more atom by another or in the presence or absence of a particular functional group), due to alterations in the gene cluster, such as replacement or alteration of an acyltransferase domain, removal, replacement or addition of a polyketide synthase module or domain, such as removal, replacement or addition of an acyltransferase, loading domain, reductive loop domain (such as one or more of a dehydratase, ketoreductase or enoylreductase domain) or ketosynthase domain (for examples, see WO 98/01546 or WO2010/034243) in particular, those generated by fermentation of *Streptomyces* sp. A92-308110 or a mutant thereof.

As used herein the term "meta-tyrosine analogue(s)" refers to chemical compounds that are structurally similar to meta-tyrosine but which differ slightly in composition (as in the replacement of one or more atom by another or in the presence or absence of a particular functional group). Examples include methyl (2S)-2-amino-3-(6-hydroxy(2-pyridyl))propanoate, L-3-aminophenylalanine methyl ester, L-4-methyl-meta-tyrosine methyl ester, L-4-fluoro-meta-tyrosine methyl ester, L-4,5-difluoro-meta-tyrosine methyl ester, DL-3-fluorophenylalanine, L-phenylalanine, DL-4-fluoro-meta-tyrosine, DL-5-fluoro-meta-tyrosine, methyl 2-amino-3-(3-fluoro-5-hydroxyphenyl)propanoate, methyl 2-amino-3-(2-fluoro-5-hydroxyphenyl)propanoate, methyl 2-amino-3-(2-fluoro-3-hydroxyphenyl)propanoate and methyl 2-amino-3-(2,6-difluoro-3-hydroxyphenyl)propanoate.

As used herein the term "sanglifehrin producing bacterium" refers to any bacterial strain that naturally makes a sanglifehrin or biosynthetically altered sanglifehrin when cultured under appropriate conditions (e.g. provision of growth media and necessary precursors). This includes, but is not limited to, *Streptomyces* sp. A92-308110, also known as DSM 9954 (see WO 97/02285 and WO 98/07743), also known as *Streptomyces flaveolus*.

As used herein, the term "HCV" refers to Hepatitis C Virus, a single stranded, RNA, enveloped virus in the viral family Flaviviridae.

As used herein, the term "HIV" refers to Human Immunodeficiency Virus, the causative agent of Human Acquired Immune Deficiency Syndrome.

As used herein, the term "bioavailability" refers to the degree to which or rate at which a drug or other substance is absorbed or becomes available at the site of biological activity after administration. This property is dependent upon a number of factors including the solubility of the compound, rate of absorption in the gut, the extent of protein binding and metabolism etc. Various tests for bioavailability that would be familiar to a person of skill in the art are described herein (see also Egorin et al. 2002).

The term "water solubility" as used in this application refers to solubility in aqueous media, e.g. phosphate buffered saline (PBS) at pH 7.4, or in 5% glucose solution. Tests for water solubility are given below in the Examples as "water solubility assay".

The pharmaceutically acceptable salts of compounds of the invention such as the compounds of formula (I) include conventional salts formed from pharmaceutically acceptable inorganic or organic acids or bases as well as quaternary ammonium acid addition salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic and the like. Hydrochloric acid salts are of particular interest. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts. References hereinafter to a compound according to the invention include both compounds of formula (I) and their pharmaceutically acceptable salts.

As used herein, the term "alkyl" represents a straight chain or branched alkyl group, containing typically 1-10 carbon atoms, for example a $C_{1-6}$ alkyl group. "Alkenyl" refers to an alkyl group containing two or more carbons (for example 2-10 carbons e.g. a $C_{2-6}$ alkenyl group) which is unsaturated with one or more double bonds.

Examples of alkyl groups include $C_{1-4}$ alkyl groups such as methyl, ethyl, n-propyl, i-propyl, and n-butyl. Examples of alkenyl groups include $C_{2-4}$alkenyl groups such as —CH═CH$_2$ and —CH$_2$CH═CH$_2$.

As used herein, the term "cycloalkyl" represents a cyclic alkyl group, containing typically 3-10 carbon atoms, optionally branched, for example cyclobutyl, cyclopentyl, cyclohexyl or cycloheptyl. A branched example is 2-methylcyclopentyl. "Cycloalkenyl" refers to a cyclic alkenyl group containing typically 5-10 carbon atoms, for example cyclopentyl, cyclohexenyl or cycloheptenyl. Cycloalkyl and cycloalkenyl groups may for example be monocyclic or bicyclic (including spirocyclic) but are suitably monocyclic.

As used herein, the term "enteric coat" means a barrier coat applied to a substance to prevent release of said substance following oral administration before it reaches the small intestine.

As used herein, the term "heterocyclyl" represents a cycloalkyl group in which one or more one or more ring carbon atoms (e.g. 1, 2 or 3 ring carbon atoms such as 1 or 2 e.g. 1) are replaced by heteroatoms selected from O, N and S. Examples include morpholinyl, piperidinyl, pyrrolidinyl, piperazinyl and N-methyl piperazinyl.

As used herein, the term "heterocyclenyl" represents a cycloalkenyl group in which one or more one or more ring carbon atoms (e.g. 1, 2 or 3 ring carbon atoms such as 1 or 2 e.g. 1) are replaced by heteroatoms selected from O, N and S.

Examples of aryl groups include (except where indicated) monocyclic groups i.e. phenyl and bicyclic rings (e.g. 9 and 10 membered rings) which are aromatic or (in the case of bicyclic rings contain at least one aromatic ring). For example a bicyclic ring may be fully aromatic e.g. naphthyl or may be partially aromatic (e.g. containing one aromatic ring), such as tetraline, indene or indane. Preferred aryl is phenyl. Aryl groups may optionally be substituted e.g. with one or more (e.g. 1, 2 or 3) substituents e.g. selected from alkyl (e.g. $C_{1-4}$alkyl), hydroxyl, $CF_3$, halogen, alkoxy (e.g. $C_{1-4}$alkoxy), nitro, —$SO_2$Me, cyano and —$CONH_2$.

Examples of heteroaryl groups include (except where indicated) monocyclic groups (e.g. 5 and 6 membered rings) and bicyclic rings (e.g. 9 and 10 membered rings) which are aromatic or (in the case of bicyclic rings contain at least one aromatic ring) and contain one or more heteroatoms (e.g. 1, 2, 3 or 4) heteroatoms selected from N, O and S. Examples of 5 membered heteroaryl rings include pyrrole, furan, thiophene, oxazole, oxadiazole, thiazole and triazole. Examples of 6 membered heteroaryl rings include pyridine, pyrimidine and pyrazine. Examples of bicyclic rings include fully aromatic rings such as quinoline, quinazoline, isoquinoline, indole, cinnoline, benzthiazole, benzimidazole, purine and quinoxaline and partially aromatic rings such as chromene, chromane, tetrahydroquinoline, dihydroquinoline, isoindoline and indoline. Monocyclic heteroaryl groups are preferred. The aforementioned heteroaryl groups may be optionally substituted as described above for aryl groups.

When bicyclic aryl and heteroaryl groups are partially aromatic, the connection to the remainder of the molecule may be through the aromatic portion or through the non-aromatic portion.

The term "treatment" includes prophylactic as well as therapeutic treatment.

FIGURE LEGEND

Figure 1B:
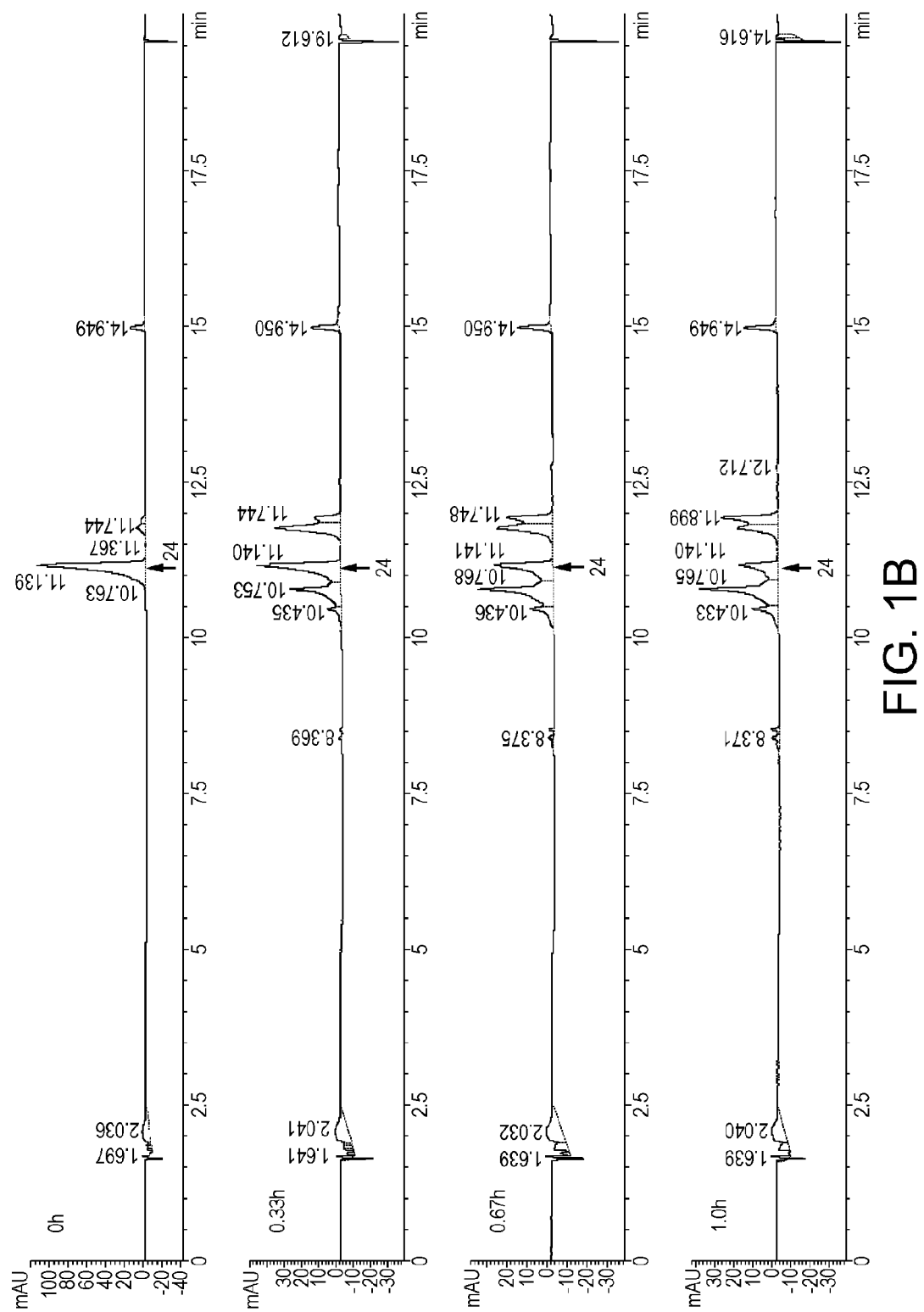

FIG. 1: Images of traces of 24 following incubation in acidic and neutral conditions. A: 24 in PBS, pH 7.3 (t=0, 8.0 hours). B: 24 in acidic conditions, pH 1.2 (t=0, 0.33, 0.67, 1.0 hours).

Figure 2:
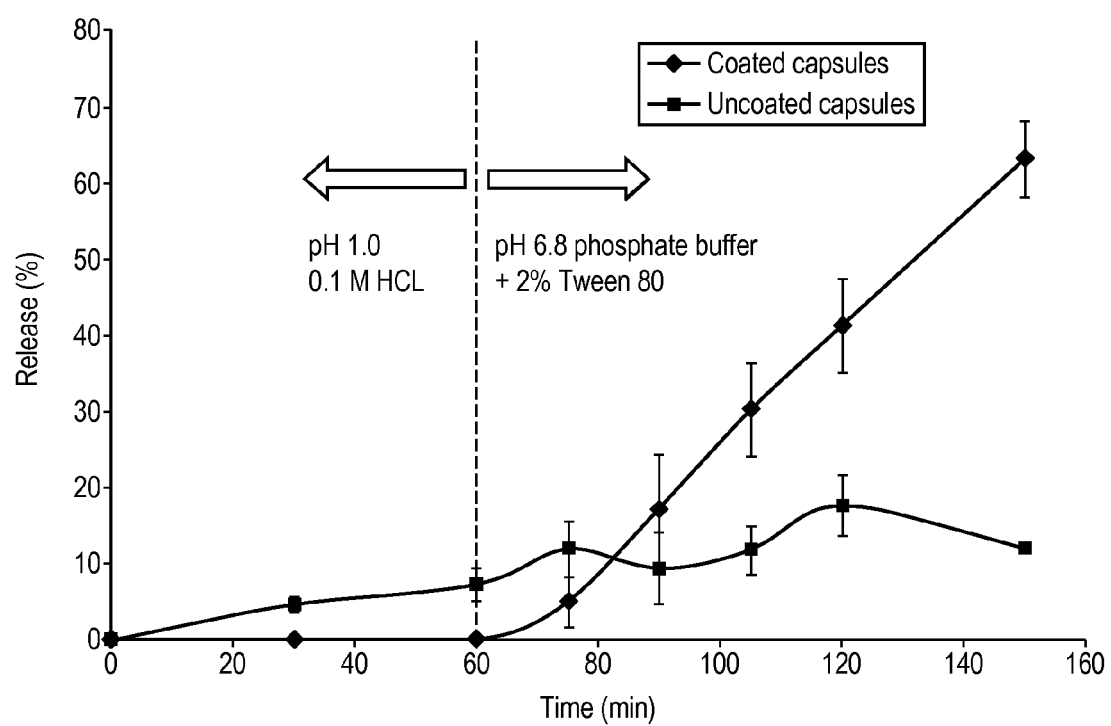

FIG. 2: Comparison of percentage of 24 in solution following dosing of a single enterically coated or uncoated capsule into pH1.0 acidic conditions, which were adjusted to pH6.8 after 60 minutes, to mimic the pH of the stomach and intestinal compartments.

DETAILED DESCRIPTION OF THE INVENTION

In one embodiment, protection of the active ingredient may be achieved by provision of a layer of enteric coat, said enteric coat being stable in the acid environment of the stomach, and adapted to release the active ingredient in the higher pH environment of the small intestine.

In one embodiment the active ingredient is particulate and the enteric coat is applied to the particles of active ingredient.

In one embodiment the active ingredient is in the form of a granulate, and the enteric coat is applied to the granules of active ingredient.

In one embodiment, the active ingredient is coated onto a non-pareil (e.g. a sugar or starch sphere) and the enteric coat is applied to the coated non-pareil. Such coated non-pareils may be formulated in tablets or capsules.

In one embodiment the active ingredient (e.g. in powder form) is contained within a capsule, said capsule being provided with an enteric coat.

In one embodiment the active ingredient (e.g. in powder form) is contained within a tablet, said tablet being provided with an enteric coat.

Sanglifehrins

In one embodiment the sanglifehrin is a natural sanglifehrin such as sanglifehrin A, B, C or D.

In one embodiment the sanglifehrin is a non-natural sanglifehrin (such as a semi-synthetic, biosynthetically altered or mutasynthetic sanglifehrin). In one embodiment, it may be a non-natural sanglifehrin prepared by chemical modification of a natural sanglifehrin. In another embodiment, it may be the product of feeding a non-natural precursor to a sanglifehrin producing bacterium. For example it may be the product of feeding a meta-tyrosine analogue to a sanglifehrin producing bacterium. In another embodiment it may be the product of feeding natural or non-natural precursors to a sanglifehrin producing bacterium in which the sanglifehrin PKS has been modified in respect of one or more modules or domains (see WO2010/034243), or it may be the direct fermentation product of a genetically altered sanglifehrin producing bacterium in which the sanglifehrin PKS has been modified in respect of one or more modules or domains, via alterations in the gene cluster, such as replacement or alteration of an acyltransferase domain, removal, replacement or addition of a polyketide synthase module or domain, such as removal, replacement or addition of an acyltransferase, loading domain, reductive loop domain (such as one or more of a dehydratase, ketoreductase or enoylreductase domain) or ketosynthase domain (for examples, see WO 98/01546 or WO2010/034243) in particular, those generated by fermentation of Streptomyces sp. A92-308110 or a mutant thereof.

In one embodiment, the sanglifehrin is a compound of formula (X) or a pharmaceutically acceptable salt thereof:

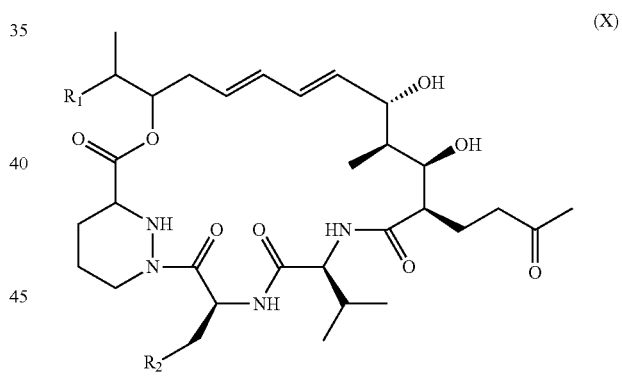

(X)

in which $R_1$ represents an organic moiety (i.e. a moiety composed of carbon and hydrogen atoms and optionally containing one or more N, O or S atoms) and $R_2$ represents an optionally substituted aryl or heteroaryl group (such as an optionally substituted phenyl, pyridine or pyrimidine group, suitably an optionally substituted phenyl group) including any tautomer thereof; and including a methanol adduct thereof in which a ketal is formed by the combination of the C-53 keto and the C-15 hydroxyl group and methanol. Optional substituents for aryl or heteroaryl may for example be selected from halogen, alkyl, F, Cl, Br, alkenyl or alkyl wherein one or more carbon atoms of said alkyl group are optionally replaced by a heteroatom selected from O, N and $S(O)_p$ in which p represents 0, 1 or 2 and wherein one or more carbon atoms of said alkyl group are optionally replaced by carbonyl and which alkyl group may optionally be substituted by one or more halogen atoms. An example substituent is hydroxyl (for example in the meta position).

In one embodiment, the non-natural sanglifehrin is a compound of formula (I) or a pharmaceutically acceptable salt thereof:

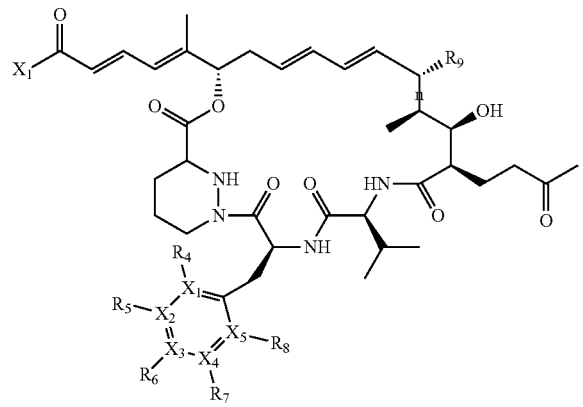

(I)

wherein:
- the moiety $X_1$ represents $-OR_1$, $-NR_1R_2$ or $R_3$;
- $R_1$, $R_2$ and $R_3$ independently represent alkyl, alkenyl, cycloalkyl, cycloalkenyl, alkylcycloalkyl, alkylcycloalkenyl, alkenylcycloalkyl, alkenylcycloalkenyl, aryl, heteroaryl, alkylaryl, alkylheteroaryl, alkenylaryl or alkenylheteroaryl any of which groups may optionally be substituted by monocylic aryl or monocyclic heteroaryl;
- and wherein one or more carbon atoms of $R_1$, $R_2$ and $R_3$ not being part of an aryl or heteroaryl group are optionally replaced by a heteroatom selected from O, N and $S(O)_p$ in which p represents 0, 1 or 2 and wherein one or more carbon atoms of $R_1$, $R_2$ and $R_3$ are optionally replaced by carbonyl;
- or $R_1$ and $R_2$ are linked such that $NR_1R_2$ represents a saturated or unsaturated heterocyclic ring containing the specified nitrogen atom and wherein one or more carbon atoms of said ring are optionally replaced by a further heteroatom selected from O, N and $S(O)_p$ in which p represents 0, 1 or 2 and wherein one or more carbon atoms of said ring are optionally replaced by carbonyl and which heterocyclic ring may optionally be fused to an aryl or heteroaryl ring;
- and wherein one or more carbon atoms of an $R_1$, $R_2$ and $R_3$ group may optionally be substituted by one or more halogen atoms;
- or $R_1$ and/or $R_2$ represents hydrogen;
- $R_9$ represents H or OH;
- n represents a single or double bond, save that when n represents a double bond $R_9$ represents H;
- $R_4$, $R_5$, $R_6$, $R_7$ and $R_8$ independently represent H, F, Cl, Br, alkenyl or alkyl wherein one or more carbon atoms of said alkyl group are optionally replaced by a heteroatom selected from O, N and $S(O)_p$ in which p represents 0, 1 or 2 and wherein one or more carbon atoms of said alkyl group are optionally replaced by carbonyl and which alkyl group may optionally be substituted by one or more halogen atoms;
- $X_2$, $X_3$, $X_4$, $X_5$ and $X_6$ independently represent C or N, and in the case of any of these groups representing N the attached substituent is absent;
- with the proviso that where $R_4$, $R_6$, $R_7$ and $R_8$ all represent H and $X_2$, $X_3$, $X_4$, $X_5$ and $X_6$ all represent C, then $R_5$ cannot represent OH, —Oalkyl or —O(CO)alkyl;
- including any tautomer thereof; and including a methanol adduct thereof in which a ketal is formed by the combination of the C-53 keto and the C-15 hydroxyl group and methanol.

For example n represents a single bond. For example $R_9$ represents OH. For example $X_2$ represents C. For example $X_3$ represents C. For example $X_4$ represents C. For example $X_5$ represents C. For example $X_6$ represents C. For example $R_4$ represents H. For example $R_8$ represents H. For example $R_5$ represents OH. For example $R_6$ represents H, Me or F. For example $R_7$ represents H or F. For example $R_6$ and/or $R_7$ represents F. For example $X_1$ represents $NR_1R_2$. For example $R_1$ represents alkyl, alkenyl, cycloalkyl, cycloalkenyl, alkylcycloalkyl, alkylcycloalkenyl, alkenylcycloalkyl, alkenylcycloalkenyl, aryl, heteroaryl, alkylaryl, alkylheteroaryl, alkenylaryl or alkenylheteroaryl and $R_2$ represents H, alkyl, alkenyl or —Oalkyl. For example $NR_1R_2$ represents morpholinyl, oxazinane or one of the groups disclosed in the following table:

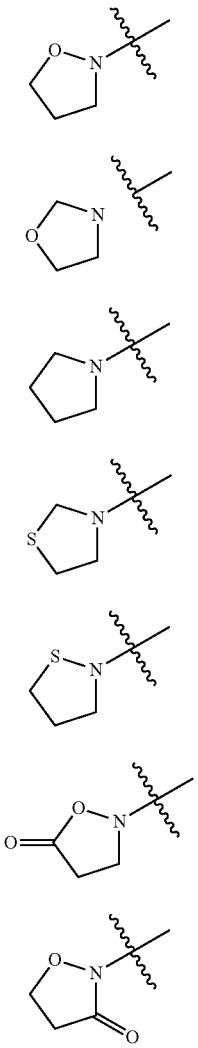

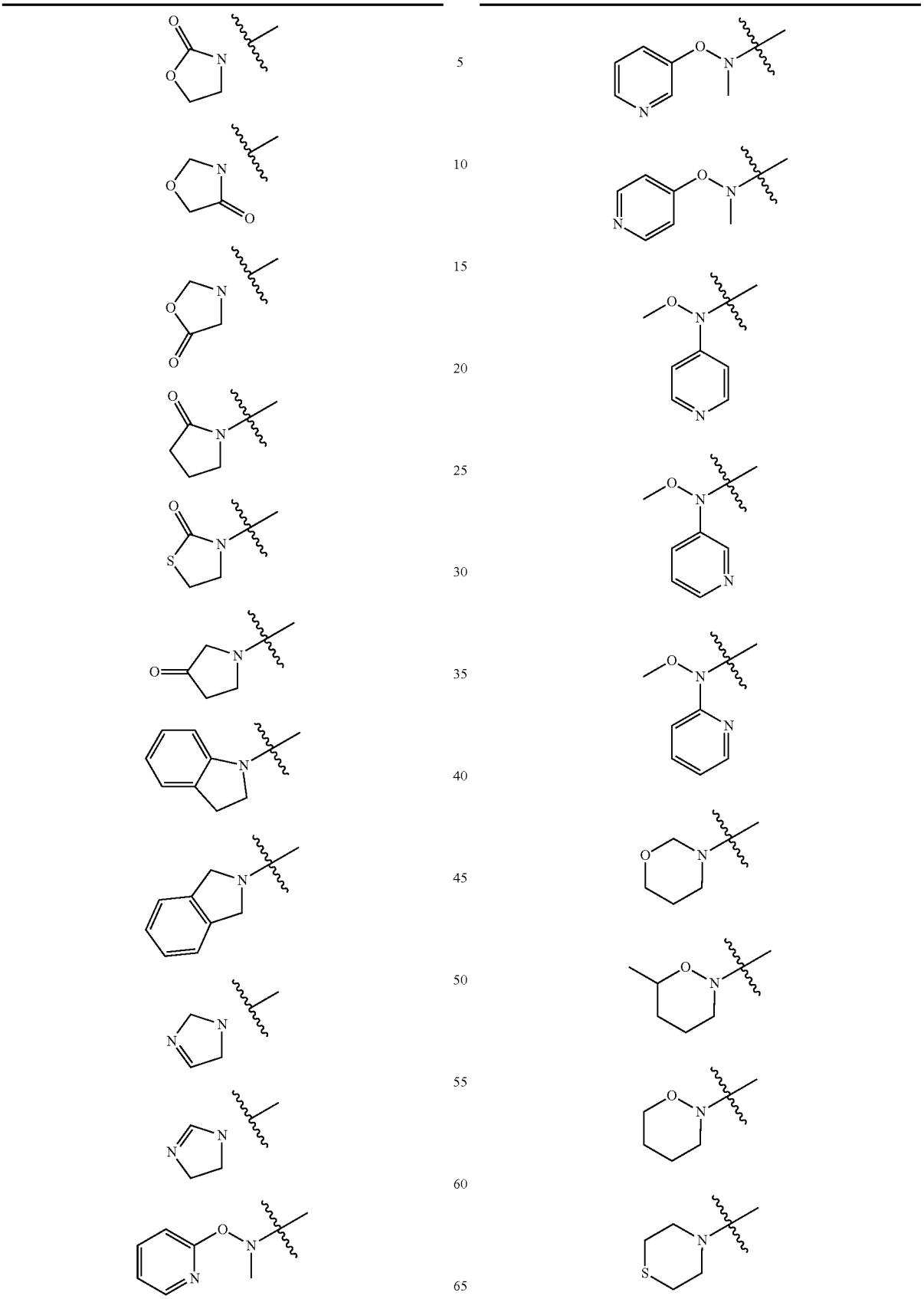

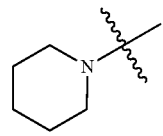
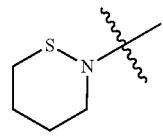 [SMILES: *N1CCCCS1]
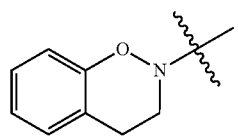 [SMILES: *N1CCc2ccccc2O1]
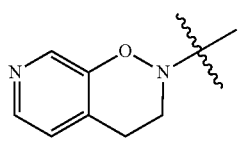 [SMILES: *N1CCc2ccncc2O1]
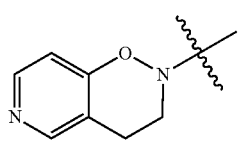 [SMILES: *N1CCc2cnccc2O1]
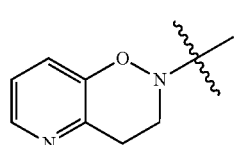
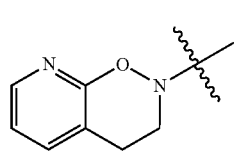
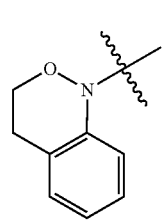 [SMILES: *N1OCCc2ccccc21]
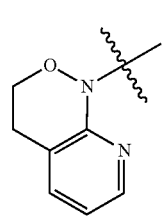 [SMILES: *N1OCCc2cccnc21]
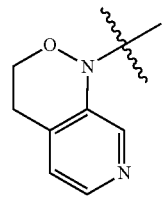 [SMILES: *N1OCCc2ccncc21]
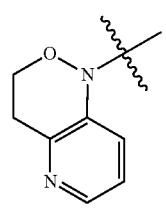 [SMILES: *N1OCCc2ncccc21]
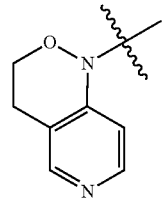 [SMILES: *N1OCCc2cnccc21]
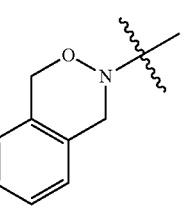
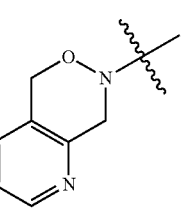
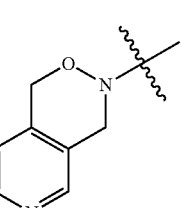
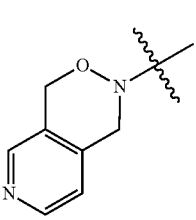

-continued
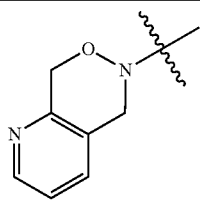
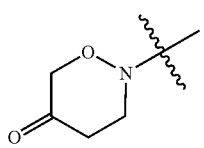 [SMILES: *N1CCC(=O)CO1]
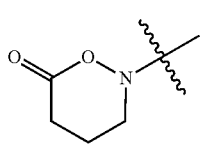
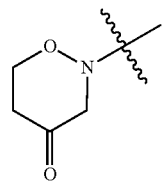 [SMILES: *N1CC(=O)CCO1]
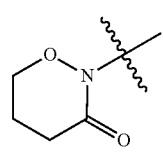 [SMILES: *N1OCCCC1=O]
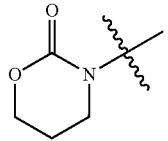
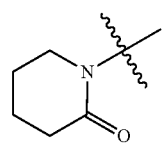 [SMILES: *N1CCCCC1=O]
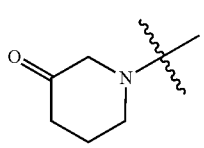 [SMILES: *N1CCCC(=O)C1]
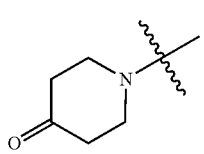 [SMILES: *N1CCC(=O)CC1]
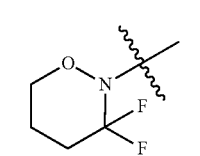 [SMILES: *N1OCCCC1(F)F]
-continued
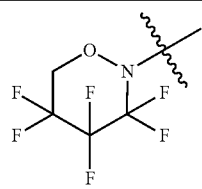
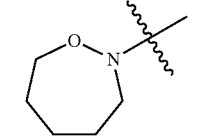
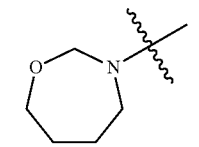 [SMILES: *N1CCCCOC1]
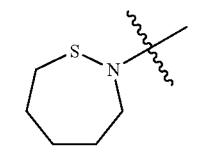
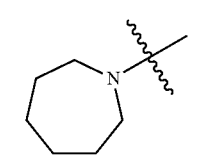 [SMILES: *N1CCCCCC1]
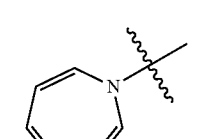
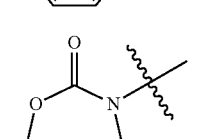
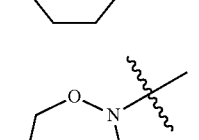
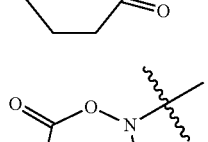
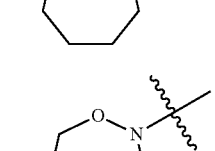

| 19 -continued | 20 -continued |
|---|---|
| 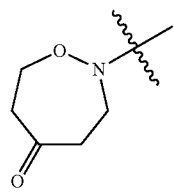 [SMILES: *N1CCC(=O)CCO1] | 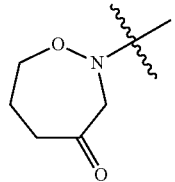 [SMILES: *N1CC(=O)CCCO1] |
A compound of formula (I) may be selected from:
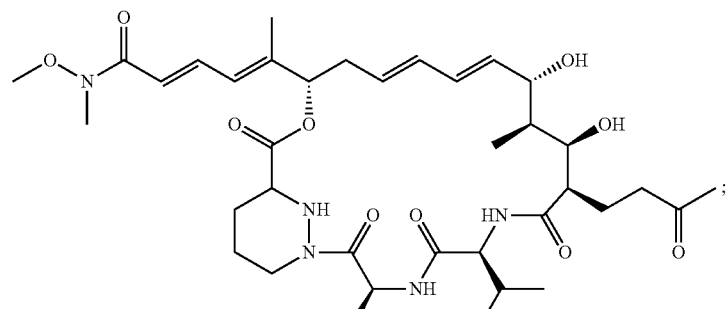
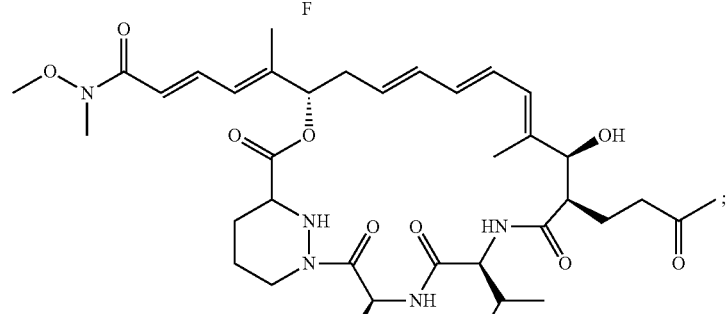
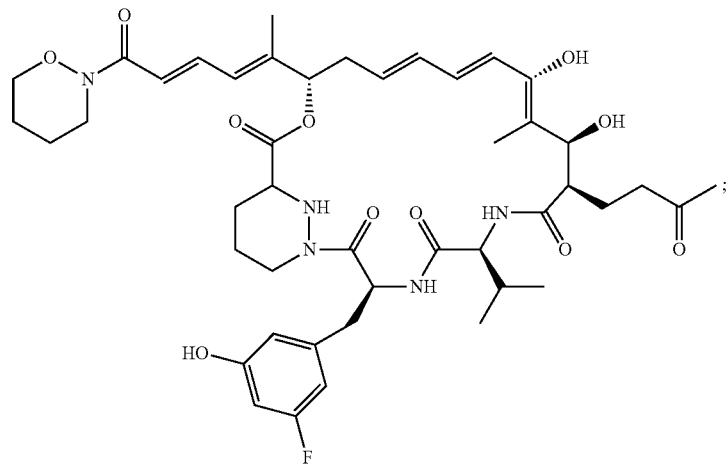

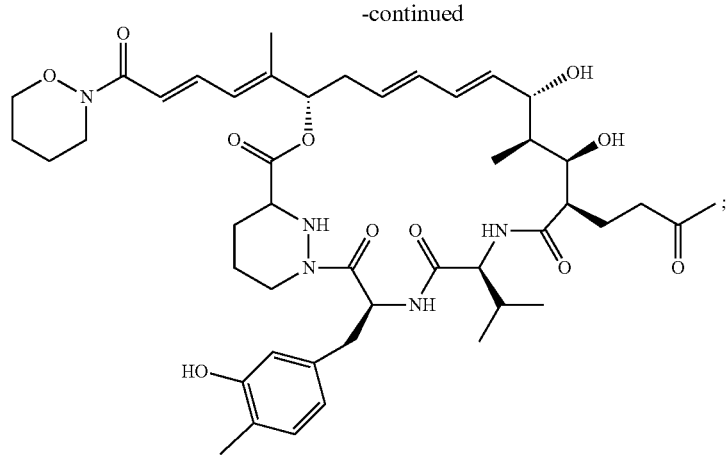
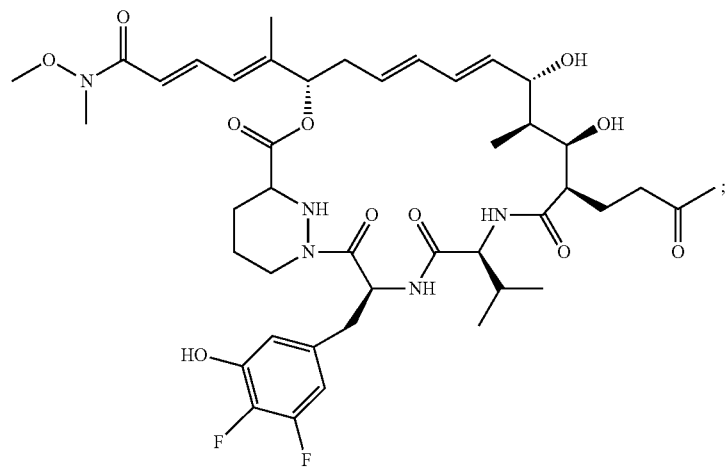
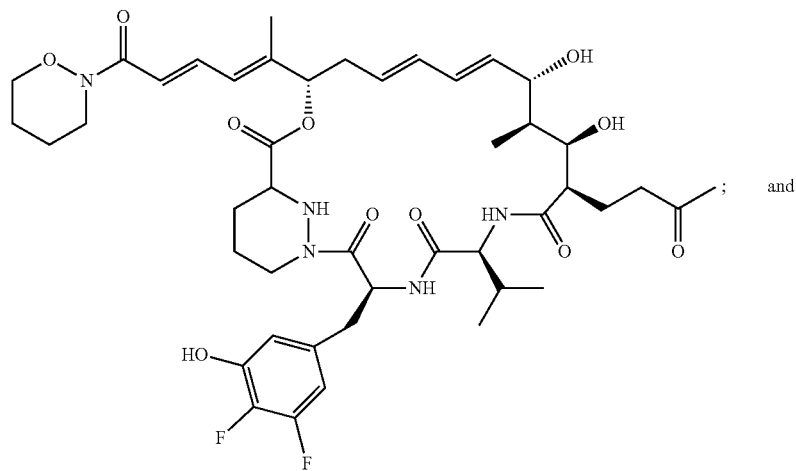

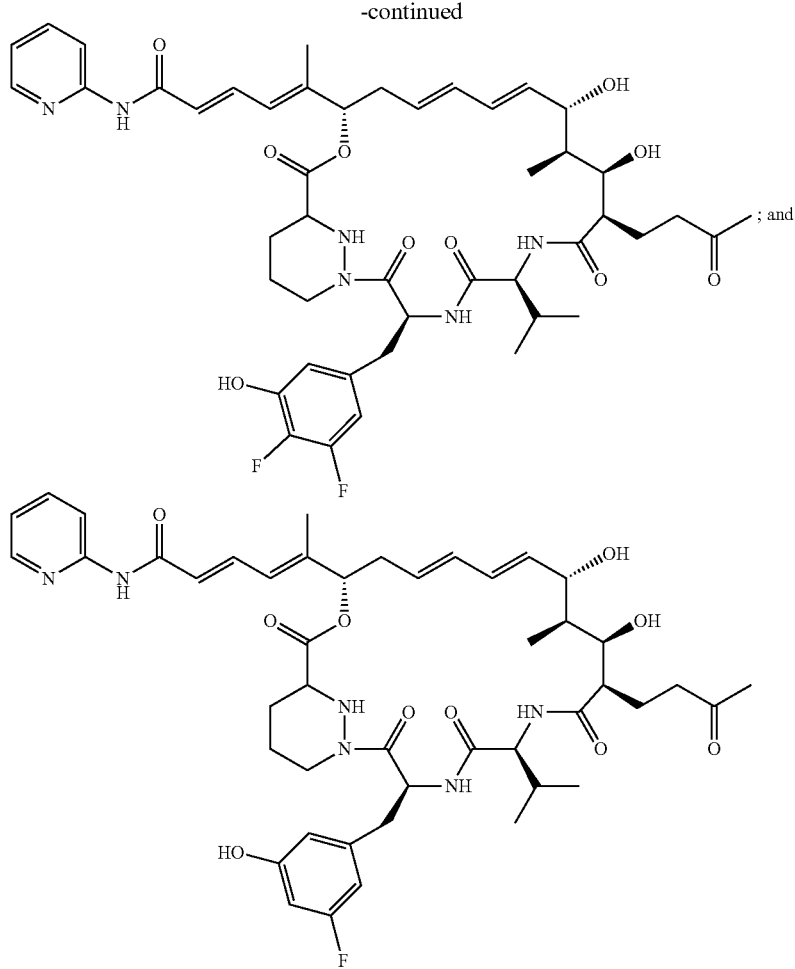

including any tautomer thereof; or an isomer thereof in which the C26, 27 C=C bond shown as trans is cis; and including a methanol adduct thereof in which a ketal is formed by the combination of the C-53 keto (if present) and the C-15 hydroxyl group and methanol;
or a pharmaceutically acceptable salt thereof.

In another embodiment, the non-natural sanglifehrin is a compound of formula (II) or (III) or a pharmaceutically acceptable salt thereof:

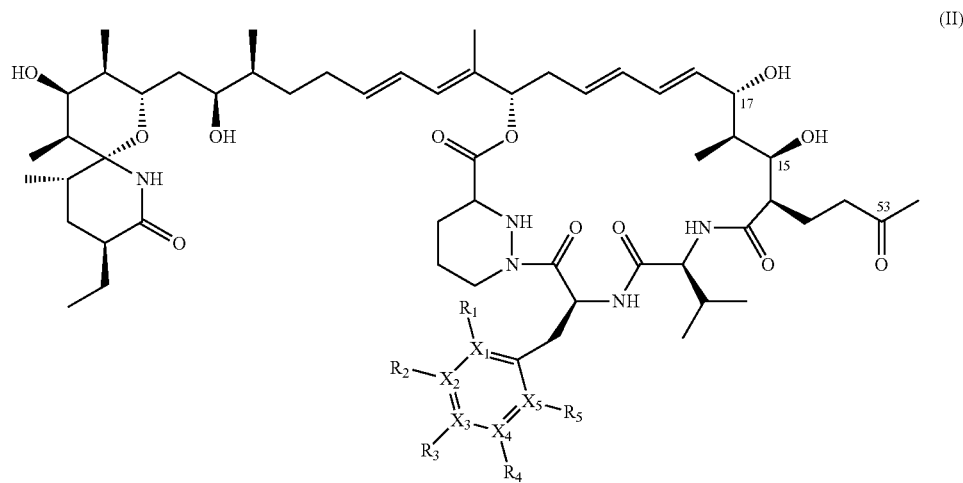

(II)

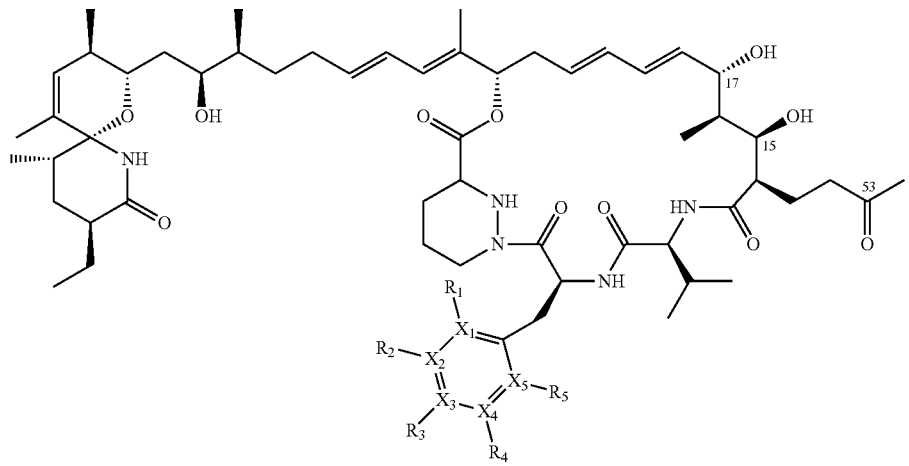

(III)

wherein:
R₁, R₂, R₃, R₄ and R₅ independently represent H, F, Cl, Br, $C_{2-6}$alkenyl or $C_{1-10}$alkyl wherein one or more carbon atoms of said alkyl group are optionally replaced by a heteroatom selected from O, N and $S(O)_p$ in which p represents 0, 1 or 2 and wherein one or more carbon atoms of said alkyl group are optionally replaced by carbonyl and which alkyl group may optionally be substituted by one or more halogen atoms;

$X_1$, $X_2$, $X_3$, $X_4$ and $X_5$ independently represent C or N, and in the case of any of these groups representing N the attached substituent is absent;

with the proviso that where R₁, R₃, R₄ and R₅ all represent H and $X_1$, $X_2$, $X_3$, $X_4$ and $X_5$ all represent C, then R₂ cannot represent OH;

including any tautomer thereof; or an isomer thereof in which the C26, 27 C=C bond shown as trans is cis; and including a methanol adduct thereof in which a ketal is formed by the combination of the C-53 keto and the C-15 hydroxyl group and methanol.

For example $X_1$ represents C. For example $X_2$ represents C. For example $X_3$ represents C. For example $X_4$ represents C. For example $X_5$ represents C. For example R₁, R₃, R₄ and R₅ are independently selected from H, F, Cl, CF₃, OH and $C_{1-6}$alkyl. For example R₂ is selected from H, F, Cl, CF₃, OH, NH₂ and $C_{1-6}$alkyl. For example R₂ represents OH.

A compound according to formula (II) or formula (III) may be selected from:

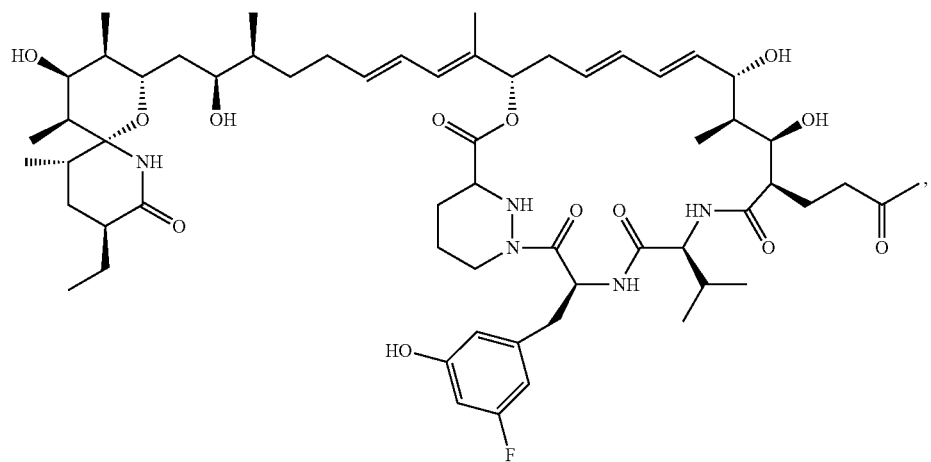

-continued
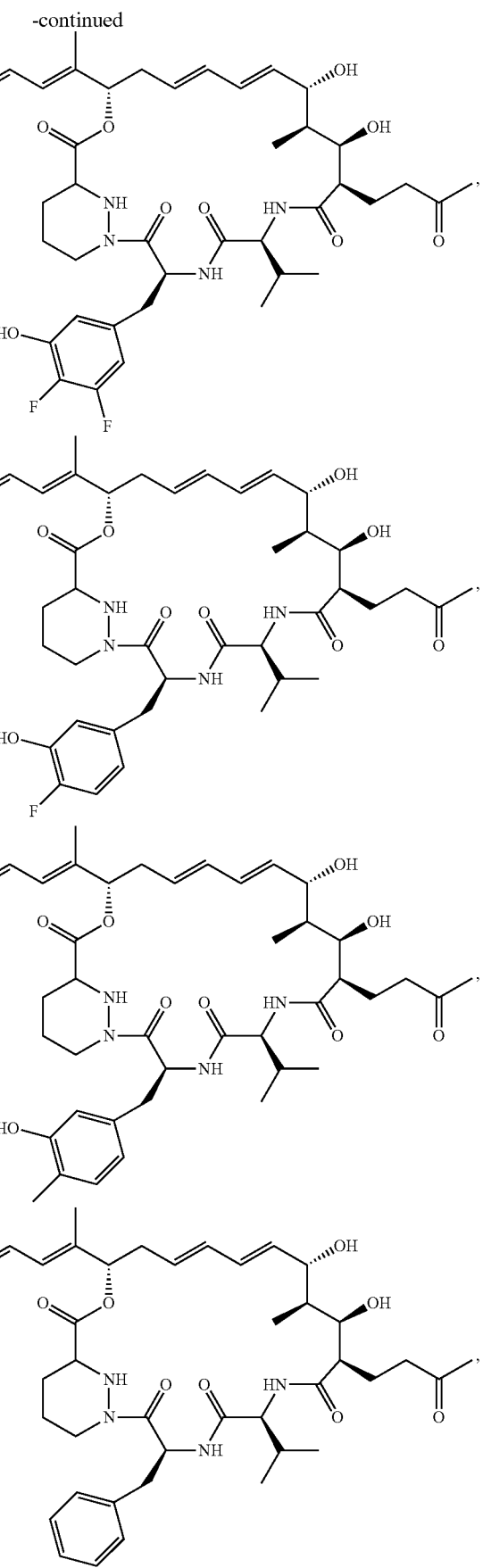

-continued
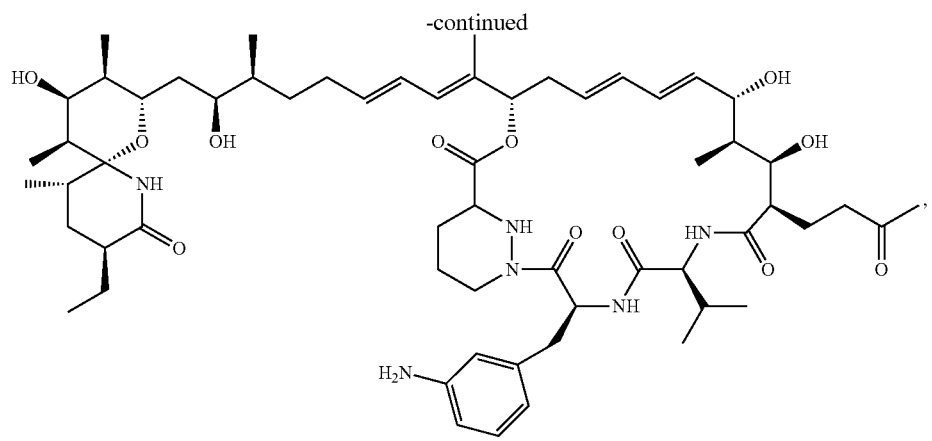
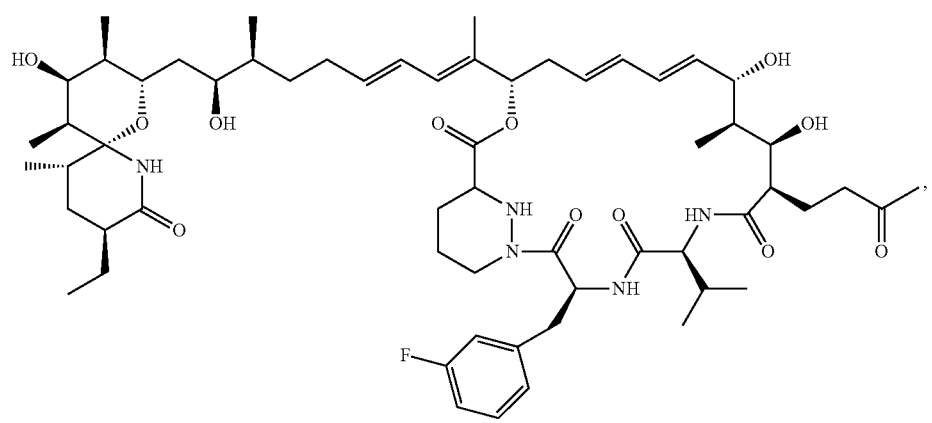
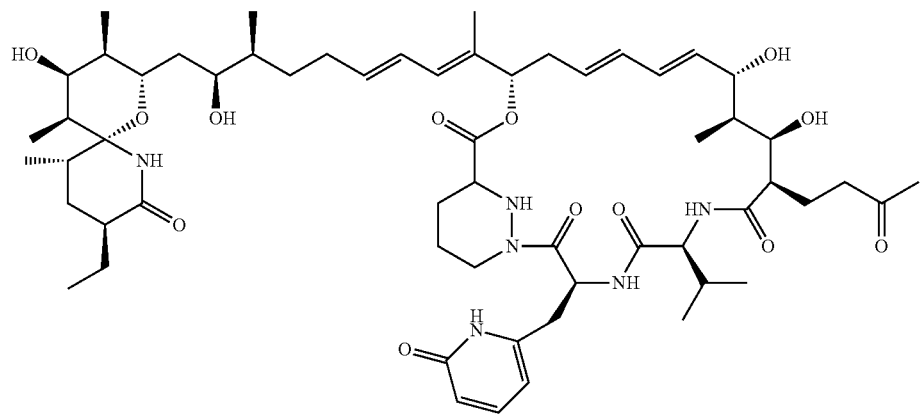 [SMILES: CC[C@H]1C[C@H](C)[C@@]2(NC1=O)O[C@@H](C[C@H](O)[C@@H](C)CC/C=C/C=C(\C)[C@@H]1C/C=C/C=C/[C@H](O)[C@H](C)[C@@H](O)[C@@H](CCC(C)=O)C(=O)N[C@@H](C(C)C)C(=O)N[C@@H](Cc3cccc(=O)[nH]3)C(=O)N3CCCC(N3)C(=O)O1)[C@H](C)[C@H](O)[C@@H]2C]

which can also be represented as
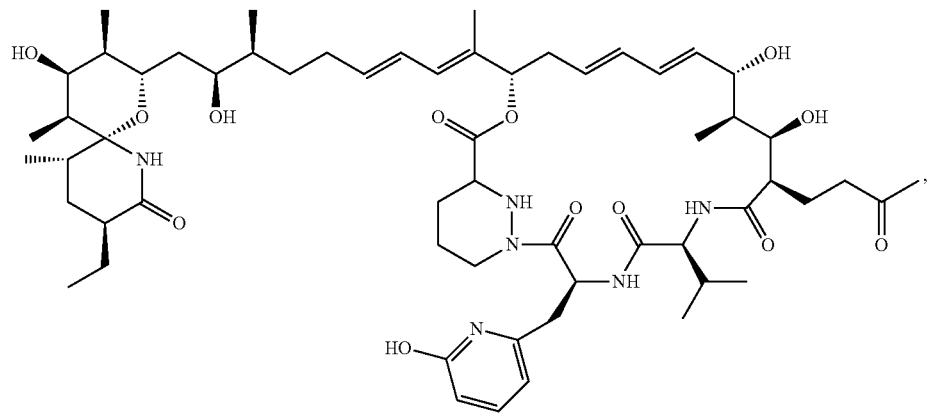
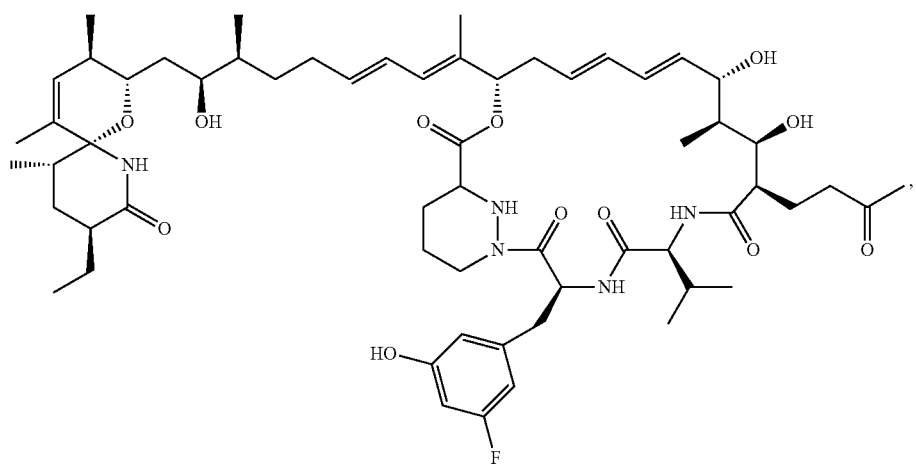
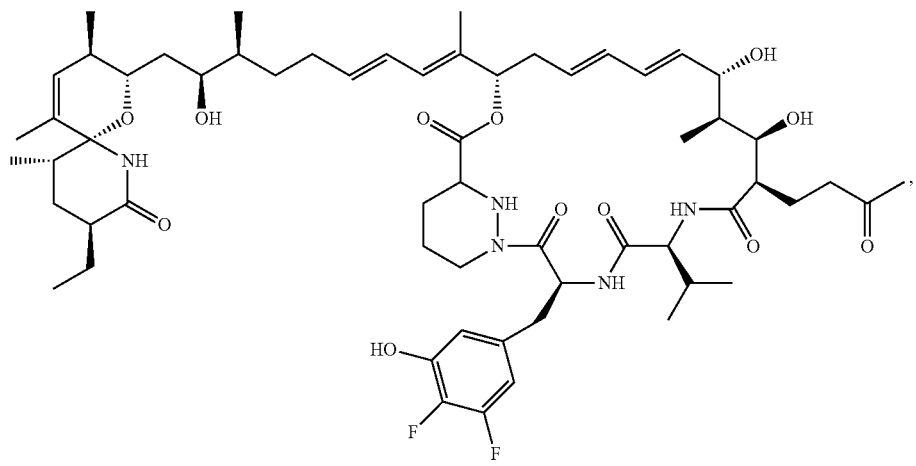

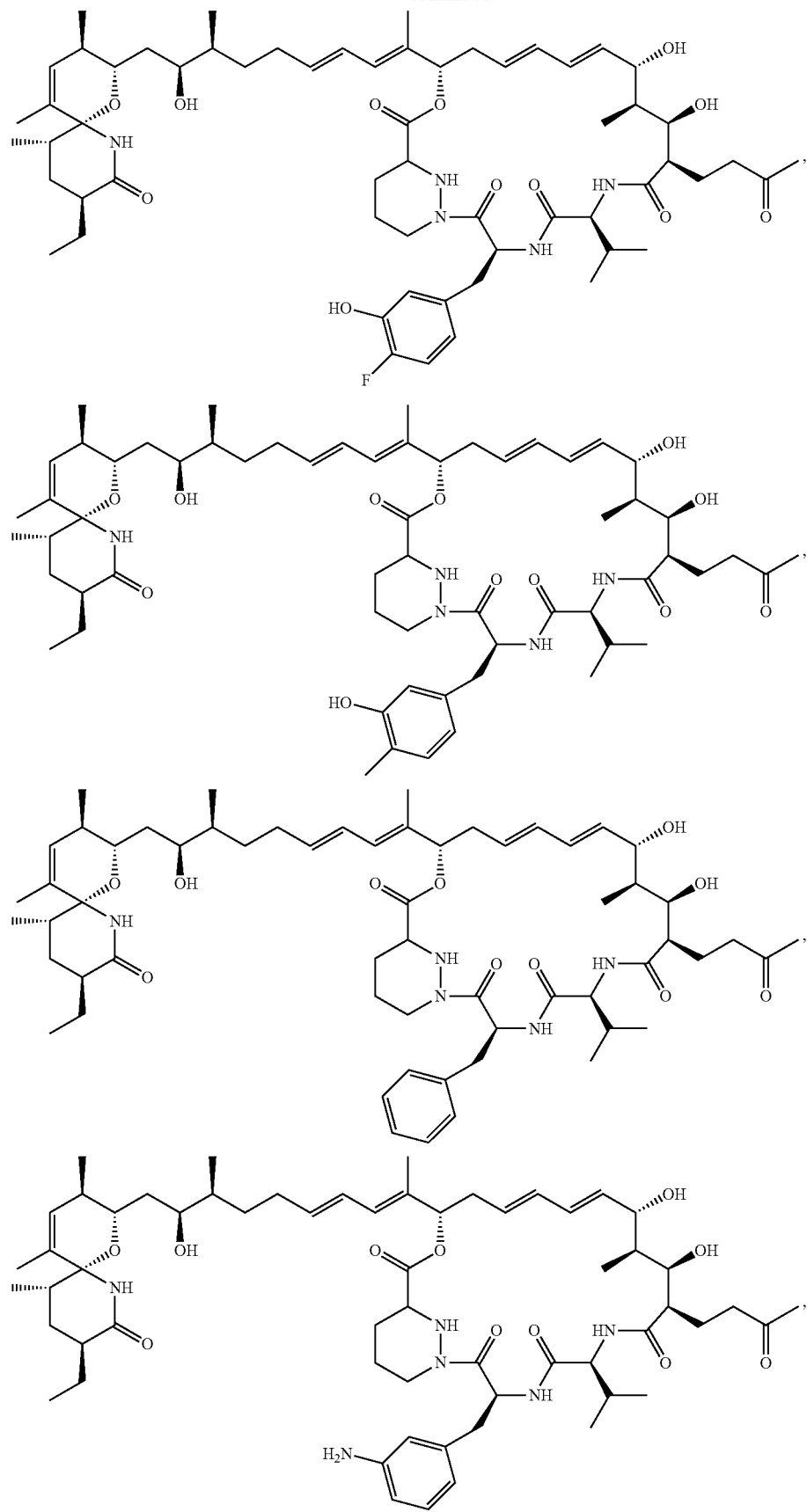

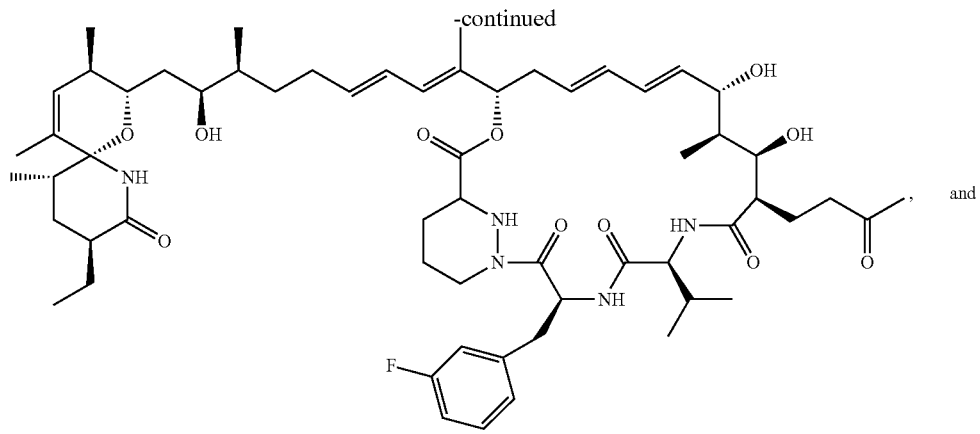
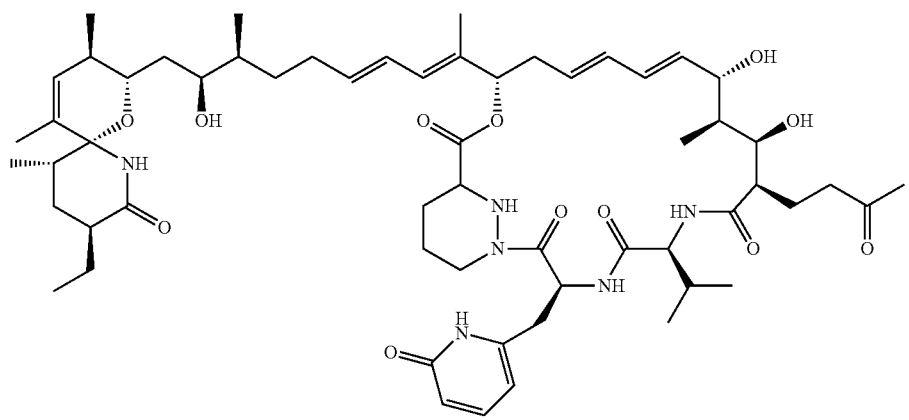 [SMILES: CC[C@H]1C[C@H](C)[C@@]2(NC1=O)O[C@@H](C[C@H](O)[C@@H](C)CC/C=C/C=C(\C)[C@@H]1C/C=C/C=C/[C@H](O)[C@H](C)[C@@H](O)[C@@H](CCC(C)=O)C(=O)N[C@@H](C(C)C)C(=O)N[C@@H](Cc3cccc(=O)[nH]3)C(=O)N3CCCC(N3)C(=O)O1)[C@H](C)C=C2C]
which can also be represented as:
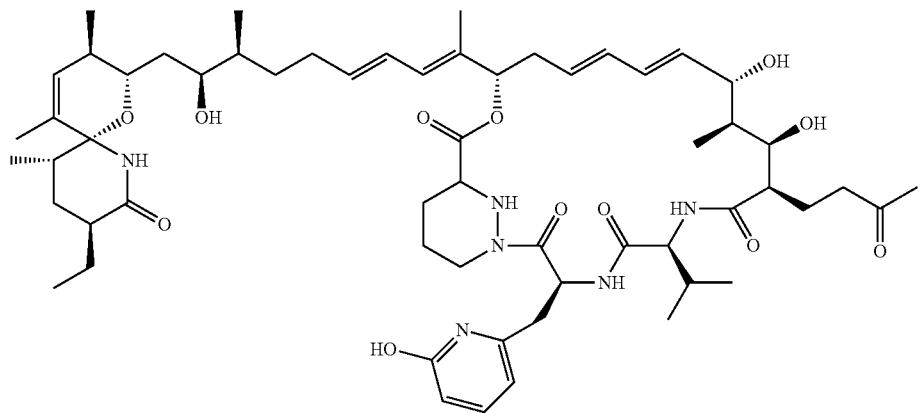 [SMILES: CC[C@H]1C[C@H](C)[C@@]2(NC1=O)O[C@@H](C[C@H](O)[C@@H](C)CC/C=C/C=C(\C)[C@@H]1C/C=C/C=C/[C@H](O)[C@H](C)[C@@H](O)[C@@H](CCC(C)=O)C(=O)N[C@@H](C(C)C)C(=O)N[C@@H](Cc3cccc(O)n3)C(=O)N3CCCC(N3)C(=O)O1)[C@H](C)C=C2C]

including any tautomer thereof; or an isomer thereof in which the C26, 27 C=C bond shown as trans is cis; and including a methanol adduct thereof in which a ketal is formed by the combination of the C-53 keto and the C-15 hydroxyl group and methanol;
or a pharmaceutically acceptable salt thereof.

In another embodiment, the non-natural sanglifehrin is a compound of formula (IV) or a pharmaceutically acceptable salt thereof:

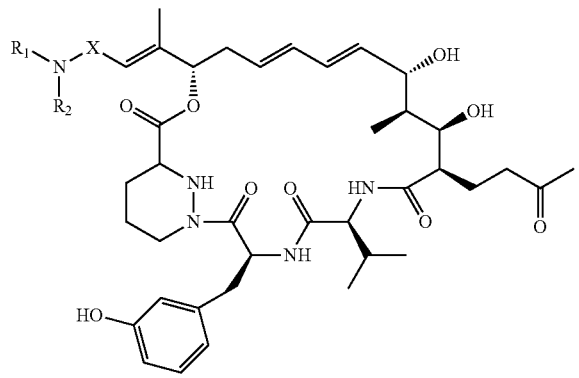

(IV)

wherein:
X represents CH$_2$ or CO
R$_1$ and R$_2$ independently represent hydrogen; or an alkyl or alkenyl group which may optionally be joined to form a saturated or unsaturated heterocyclic ring containing the nitrogen atom shown and wherein one or more carbon atoms of R$_1$ and/or R$_2$ are optionally replaced by a heteroatom selected from O, N and S(O)$_p$ in which p represents 0, 1 or 2 and wherein one or more carbon atoms of R$_1$ and/or R$_2$ are optionally replaced by carbonyl; or one of R$_1$ and R$_2$ represents -alkylaryl, -alkenylaryl, -alkylheteroaryl or -alkenylheteroaryl and the other represents H, alkyl or alkenyl;
including any tautomer thereof; and including a methanol adduct thereof in which a ketal is formed by the combination of the C-53 keto and the C-15 hydroxyl groups and methanol.

For example, R$_1$ and R$_2$ independently represent hydrogen; or an alkyl or alkenyl group wherein one or two carbon atoms of R$_1$ and/or R$_2$ are optionally replaced by a heteroatom selected from O, N and S(O)$_p$ and wherein one or two carbon atoms of R$_1$ and/or R$_2$ are optionally replaced by carbonyl. For example R$_1$ represents hydrogen and R$_2$ represents an alkyl group. For example R$_1$ represents hydrogen and R$_2$ represents an alkenyl group. For example R$_1$ and R$_2$ independently represent an alkyl or alkenyl group which is joined to form a saturated or unsaturated heterocyclic ring containing the nitrogen atom shown and wherein one or two carbon atoms of R$_1$ and/or R$_2$ are optionally replaced by a heteroatom selected from O, N and S(O)$_p$ in which p represents 0, 1 or 2 and wherein one or two carbon atoms of R$_1$ and/or R$_2$ are optionally replaced by carbonyl. For example R$_1$ and R$_2$ independently represent an alkyl group which are joined to form a saturated heterocyclic ring containing the nitrogen atom shown. For example R$_1$ and R$_2$ independently represent an alkyl or alkenyl group which are joined to form a saturated or unsaturated heterocyclic ring containing the nitrogen atom shown and wherein one or two carbon atoms of R$_1$ and/or R$_2$ are replaced by a heteroatom selected from O, N and S(O)$_p$. For example, if a carbon atom is replaced with a heteroatom, it is replaced with N or O. For example X represents CH$_2$.

A compound according to formula (IV) may be selected from:

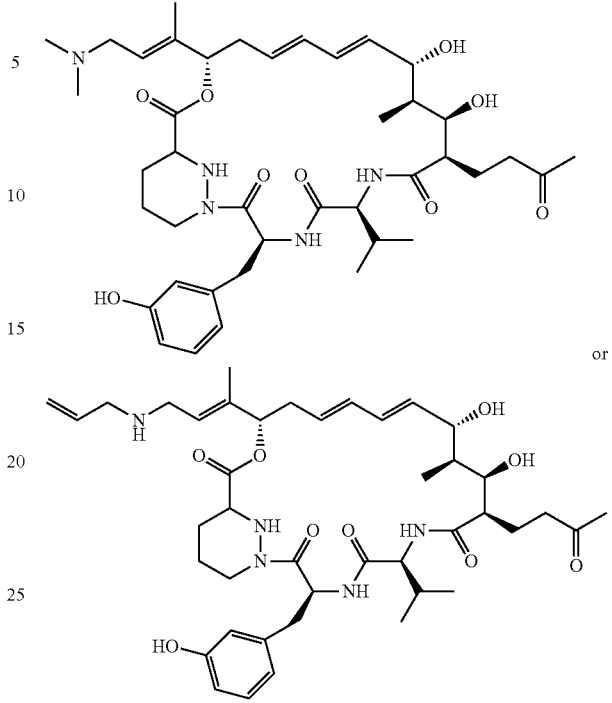

or or a pharmaceutically acceptable salt thereof.

In another embodiment, the non-natural sanglifehrin is a compound of formula (V) or a pharmaceutically acceptable salt thereof:

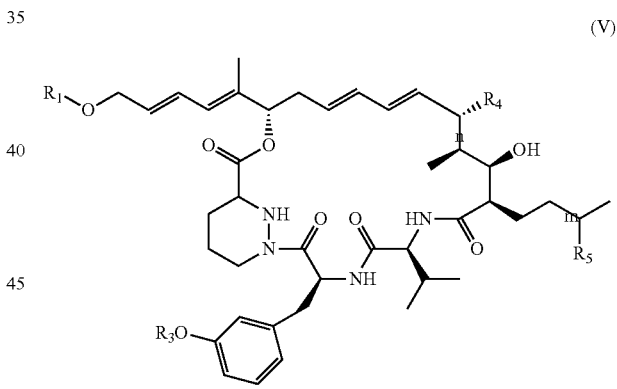

(V)

wherein:
R$_1$ represents alkyl, alkenyl, cycloalkyl, cycloalkenyl, alkylcycloalkyl, alkylcycloalkenyl, alkenylcycloalkyl, alkenylcycloalkenyl, aryl, heteroaryl, alkylaryl, alkylheteroaryl, alkenylaryl or alkenylheteroaryl any of which groups may optionally be substituted by monocylic aryl or monocyclic heteroaryl;
or R$_1$ represents hydrogen;
and wherein one or more carbon atoms of R$_1$ not being part of an aryl or heteroaryl group are optionally replaced by a heteroatom selected from O, N and S(O)$_p$ in which p represents 0, 1 or 2 and wherein one or more carbon atoms of R$_1$ are optionally replaced by carbonyl;
provided that R$_1$ does not represent methyl or —CHMe$_2$;
and wherein one or more carbon atoms of an R$_1$ group may optionally be substituted by one or more halogen atoms;

$R_3$ represents H or $(CO)_x$alkyl;
$R_4$ represents H or OH;
$R_5$ represents H, OH or =O;
n represents a single or double bond save that when n represents a double bond $R_4$ represents H; and
m represents a single or double bond save that when m represents a double bond $R_5$ represents H;
x represents 0 or 1;
including any tautomer thereof; or an isomer thereof in which the C26, 27 C=C bond shown as trans is cis; and including a methanol adduct thereof in which a ketal is formed by the combination of the C-53 keto (if present) and the C-15 hydroxyl group and methanol.

For example, $R_1$ represents alkyl, alkenyl, cycloalkyl, cycloalkenyl, alkylcycloalkyl, alkylcycloalkenyl, alkenylcycloalkyl, alkenylcycloalkenyl, aryl, heteroaryl, alkylaryl, alkylheteroaryl, alkenylaryl or alkenylheteroaryl any of which groups may optionally be substituted by monocylic aryl or monocyclic heteroaryl; or $R_1$ represents hydrogen; and wherein one or more carbon atoms of $R_1$ not being part of an aryl or heteroaryl group are optionally replaced by a heteroatom selected from O, N and $S(O)_p$ in which p represents 0, 1 or 2 and wherein one or more carbon atoms of $R_1$ are optionally replaced by carbonyl; provided that $R_1$ does not represent methyl or —$CHMe_2$.

For example $R_1$ represents $C_{4-10}$ alkyl, alkenyl, cycloalkyl, cycloalkenyl, alkylcycloalkyl, alkylcycloalkenyl, alkenylcycloalkyl, alkenylcycloalkenyl, aryl, heteroaryl, alkylaryl, alkylheteroaryl, alkenylaryl or alkenylheteroaryl any of which groups may optionally be substituted by monocylic aryl or monocyclic heteroaryl; or $R_1$ represents hydrogen; and wherein one or more carbon atoms of $R_1$ not being part of an aryl or heteroaryl group are optionally replaced by a heteroatom selected from O, N and $S(O)_p$ in which p represents 0, 1 or 2 and wherein one or more carbon atoms of $R_1$ are optionally replaced by carbonyl.

For example $R_1$ is selected from $C_{2-10}$ alkyl, $C_{2-10}$ alkenyl and aryl. For example $R_1$ is selected from $C_{2-6}$ alkyl, $C_{2-6}$ alkenyl and aryl. For example $R_1$ is selected from $C_{4-6}$ alkyl, $C_{2-6}$ alkenyl and aryl.

For example, independently or in any combination: $R_3$ represents H or $(CO)_xC_{1-4}$alkyl, wherein x is as defined in claim 1; n represents a single bond; m represents a single bond; $R_4$ represents OH; and $R_5$ represents =O.

For example x represents 0. For example $R_3$ represents H or methyl. For example $R_5$ represents C=O.

For example a compound of formula (V) is selected from a compound in which:
$R_1$ represents $CH_2CH=CH_2$, $R_3$ represents H, $R_4$ represents OH, n represents a single bond, m represents a single bond and $R_5$ represents =O as represented by the following structure:

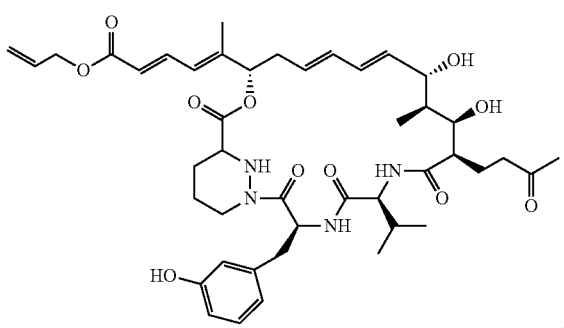

;

or $R_1$ represents $CH_2CH_3$, $R_3$ represents H, $R_4$ represents OH, n represents a single bond, m represents a single bond and $R_5$ represents =O as represented by the following structure:

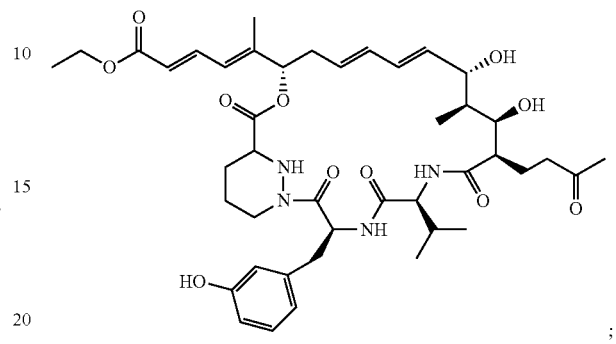

;

or $R_1$ represents $C(CH_3)_3$, $R_3$ represents H, $R_4$ represents OH, n represents a single bond, m represents a single bond and $R_5$ represents =O as represented by the following structure:

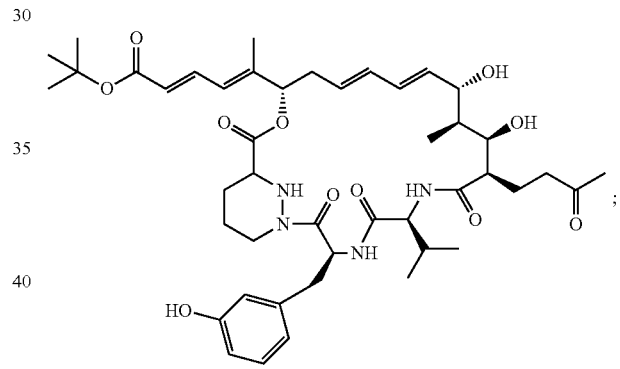

;

or $R_1$ represents phenyl, $R_3$ represents H, $R_4$ represents OH, n represents a single bond, m represents a single bond and $R_5$ represents =O as represented by the following structure:

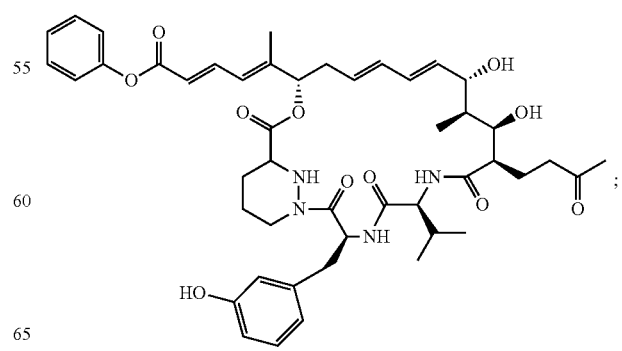

;

or
R₁ represents C(CH₃)₃, R₃ represents H, R₄ represents H, n represents a double bond, m represents a single bond and R₅ represents =O as represented by the following structure:

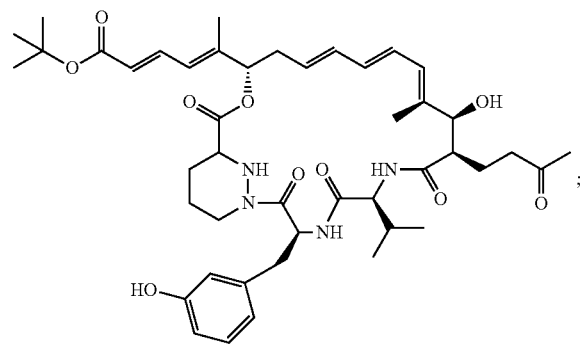

or
R₁ represents C(CH₃)₃, R₃ represents H, R₄ represents H, n represents a single bond, m represents a single bond and R₅ represents =O as represented by the following structure:

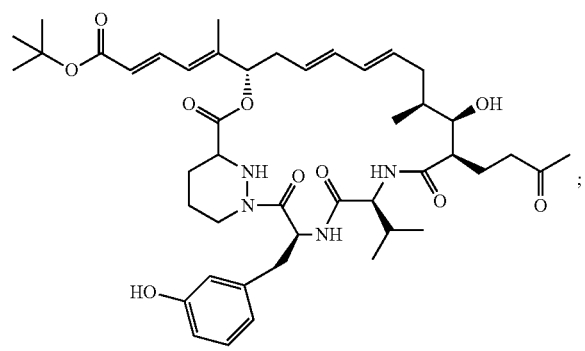 [SMILES: CC(=O)CC[C@H]1C(=O)N[C@@H](C(C)C)C(=O)N[C@@H](Cc2cccc(O)c2)C(=O)N2CCCC(N2)C(=O)O[C@H](/C(C)=C/C=C/C(=O)OC(C)(C)C)C/C=C/C=C/C[C@H](C)[C@H]1O]

or
R₁ represents CH₂CH=CH₂, R₃ represents H, R₄ represents H, n represents a single bond, m represents a single bond and R₅ represents =O as represented by the following structure:

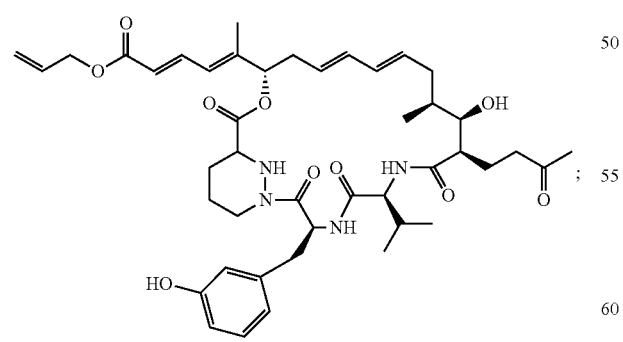

or
R₁ represents CH₂CH₃, R₃ represents H, R₄ represents H, n represents a single bond, m represents a single bond and R₅ represents =O as represented by the following structure:

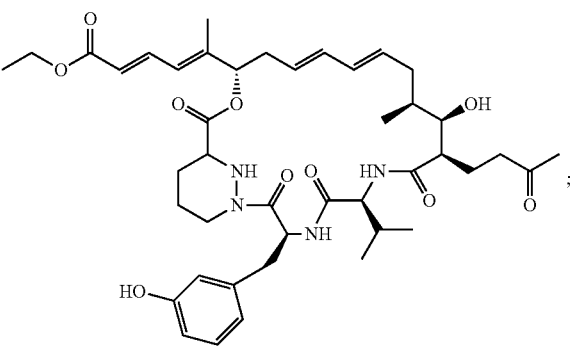 [SMILES: CCOC(=O)/C=C/C=C(\C)[C@@H]1C/C=C/C=C/C[C@H](C)[C@@H](O)[C@@H](CCC(C)=O)C(=O)N[C@@H](C(C)C)C(=O)N[C@@H](Cc2cccc(O)c2)C(=O)N2CCCC(N2)C(=O)O1]

or
R₁ represents phenyl R₃ represents H, R₄ represents H, n represents a single bond, m represents a single bond and R₅ represents =O as represented by the following structure:

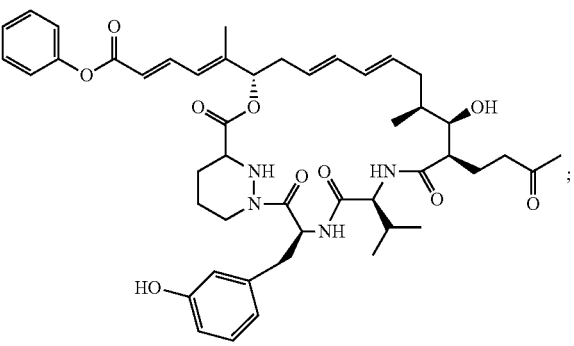 [SMILES: CC(=O)CC[C@H]1C(=O)N[C@@H](C(C)C)C(=O)N[C@@H](Cc2cccc(O)c2)C(=O)N2CCCC(N2)C(=O)O[C@H](/C(C)=C/C=C/C(=O)Oc2ccccc2)C/C=C/C=C/C[C@H](C)[C@H]1O]

including any tautomer thereof; or an isomer thereof in which the C26, 27 C=C bond shown as trans is cis; and including a methanol adduct thereof in which a ketal is formed by the combination of the C-53 keto (if present) and the C-15 hydroxyl group and methanol.

For example, R₃ represents H, R₄ represents OH, n represents a single bond, m represents a single bond and R₅ represents =O as represented by the following structure:

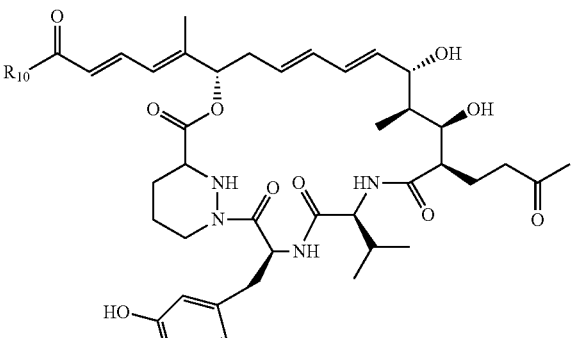

wherein R₁₀ represents —OR₁ and R₁ is as defined above, including any tautomer thereof; or an isomer thereof in which the C26, 27 C=C bond shown as trans is cis; and including a methanol adduct thereof in which a ketal is formed by the combination of the C-53 keto (if present) and the C-15 hydroxyl group and methanol.

For example, $R_{10}$ is selected from a group listed in the following table:
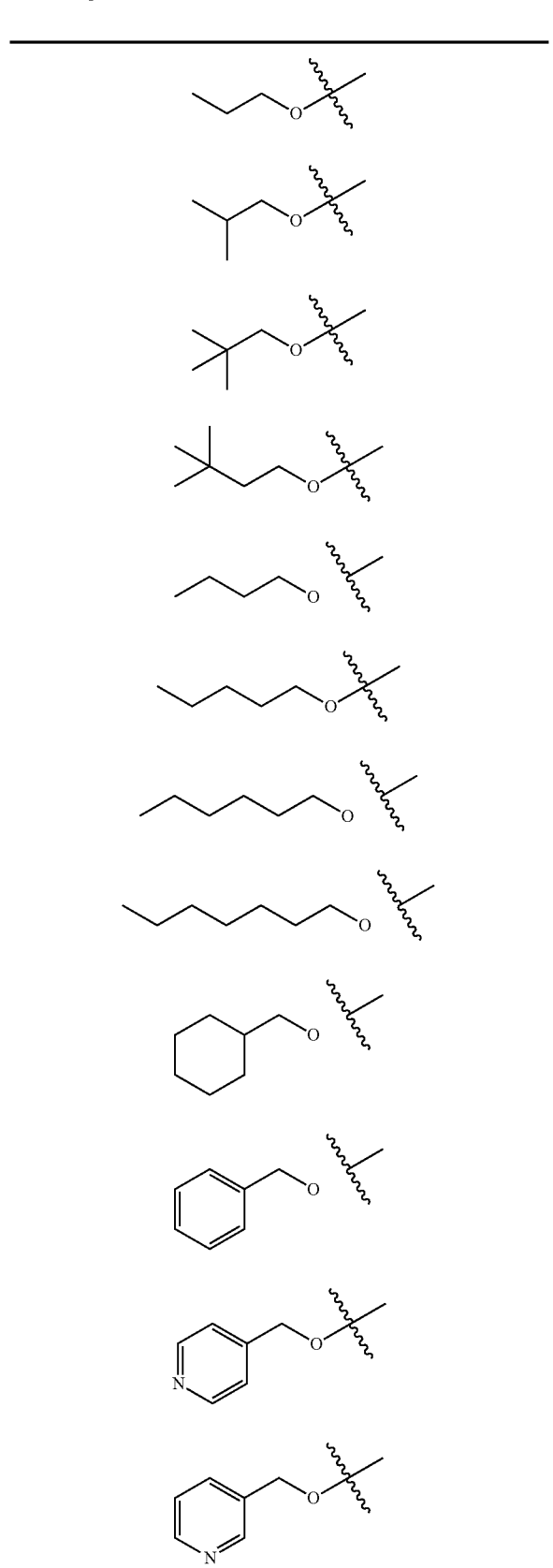
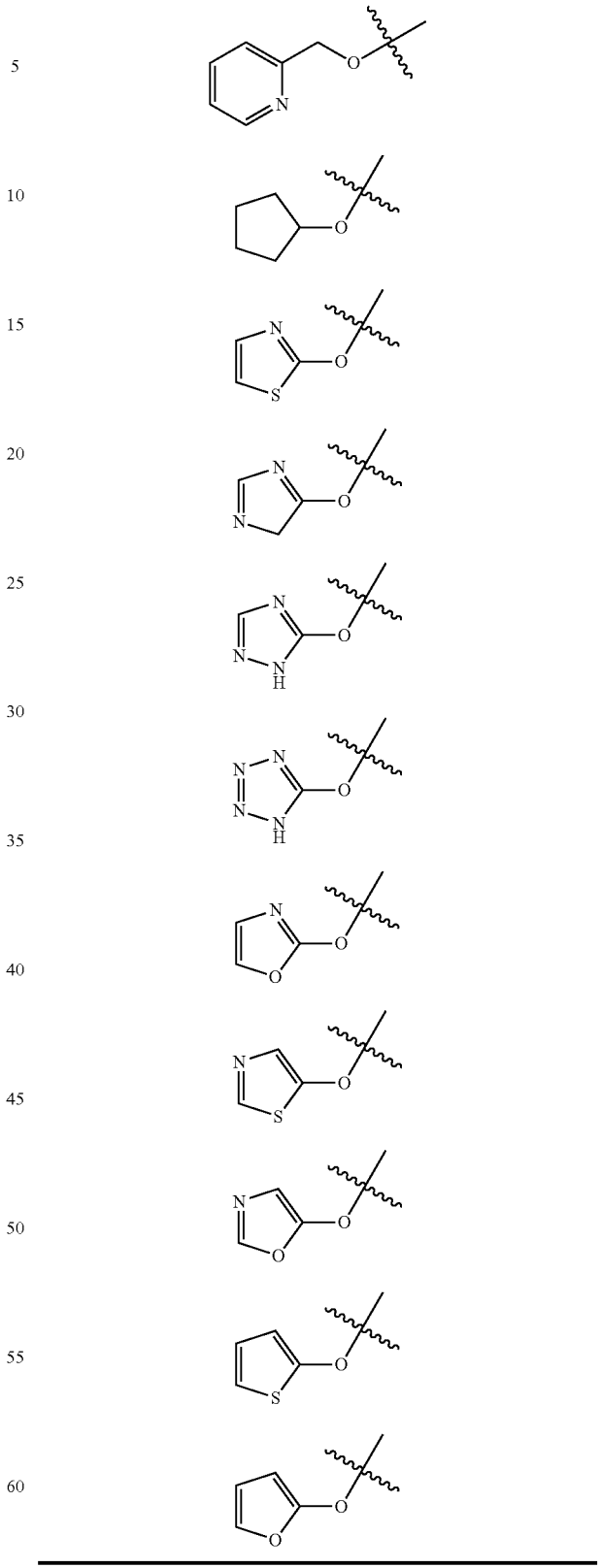
Compounds of formula (V) may be prepared according to methods disclosed in WO2011/098805 which is herein incorporated by reference in its entirety.

In another embodiment, the non-natural sanglifehrin is a compound of formula (VI) or a pharmaceutically acceptable salt thereof:

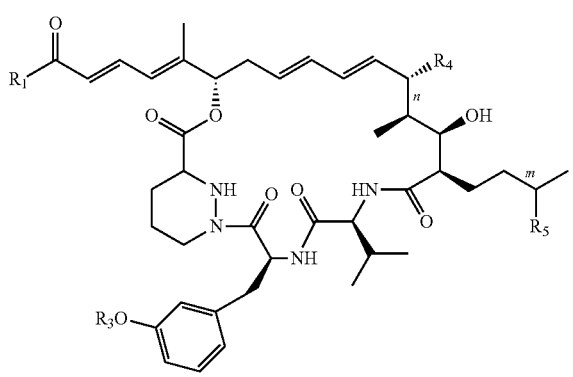

(VI)

wherein:
- $R_1$ represents alkyl, alkenyl, cycloalkyl, cycloalkenyl, alkylcycloalkyl, alkylcycloalkenyl, alkenylcycloalkyl, alkenylcycloalkenyl, aryl, heteroaryl, alkylaryl, alkylheteroaryl, alkenylaryl or alkenylheteroaryl any of which groups may optionally be substituted by monocylic aryl or monocyclic heteroaryl;
- and wherein one or more carbon atoms of $R_1$ not being part of an aryl or heteroaryl group are optionally replaced by a heteroatom selected from O, N and $S(O)_p$ in which p represents 0, 1 or 2 save that the atom adjacent to the carbonyl group to which $R_1$ is attached is not O or N and wherein one or more carbon atoms of $R_1$ are optionally replaced by carbonyl;
- and wherein one or more carbon atoms of an $R_1$ group may optionally be substituted by one or more halogen atoms;
- $R_3$ represents H or $(CO)_x$alkyl;
- $R_4$ represents H or OH;
- $R_5$ represents H, OH or =O;
- n represents a single or double bond save that when n represents a double bond $R_4$ represents H; and
- m represents a single or double bond save that when m represents a double bond $R_5$ represents H;
- x represents 0 or 1;
- including any tautomer thereof; or an isomer thereof in which the C26, 27 C=C bond shown as trans is cis; and including a methanol adduct thereof in which a ketal is formed by the combination of the C-53 keto (if present) and the C-15 hydroxyl group and methanol.

For example $R_1$ represents alkyl, alkenyl, cycloalkyl, cycloalkenyl, alkylcycloalkyl, alkylcycloalkenyl, alkenylcycloalkyl, alkenylcycloalkenyl, aryl, heteroaryl, alkylaryl, alkylheteroaryl, alkenylaryl or alkenylheteroaryl any of which groups may optionally be substituted by monocylic aryl or monocyclic heteroaryl;

and wherein one or more carbon atoms of $R_1$ not being part of an aryl or heteroaryl group are optionally replaced by a heteroatom selected from O, N and $S(O)_p$ in which p represents 0, 1 or 2 save that the atom adjacent to the carbonyl group to which $R_1$ is attached is not O or N and wherein one or more carbon atoms of $R_1$ are optionally replaced by carbonyl.

For example $R_1$ represents $C_{1-6}$alkyl, $C_{2-6}$alkenyl, $C_{1-4}$alkyl$C_{4-7}$cycloalkyl or $C_{1-4}$alkyl$C_{5-7}$cycloalkenyl.

For example independently or in any combination: $R_3$ represents H or $(CO)_xC_{1-4}$alkyl; n represents a single bond; m represents a single bond; $R_4$ represents OH; and $R_5$ represents =O.

For example x represents 0. For example $R_3$ represents H or methyl.

For example a compound of formula (VI) is selected from a compound in which:
- $R_1$ represents $CH_2CH_3$, $R_3$ represents H, $R_4$ represents OH, n represents a single bond, m represents a single bond and $R_5$ represents =O as represented by the following structure:

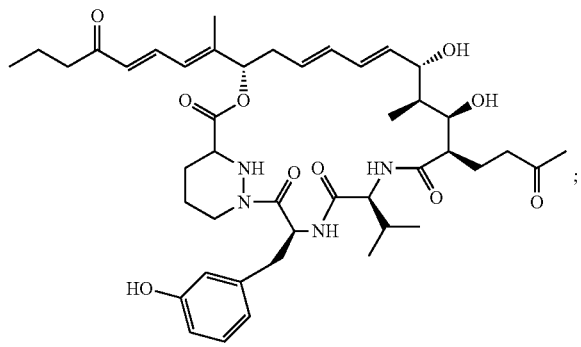 [SMILES: CCCC(=O)/C=C/C=C(\C)[C@@H]1C/C=C/C=C/[C@H](O)[C@H](C)[C@@H](O)[C@@H](CCC(C)=O)C(=O)N[C@@H](C(C)C)C(=O)N[C@@H](Cc2cccc(O)c2)C(=O)N2CCCC(N2)C(=O)O1]

or
- $R_1$ represents ethylcyclohexyl, $R_3$ represents H, $R_4$ represents OH, n represents a single bond, m represents a single bond and $R_5$ represents =O as represented by the following structure:

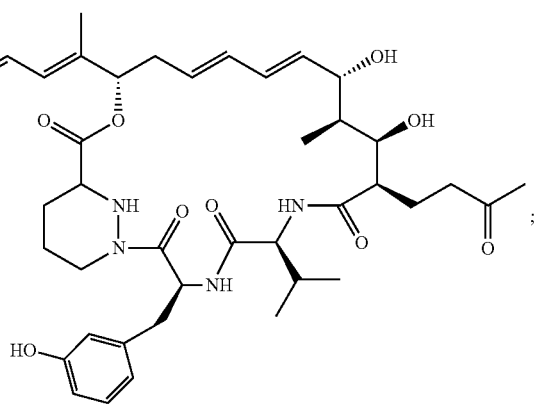

or
$R_1$ represents t-butyl, $R_3$ represents H, $R_4$ represents OH, n represents a single bond, m represents a single bond and $R_5$ represents =O as represented by the following structure:

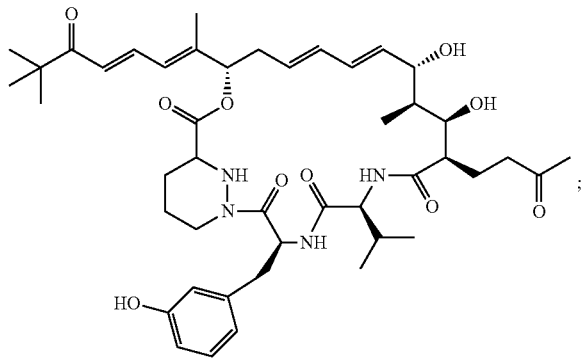 [SMILES: CC(=O)CC[C@H]1C(=O)N[C@@H](C(C)C)C(=O)N[C@@H](Cc2cccc(O)c2)C(=O)N2CCCC(N2)C(=O)O[C@H](/C(C)=C/C=C/C(=O)C(C)(C)C)C/C=C/C=C/[C@H](O)[C@H](C)[C@H]1O]

or
$R_1$ represents $CH_2CH_3$, $R_3$ represents H, $R_4$ represents H, n represents a single bond, m represents a single bond and $R_5$ represents =O as represented by the following structure:

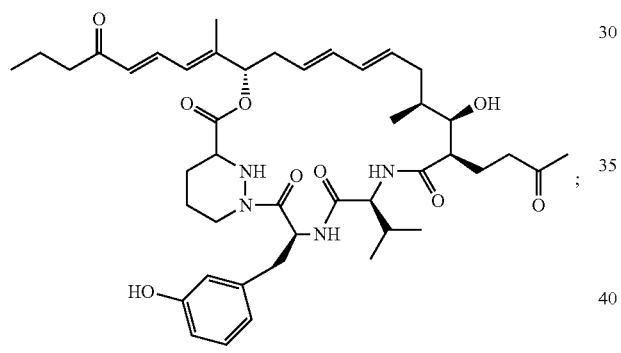

or
$R_1$ represents ethylcyclohexyl, $R_3$ represents H, $R_4$ represents H, n represents a single bond, m represents a single bond and $R_5$ represents =O as represented by the following structure:

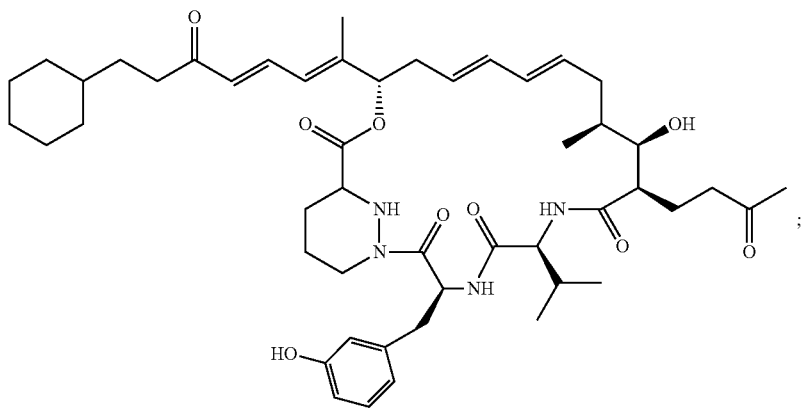 [SMILES: CC(=O)CC[C@H]1C(=O)N[C@@H](C(C)C)C(=O)N[C@@H](Cc2cccc(O)c2)C(=O)N2CCCC(N2)C(=O)O[C@H](/C(C)=C/C=C/C(=O)CCC2CCCCC2)C/C=C/C=C/C[C@H](C)[C@H]1O]

or
$R_1$ represents t-butyl, $R_3$ represents H, $R_4$ represents H, n represents a single bond, m represents a single bond and $R_5$ represents =O as represented by the following structure:

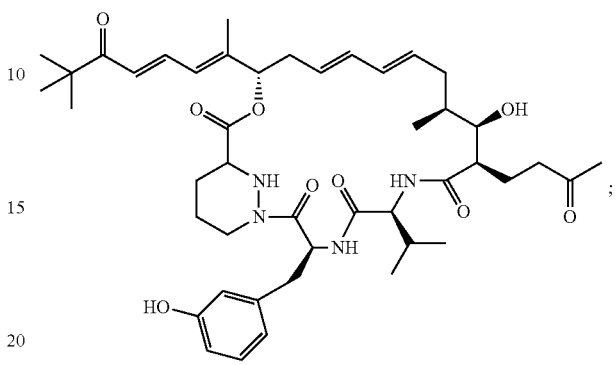

or
$R_3$ represents H, $R_4$ represents OH, n represents a single bond, m represents a single bond and $R_5$ represents =O as represented by the following structure:

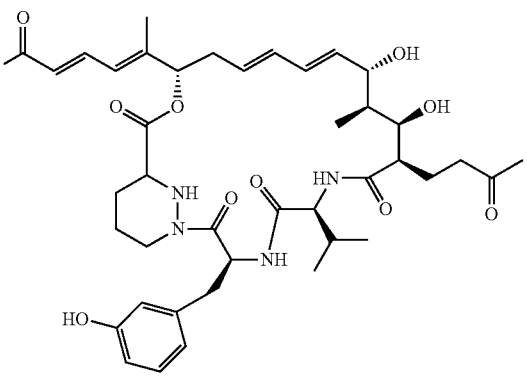

wherein $R_1$ is as defined above;
including any tautomer thereof; or any isomer thereof in which the C26, 27 C=C bond shown as trans is cis; and including a methanol adduct thereof in which a ketal is formed by the combination of the C-53 keto (if present) and the C-15 hydroxyl groups and methanol.
For example $R_1$ is selected from a group listed in the following table:
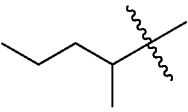
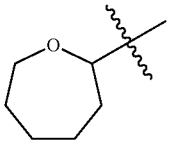
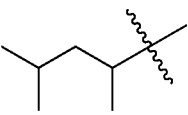 [SMILES: *C(C)CC(C)C]
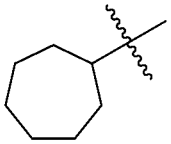 [SMILES: *C1CCCCCC1]
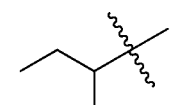
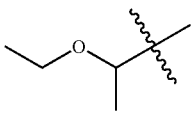 [SMILES: *C(C)OCC]
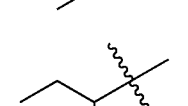
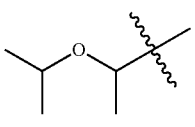 [SMILES: *C(C)OC(C)C]
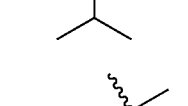
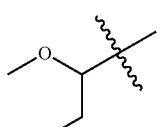
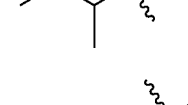
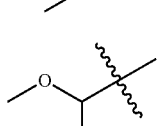
-continued
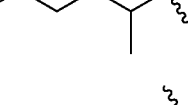
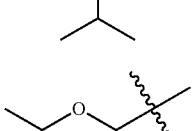
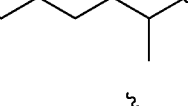
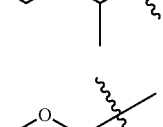
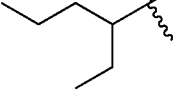
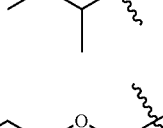
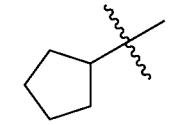
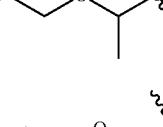
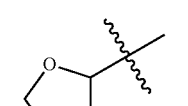
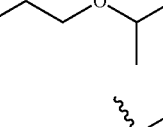
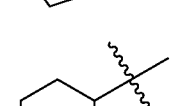
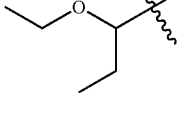
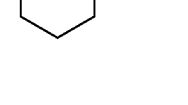
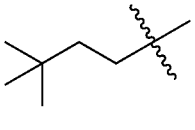 [SMILES: *CCC(C)(C)C]

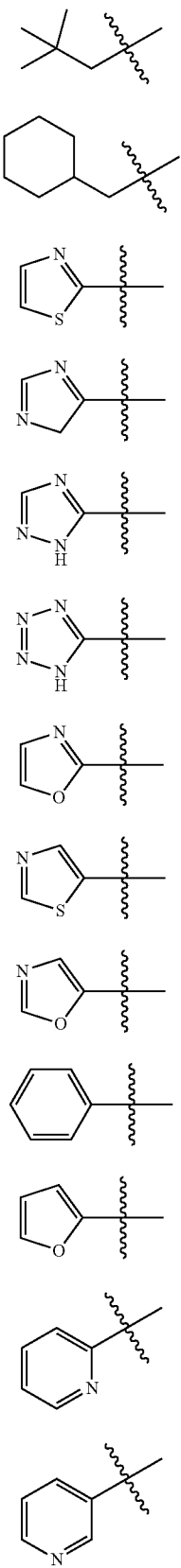

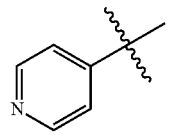 [SMILES: *c1ccncc1]

Compounds of formula (VI) may be prepared according to methods disclosed in WO2011/098808 which is herein incorporated by reference in its entirety.

In another embodiment, the non-natural sanglifehrin is a compound of formula (VII) or a pharmaceutically acceptable salt thereof:

(VII)

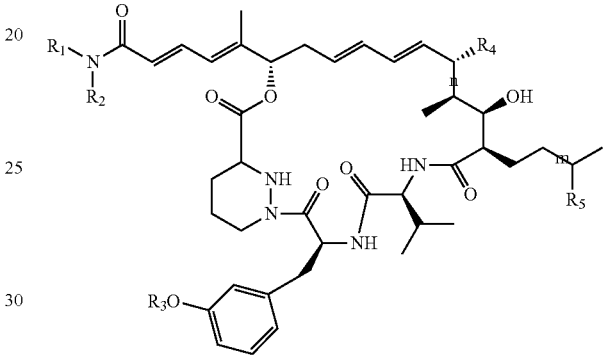

wherein:
$R_1$ and $R_2$ independently represent alkyl, alkenyl, cycloalkyl, cycloalkenyl, alkylcycloalkyl, alkylcycloalkenyl, alkenylcycloalkyl, alkenylcycloalkenyl, aryl, heteroaryl, alkylaryl, alkylheteroaryl, alkenylaryl or alkenylheteroaryl any of which groups may optionally be substituted by monocylic aryl or monocyclic heteroaryl;
  or $R_1$ represents hydrogen; and wherein one or more carbon atoms of $R_1$ and/or $R_2$ not being part of an aryl or heteroaryl group are optionally replaced by a heteroatom selected from O, N and $S(O)_p$ in which p represents 0, 1 or 2 and wherein one or more carbon atoms of $R_1$ and/or $R_2$ are optionally replaced by carbonyl;
  or $R_1$ and $R_2$ are joined to form a saturated or unsaturated heterocyclic ring containing the nitrogen atom shown and wherein one or more carbon atoms of said ring are optionally replaced by a heteroatom selected from O, N and $S(O)_p$ in which p represents 0, 1 or 2 and wherein one or more carbon atoms of said ring are optionally replaced by carbonyl and which heterocyclic ring may optionally be fused to an aryl or heteroaryl ring;
  and wherein one or more carbon atoms of an $R_1$ and/or $R_2$ group may optionally be substituted by one or more halogen atoms;
$R_3$ represents H, —(CO)$_x$alkyl;
$R_4$ represents H or OH;
$R_5$ represents H, OH or =O;
n represents a single or double bond save that when n represents a double bond $R_4$ represents H; and
m represents a single or double bond save that when m represents a double bond $R_5$ represents H;
x represents 0 or 1;

including any tautomer thereof; or an isomer thereof in which the C26, 27 C═C bond shown as trans is cis; and including a methanol adduct thereof in which a ketal is formed by the combination of the C-53 keto (if present) and the C-15 hydroxyl groups and methanol.

For example $R_1$ and $R_2$ independently represent alkyl, alkenyl, cycloalkyl, cycloalkenyl, alkylcycloalkyl, alkylcycloalkenyl, alkenylcycloalkyl, alkenylcycloalkenyl, aryl, heteroaryl, alkylaryl, alkylheteroaryl, alkenylaryl or alkenylheteroaryl any of which groups may optionally be substituted by monocyclic aryl or monocyclic heteroaryl;

or $R_1$ represents hydrogen; and wherein one or more carbon atoms of $R_1$ and/or $R_2$ not being part of an aryl or heteroaryl group are optionally replaced by a heteroatom selected from O, N and $S(O)_p$ in which p represents 0, 1 or 2 and wherein one or more carbon atoms of $R_1$ and/or $R_2$ are optionally replaced by carbonyl;

or $R_1$ and $R_2$ are joined to form a saturated or unsaturated heterocyclic ring containing the nitrogen atom shown and wherein one or more carbon atoms of said ring are optionally replaced by a heteroatom selected from O, N and $S(O)_p$ in which p represents 0, 1 or 2 and wherein one or more carbon atoms of said ring are optionally replaced by carbonyl and which heterocyclic ring may optionally be fused to an aryl or heteroaryl ring.

For example $R_1$ represents aryl or heteroaryl substituted by monocyclic aryl or monocyclic heteroaryl, —$C_{1-4}$alkyl, —$OC_{1-4}$alkyl, —$COC_{1-4}$alkyl or —$C_{2-4}$alkenyl. For example $R_2$ represents hydrogen, $C_{1-4}$ alkyl or $C_{1-4}$ alkenyl. For example $R_2$ represents hydrogen or $C_{1-4}$ alkyl.

For example $R_1$ and $R_2$ together with the nitrogen to which they are attached represent a 5-7 membered heterocyclic ring, such as a pyrrolidine, piperidine, morpholine or piperazine ring in which the 4-nitrogen of piperazine is optionally substituted by $C_{1-4}$alkyl and in which a carbon atom adjacent to a nitrogen atom within the ring is optionally replaced with carbonyl.

For example independently or in any combination: $R_3$ represents H or $(CO)_xC_{1-4}$alkyl, wherein x is as defined above; n represents a single bond; m represents single bond; $R_4$ represents OH; $R_5$ represents ═O.

For example x represents 0.

For example a compound of formula (VII) is selected from a compound in which:

$R_1$ represents $OCH_3$, $R_2$ represents Me, $R_3$ represents H, $R_4$ represents OH, n represents a single bond, m represents a single bond and $R_5$ represents ═O as represented by the following structure:

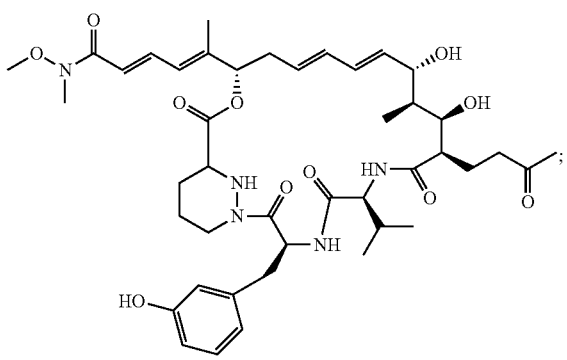 [SMILES: CON(C)C(=O)/C=C/C=C(\C)[C@@H]1C/C=C/C=C/[C@H](O)[C@H](C)[C@@H](O)[C@@H](CCC(C)=O)C(=O)N[C@@H](C(C)C)C(=O)N[C@@H](Cc2cccc(O)c2)C(=O)N2CCCC(N2)C(=O)O1]

or $R_1$ represents ethyl, $R_2$ represents ethyl, $R_3$ represents H, $R_4$ represents OH, n represents a single bond, m represents a single bond and $R_5$ represents ═O as represented by the following structure:

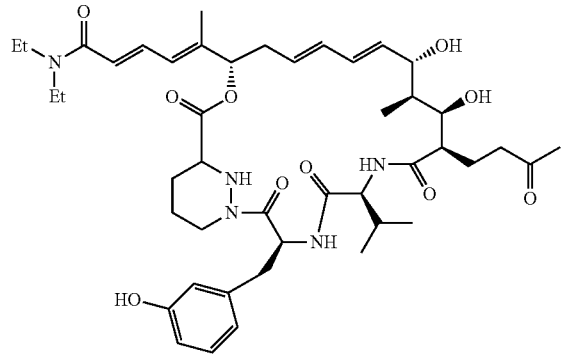 [SMILES: CCN(CC)C(=O)/C=C/C=C(\C)[C@@H]1C/C=C/C=C/[C@H](O)[C@H](C)[C@@H](O)[C@@H](CCC(C)=O)C(=O)N[C@@H](C(C)C)C(=O)N[C@@H](Cc2cccc(O)c2)C(=O)N2CCCC(N2)C(=O)O1]

or $R_1$ represents —$CHMe_2$, $R_2$ represents H, $R_3$ represents H, $R_4$ represents OH, n represents a single bond, m represents a single bond and $R_5$ represents ═O as represented by the following structure:

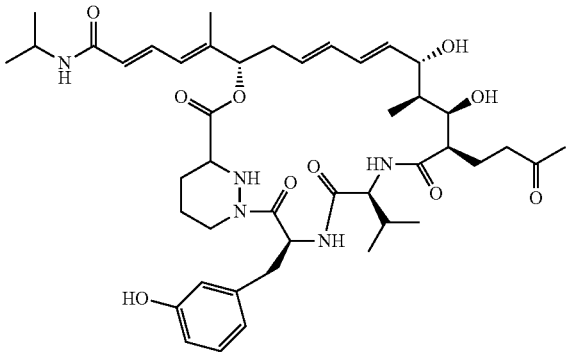 [SMILES: CC(=O)CC[C@H]1C(=O)N[C@@H](C(C)C)C(=O)N[C@@H](Cc2cccc(O)c2)C(=O)N2CCCC(N2)C(=O)O[C@H](/C(C)=C/C=C/C(=O)NC(C)C)C/C=C/C=C/[C@H](O)[C@H](C)[C@H]1O]

or $R_1$ represents methyl, $R_2$ represents H, $R_3$ represents H, $R_4$ represents OH, n represents a single bond, m represents a single bond and $R_5$ represents ═O as represented by the following structure:

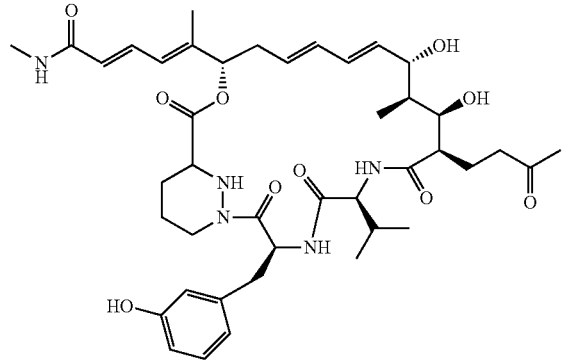 [SMILES: CNC(=O)/C=C/C=C(\C)[C@@H]1C/C=C/C=C/[C@H](O)[C@H](C)[C@@H](O)[C@@H](CCC(C)=O)C(=O)N[C@@H](C(C)C)C(=O)N[C@@H](Cc2cccc(O)c2)C(=O)N2CCCC(N2)C(=O)O1]

or
- $R_1$ represents methyl, $R_2$ represents H, $R_3$ represents Me, $R_4$ represents OH, n represents a single bond, m represents a single bond and $R_5$ represents =O as represented by the following structure:

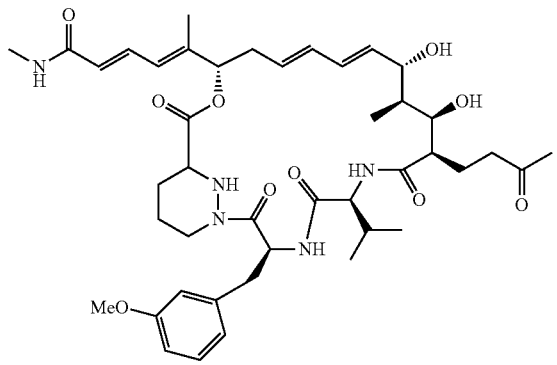 [SMILES: CNC(=O)/C=C/C=C(\C)[C@@H]1C/C=C/C=C/[C@H](O)[C@H](C)[C@@H](O)[C@@H](CCC(C)=O)C(=O)N[C@@H](C(C)C)C(=O)N[C@@H](Cc2cccc(OC)c2)C(=O)N2CCCC(N2)C(=O)O1]

or
- $R_1$ represents —CH$_2$CH=CH$_2$, $R_2$ represents H, $R_3$ represents H, $R_4$ represents OH, n represents a single bond, m represents a single bond and $R_5$ represents =O as represented by the following structure:

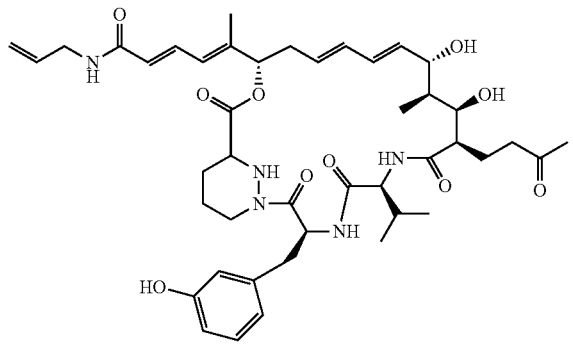 [SMILES: C=CCNC(=O)/C=C/C=C(\C)[C@@H]1C/C=C/C=C/[C@H](O)[C@H](C)[C@@H](O)[C@@H](CCC(C)=O)C(=O)N[C@@H](C(C)C)C(=O)N[C@@H](Cc2cccc(O)c2)C(=O)N2CCCC(N2)C(=O)O1]

or
- $R_1$ represents methyl, $R_2$ represents methyl, $R_3$ represents H, $R_4$ represents OH, n represents bond, m represents bond and $R_5$ represents =O as represented by the following structure:

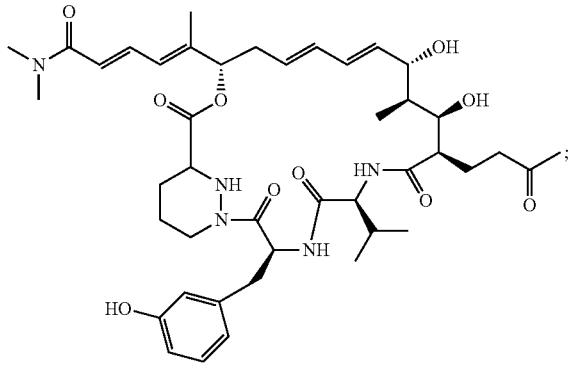 [SMILES: CC(=O)CC[C@H]1C(=O)N[C@@H](C(C)C)C(=O)N[C@@H](Cc2cccc(O)c2)C(=O)N2CCCC(N2)C(=O)O[C@H](/C(C)=C/C=C/C(=O)N(C)C)C/C=C/C=C/[C@H](O)[C@H](C)[C@H]1O]

or
- $R_1$ represents —CH$_2$CHMe$_2$, $R_2$ represents —CH$_2$CHMe$_2$, $R_3$ represents H, $R_4$ represents OH, n represents a single bond, m represents a single bond and $R_5$ represents =O as represented by the following structure:

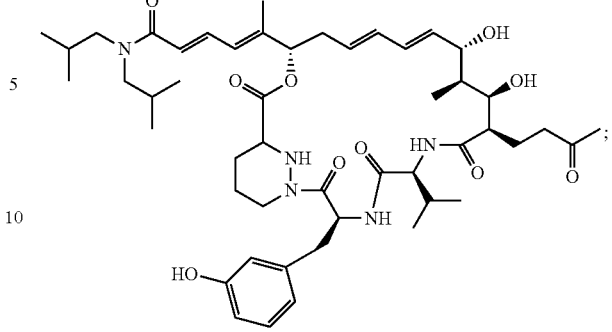

or
- $R_1$ represents OCH$_3$, $R_2$ represents Me, $R_3$ represents H, $R^4$ represents OH, n represents a single bond, m represents a double bond and $R_5$ represents H as represented by the following structure:

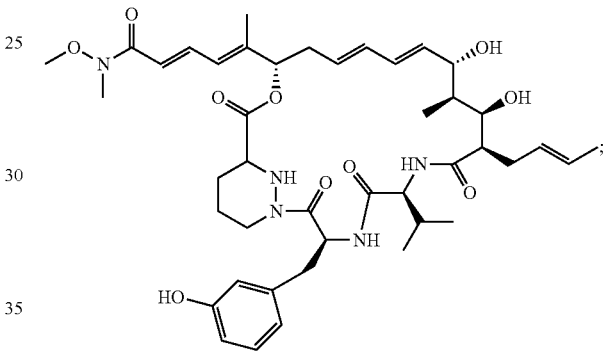

or
- $R_1$ represents OCH$_3$, $R_2$ represents Me, $R_3$ represents H, $R_4$ represents H, n represents a double bond, m represents a single bond and $R_5$ represents =O as represented by the following structure:

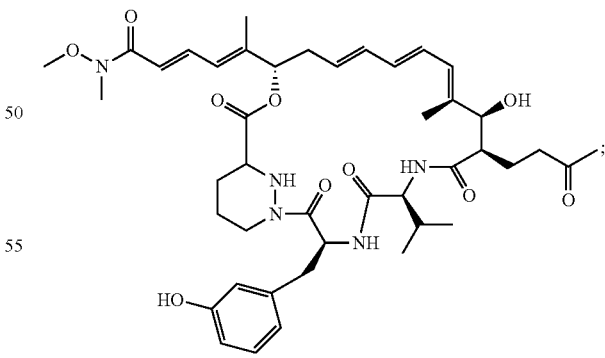

or
- $R_1$ and $R_2$ together represent —CH$_2$CH$_2$OCH$_2$CH$_2$— connected in a 6-membered heterocycle, $R_3$ represents H, $R_4$ represents OH, n represents a single bond, m represents a single bond and $R_5$ represents =O as represented by the following structure:

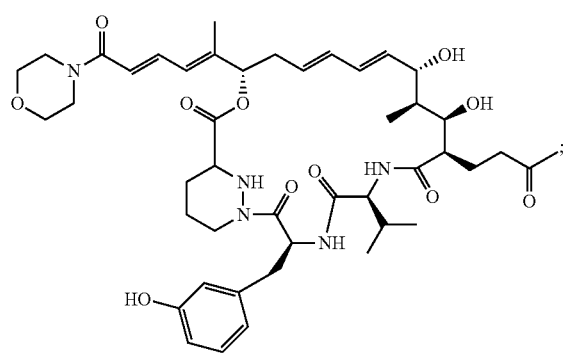 [SMILES: CC(=O)CC[C@H]1C(=O)N[C@@H](C(C)C)C(=O)N[C@@H](Cc2cccc(O)c2)C(=O)N2CCCC(N2)C(=O)O[C@H](/C(C)=C/C=C/C(=O)N2CCOCC2)C/C=C/C=C/[C@H](O)[C@H](C)[C@H]1O]

or
R$_1$ represents 4-biphenylyl, R$_2$ represents H, where, R$_3$ represents H, R$_4$ represents OH, n represents a single bond, m represents a single bond and R$_5$ represents =O as represented by the following structure:

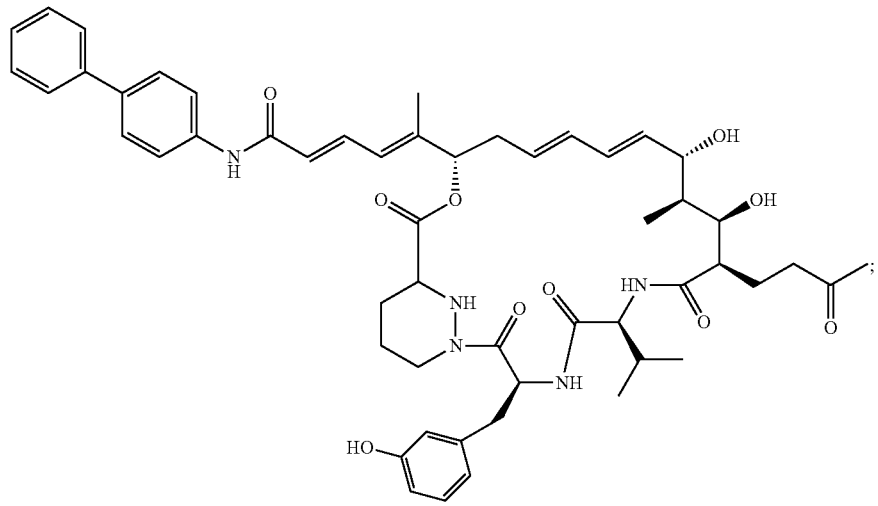 [SMILES: CC(=O)CC[C@H]1C(=O)N[C@@H](C(C)C)C(=O)N[C@@H](Cc2cccc(O)c2)C(=O)N2CCCC(N2)C(=O)O[C@H](/C(C)=C/C=C/C(=O)Nc2ccc(-c3ccccc3)cc2)C/C=C/C=C/[C@H](O)[C@H](C)[C@H]1O]

or
R$_1$ represents cyclohexyl, R$_2$ represents Me, R$_3$ represents H, R$_4$ represents OH, n represents a single bond, m represents a single bond and R$_5$ represents =O as represented by the following structure:

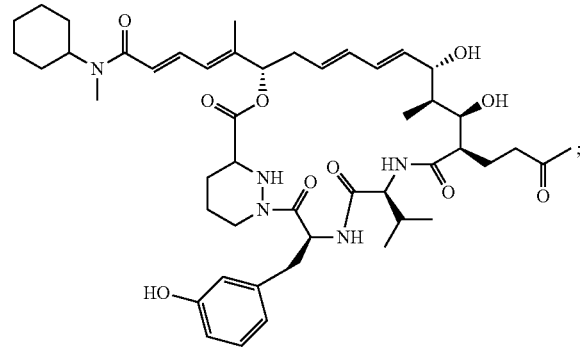 [SMILES: CC(=O)CC[C@H]1C(=O)N[C@@H](C(C)C)C(=O)N[C@@H](Cc2cccc(O)c2)C(=O)N2CCCC(N2)C(=O)O[C@H](/C(C)=C/C=C/C(=O)N(C)C2CCCCC2)C/C=C/C=C/[C@H](O)[C@H](C)[C@H]1O]

or
R$_1$ and R$_2$ together represent —OCH$_2$CH$_2$CH$_2$CH$_2$— connected in a 6-membered heterocycle, R$_3$ represents H, R$_4$ represents H, n represents a single bond, m represents a single bond and R$_5$ represents =O as represented by the following structure:

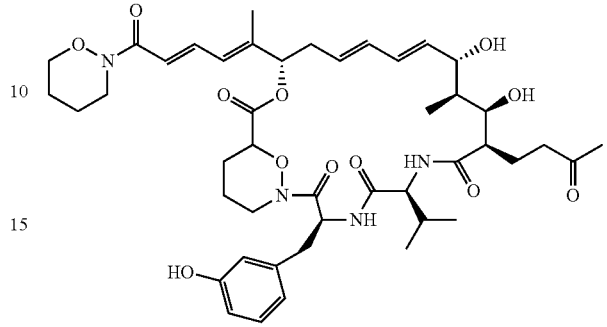

or
R$_1$ represents 2-pyridinyl, R$_2$ represents H, R$_3$ represents H, R$_4$ represents OH, n represents a single bond, m represents a single bond and R$_5$ represents =O as represented by the following structure:

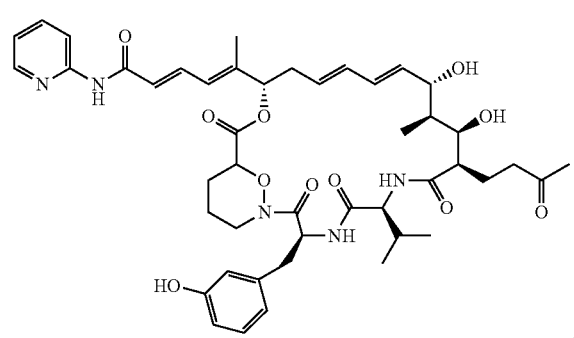

or
R$_1$ represents cyclohexyl, R$_2$ represents H, R$_3$ represents H, R$_4$ represents OH, n represents a single bond, m represents a single bond and R₅ represents =O as represented by the following structure:

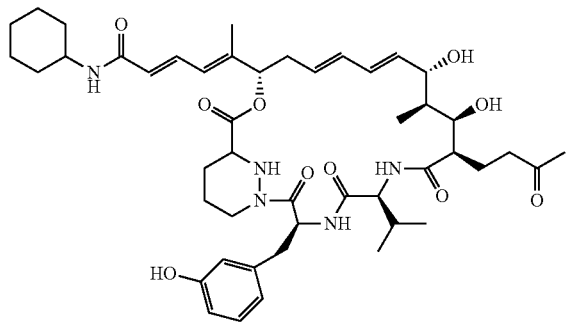 [SMILES: CC(=O)CC[C@H]1C(=O)N[C@@H](C(C)C)C(=O)N[C@@H](Cc2cccc(O)c2)C(=O)N2CCCC(N2)C(=O)O[C@H](/C(C)=C/C=C/C(=O)NC2CCCCC2)C/C=C/C=C/[C@H](O)[C@H](C)[C@H]1O]

or

R₁ represents OCH₃, R₂ represents Me, R₃ represents H, R₄ represents OH, n represents a single bond, m represents a single bond and R₅ represents OH as represented by the following structure:

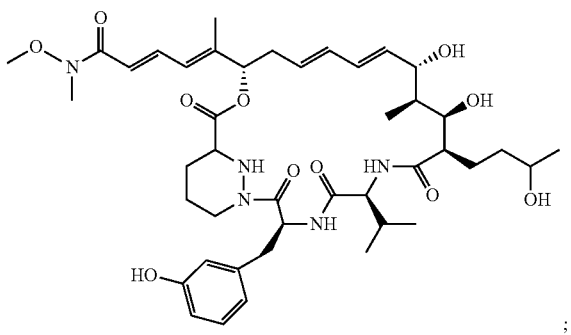 [SMILES: CON(C)C(=O)/C=C/C=C(\C)[C@@H]1C/C=C/C=C/[C@H](O)[C@H](C)[C@@H](O)[C@@H](CCC(C)O)C(=O)N[C@@H](C(C)C)C(=O)N[C@@H](Cc2cccc(O)c2)C(=O)N2CCCC(N2)C(=O)O1]

;

or

R₁ represents OCH₃, R₂ represents Me, R₃ represents H, R₄ represents H, n represents a single bond, m represents a single bond and R₅ represents =O as represented by the following structure:

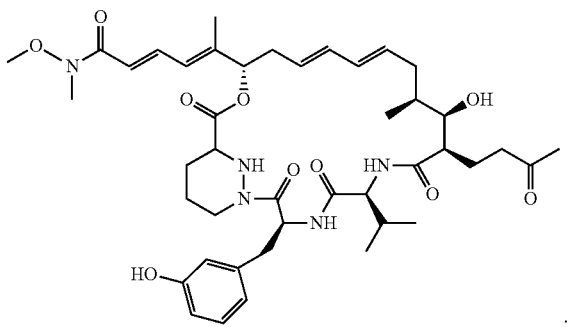

;

or

R₁ represents ethyl, R₂ represents ethyl, R₃ represents H, R₄ represents H, n represents a single bond, m represents a single bond and R₅ represents =O as represented by the following structure:

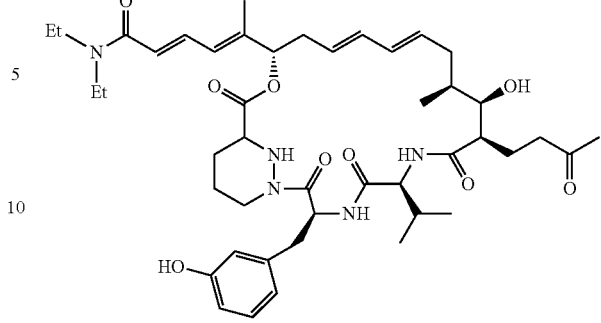

;

or

R₁ represents —CHMe₂, R₂ represents H, R₃ represents H, R₄ represents H, n represents a single bond, m represents a single bond and R₅ represents =O as represented by the following structure:

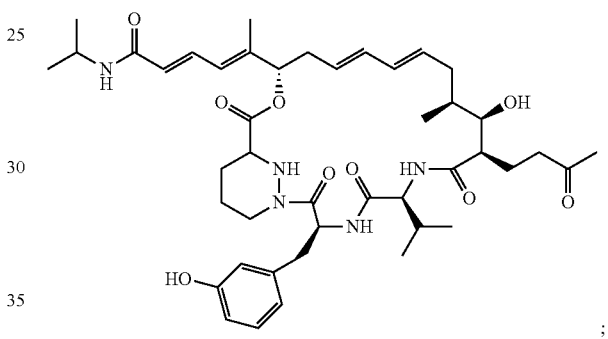

;

or

R₁ represents methyl, R₂ represents H, R₃ represents H, R₄ represents H, n represents a single bond, m represents a single bond and R₅ represents =O as represented by the following structure:

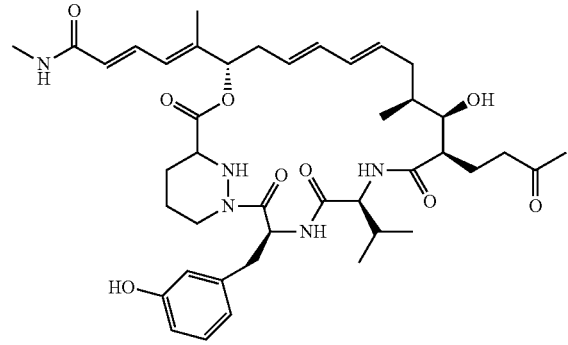

;

or

R₁ represents methyl, R₂ represents H, R₃ represents Me, R₄ represents H, n represents a single bond, m represents a single bond and R₅ represents =O as represented by the following structure:

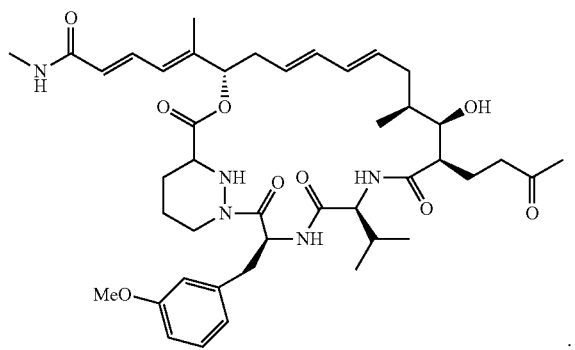

;

or

R₁ represents —CH₂CH═CH₂, R₂ represents H, R₃ represents H, R₄ represents H, n represents a single bond, m represents a single bond and R₅ represents ═O as represented by the following structure:

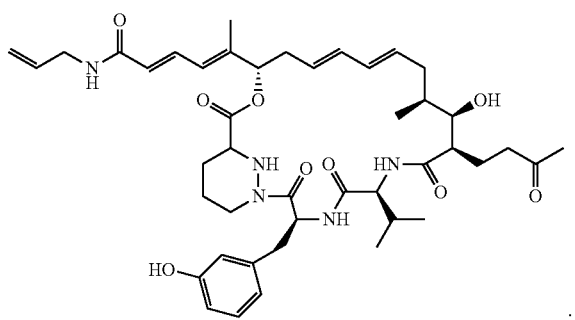

;

or

R₁ represents methyl, R₂ represents methyl, R₃ represents H, R₄ represents H, n represents bond, m represents bond and R₅ represents ═O as represented by the following structure:

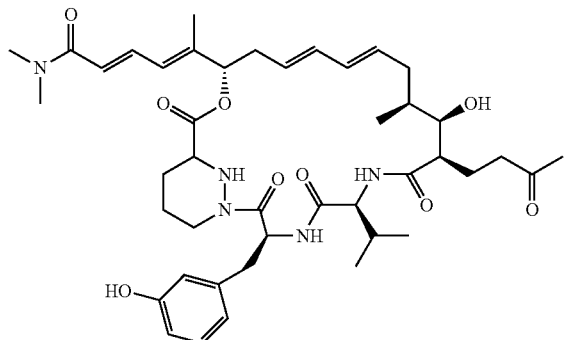

;

or

R₁ represents —CH₂CHMe₂, R₂ represents —CH₂CHMe₂, R₃ represents H, R₄ represents H, n represents a single bond, m represents a single bond and R₅ represents ═O as represented by the following structure:

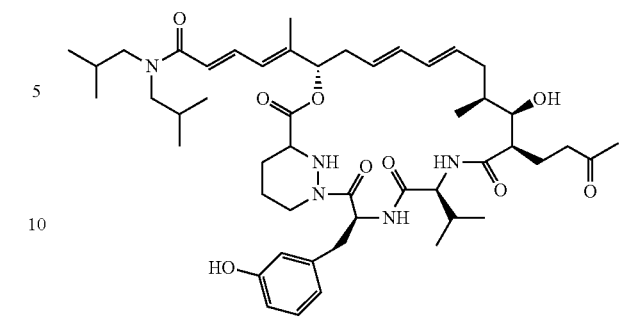

;

or

R₁ represents OCH₃, R₂ represents Me, R₃ represents H, R₄ represents H, n represents a single bond, m represents a double bond and R₅ represents H as represented by the following structure:

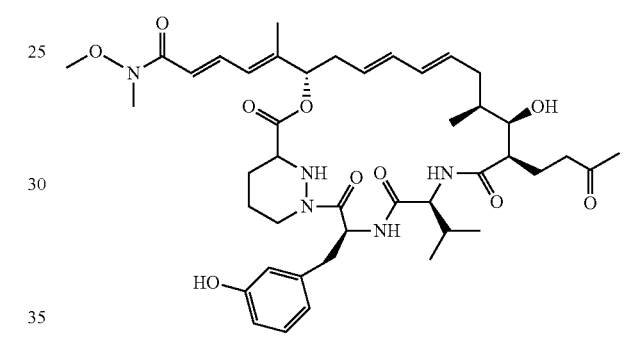

;

or

R₁ and R₂ together represent —CH₂CH₂OCH₂CH₂— connected in a 6-membered heterocycle, R₃ represents H, R₄ represents H, n represents a single bond, m represents a single bond and R₅ represents ═O as represented by the following structure:

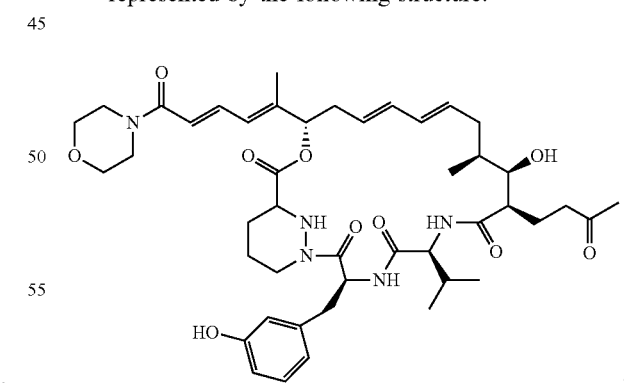

;

or

R₁ represents 4-biphenylyl, R₂ represents H, where, R₃ represents H, R₄ represents H, n represents a single bond, m represents a single bond and R₅ represents ═O as represented by the following structure:

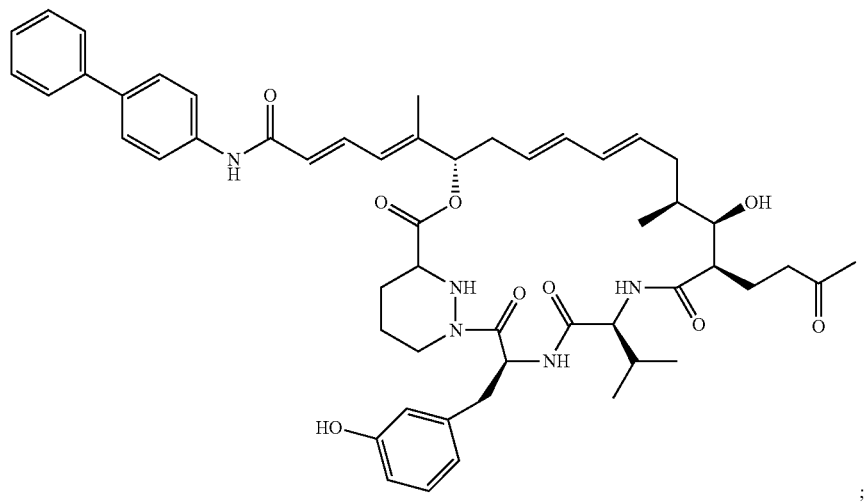 [SMILES: CC(=O)CC[C@H]1C(=O)N[C@@H](C(C)C)C(=O)N[C@@H](Cc2cccc(O)c2)C(=O)N2CCCC(N2)C(=O)O[C@H](/C(C)=C/C=C/C(=O)Nc2ccc(-c3ccccc3)cc2)C/C=C/C=C/C[C@H](C)[C@H]1O]

or $R_1$ represents cyclohexyl, $R_2$ represents Me, $R_3$ represents H, $R_4$ represents H, n represents a single bond, m represents a single bond and $R_5$ represents =O as represented by the following structure:

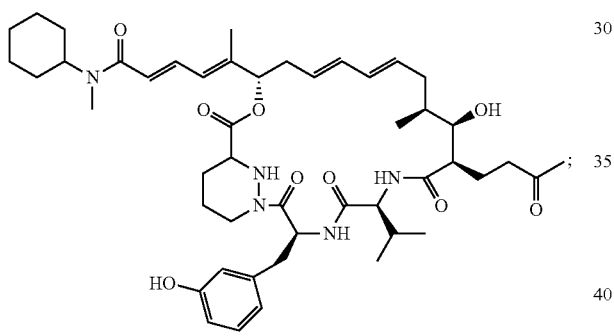

or $R_1$ represents cyclohexyl, $R_2$ represents H, $R_3$ represents H, $R_4$ represents H, n represents a single bond, m represents a single bond and $R_5$ represents =O as represented by the following structure:

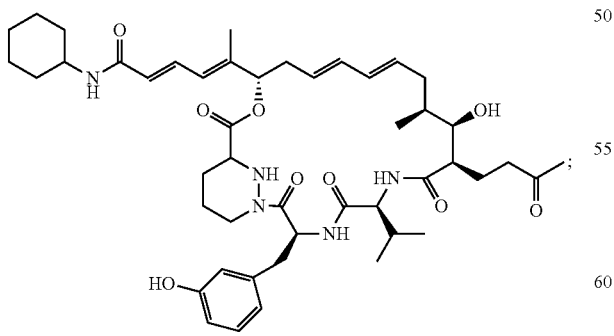

or $R_1$ and $R_2$ together represent —OCH$_2$CH$_2$CH$_2$CH$_2$— connected in a 6-membered heterocycle. $R_3$ represents H, $R_4$ represents H, n represents a single bond, m represents a single bond and $R_5$ represents =O as represented by the following structure:

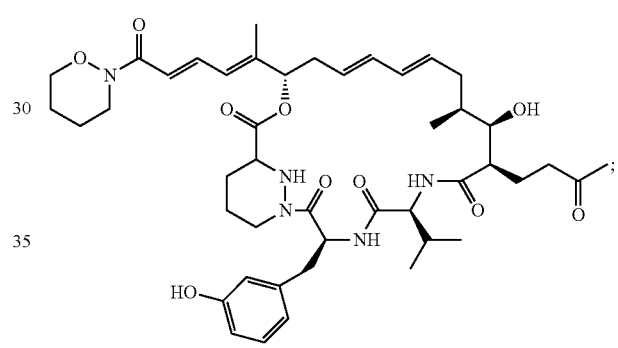

or $R_1$ represents 2-pyridinyl, $R_2$ represents H, $R_3$ represents H, $R_4$ represents H, n represents a single bond, m represents a single bond and $R_5$ represents =O as represented by the following structure:

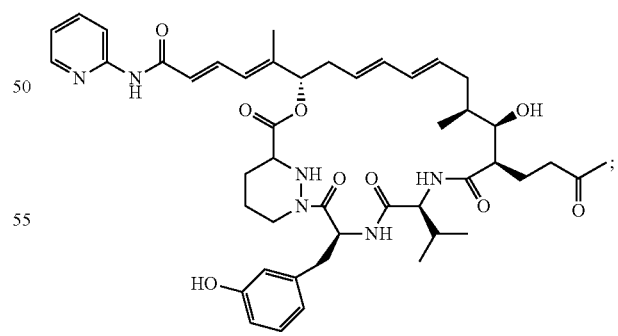

or or a pharmaceutically acceptable salt of any one thereof; including any tautomer thereof; or an isomer thereof in which the C26, 27 C=C bond shown as trans is cis; and including a methanol adduct thereof in which a ketal is formed by the combination of the C-53 keto (if present) and the C-15 hydroxyl groups and methanol.

For example R₃ represents H, R₄ represents OH, n represents a single bond, m represents a single bond and R₅ represents =O as represented by the following structure:
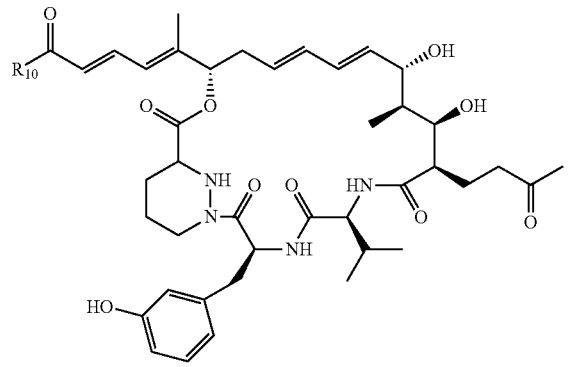
wherein R₁₀ represents a group as shown in the following table:
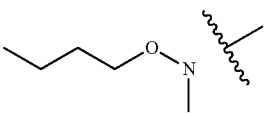
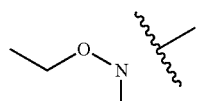
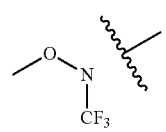
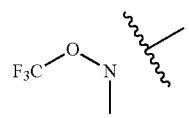
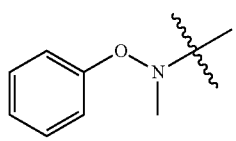 [SMILES: *N(C)Oc1ccccc1]
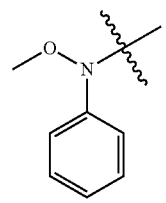 [SMILES: *N(OC)c1ccccc1]
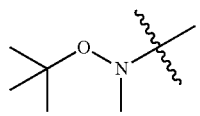 [SMILES: *N(C)OC(C)(C)C]
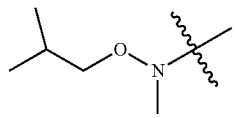 [SMILES: *N(C)OCC(C)C]
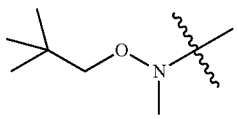 [SMILES: *N(C)OCC(C)(C)C]
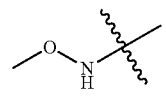
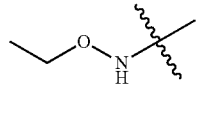 [SMILES: *NOCC]
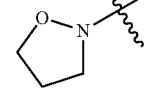

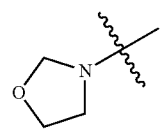 [SMILES: *N1CCOC1]
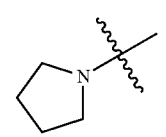 [SMILES: *N1CCCC1]
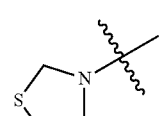
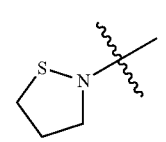 [SMILES: *N1CCCS1]
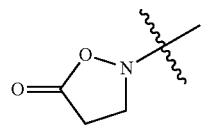 [SMILES: *N1CCC(=O)O1]
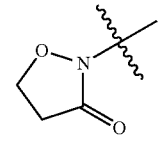 [SMILES: *N1OCCC1=O]
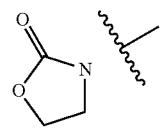
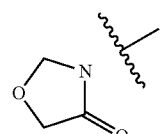
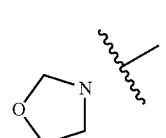
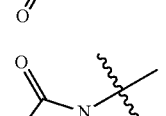
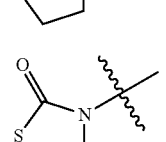
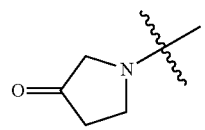 [SMILES: *N1CCC(=O)C1]
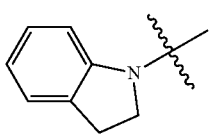 [SMILES: *N1CCc2ccccc21]
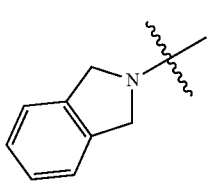 [SMILES: *N1Cc2ccccc2C1]
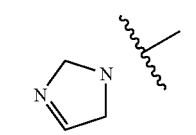
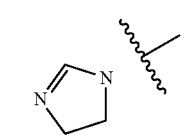
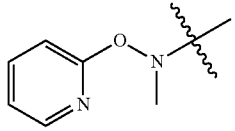 [SMILES: *N(C)Oc1ccccn1]
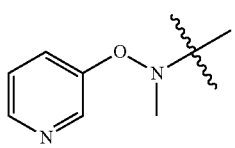 [SMILES: *N(C)Oc1cccnc1]
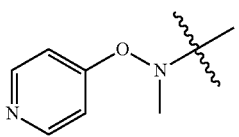 [SMILES: *N(C)Oc1ccncc1]
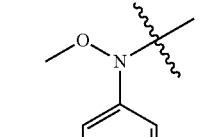
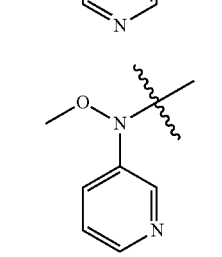

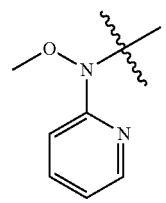 [SMILES: *N(OC)c1ccccn1]
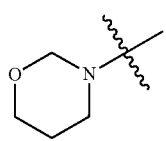 [SMILES: *N1CCCOC1]
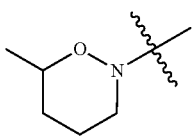 [SMILES: *N1CCCC(C)O1]
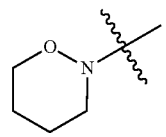 [SMILES: *N1CCCCO1]
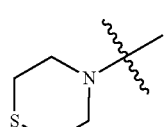
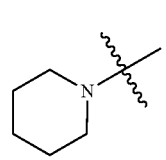 [SMILES: *N1CCCCC1]
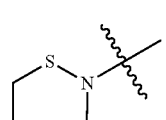
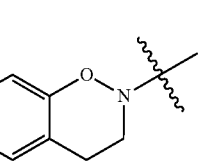
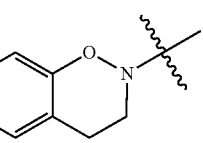
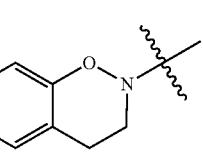
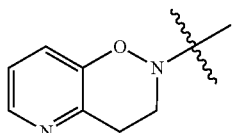 [SMILES: *N1CCc2ccccc2O1]
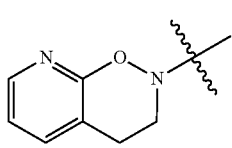 [SMILES: *N1CCc2cccnc2O1]
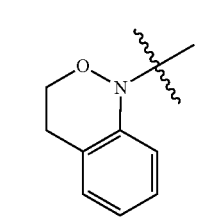 [SMILES: *N1OCCc2ccccc21]
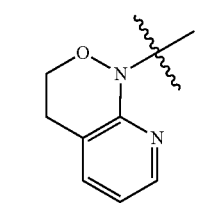 [SMILES: *N1OCCc2cccnc21]
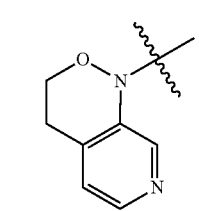 [SMILES: *N1OCCc2ccncc21]
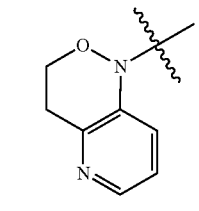 [SMILES: *N1OCCc2ncccc21]
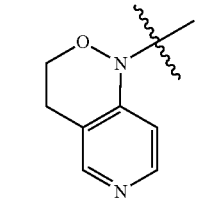 [SMILES: *N1OCCc2cnccc21]
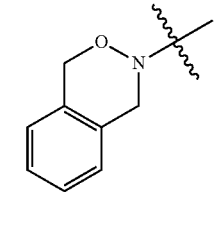 [SMILES: *N1Cc2ccccc2CO1]

-continued
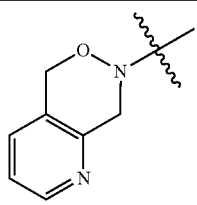
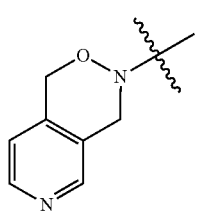 [SMILES: *N1Cc2cnccc2CO1]
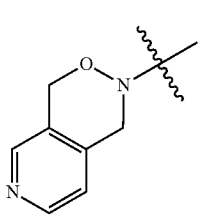 [SMILES: *N1Cc2ccncc2CO1]
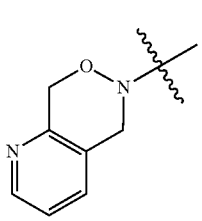
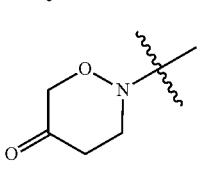
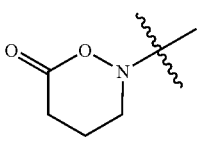 [SMILES: *N1CCCC(=O)O1]
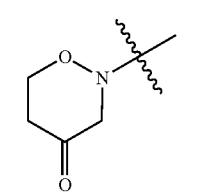 [SMILES: *N1CC(=O)CCO1]
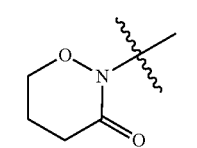 [SMILES: *N1OCCCC1=O]
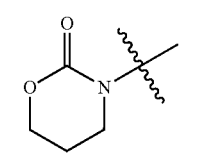 [SMILES: *N1CCCOC1=O]
-continued
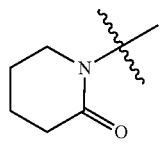 [SMILES: *N1CCCCC1=O]
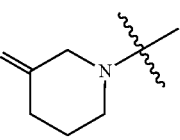
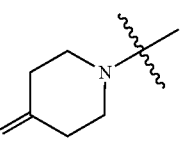
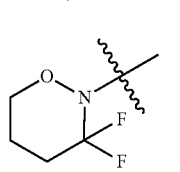
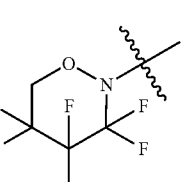
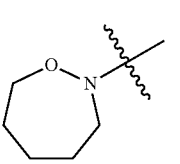 [SMILES: *N1CCCCCO1]
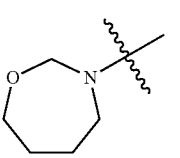 [SMILES: *N1CCCCOC1]
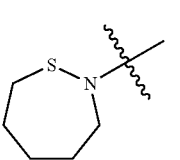 [SMILES: *N1CCCCCS1]
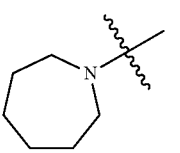 [SMILES: *N1CCCCCC1]
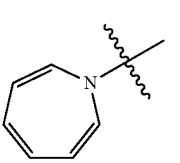 [SMILES: *N1C=CC=CC=C1]

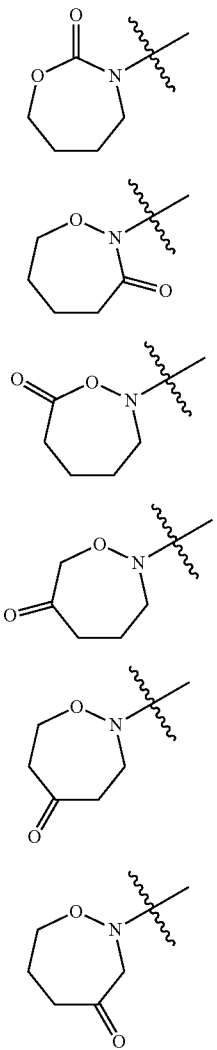

or a pharmaceutically acceptable salt of any one thereof; including any tautomer thereof; or an isomer thereof in which the C26, 27 C=C bond shown as trans is cis; and including a methanol adduct thereof in which a ketal is formed by the combination of the C-53 keto (if present) and the C-15 hydroxyl groups and methanol.

Compounds of formula (VII) may be prepared according to methods disclosed in WO2011/098809 which is herein incorporated by reference in its entirety.

Compounds of formula (X) and (I) to (IV) may generally be prepared by methods analogous to those described in WO2010/034243, WO2011/098805, WO2011/098808 and WO2011/098809. This may involve semi-synthetic alteration of a fermentation-produced sanglifehrin template, for example by modified Sharpless asymmetric dihydroxylation and oxidative cleavage, followed by Homer Wadsworth Emmons coupling of a suitable phosphonate.

Formulations

Pharmaceutical formulations of sanglifehrins may conveniently be presented in unit dosage form and may be prepared by any of the methods well known in the art of pharmacy. Such methods include the step of bringing into association the active ingredient (sanglifehrin) with the carrier which constitutes one or more accessory ingredients.

In general the formulations are prepared by uniformly and intimately bringing into association the active ingredient with liquid carriers or finely divided solid carriers or both, and then, if necessary, shaping the product.

According to the invention the sanglifehrins will normally be administered orally in the form of a pharmaceutical formulation comprising the active ingredient, optionally in the form of a non-toxic organic, or inorganic, acid, or base, addition salt, in a pharmaceutically acceptable dosage form.

Depending upon the disorder and patient to be treated, as well as the route of administration, the compositions may be administered at varying doses.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycolate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethylcellulose in varying proportions to provide desired release profile.

Formulations in accordance with the present invention suitable for oral administration may be presented as discrete units such as capsules, cachets or tablets, each containing a predetermined amount of the active ingredient; or as a powder or granules.

It should be understood that in addition to the ingredients particularly mentioned above the formulations of this invention may include other agents conventional in the art having regard to the type of formulation in question, for example those suitable for oral administration may include flavouring agents.

The dosage form will contain the sanglifehrin as active ingredient in a form in which it is protected from acid degradation in the stomach (most preferably by provision of an enteric coating and discussed elsewhere herein).

The dosage to be administered of a sanglifehrin will vary according to the particular compound, the disease involved, the subject, and the nature and severity of the disease and the physical condition of the subject, and the selected route of administration. The appropriate dosage can be readily determined by a person skilled in the art.

The compositions may contain from 0.1% by weight, preferably from 5-60%, more preferably from 10-30% by weight, of a sanglifehrin, depending on the method of administration.

It will be recognized by one of skill in the art that the optimal quantity and spacing of individual dosages of a sanglifehrin will be determined by the nature and extent of the condition being treated, the form, route and site of administration, and the age and condition of the particular subject being treated, and that a physician will ultimately determine appropriate dosages to be used. This dosage may be repeated as often as appropriate. If side effects develop the amount and/or frequency of the dosage can be altered or reduced, in accordance with normal clinical practice.

Enteric Coating Technologies

In general, when substrates (such as particles, granules, capsule or tablets) are to be enteric coated they are coated with an enteric coating layer with the optional presence of a separating layer between the substrate and the enteric coating layer and with the optional presence of a finishing layer applied on top of the enteric coating layer.

Separating layers may optionally be used to avoid issues of possible chemical interaction between the enteric coating layer (or its carrier used in the process of application) and the active ingredient (or another component of the substrate). A separating layer may also be used when the active ingredient (or another component of the substrate) may be partially or substantially dissolved during the process of application of the enteric coating layer.

A separating layer may, for example, contain a polymer such as hydroxymethylcellulose (HPMC).

Finishing layers may optionally be used, for example to protect the enteric layer or, by inclusion of whitening agents or colorants, to modify the colour of the coated material. A finishing layer may, for example, contain a polymer such as hydroxymethylcellulose (HPMC) and a whitening agent such as titanium dioxide.

Suitably separating layer and finishing layer coating materials are available under the Opadry brand name from Colorcon.

The enteric coating layer will typically comprise a substance, such as a fatty acid, wax, shellac, polymers, plant fibres and the like, which is stable to the acid pH of the stomach (particularly pH below 5 and especially pH around 3 or less) but breaks down in alkaline environment (e.g. pH 7-9) of the small intestine.

One class of enteric coating materials is the phthalates. Examples include cellulose acetate phthalate, hydroxypropylmethylcellulose phthalate and polyvinylacetate phthalate.

Sureteric™ is a proprietory aqueous enteric coating system from Colorcon that comprises polyvinylacetate phthalate, plasticisers and other ingredients in a dry powder system.

Opadry™ Enteric is a proprietory enteric coating system from Colorcon based on polyvinylacetate phthalate that is suitable for application by alcoholic or hydroalcoholic processing techniques. An example thickness of coating of Opadry Enteric is that of 11 mg Opadry Enteric applied to a size 0 capsule (21.7 mm diameter×7.65 mm height) scaled according to size of article coated.

Another class of enteric coating materials is the acetate succinates. Examples include hydroxypropylmethylcellulose acetate succinate and cellulose acetate succinate.

Another class of enteric coating materials include alginates and alginic acid derivatives.

Another class of enteric coating materials includes methylacrylate—methacrylic acid copolymers and methylmethylacrylate—methacrylic acid copolymers. Acryl EZE™ is a is a proprietory aqueous acrylic enteric coating system from Colorcon.

A further example enteric coating material is Eudragit™ L-30 D55 from Evonik Röhm GmbH Coating, such as separating coatings, enteric coatings and finishing coatings are typically applied to the substrate (particle, granule, capsule or tablet) by spray coating. Spray coating may be performed in line with manufacturer's directions.

Further details of example coating layers and methods of applying coating layers (including suitable thicknesses) may be gleaned by reference to "Aqueous Polymeric Coatings for Pharmaceutical Dosage Forms" $3^{nd}$ Edition (2008) Editors: James W McGinity and Linda A Felton; Publisher: Informa Healthcare USA, Inc, the contents of which are herein incorporated in their entirety by reference.

Further information may also be gleaned by reference to Remington, The Science and Practice of Pharmacy, $21^{st}$ Edition, the contents of which are herein incorporated in their entirety by reference.

The type and thicknesses of the respective layers may also be selected according to manufacturer's instructions.

Therapeutic Use

A sanglifehrin according to the invention is expected to be useful in the treatment of viral infections (especially RNA virus infections) such as HCV or HIV infection, for use as an anti-inflammatory agent or for prophylaxis of organ transplant rejection.

Aspects of the invention include:
A pharmaceutical dosage form according to this invention for use in the treatment of viral infections (especially RNA virus infections) such as HCV or HIV infection, or for use as an anti-inflammatory agent or for prophylaxis of organ transplant rejection, by oral administration.

A method of treatment of viral infections (especially RNA virus infections) such as HCV or HIV infection, or a method of treatment of inflammation or a method of prophylaxis of organ transplant rejection which comprises orally administering to a subject in need therefore an effective amount of a pharmaceutical dosage form according to this invention.

An effective amount is an amount which gives rise to a biologically meaningfull response (e.g. reduction in viral load, reduction in inflammation etc) and may be determined experimentally by a skilled person. An effective amount may typically be in the range 1-1500 mg/day, most preferably 25-600 mg/day (or 0.015-20 mg/kg, most preferably 0.35-9 mg/kg/day) said weight amount referring to the amount of sanglifehrin active ingredient in the dosage form.

Combination Therapy

A sanglifehrin according to the invention may be administered alone or in combination with other therapeutic agents. Co-administration of two (or more) agents may allow for lower doses of each to be used, thereby reducing side effect, can lead to improved potency and therefore higher SVR, and a reduction in resistance.

Therefore in one embodiment, the sanglifehrin is co-administered with one or more therapeutic agent/s for the treatment of HCV infection, taken from the standard of care treatments. This could be an interferon (e.g. pIFNα and/or ribavirin).

In an alternative embodiment, a sanglifehrin is co-administered with one or more other anti-viral agents, such as a STAT-C (specifically targeted agent for treatment of HCV) or DAA (direct acting antivirals), which could be one or more of the following: Non-nucleoside Polymerase inhibitors (e.g. ABT-333, ABT-072, BMS 791325, IDX375, VCH-222, BI 207127, ANA598, VCH-916, GS 9190, PF-00868554 (Filibuvir) or VX-759), Nucleoside or nucleotide polymerase inhibitors (e.g. 2'-C-methylcytidine, 2'-C-methyladenosine, R1479, PSI-6130, R7128, R1626, PSI 7977 or IDX 184), Protease inhibitors (e.g. ABT-450, ACH-1625, BI 201355, BILN-2061, BMS-650032, CTS 1027, Danoprevir, GS 9256, GS 9451, MK 5172, IDX 320, VX-950 (Telaprevir), SCH503034 (Boceprevir), TMC435350, MK-7009 (Vaneprivir), R7227/ITMN-191, EA-058, EA-063 or VX 985), NS5A inhibitors (e.g. A-831, BMS 790052, BMS 824393, CY-102 or PPI-461), silymarin, NS4b inhibitors, serine C-palmitoyltransferase inhibitors, Nitazoxanide or viral entry inhibitors (e.g. PRO 206).

In an alternative embodiment, a sanglifehrin is co-administered with one or more other anti-viral agents (such as highly active antiretroviral therapy (HAART)) for the treatment of HIV, which could be one or more of the following: nucleoside reverse transcriptase inhibitors (NRTI) (e.g. Emtricitabine or Tenofovir), non-nucleoside reverse transcriptase inhibitors (NNRTI) (e.g. Rilipivirine or Efavirenz), protease inhibitors (PI) (e.g. Ritonavir or Lopinavir), fusion inhibitors (e.g. Maraviroc or Enfuvirtide), CCR5 inhibitors (e.g. Aplaviroc or Vicriviroc), maturation inhibitors (e.g. Bevirimat), CD4 monoclonal antibodies (e.g. Ibalizumab) and integrase inhibitors (e.g. Eltiegravir).

In an alternative embodiment, a sanglifehrin is co-administered with one or more other anti-viral agents for the treatment of HBV, which could be one or more of the following: interferons (e.g. interferon alpha or pegylated interferon alpha), nucleoside or nucleotide analogues (e.g. lamivudine, entecavir, adefovir dipivoxil or telbivudine), other immunomodulators (e.g. Thymosin alpha, CYT107 or DV-601) or HMG CoA reductase inhibitors (e.g. Simvastatin).

Optionally, the pharmaceutical dosage form according to the invention may comprise one or more other therapeutic agents, for example one or more other anti-viral agents and/or one of more other therapeutic agents mentioned above.

Alternatively, the pharmaceutical dosage form of the invention may form a kit of parts together with one or more other pharmaceutical dosage forms containing one or more other anti-viral agents and/or one of more other therapeutic agents mentioned above General Methods
Materials and Methods
Bacterial Strains and Growth Conditions The sanglifehrin producer *Streptomyces* sp. A92-308110 (DSM no 9954, purchased from DSMZ, Braunschweig, Germany) also termed BIOT-4253 and BIOT-4370 or its derivatives, such as BIOT-4585 are maintained on medium oatmeal agar, MAM, ISP4 or ISP2 (see below) at 28° C.

BIOT-4585 was grown on oatmeal agar at 28° C. for 7-10 days. Spores from the surface of the agar plate were collected into 20% w/v sterile glycerol in distilled and stored in 0.5-ml aliquots at −80° C. Frozen spore stock was used for inoculating seed media SGS or SM25-3. The inoculated seed medium was incubated with shaking between 200 and 300 rpm at 5.0 or 2.5 cm throw at 27° C. for 24 hours. The fermentation medium SGP-2 or BT6 were inoculated with 2.5%-10% of the seed culture and incubated with shaking between 200 and 300 rpm with a 5 or 2.5 cm throw at 24° C. for 4-5 days. The culture was then harvested for extraction.

Meta-Tyrosine Analogues

Methyl (2S)-2-amino-3-(6-hydroxy(2-pyridyl))propanoate, L-3-aminophenylalanine methyl ester, L-4-methyl-meta-tyrosine methyl ester, L-4-fluoro-meta-tyrosine methyl ester and L-4,5-difluoro-meta-tyrosine methyl ester were purchased from Netchem (USA).

DL-3-fluorophenylalanine and L-phenylalanine were purchased from Sigma (UK).

DL-meta-tyrosine was purchased from Fluorochem (UK).
L-meta-tyrosine was purchased from Alfa Aesar (UK).

DL-4-fluoro-meta-tyrosine (8), DL-5-fluoro-meta-tyrosine (9), methyl 2-amino-3-(3-fluoro-5-hydroxyphenyl)propanoate (10), methyl 2-amino-3-(2-fluoro-5-hydroxyphenyl)propanoate (11), methyl 2-amino-3-(2-fluoro-3-hydroxyphenyl)propanoate (12) and methyl 2-amino-3-(2,6-difluoro-3-hydroxyphenyl)propanoate (13) were synthesised as follows:

DL-4-fluoro-meta-tyrosine (8)

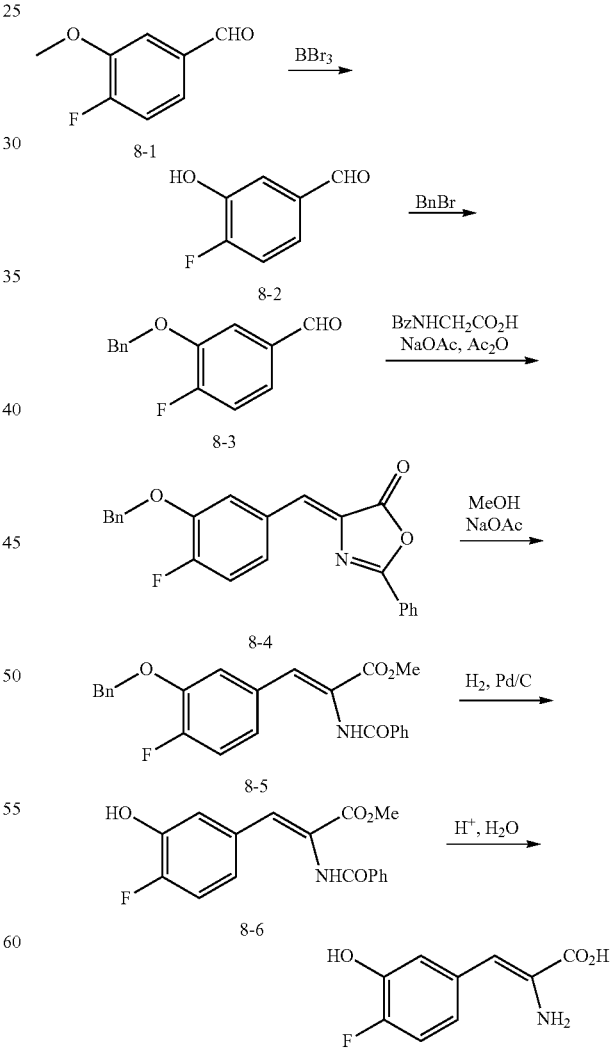

To a solution of 8-1 (3 g, 19.5 mmol) in dry DCM (150 mL) was added dropwise BBr$_3$ (4 M in DCM, 14.6 ml, 58.5 mmol) at −70° C. After the addition, the reaction mixture was stirred at −20° C. for 3 h, ice-water was added carefully, and extracted with DCM. The organic layers were washed with water and brine, dried over Na$_2$SO$_4$, filtered and concentrated. The residue was purified by flash chromatographed on silica to give the desired compound 8-2.

To a solution of 8-2 (0.9 g, 6.4 mmol) in acetone (40 mL) was added K$_2$CO$_3$ (2.2 g, 16 mmol) at room temperature. The reaction mixture was stirred at room temperature overnight. Water was added and acetone was removed under vacuum, and then extracted with EtOAc, the organic layers were washed with water and brine, dried over Na$_2$SO$_4$, filtered and concentrated. The residue was purified by flash chromatographed on silica to give the desired compound 8-3.

A mixture of 8-3 (1 g, 4.34 mmol), hippuric acid (860 mg, 4.80 mmol), NaOAc (400 mg) and Ac$_2$O (2.2 mL) was stirred at 80° C. for 2 h. The yellow reaction mixture was cooled and cold EtOH (10 mL) was added, the mixture was cooled in an ice bath for 15 min and then was poured into 30 mL of ice water, chilled and the product was collected by filtration. The solid was dried in vacuo to yield 8-4.

A solution of 8-4 (300 mg, 0.8 mmol) and NaOAc (71 mg, 0.87 mmol) in MeOH (50 mL) was stirred at room temperature overnight. The solvent was removed by rotary evaporation and the reside was dissolved in 50 mL of EtOAc, the EtOAc solution was washed two times with water and concentrated to give 8-5.

A solution of 8-5 (360 mg, 0.89 mmol) in MeOH (50 mL) was hydrogenated over 10% Pd/C (77 mg) at normal pressure for 20 h. After removal of the catalyst by filtration, the solvent was evaporated to give the product 8-6.

A solution of 8-6 (210 mg) in 3 N HCl (10 mL) was refluxed for 24 h. the solution was concentrated to dryness and the residue was purified by reverse-combiflash to give the target product 8.

DL-5-fluoro-meta-tyrosine (9) and methyl 2-amino-3-(3-fluoro-5-hydroxyphenyl)propanoate (10)

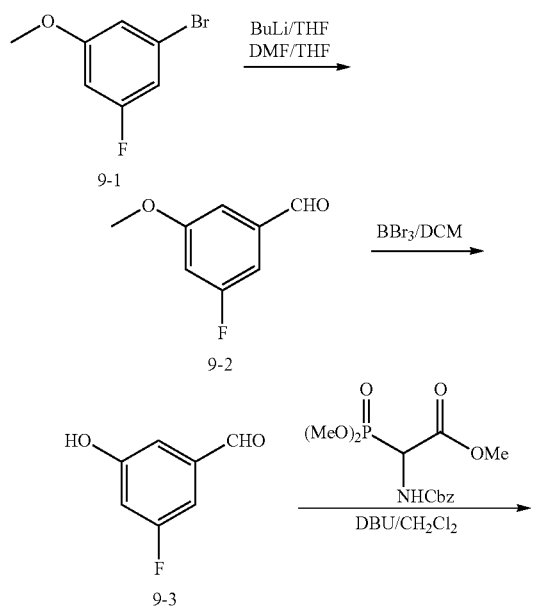

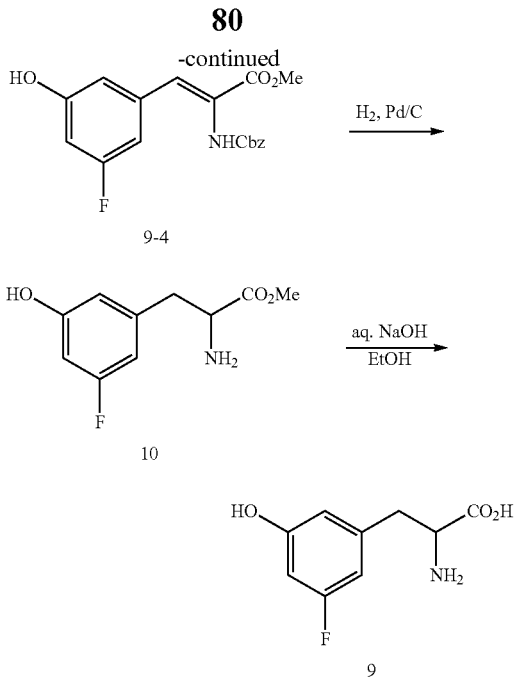

To a solution of 9-1 (20 g, 97.55 mmol) in tetrahydrofuran (100 mL) was added dropwise n-butyl lithium (43 mL, 2.5 M, 107.3 mmol) at −78° C. It was stirred for 30 minutes and N,N-dimethylformamide (15.1 mL, 195.1 mmol) was added at this temperature. It was stirred for another 30 minutes and the cold bath was removed. After 1 hour, the reaction was quenched with saturated aqueous ammonium chloride. The organic layer was washed with water and saturated aqueous sodium chloride, dried (sodium sulfate), filtered and concentrated. The residue was purified by chromatography on silica to give 9-2.

To a solution of 9-2 (6 g, 38.9 mmol) in dry DCM (200 mL) was added dropwise BBr$_3$ (4 M in DCM, 30 ml, 116.8 mmol) at −70° C. After the addition, the reaction mixture was stirred at −20° C. for 3 hours, ice-water was added carefully, and extracted with DCM. The organic layers were washed with water and brine, dried over Na$_2$SO$_4$, filtered and concentrated. The residue was purified by flash chromatographed on silica to give the desired compound 9-3.

To a solution of methyl 2-(benzyloxycarbonylamino)-2-(dimethoxyphosphoryl)acetate (4.64 g, 14 mmol) in DCM (150 mL) was added DBU (4.26 g, 28 mmol) at room temperature. After 10 min, 9-3 (1.95 g, 14 mmol) was added and the resulting mixture was stirred at room temperature overnight. The solution was diluted with EtOAc (150 mL), separated and the organic layer was washed with 1 N HCl, dried over Na$_2$SO$_4$, filtered and concentrated. The residue was purified by flash chromatography on silica to give 9-4.

A solution of 9-4 (1 g) in MeOH (20 mL) was hydrogenated over 200 mg of 10% Pd/C at normal pressure overnight. After removal of the catalyst by filtration, the solvent was evaporated to give 10.

To a solution of 10 (300 mg, 1.4 mmol) in EtOH (30 mL) was added aq. NaOH (2 N, 4 mL), the reaction was stirred at room temperature for 30 minutes. The solvent was removed and the residue was neutralized to pH=6 with 2 N HCl and the white crystals that formed were collected by filtration to give the target compound 9.

81

Methyl
2-amino-3-(2-fluoro-5-hydroxyphenyl)propanoate
(11)

82

Methyl
2-amino-3-(2-fluoro-3-hydroxyphenyl)propanoate
(12)

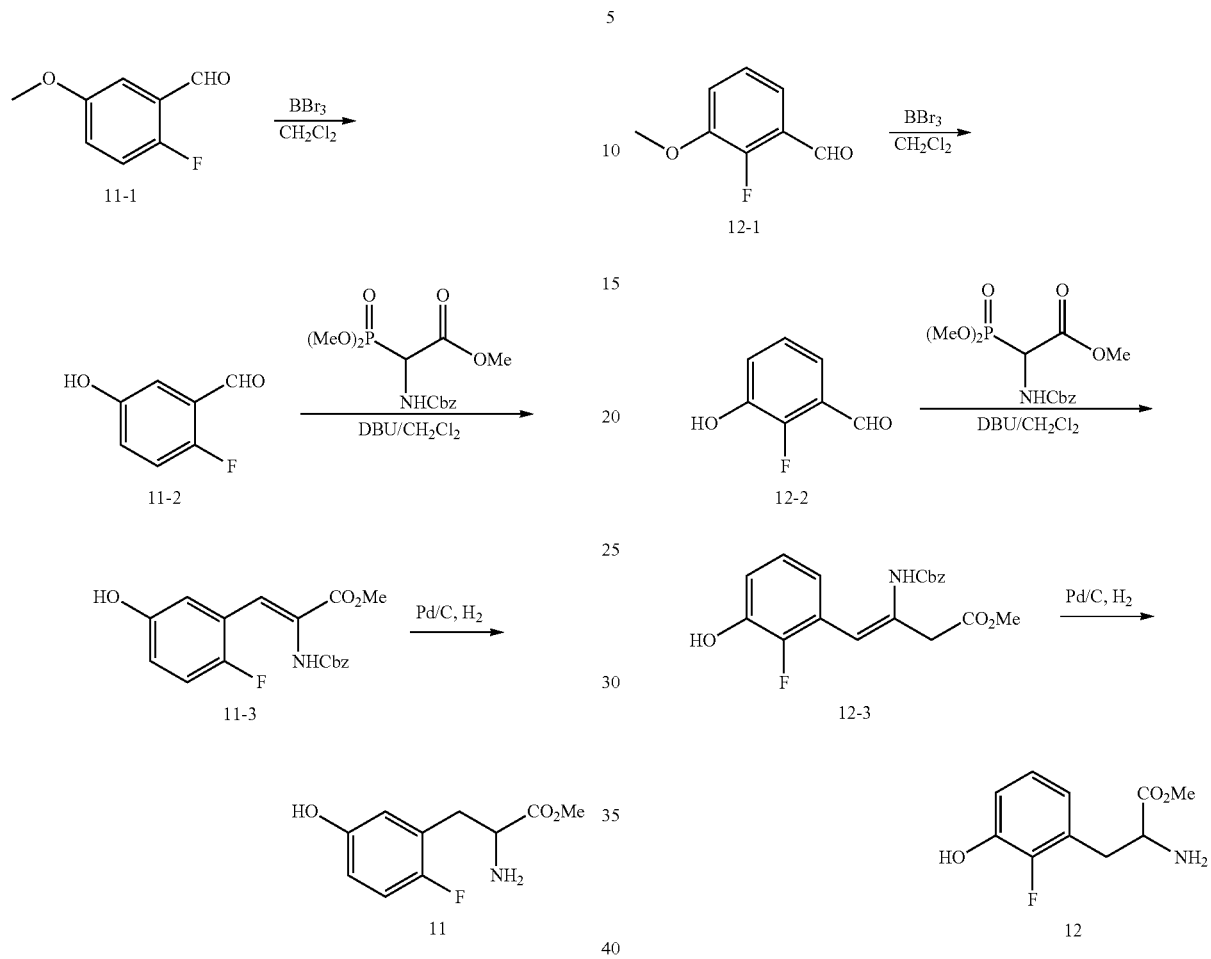

To a solution of the compound 11-1 (1.4 g, 9 mmol) in 50 mL DCM was added dropwise BBr$_3$ (4M in DCM, 3.6 mL, 13.5 mmol) at −78° C. After the addition, the reaction was stirred at −20° C. for 4 hours. Then slow addition of ice/water, the layers was separated, the organic layers was washed with water and brine, dried over Na$_2$SO$_4$ and evaporated to dryness. The residue was used to next step without further purification.

To a solution of methyl 2-(benzyloxycarbonylamino)-2-(dimethoxyphosphoryl)acetate (3 g, 9 mmol) in 100 mL DCM was added DBU (2.8 g, 18 mmol) at room temperature, after 10 mins, the compound 11-2 (crude compound from last step) was added, stirred at room temperature for 2 hours. The solution was then diluted with DCM (50 mL), washed with 1N HCl (20 mL), dried over Na$_2$SO$_4$ and evaporated to dryness. The residue was purified by silica gel chromatography (petroleum ether/ethyl acetate=5/1) to give 11-3.

A mixture of the compound 11-3 (500 mg, 1.5 mmol) in MeOH (20 mL) was hydrogenated over 50 mg of 10% Pd/C at normal pressure overnight. After removal of the catalyst by filtration, the solvent was evaporated to get the crude product, which was purified by reverse-combiflash to get 11 as a white solid.

To a solution of the compound 12-1 (1.4 g, 9 mmol) in 50 mL DCM was added dropwise BBr$_3$ (4M in DCM, 3.6 mL, 13.5 mmol) at −78° C. After the addition, the reaction was stirred at −20° C. for 4 hours. After slow addition of ice/water, the layers were separated, the organic layer was washed with water and brine, dried over Na$_2$SO$_4$ and evaporated to dryness. The residue was used to next step without further purification.

To a solution of methyl 2-(benzyloxycarbonylamino)-2-(dimethoxyphosphoryl)acetate (3 g, 9 mmol) in 100 mL DCM was added DBU (2.7 mL, 18 mmol) at room temperature, after 10 mins, the compound 12-2 (crude compound from last step) was added, stirred at room temperature for 2 hours. The solution was then diluted with DCM (100 mL), washed with 1N HCl (30 mL), dried over Na$_2$SO$_4$ and evaporated to dryness. The residue was purified by silica gel chromatography (petroleum ether/ethyl acetate=5/1) to give 12-3.

A mixture of the compound 12-3 (500 mg, 1.44 mmol) in MeOH (10 mL) was hydrogenated over 100 mg of 10% Pd/C at normal pressure overnight. After removal of the catalyst by filtration, the solvent was evaporated to get the crude product, which was purified by reverse-combiflash to get the desired compound 12 as a white solid.

Methyl 2-amino-3-(2,6-difluoro-3-hydroxyphenyl)propanoate (13)

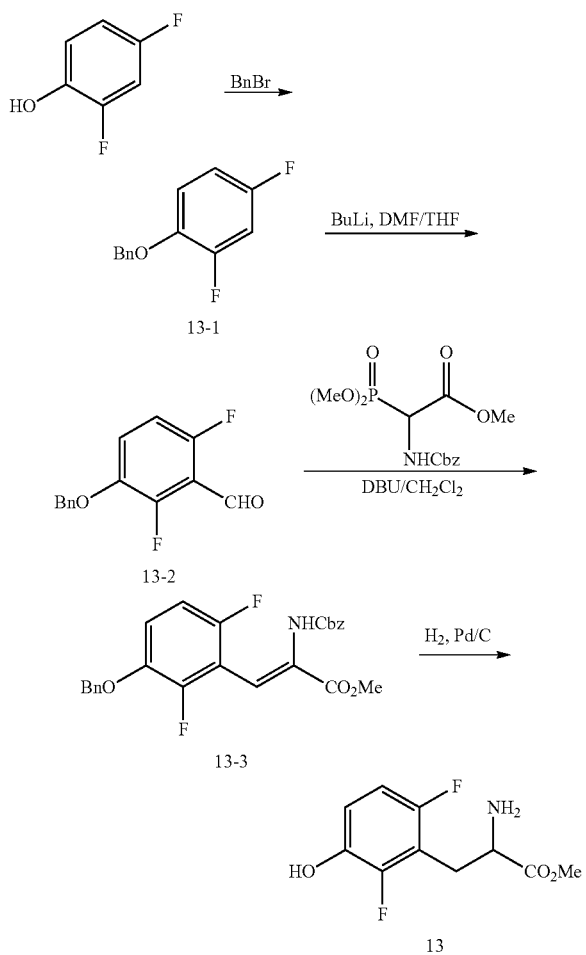

To a solution of 2,4-difluorophenol (2 g, 15.4 mmol) in 50 mL DMF was added $K_2CO_3$ (3.2 g, 23.1 mmol) and BnBr (2.2 mL, 18.5 mmol) at 0° C. The reaction was stirred at room temperature for 2 hours. Water (100 mL) and EA (200 mL) was added, the organic layers was washed with water (50 mL) and brine (50 mL), dried over $Na_2SO_4$ and evaporated to dryness. The residue was purified by silica gel chromatography (petroleum ether/ethyl acetate=10/1) to give the crude 13-1.

To a solution of the compound 13-1 (2 g, 9 mmol) in 10 mL THF was added dropwise n-BuLi (4 mL, 2.5 M) at −78° C. and stirred for 30 mins. DMF (1.3 g, 0.018 mmol) was added and stirred for 30 mins again. The cold bath was then removed and the reaction mixture was stirred at room temperature for 1 hour before being quenched with water. It was extracted with ethyl acetate (20 mL×3), dried over $Na_2SO_4$ and evaporated to dryness. The residue was purified by silica gel chromatography (petroleum ether/ethyl acetate=10/1) to give 13-2 as a yellow solid.

To a solution of methyl 2-(benzyloxycarbonylamino)-2-(dimethoxyphosphoryl)acetate (728 mg, 2.2 mmol) in 20 mL DCM was added DBU (319 mg, 2.1 mmol) at room temperature. After 10 mins, the compound 13-2 (500 mg, 2 mmol) was added and stirred at room temperature for 2 hours. The solution was then diluted with DCM (50 mL), washed with 1N HCl (20 mL), dried over $Na_2SO_4$ and evaporated to dryness. The residue was purified by silica gel chromatography (petroleum ether/ethyl acetate=5/1) to give 13-3 as a yellow oil.

The compound 13-3 (600 mg, 1.32 mmol) in MeOH (20 mL) was hydrogenated over 60 mg of 10% Pd/C at normal pressure overnight. After removal of the catalyst by filtration, the solvent was evaporated to get the crude product, which was purified by reverse-combiflash to get the desired compound 13 as a white solid.

Media Recipes

Water used for preparing media was prepared using Millipore Elix Analytical Grade Water Purification System

SGS Seed Medium

| Ingredient (and supplier) | Recipe |
|---|---|
| Glucose (Sigma, G7021) | 7.50 g |
| Glycerol (Fisher scientific, G/0650/25) | 7.50 g |
| yeast extract (Becton Dickinson, 212770) | 1.35 g |
| malt extract (Becton Dickinson, 218630) | 3.75 g |
| potato starch (soluble) (Signma, S2004) | 7.50 g |
| NZ-amine A (Sigma, C0626) | 2.50 g |
| toasted soy flour, Nutrisoy (ADM, 063-160) | 2.50 g |
| L-asparagine (Sigma, A0884) | 1.00 g |
| $CaCO_3$(Calcitec, V/40S) | 0.05 g |
| NaCl (Fisher scientific, S/3160/65) | 0.05 g |
| $KH_2PO_4$ (Sigma, P3786) | 0.25 g |
| $K_2HPO_4$ (Sigma, P5379) | 0.50 g |
| $MgSO_4 \cdot 7H_2O$ (Sigma, M7774) | 0.10 g |
| trace element solution B | 1.00 mL |
| agar | 1.00 g |
| SAG471 Antifoam (GE Silicones, SAG471) | * 0.20 mL |
| RO $H_2O$ to final vol. of | ** 1.00 L | pre-sterilisation pH was adjusted to pH 7.0 with 10M NaOH/10M $H_2SO_4$
sterilised by heating 121° C., 20-30 min (autoclaving)
Notes
* antifoam only used in seed fermenters, NOT seed flasks
** final volume adjusted accordingly to account for seed volume

Trace Element Solution B

| Ingredient | Recipe |
|---|---|
| $FeSO_4 \cdot 7H_2O$ (Sigma, F8633) | 5.00 g |
| $ZnSO_4 \cdot 7H_2O$ (Sigma, Z0251) | 4.00 g |
| $MnCl_2 \cdot 4H_2O$ (Sigma, M8530) | 2.00 g |
| $CuSO_4 \cdot 5H_2O$ (Aldrich, 20,919-8) | 0.20 g |
| $(NH_4)_6Mo_7O_{24}$ (Fisher scientific, A/5720/48) | 0.20 g |
| $CoCl_2 \cdot 6H_2O$ (Sigma, C2644) | 0.10 g |
| $H_3BO_3$ (Sigma, B6768) | 0.10 g |
| KI (Alfa Aesar, A12704) | 0.05 g |
| $H_2SO_4$ (95%) (Fluka, 84720) | 1.00 mL |
| RO $H_2O$ to final vol. of | 1.00 L |

SGP2 Production Medium

| Ingredient | Recipe |
|---|---|
| toasted soy flour (Nutrisoy) (ADM, 063-160) | 20.00 g |
| Glycerol (Fisher scientific, G/0650/25) | 40.00 g |
| MES buffer (Acros, 172595000) | 19.52 g |

| Ingredient | Recipe |
|---|---|
| SAG471 Antifoam (GE Silicones, SAG471) | *0.20 mL |
| RO H₂O to final vol. of | **1.00 L | pre-sterilisation pH adjusted to pH 6.8 with 10M NaOH
sterilised by heating 121° C., 20-30 min (autoclaving)
Notes
*final volume adjusted accordingly to account for seed volume
**antifoam was used only in fermentors not flasks SM25-3 Medium (also termed SM25)
Ingredient

| Glycerol (Fisher scientific, G/0650/25) | 40 g |
|---|---|
| Soy Peptone A3 SC (Organotechnie) | 10 g |
| Malt extract (Difco) | 21 g |
| to final vol. of | 1 L | pre-sterilisation pH not adjusted (i.e. pH 7.0)

ISP4 Medium
Ingredient

| Soluble Starch (Difco) | 10 g |
|---|---|
| K2HPO4 | 1 g |
| MgSO4•7H20 | 1 g |
| NaCl | 1 g |
| (NH4)2SO4 | 2 g |
| CaCO3 | 2 g |
| ISP Trace Salts Solution | 1 mL |
| Agar | 20 g |
| to final vol. of | 1 L |

Make a paste with the starch in a small volume of cold water and bring to volume of 500 ml Add other ingredients to solution II in 500 mls water pH should be between pH 7.0 and pH 7.4 (pH 7.3) Mix two solutions together and add agar ISP Trace Salts
Ingredient

| FeSO4•7H20 | 1 g |
|---|---|
| MnCl2•4H20 | 1 g |
| ZnSO4•7H20 | 1 g |
| to final vol. of | 1 L |

Store at 4 degrees C.

General Fermentation Method

Cryopreserved spore stocks of BIOT-4585 were thawed at room temperature. Vegetative cultures (seed cultures) were prepared by transferring 4.0 mL of spore stock into 400 mL medium SM25 in 2 L Erlenmeyer flasks with foam plug. Cultivation was carried out for 48 hours at 27° C. and 250 rpm (5.0 cm throw). From the seed culture 25 mL was transferred into 250 mL production medium SGP2+5% HP20 in 2 L Erlenmeyer flasks with foam plug. After 24 hours cultivation at 24° C. and 250 rpm (2.5 cm throw), 2 mL of a 250 mM racemic or 125 mM enantiomerically pure solution of the desired precursor in 1M hydrochloric acid and 2 mL of a 250 mM methanolic solution of DL-piperazic acid was added to each production flask to give a final 1 mM concentration of the individual enantiomers of the precursors. Cultivation was continued for further four days at 24° C. and 250 rpm (2.5 cm throw).

Analysis of Culture Broths by LC-UV and LC-UV-MS

Culture broth (1 mL) and ethyl acetate (1 mL) is added and mixed for 15-30 min followed by centrifugation for 10 min. 0.4 mL of the organic layer is collected, evaporated to dryness and then re-dissolved in 0.20 mL of acetonitrile.

HPLC conditions:
C18 Hyperclone BDS C18 Column 3u, 4.6 mm×150 mm
Fitted with a Phenomenex Analytical C18 Security Guard Cartridge (KJ0-4282)
Column temp at 50° C.
Flow rate 1 mL/min
Monitor UV at 240 nm
Inject 20 uL aliquot
Solvent gradient:
0 min: 55% B
1.0 min: 55% B
6.5 min: 100% B
10.0 min: 100% B
10.05 min: 55% B
13.0 min: 55% B
Solvent A is Water+0.1% Formic Acid
Solvent B is Acetonitrile+0.1% Formic Acid
Under these conditions SfA elutes at 5.5 min
Under these conditions SfB elutes at 6.5 min LCMS is performed on an integrated Agilent HP1100 HPLC system in combination with a Bruker Daltonics Esquire 3000+ electrospray mass spectrometer operating in positive ion mode using the chromatography and solvents described above.

QC LC-MS Method
HPLC conditions:
C18 Hyperclone BDS C18 Column 3u, 4.6 mm×150 mm
Fitted with a Phenomenex Analytical C18 Security Guard Cartridge (KJ0-4282)
Column temp at 50° C.
Flow rate 1 mL/min
Monitor UV at 210, 240 and 254 nm
Solvent gradient:
0 min: 10% B
2.0 min: 10% B
15 min: 100% B
17 min: 100% B
17.05 min: 10% B
20 min: 10% B
Solvent A is Water+0.1% Formic Acid
Solvent B is Acetonitrile+0.1% Formic Acid
MS conditions:
MS operates in switching mode (switching between positive and negative), scanning from 150 to 1500 amu.

Analysis of 24 by HPLC in Capsule Study 24 was analysed by HPLC using the following parameters

| Parameter | Setting |
|---|---|
| System: | Agilent 1200 Series |
| Column: | Phenomenex Hyperclone BDS C18 Column 3u, 4.6 mm × 150 mm |
| Mobile phase: | Solvent A is Water + 0.1% Formic Acid |
| | Solvent B is Acetonitrile + 0.1% Formic Acid |
| Injection volume: | 20 μL |
| Flow rate: | 1 mL/min |
| Column temperature: | 50° C. |
| Run time: | 20 min |
| Detection: | Agilent UV detector, 276 nm |
| Gradient: | 0 min: 10% B |
| | 2.0 min: 10% B |
| | 15 min: 100% B |
| | 17 min: 100% B |

| Parameter | Setting |
|---|---|
| | 17.05 min: 10% B |
| | 20 min: 10% B |

In Vivo Assessment of Oral and Intravenous Pharmacokinetics

For sanglifehrins, whole blood is analysed. Compounds are formulated in 5% ethanol/5% cremophor EL/90% saline for both p.o. and i.v. administration. Groups of 3 male CD1 mice are dosed with either 1 mg/kg i.v. or 5 or 10 mg/kg p.o. Blood samples (40 µL) are taken via saphenous vein, pre-dose and at 0.25, 0.5, 2, 8, and 24 hours, and diluted with an equal amount of $dH_2O$ and put on dry ice immediately. Samples are stored at −70° C. until analysis. The concentration of the sanglifehrin or parent compound in the sample is determined via LCMS as follows: 20 µL of blood:$H_2O$ (1:1, v/v)/PK sample is added with 20 µL Internal standard (hydroxyl macrocycle, 6) at 100 ng/mL, 20 µL working solution/MeOH and 150 µL of ACN, vortexed for 1 minute at 1500 rpm, and centrifuged at 12000 rpm for 5 min. The supernatant is then injected into LC-MS/MS. The time-course of blood concentrations is plotted and used to derive area under the whole blood concentration-time curve (AUC—which is directly proportional to the total amount of unchanged drug that reaches the systemic circulation). These values are used to generate PK parameters where possible.

In Vitro Assessment of Stability in Acidic and Neutral Conditions

Test Compound DMSO Solutions 1 mM DMSO solutions were made of compounds to be tested and mixed on vibrax to ensure compound was fully dissolved.

Test Solutions

The following solutions were made to test the compounds in:

PBS Solution: 2 tablets of Phosphate Buffered Saline (Dulbecco A) tablets (Oxoid, BR0014G) were added to 200 mL distilled water and stirred to mix. pH was measured at 7.28.

Simulated Gut Fluid (SGF): 300 uL conc. HCl added to 50 mL distilled water and mixed. pH was measured at 1.21.

Simulated gut fluid+pepsin: 300 uL conc. HCl and 1 g of Pepsin (from Porcine gastric mucosa, Sigma) were added to 50 mL distilled water and mixed by stirring for 1 hr.

SGF+denatured pepsin: 900 uL of Acidic Enzyme Solution taken into a 2 mL eppendorf tube and heated at 99° C. in a water bath for 30 mins.

Acidic Enzyme and Acidic Denatured Enzyme solutions were made fresh each day, whereas PBS and Acid Solutions were stored at 4° C. when not in use.

Eppendorfs containing 900 uL of test solutions were pre-warmed in a 37° C. water bath. At t=0, 100 uL of test compound (1 mM DMSO solution) was added to test solution and mixed. 100 uL was taken immediately and mixed into 900 uL acetonitrile in an amber glass LC vial. 50-100 uL of the sample was analysed by HPLC, integrating the compounds' UV peaks to determine degradation over time. Sanglifehrin A was measured at its λmax of 240 nm; 33, 45 and 24 were measured at their λmax of 276 nm.

Further samples were taken in the same manner for analysis at approximately t=0.33, 0.67, 1.0, 2.67, and 4.67 hr. A final analysis was run at t=>30 to confirm end point of reaction.

Controls of test compound DMSO solutions in 900 uL DMSO were also prepared and treated in the same manner, with samples analysed at t=0, t=8 and t=>30 hr. Half lives were calculated from the data generated.

Assessment of Hepatocyte Stability

Cryopreserved hepatocytes, previously stored in liquid nitrogen are placed in a 37±1° C. shaking water bath for 2 min±15 sec. The hepatocytes are then added to 10× volume of pre-warmed Krebs-Henseleit bicarbonate (KHB) buffer (2000 mg/L glucose, no calcium carbonate and sodium bicarbonate, Sigma), mixed gently and centrifuged at 500 rpm for 3 minutes. After centrifugation, the supernatant is carefully removed and a 10× volume of pre-warmed KHB buffer added to resuspend the cell pellet. This is mixed gently and centrifuged at 500 rpm for 3 minutes. The supernatant is then removed and discarded. The cell viability and yield are then determined by cell counts, and these values used to generate human hepatocyte suspensions to the appropriate seeding density (viable cell density=2×106 cells/mL). A 2× dosing solution is prepared in pre-warmed KHB (1% DMSO) (200 µM spiking solution: 20 µL of substrate stock solution (10 mM) in 980 µL of DMSO, 2× dosing solution: 10 µL of 200 µM spiking solution in 990 µL of KHB (2 µM after dilution).

50 µL of pre-warmed 2× dosing solution is added to the wells and 50 µL of pre-warmed hepatocyte solution (2×106 cells/mL) added and timing started. The plate is then incubated at 37° C. 100 µL of acetonitrile containing internal standard is added to each the wells after completion of incubation time (0, 15, 30, 60 and 120 minutes) mixed gently, and 50 µL of pre-warmed hepatocyte solution added (2×106 cells/mL). At the end of the incubation, cell viability is determined. Samples are centrifuged at 4000 rpm for 15 minutes at 4° C., supernatants diluted 2-fold with ultrapure water and compound levels analysed by LC-MS/MS.

EXAMPLES

Example 1

Construction of an sfaA Deletion Mutant of *Streptomyces* Sp. A92-308110 (DSM9954)

1.1 Construction of the sfaA Deletion Construct

The ~7 kb EcoRV-StuI fragment of cosmid TL3006 (SEQ ID NO. 3) encompassing sfaA (nucleotide position 14396-21362, NCBI sequence accession number FJ809786) was excised by digestion with EcoRV and StuI and the resulting isolated fragment ligated directly into pKC1139 that had previously been digested with EcoRV and treated with shrimp alkaline phosphatase (Roche). This plasmid was designated pSGK268.

An in frame deletion of the sfaA gene contained within this clone was performed using the Red/ET recombination kit supplied by Gene Bridges (catalog number K006).

(SEQ ID NO. 1)
SfaA17161f
5'-CGCTCTGTGGCGCCTGGTTTCCAAGCGGCTCGCGGACCGGCACCGGC

ACATGCATAATTAACCCTCACTAAAGGGCG-3'

(SEQ ID NO. 2)
SfaA17825r
5'-TGGATGTATCGTCGCAGGACGCCCAGAATTCACCTGCGACGTCCTCC

AGATGCATTAATACGACTCACTATAGGGCTC-3'

Two oligonucleotides, SfaA17161f and SfaA17825r were used to amplify the neomycin marker from the FRT-PGK-gb2-neo-FRT template DNA supplied in the kit using KOD DNA polymerase. The resulting ~1.7 kb amplified product was isolated by gel electrophoresis and purified from the gel with QiaEX resin.

Plasmid pSGK268 was transformed into E. coli DH10B using standard techniques and selected on plates containing apramycin (50 μg/ml). Introduction of the deletion construct was performed essentially following the Gene Bridges kit protocol. A single colony was grown overnight in 2TY apramycin (50 μg/ml) and transformed with the pRedET (tet) plasmid and selected on apramycin (50 μg/ml) and tetracycline (3 μg/ml) at 30° C. A single colony was used to prepare an overnight culture of this strain in 3 ml 2TY apramycin (50 μg/ml) and tetracycline (3 μg/ml) at 30 C. 0.5 ml of this culture was used to inoculate 10 ml 2TY apramycin (50 μg/ml) and tetracycline (3 μg/ml) at 30° C. and grown to an $OD_{600nm}$ ~0.5. 1.4 ml of this culture was transferred to each of 2 eppendorf tubes and 50 μl 10% arabinose added to one tube to induce expression of the Red/ET recombination proteins. Tubes were shaken for ~1 hour at 37° C. Induced and non-induced cells were pelleted in a bench top centrifuge and washed twice with chilled sterile water; resuspending and centrifuging to pellet the cells each time. The resulting pellets were suspended in about 30-40 μl of water and kept on ice. The 1.7 kb disruption fragment isolated previously was added to the induced and non-induced tubes and transferred to 1 mm Biorad electrocuvettes on ice. The samples were electroporated (Biorad Micropulser at 1.8 kV, resulting time constant ~4 ms) and 1 ml 2TY (no antibiotics) added and mixed to remove the cells from the cuvette. Cells were incubated for ~3 hours at 37° C. with shaking (1100 rpm, eppendorf thermomixer compact) before plating onto 2TY plates containing apramycin (50 μg/ml and kanamycin 25 μg/ml and incubating over night at 37° C. Colonies from the induced sample plates were streaked onto 2TY plates containing kanamycin at 50 μg/ml to purify and confirm introduction of the kanamycin resistance cassette. PCR on individual bacterial colonies was used to confirm the introduction of the cassette. Plasmids were prepared from these cultures and digested to confirm the expected plasmid pSGK270. Plasmids were then digested with NsiI to remove the marker fragment, and the remainder religated to produce the sfaA in-frame deletion construct pSGK271.

1.2 Conjugation of *Streptomyces* Sp. A92-308110 (DSM9954) and Introduction of an sfaA Deletion Plasmid pSGK271 was transformed into E. coli ET12567 pUZ8002 using standard techniques and selected on 2TY plates containing apramycin (50 μg/ml), kanamycin (25 μg/ml) and chloroamphenicol (10 μg/ml). The resulting strain was inoculated into 3 ml liquid 2TY containing apramycin (50 μg/ml), kanamycin (25 μg/ml) and chloroamphenicol (10 μg/ml) and incubated overnight at 37° C., 250 rpm. 0.8 ml of this culture was used to inoculate 10 ml liquid 2TY containing apramycin (50 μg/ml), kanamycin (25 μg/ml) and chloroamphenicol (10 μg/ml) in a 50 ml Falcon tube and incubated at 37° C. 250 rpm until $OD_{600nm}$ ~0.5 was reached. The resulting culture was centrifuged at 3500 rpm for 10 minutes at 4° C., washed twice with 10 ml 2TY media using centrifugation to pellet the cells after each wash. The resulting pellet was resuspended in 0.5 ml 2TY and kept on ice before use. This process was timed to coincide with the complete preparation of *Streptomyces* spores described below.

Spores of *Streptomyces* sp. A92-308110 (DSM9954) (Biot-4370) were harvested from a 1-2 week old confluent plate by resuspending in ~3 ml 20% glycerol. Spores were centrifuged (5000 rpm, 10 minutes room temperature) and washed twice with 50 mM TES buffer before resuspending in 1 ml 50 mM TES buffer and splitting between 2 eppendorf tubes. These tubes were heat shocked at 50° C. for 10 minutes in a water bath before adding 0.5 ml 2TY and incubating in an Eppendorf Thermomixer compact at 37° C. for 4-5 hours.

The prepared E. coli ET12567 pUZ8002 pSGK271 and Biot-4370 were mixed at ratios 1:1 (250 μL each strain) and 1:3 (100 μL E. coli) and immediately spread on R6 plates and transferred to a 37° C. incubator. After approximately 2 hours incubation these plates were overlaid with 2 ml of sterile water containing nalidixic acid to give a final in-plate concentration of 25 μg/L. Plates were returned to the 37° C. incubator overnight before overlaying with 2 ml of sterile water containing apramycin to give a final in-plate concentration of 20-25 μg/L. Ex-conjugant colonies appearing after ~4-7 days were patched to ISP4 media containing apramycin (25 μg/L) and nalidixic acid (25 μg/L) and incubated at 37° C. Once adequate mycelial growth was observed strains were repatched to ISP4 media containing apramycin (25 μg/L) at 37° C. and allowed to sporulate. Strains were then subcultured three times (to promote removal of the temperature sensitive plasmid) by patching to ISP4 (without antibiotic) and incubating at 37° C. for 3-4 days. Strains were finally patched to ISP4 and incubated at 28° C. to allow full sporulation (5-7 days). Spores were harvested and serially diluted onto ISP4 plates at 28° C. to allow selection of single colonies. Sporulated single colonies were doubly patched to ISP4 plates with or without apramycin (25 μg/L) to confirm loss of plasmid and allowed to grow ~7 days before testing for production of sanglifehrins.

1.3 Screening Strains for Production of Sanglifehrins in Falcon Tubes

A single ~7 mm agar plug of a well sporulated strain was used to inoculate 7 ml of sterile SM25-3 media and incubated at 27° C. 200 rpm in a 2" throw shaker. After 48 hours of growth 0.7 ml of this culture was transferred to a sterilised falcon tube containing 7 ml of SGP2 media with 5% HP20 resin. Cultures were grown at 24° C. 300 rpm on a 1 inch throw shaking incubator for 5 days before harvest. 0.8 ml bacterial culture was removed and aliquoted into a 2 ml eppendorf tube ensuring adequate dispersal of the resin in throughout the culture prior to aliquoting. 0.8 ml acetonitrile and 15 μl of formic acid were added and the tube mixed for about 30 minutes.

The mixture was cleared by centrifugation and 170 μl of the extract removed into a HPLC vial and analysed by HPLC.

1.4 Analysis of Strains for Reversion to Wild Type or sfaA Phenotype.

Extracts of strains were analysed by HPLC. Strains that produced sanglifehrin A and B were not analysed further as these had reverted to wild type. Strains lacking sanglifehrin A and B production showed small levels (~1-2 mg/L) of a peak retention time 6.5 minutes that displayed a sanglifehrin like chromophore. Analysis by LCMS indicated this peak had a m/z 1073, −16 units from the expected m/z of sanglifehrin. It was postulated this peak was due to incorporation of phenylalanine in absence of meta-hydroxytyrosine.

Eight strains showing loss of sanglifehrin production were subsequently regrown to assess whether the potential sfaA mutation could be complemented chemically allowing a mutasynthetic process to novel sanglifehrins. Strains were grown in SM25-3 seed media for 48 hours before transferring to SGP2 production media with 5% resin. After a further 24 hours growth strains were fed in triplicate with 2 mM DL meta-hydroxytyrosine (addition of 100 ul of a 0.16M solution in 1M HCL) or 2 mM L-phenylalanine with an unfed strain used as control. Strains were also fed pipecolic acid (2 mM) in methanol) to enhance product yields. Strains were harvested after a further 4 days growth and extracted and analysed by HPLC. Meta-hydroxy tyrosine was shown to completely complement the sfaA mutation and addition of L-phenylalanine increased levels of the −16 amu compound. Strain Biot-4585 was chosen for further study as the sfaA deletion mutant.

Example 2

Other Methods for Construction of the sfaA Deletion Construct

Other methods can be used to generate sfaA deletion mutants. Examples include sfaA insertional inactivation mutants (such as example 12 from WO2010/034243). This strain was generated as described in WO2010/034243, and given the strain designation BIOT-4452.

Example 3

Array Feed of the sfaA Deletion Mutant

Spore stocks of a mutant disrupted in sfaA (BIOT-4452 or BIOT-4585) were prepared after growth on MAM, ISP4, ISP3 or ISP2 medium, and preserved in 20% w/v glycerol in distilled water and stored at −80° C. Vegetative cultures (seed cultures) were prepared by inoculating spore stock (1% v/v) into 7 mL seed medium (SM25 medium) in 50 mL centrifuge tubes with foam plugs. The culture tubes were incubated at 27° C., 250 rpm (5 cm throw) for 48 h. From the seed culture 10% (v/v) was transferred into 7 mL production medium SGP-2 in 50 mL centrifuge tubes with foam plugs. Cultivation was carried out at 24° C. and 300 rpm (2.5 cm throw). For production of mutasynthetic sanglifehrins, 0.05 mL of a 0.32 M solution (in 1N HCl) of the feed compound (mutasynthon) was added to each tube at 24 hours post inoculation to give a final concentration of 2 mM. Additionally, 0.05 ml of a 0.32 M solution of piperazic acid (in methanol) was added to each tube at 24 hours to give a final concentration of 2 mM. Cultivation was continued for an additional four days post feeding.

Samples were extracted by transferring 0.8 ml of the whole broth into a 2 ml capped eppendorf tube. 0.8 ml of acetonitrile was added, along with 0.015 ml of formic acid. The mixture was then shaken for 30 minutes on a vibrax. The tube was then centrifuged at 13000 rpm for 10 minutes and 0.15 ml of the supernatant was removed for analysis. Extracts were analysed as described in general methods.

Table 1 shows the mutasynthons that were fed in this way, along with the LCMS H+ and Na+ adducts, anticipated molecular mass and retention time of the sanglifehrin mutasynthetic products observed. The major peaks, relating to the sanglifehrin A analogues, are shown. In all cases, LCMS peaks were also seen for the sanglifehrin B analogues (Mass—18).

TABLE 1

| mutasynthon fed | mutasynthon name | $[M - H]^-$ observed (m/z) | $[M + Na]^+$ observed (m/z) | molecular mass (amu) | retention time (minutes) |
|---|---|---|---|---|---|
| (HO, F on phenyl ring with CH₂-CH(NH₂)-CO₂H) | 2-amino-3-(4-fluoro-3-hydroxyphenyl)propanoic acid | 1106.4 | 1130.4 | 1107.4 | 5.5 |
| (HO, F on phenyl ring with CH₂-CH(NH₂)-CO₂H) | 2-amino-3-(3-fluoro-5-hydroxyphenyl)propanoic acid | 1106.4 | 1130.4 | 1107.4 | 5.7 |
| (HO, F on phenyl ring with CH₂-CH(NH₂)-CO₂Me) | methyl 2-amino-3-(3-fluoro-5-hydroxyphenyl)proprionate | 1106.4 | 1130.4 | 1107.4 | 5.7 |
| (HO, Me on phenyl ring with CH₂-CH(NH₂)-CO₂Me) | methyl (S)-2-amino-3-(3-hydroxy-4-methylphenyl)propanoate | 1102.5 | 1126.7 | 1103.5 | 6.0 |
| (F on phenyl ring with CH₂-CH(NH₂)-CO₂H) | 2-amino-3-(3-fluorophenyl)propanoic acid | 1090.4 | 1114.5 | 1091 | 6.1 |

TABLE 1-continued

| mutasynthon fed | mutasynthon name | [M − H]⁻ observed (m/z) | [M + Na]⁺ observed (m/z) | molecular mass (amu) | retention time (minutes) |
|---|---|---|---|---|---|
| (structure) | methyl (2S)-2-amino-3-(3-hydroxy(2-pyridyl)propanoate | 1089.5 | 1113.7 | 1090.5 | 4.4 |
| (structure) | methyl 2-amino-3-(2-fluoro-5-hydroxyphenyl)propanoate | 1106.5 | 1130.6 | 1107.5 | 5.5 |
| (structure) | methyl 2-amino-3-(2-fluoro-3-hydyoxyphenyl)propanoate | 1106.5 | 1130.6 | 1107.5 | 5.1 |
| (structure) | methyl 2-amino-3-(2,6-difluoro-3-hydroxyphenyl)propanoate | 1124.4 | 1148.5 | 1125.5 | 5.1 |

Example 4

Isolation of 63-Fluoro Sanglifehrin a, Compound 14

Fermentation carried out as described in general methods utilising methyl 2-amino-3-(3-fluoro-5-hydroxyphenyl)propanoate and DL-piperazic acid as precursors, both were added at 26 hours.

After harvesting the culture broths were pooled and adjusted to approx. pH 3 with formic acid and centrifuged (3300 g) for 25 mins to separate the cells and resin from the clarified broth. The clarified broth was discarded after assay having confirmed less than 5% of target compound present. The cells and resin were stirred with 2 volumes of acetonitrile for 1 hr using a magnetic stirrer. The acetonitrile extract was recovered either by centrifugation or by allowing it to settle under gravity. A second acetonitrile extraction of the cells and resin was then performed under the same conditions. The combined acetonitrile extracts were concentrated to a residual aqueous volume under reduced pressure and then adjusted to pH 6. This was extracted twice with ethyl acetate and the combined organics taken to dryness under reduced pressure to give the final crude (1.3 g).

The crude extract (1.3 g) was dissolved in ethyl acetate (2 ml) and loaded onto a silica gel column (10×2 cm) conditioned with ethyl acetate (500 ml). The column was eluted with ethyl acetate and then with stepwise increases in acetone (10%, 20%, 30%, etc. in ethyl acetate). Approx. 250 mL fractions were collected and the target compound identified by analytical LC, combined and taken to dryness. This material (278 mg) was dissolved in methanol (1.8 ml) and purified by preparative HPLC. A Waters Xterra MSC18 column (10 micron, 19 cm×250 mm) was used with solvent pumped at 21 mL/min. Solvent A was water and solvent B was acetonitrile. The column was run isocratically at 50% B for 6 minutes following the injection followed by a gradient to 100% B at 30 minutes. Pure fractions were identified by HPLC-UV and combined. These fractions were taken to dryness under reduced pressure to yield the target compound as an off-white amorphous solid (20 mg).

Example 5

Isolation of 62,63-fluoro sanglifehrin A, Compound 15

Fermentation carried out as described in general methods utilising methyl (S)-2-amino-3-(3,4-difluoro-5-hydroxyphenyl)propanoate and DL-piperazic acid as precursors, both were added at 26 hours.

After harvesting the culture broths were pooled and adjusted to approx. pH 3 with formic acid and centrifuged (3300 g) for 25 mins to separate the cells and resin from the clarified broth. The clarified broth was discarded after assay having confirmed less than 5% of target compound present. The cells and resin were stirred with 2 volumes of acetonitrile for 1 hr using a magnetic stirrer. The acetonitrile extract was recovered either by centrifugation or by allowing it to settle under gravity. A second acetonitrile extraction of the cells and resin was then performed under the same conditions. The combined acetonitrile extracts were concentrated to a residual aqueous volume under reduced pressure and then adjusted to pH 6. This was extracted twice with ethyl acetate and the combined organics taken to dryness under reduced pressure to give the final crude (1.6 g).

The crude extract (1.6 g) was dissolved in 2 ml ethyl acetate and loaded onto a silica gel column (10×2 cm) conditioned with 500 ml ethyl acetate. The column was eluted with ethyl acetate and then with stepwise increases in acetone (10%, 20%, 30%, etc. in ethyl acetate). Approx. 250 mL fractions were collected and the target compound identified by analytical LC, combined and taken to dryness. This material (188 mg) was dissolved in 1.8 ml methanol and purified by preparative HPLC. A Waters Xterra MSC18 column (10 micron, 19 cm×250 mm) was used with solvent pumped at 21 mL/min. Solvent A was water and solvent B was acetonitrile. The column was run isocratically at 50% B for 6 minutes following the injection followed by a gradient to 100% B at 30 minutes. These fractions were taken to dryness under reduced pressure to yield the target compound as an off-white amorphous solid (15 mg).

Example 6

Isolation of 62-fluoro sanglifehrin A, Compound 16

Employed methyl (S)-2-amino-3-(4-fluoro-3-hydroxyphenyl)propanoate and DL-piperazic acid precursors. Carried out in accordance with general method with exception that precursors were added at 27 hours.

After harvesting the culture broths were pooled and adjusted to approx. pH 3 with formic acid and centrifuged (3300 g) for 25 mins to separate the cells and resin from the clarified broth. The clarified broth was discarded after assay having confirmed less than 5% of target compound present. The cells and resin were stirred with 2 volumes of acetonitrile for 1 hr using magnetic stirrer. The acetonitrile extract was recovered either by centrifugation or by allowing it to settle under gravity. A second acetonitrile extraction of the cells and resin was then performed under the same conditions.

The combined acetonitrile extracts were concentrated to a residual aqueous volume under reduced pressure and then adjusted to pH 6. This was extracted twice with ethyl acetate and the combined organics taken to dryness under reduced pressure to give the final oily crude (4.2 g).

The crude extract (4.2 g) was dissolved in 4 ml ethyl acetate and loaded onto a silica gel column (15×2 cm) conditioned with 500 ml ethyl acetate. The column was eluted with ethyl acetate and then with stepwise increases in acetone (10%, 20%, 30%, etc. in ethyl acetate). Approx. 250 mL fractions were collected and the target compound identified by analytical LC, combined and taken to dryness. This material (390 mg) was dissolved in 2.4 ml methanol and purified by preparative HPLC. A Waters Xterra MSC18 column (10 micron, 19 cm×250 mm) was used with solvent pumped at 21 mL/min. Solvent A was water and solvent B was acetonitrile. The column was run isocratically at 50% B for 6 minutes following the injection followed by a gradient to 100% B at 30 minutes. Pure fractions were identified by HPLC-UV and combined. These fractions were taken to dryness under reduced pressure to yield the target compound as an off-white amorphous solid (38 mg).

Example 7

Isolation of 62-Methyl Sanglifehrin A, Compound/7

Cryopreserved spore stocks of BIOT-4585 were thawed at room temperature. Vegetative cultures (seed cultures) were prepared by transferring 0.4 mL of spore stock into 400 mL medium SM25 in 2 L Erlenmeyer flasks with foam plug. Cultivation was carried out for 48 hours at 27° C. and 250 rpm (2.5 cm throw). From the seed culture 20 mL was transferred into 400 mL production medium SGP2+5% HP20 in 2 L Erlenmeyer flasks with foam plug. After 24 hours cultivation at 24° C. and 250 rpm (2.5 cm throw), 2 mL of a 200 mM solution of methyl (S)-2-amino-3-(3-hydroxy-4-methylphenyl)propanoate in 1M hydrochloric acid and 2 mL of a 400 mM methanolic solution of DL-piperazic acid was added to each production flask to give a final 1 mM concentration of the individual enantiomers of the precursors. Cultivation was continued for further four days at 24° C. and 250 rpm (2.5 cm throw).

The culture broths were pooled and adjusted to approx. pH 3 with formic acid and centrifuged (3300 g) for 25 mins to separate the cells and resin from the clarified broth. The clarified broth was discarded after assay having confirmed less than 5% of target compound present. The cells and resin were stirred with 2 volumes of acetonitrile for 1 hr using an overhead paddle stirrer. The acetonitrile extract was recovered by allowing it to settle under gravity. A second acetonitrile extraction of the cells and resin was then performed under the same conditions. The combined acetonitrile extracts were concentrated to a residual aqueous volume under reduced pressure and then adjusted to pH 6. This was extracted twice with ethyl acetate and the combined organics taken to dryness under reduced pressure to give the final crude (7.6 g).

The crude extract (7.6 g) was dissolved in 5 ml ethyl acetate and loaded onto a silica gel column (15×2 cm) conditioned with 500 ml ethyl acetate. The column was eluted with ethyl acetate and then with stepwise increases in acetone (10%, 20%, 30%, etc. in ethyl acetate). Approx. 250 mL fractions were collected and the target compound identified by analytical LC, combined and taken to dryness. This material (319 mg) was dissolved in 2.4 ml methanol and purified by preparative HPLC. A Waters Xterra MSC18 column (10 micron, 19 cm×250 mm) was used with solvent pumped at 21 mL/min. Solvent A was water and solvent B was acetonitrile. The column was run isocratically at 50% B for 6 minutes following the injection followed by a gradient to 100% B at 30 minutes. Pure fractions were identified by HPLC-UV and combined. These fractions were taken to dryness under reduced pressure to yield the target compound as an off-white amorphous solid (14.9 mg).

Example 8

Isolation of 61-deshydroxy sanglifehrin A, Compound 18

Cryopreserved spore stocks of BIOT-4585 were thawed at room temperature. Vegetative cultures (seed cultures) were prepared by transferring 0.4 mL of spore stock into 400 mL medium SM25 in 2 L Erlenmeyer flasks with foam plug. Cultivation was carried out for 48 hours at 27° C. and 250 rpm (2.5 cm throw). From the seed culture 500 mL was transferred into 4.5 L production medium SGP2+5% HP20 in a 7 L Applikon fermenter and cultivated at 24° C., 400 rpm (cascade DOT control), 2.5 L/min air flow and 30% DOT (cascade agitation control). After 24 hours cultivation, 7.5 mL of a 667 mM solution of (S)-2-amino-3-phenylpropanoic acid in 1M hydrochloric acid was added to the fermenter to give a final 1 mM concentration of the precursor. Cultivation was continued for further four days at 24° C., 400 rpm (cascade DOT control), 2.5 L/min air flow and 30% DOT (cascade agitation control).

The culture broths were pooled and adjusted to approx. pH 3 with formic acid and centrifuged (3300 g) for 25 mins to separate the cells and resin from the clarified broth. The clarified broth was discarded after assay having confirmed less than 5% of target compound present. The cells and resin were stirred with 2 volumes of acetonitrile for 1 hr using an overhead paddle stirrer. The acetonitrile extract was recovered by allowing it to settle under gravity. A second acetonitrile extraction of the cells and resin was then performed under the same conditions, but with the second extract being recovered by centrifugation. The combined acetonitrile extracts were concentrated to a residual aqueous volume under reduced pressure and then adjusted to pH 6. This was extracted twice with ethyl acetate and the combined organics taken to dryness under reduced pressure to give the final crude (55 g).

The crude extract (55 g) was suspended in 80% methanol in water and extracted with 300 ml hexane twice. The target compound was found in methanol/water part and which were taken to dryness. This dried extract (48 g) dissolved in 30 ml ethyl acetate and loaded onto a silica gel column (20×5 cm) conditioned with 1 L ethyl acetate. The column was eluted with ethyl acetate and then with stepwise increases in acetone (10%, 20%, 30%, etc. in ethyl acetate). Approx. 250 mL fractions were collected and the target compound identified by analytical LC, combined and taken to dryness. This material (813 mg) was dissolved in methanol and purified by preparative HPLC. A Waters Xterra MSC18 column (10 micron, 19 cm×250 mm) was used with solvent pumped at 21 mL/min. Solvent A was water and solvent B was acetonitrile. The column was run isocratically at 50% B for 6 minutes following the injection followed by a gradient to 100% B at 30 minutes. Pure fractions were identified by HPLC-UV and combined. These fractions were taken to dryness under reduced pressure to yield the target compound as an off-white amorphous solid (34 mg).

Example 9

Isolation 58-des(3-hydroxyphenyl)-58-(3-hydroxy (2-pyridyl)-sanglifehrin A, Compound 19

Employed methyl (2S)-2-amino-3-(3-hydroxy(2-pyridyl))propanoate and DL-piperazic acid precursors. Carried out in accordance with general method with exception that the incubator throw during vegetative (seed) cultivation was 2.5 cm.

The culture broths were pooled and adjusted to approx. pH 3 with formic acid and centrifuged (3300 g) for 25 mins to separate the cells and resin from the clarified broth. The clarified broth was discarded after assay having confirmed less than 5% of target compound present. The cells and resin were stirred with 2 volumes of acetonitrile for 1 hr using an overhead paddle stirrer. The acetonitrile extract was recovered by allowing it to settle under gravity. A second acetonitrile extraction of the cells and resin was then performed under the same conditions. The combined acetonitrile extracts were concentrated to a residual aqueous volume under reduced pressure and then adjusted to pH 6. This was extracted twice with ethyl acetate and the combined organics taken to dryness under reduced pressure to give the final crude (7 g).

The crude extract (7 g) was dissolved in 4 ml ethyl acetate and loaded onto a silica gel column (15×2 cm) conditioned with 500 ml ethyl acetate. The column was eluted with ethyl acetate and then with stepwise increases in acetone (10%, 20%, 30%, etc. in ethyl acetate to 100% acetone then 1% methanol to stepwise 5% methanol in acetone). Approx. 250 mL fractions were collected and the target compound identified by analytical LC, combined and taken to dryness. This material (204 mg) was dissolved in methanol and purified by preparative HPLC. A Waters Xterra MSC18 column (10 micron, 19 cm×250 mm) was used with solvent pumped at 21 mL/min. Solvent A was water and solvent B was acetonitrile. The column was run isocratically at 50% B for 6 minutes following the injection followed by a gradient to 100% B at 30 minutes. Pure fractions were identified by HPLC-UV and combined. These fractions were taken to dryness under reduced pressure to yield the target compound as an off-white amorphous solid (4 mg).

Example 10

Isolation of 61-deshydroxy-61-fluoro sanglifehrin A, Compound 20

Cryopreserved spore stocks of BIOT-4585 were thawed at room temperature. Vegetative cultures (seed cultures) were prepared by transferring 0.4 mL of spore stock into 400 mL medium SM25 in 2 L Erlenmeyer flasks with foam plug. Cultivation was carried out for 48 hours at 27° C. and 250 rpm (2.5 cm throw). From the seed culture 20 mL was transferred into 400 mL production medium SGP2+5% HP20 in 2 L Erlenmeyer flasks with foam plug. After 24 hours cultivation at 24° C. and 250 rpm (2.5 cm throw), 2 mL of a 400 mM solution of 2-amino-3-(3-fluorophenyl) propanoic acid in 1M hydrochloric acid and 2 mL of a 400 mM methanolic solution of DL-piperazic acid was added to each production flask to give a final 1 mM concentration of the individual enantiomers of the precursors. Cultivation was continued for further four days at 24° C. and 250 rpm (2.5 cm throw).

The culture broths were pooled and adjusted to approx. pH 3 with formic acid and centrifuged (3300 g) for 25 mins to separate the cells and resin from the clarified broth. The clarified broth was discarded after assay having confirmed less than 5% of target compound present. The cells and resin were stirred with 2 volumes of acetonitrile for 1 hr using an overhead paddle stirrer. The acetonitrile extract was recovered either by allowing it to settle under gravity. A second acetonitrile extraction of the cells and resin was then performed under the same conditions. A third extract was obtained by centrifugation of the residual cell and resin mix. The combined acetonitrile extracts were concentrated to a residual aqueous volume under reduced pressure and then adjusted to pH 6. This was extracted twice with ethyl acetate and the combined organics taken to dryness under reduced pressure to give the final crude (10.5 g).

The crude extract (10.5 g) was dissolved in 7 ml ethyl acetate and loaded onto a silica gel column (15×2 cm) conditioned with 500 ml ethyl acetate. The column was eluted with ethyl acetate and then with stepwise increases in acetone (10%, 20%, 30%, etc. in ethyl acetate). Approx. 250 mL fractions were collected and the target compound identified by analytical LC, combined and taken to dryness. This material (342 mg) was dissolved in methanol and purified by preparative HPLC. A Waters Xterra MSC18 column (10 micron, 19 cm×250 mm) was used with solvent pumped at 21 mL/min. Solvent A was water and solvent B was acetonitrile. The column was run isocratically at 53% B for 30 minutes following the injection. Pure fractions were identified by HPLC-UV and combined. These fractions were taken to dryness under reduced pressure to yield the target compound as an off-white amorphous solid (6 mg).

Example 11

Synthesis of diethyl (2-(1,2-oxazinan-2-yl)-2-oxoethyl)phosphonate

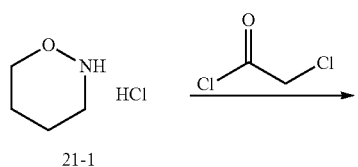

21-1

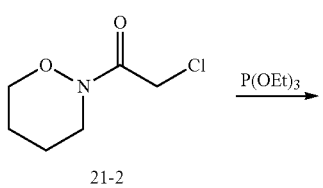

21-2

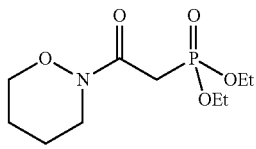

21

To a solution of 21-1 (ChemCollect, Germany) (100 mg, 0.81 mmol), Et₃N (246 mg, 2.43 mmol) in dry DCM (5 mL) was added dropwise chloroacetyl chloride (138 mg, 1.22 mmol). The reaction mixture was stirred at room temperature for 3 h, poured into ice water, and extracted with ethyl acetate. The organic layer was washed with brine and dried over Na₂SO₄, filtered, concentrated in vacuo. The residue (21-2) was used to the next step without any further purification. (123 mg, 90% yield).

A mixture of 21-2 (123 mg, 0.75 mmol) and triethyl phosphite (250 mg, 1.50 mmol) were stirred at 140° C. for 6 h. The reaction mixture was cooled to room temperature and was purified by flash chromatography to yield 21.

Example 12

Synthesis of diethyl (2-oxo-2-(pyridin-2-ylamino)ethyl)phosphonate

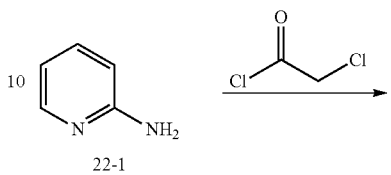

22-1

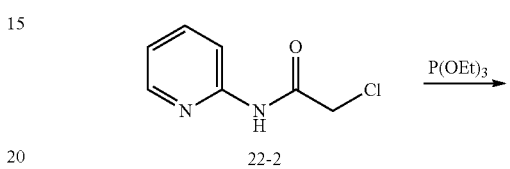

22-2

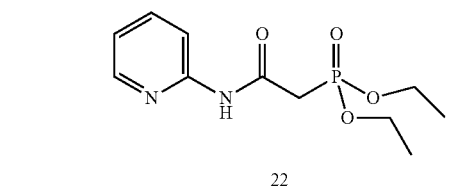

22

To a solution of 22-1 (1 g, 10.6 mmol), Et₃N (1.075 g, 10.6 mmol) in dry methylene chloride (50 mL) was added dropwise chloroacetyl chloride (1.2 g, 10.6 mmol). The reaction mixture was stirred at room temperature for 3 h, poured into ice water, and extracted with ethyl acetate. The organic layer was washed with brine and dried over Na₂SO₄, filtered and concentrated in vacuo. The residue was purified by reversed phase-combiflash to yield 22-2.

A mixture of 22-2 (170 mg, 1.00 mmol) and triethyl phosphite (332 mg, 2.00 mmol) was stirred at 140° C. for 6 h. The reaction mixture was cooled to room temperature and was purified by flash chromatography to yield 22.

Example 13

Preparation of Compound 23

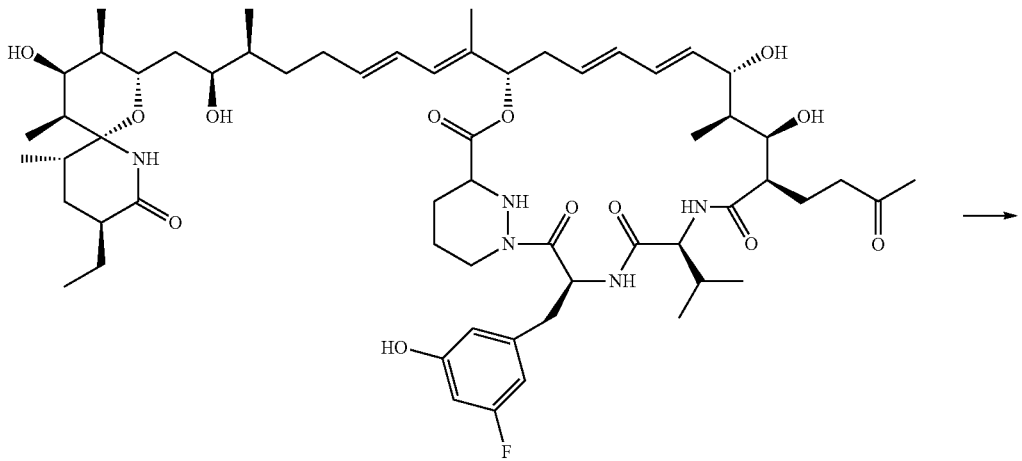

14

-continued

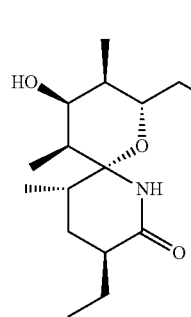
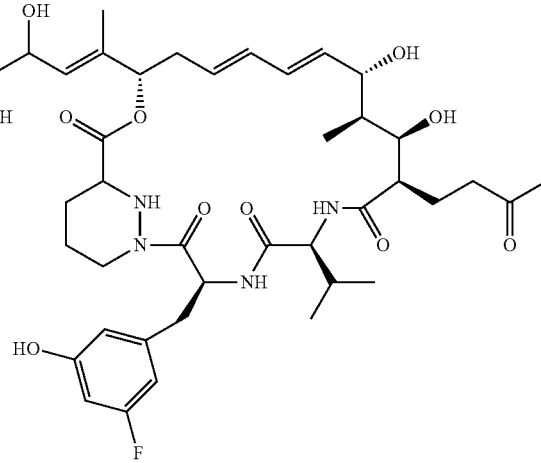

23-2

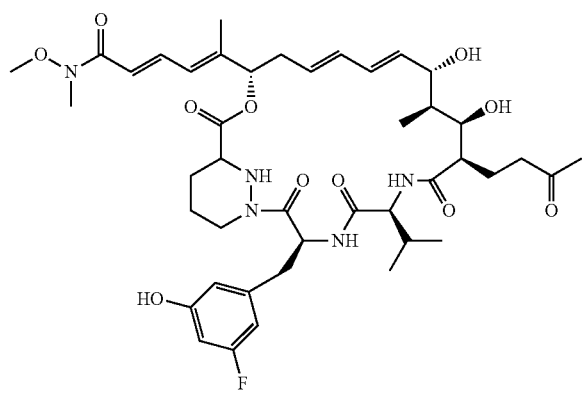

23

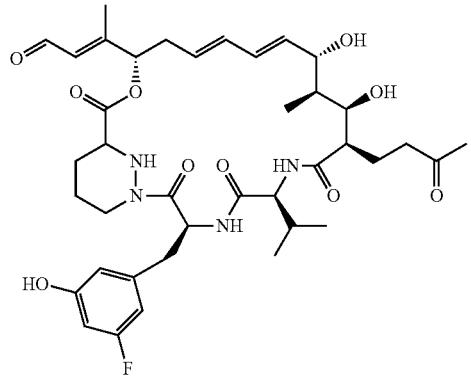

23-3

To a stirred solution of 14 (430 mg, 0.38 mmol), (DHQ)$_2$PHAL (18.6 mg, 0.024 mmol), osmium tetroxide (0.156 mL, 0.012 mmol) in tert-butyl alcohol (2.5 wt %, 0.079 mmol/ml), and methanesulfonamide (74 mg, 0.77 mmol) in 20 mL tert-butyl alcohol were added at room temperature, a solution of potassium ferricyanide (382 mg, 1.16 mmol) and potassium carbonate (160 mg, 1.16 mmol) in 20 mL water, resulting in a brown emulsion. After 2 h a solution of sodium sulfite was added, and stirring was continued for 20 min. The resulting mixture was extracted with ethyl acetate (3×50 ml). The combined organic layers were washed with brine, dried over anhydrous sodium sulfate, filtered, and concentrated under reduced pressure, purified by reverse-phase flash chromatography to yield 23-2 as a white solid.

To a stirred solution of 23-2 (240 mg, 0.21 mmol) in 24 mL of a 2:1 mixture of THF and water was added sodium periodate (91 mg, 0.42 mmol). The resulting mixture was stirred at room temperature for 3 h, and then saturated aqueous sodium bicarbonate was added. This mixture was extracted with three portions of ethyl acetate. The combined organic layers were washed with one portion of water and two portions of saturated brine, dried over anhydrous sodium sulfate, filtered, and concentrated under reduced pressure. The residue was purified by reverse-phase flash chromatography to yield 23-3.

To a solution of diethyl (2-(methoxy(methyl)amino)-2-oxoethyl)phosphonate (91 mg, 0.368 mmol) in THF (5.0 mL) was added NaH (2.8 mg, 0.1104 mmol) in anhydrous THF (0.2 mL) at 0° C. with stirring. The solution was then stirred at 20° C. until it became clear. Then 23-3 (70 mg, 0.092 mmol) was added to the clear solution and the mixture stirred at 20° C. for 2 h. The mixture was quenched with water (10 mL) and extracted with ethyl acetate (3×30 mL). The organic layer was washed with brine and dried over Na$_2$SO$_4$, filtered and reduced in vacuo. The residue was purified by preparative HPLC to obtained 23 as a white solid.

Example 14

Preparation of Compound 24

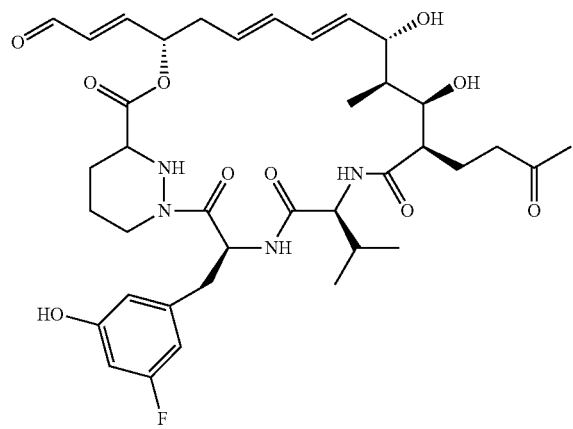

23-3

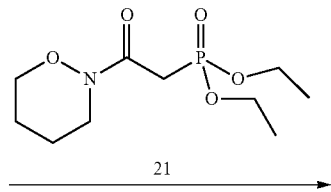

21

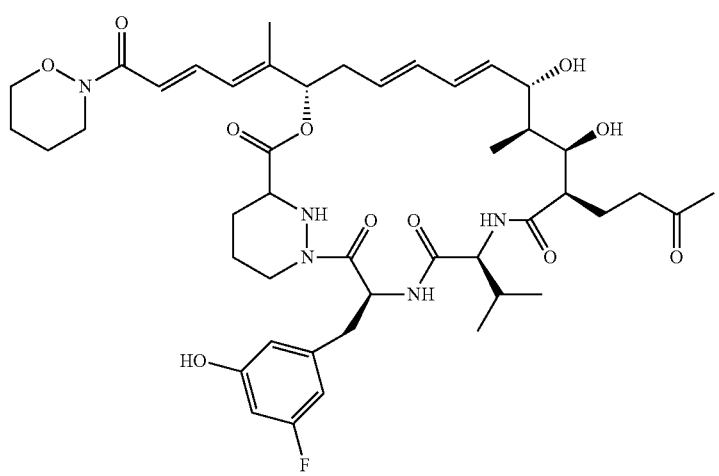

24

To a solution of 21 (42 mg, 0.168 mmol) in THF (2.0 mL) was added NaH (1.2 mg, 0.05 mmol) in anhydrous THF (0.2 mL) at 0° C. with stirring. The solution was then stirred at 20° C. until it became clear. Then 23-3 (30 mg, 0.042 mmol) was added to the clear solution and the mixture stirred at 20° C. for 2 h. The mixture was quenched with water (10 mL) and extracted with ethyl acetate (3×20 mL). The organic layer was washed with brine and dried over $Na_2SO_4$, filtered and reduced in vacuo. The residue was purified by preparative HPLC to obtained 24 as a white solid.

Example 15

Preparation of Compound 25

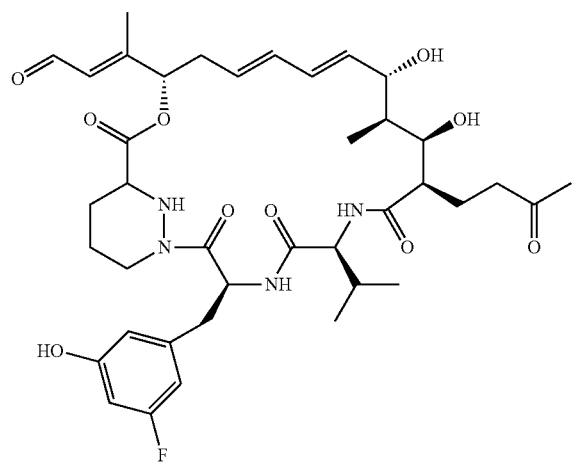

23-3

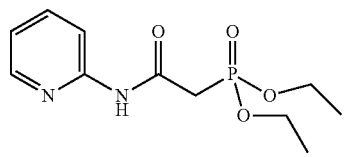

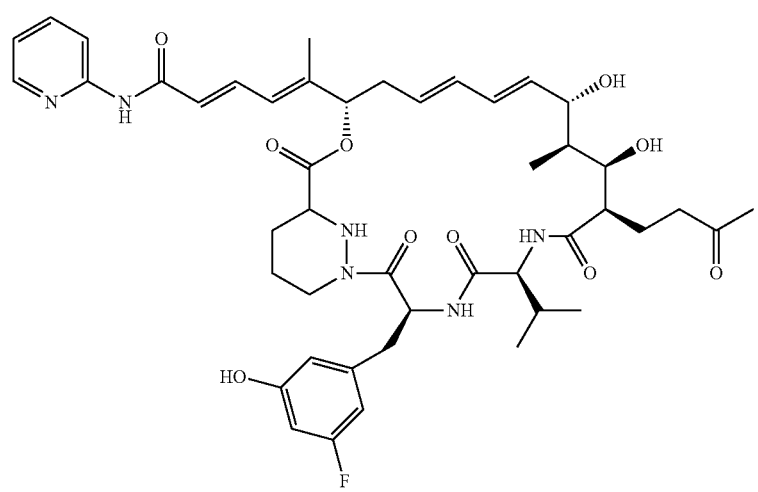

25

To a solution of 22 (48 mg, 0.168 mmol) in THF (2.0 mL) was added NaH (1.2 mg, 0.05 mmol) in anhydrous THF (0.2 mL) at 0° C. with stirring. The solution was then stirred at 20° C. until it became clear. Then 23-3 (30 mg, 0.042 mmol) was added to the clear solution and the mixture stirred at 20° C. for 2 h. The mixture was quenched with water (10 mL) and extracted with ethyl acetate (3×20 mL). The organic layer was washed with brine and dried over $Na_2SO_4$, filtered and reduced in vacuo. The residue was purified by preparative HPLC to obtained 25 as a white solid.

Example 16

Preparation of Compound 26

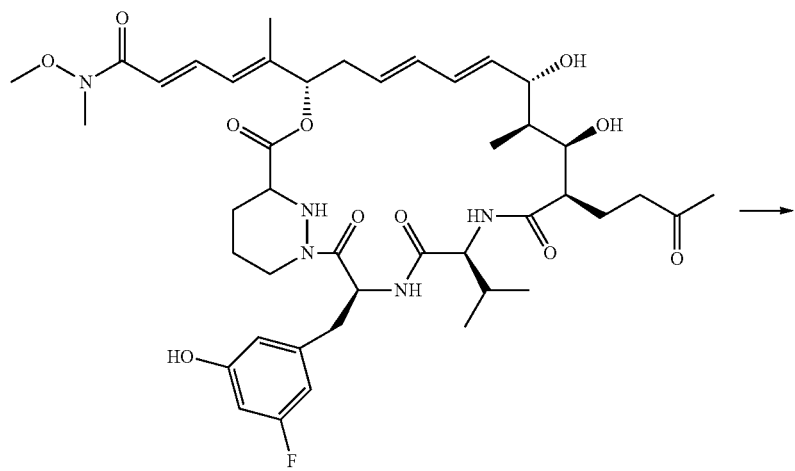

23

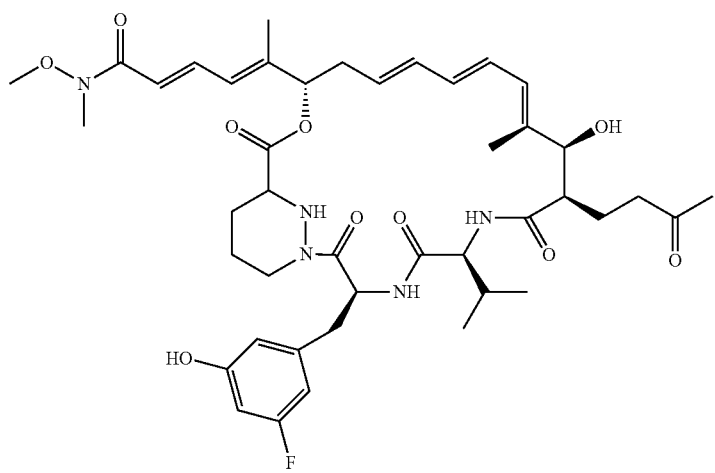

26

To a solution of 23 (13 mg, 0.015 mmol) dissolved in dioxane (1 mL) was added aqueous HCl solution (2 M, 0.080 ml, 0.16 mmol). The reaction was stirred at 20° C. for 24 h and the reaction was quenched with water and extracted with ethyl acetate (3×10 mL). The organic phase was dried over sodium sulfate and evaporated. The residue was purified by preparative HPLC to obtained 26 as a white solid.

Example 17

Preparation of Compound 27

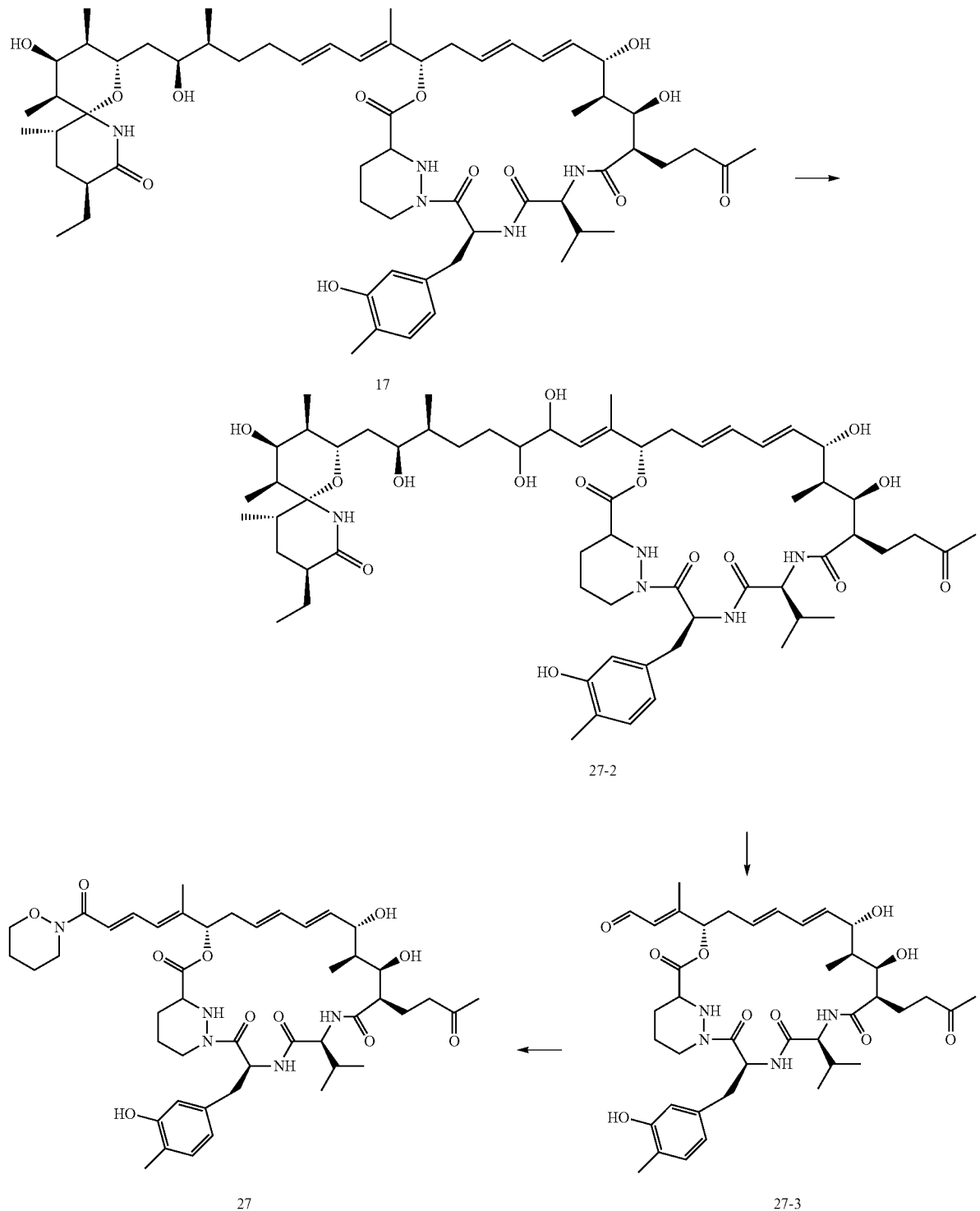

To a stirred solution of 17 (99 mg, 0.09 mmol), (DHQ)₂PHAL (4.2 mg, 0.0054 mmol), osmium tetroxide (0.034 mL, 0.0027 mmol) in tert-butyl alcohol (2.5 wt %, 0.079 mmol/ml), and methanesulfonamide (18 mg, 0.18 mmol) in 5 mL tert-butyl alcohol were added at room temperature, a solution of potassium ferricyanide (90 mg, 0.27 mmol) and potassium carbonate (37 mg, 0.27 mmol) in 5 mL water, resulting in a brown emulsion. After 2 h a solution of sodium sulfite was added, and stirring was continued for 20 min. The resulting mixture was extracted with ethyl acetate (3×20 ml). The combined organic layers were washed with brine, dried over anhydrous sodium sulfate, filtered, and concentrated under reduced pressure, purified by reverse-phase flash chromatography to yield 27-2 as a white solid.

To a stirred solution of 27-2 (40 mg, 0.035 mmol) in 3 mL of a 2:1 mixture of THF and water was added sodium periodate (15 mg, 0.07 mmol). The resulting mixture was stirred at room temperature for 3 h, and then saturated aqueous sodium bicarbonate was added. This mixture was extracted with three portions of ethyl acetate. The combined organic layers were washed with one portions of water and two portions of saturated brine, dried over anhydrous sodium sulfate, filtered, and concentrated under reduced pressure. The residue was purified by reverse-phase flash chromatography to yield 27-3 as a white solid To a solution of 21 (28 mg, 0.104 mmol) in THF (2.0 mL) was added NaH (0.75 mg, 0.0312 mmol) in anhydrous THF (0.2 mL) at 0° C. with stirring. The solution was then stirred at 20° C. until it became clear. Then 27-3 (19.6 mg, 0.026 mmol) was added to the clear solution and the mixture stirred at 20° C. for 2 h. The mixture was quenched with water (10 mL) and extracted with ethyl acetate (3×10 mL). The organic layer was washed with brine and dried over $Na_2SO_4$, filtered, and concentrated under reduced pressure. The residue was purified by preparative HPLC to obtained 27 as a white solid.

Example 18

Preparation of Compound 28

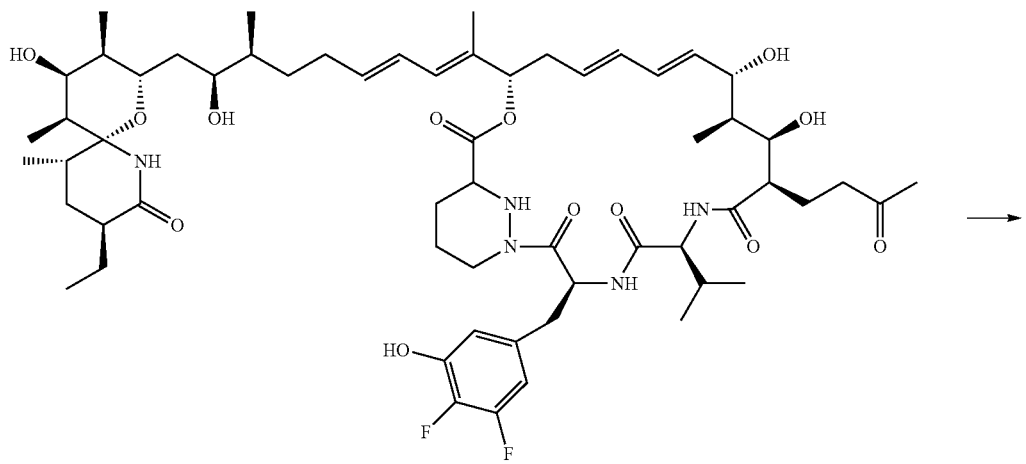

15

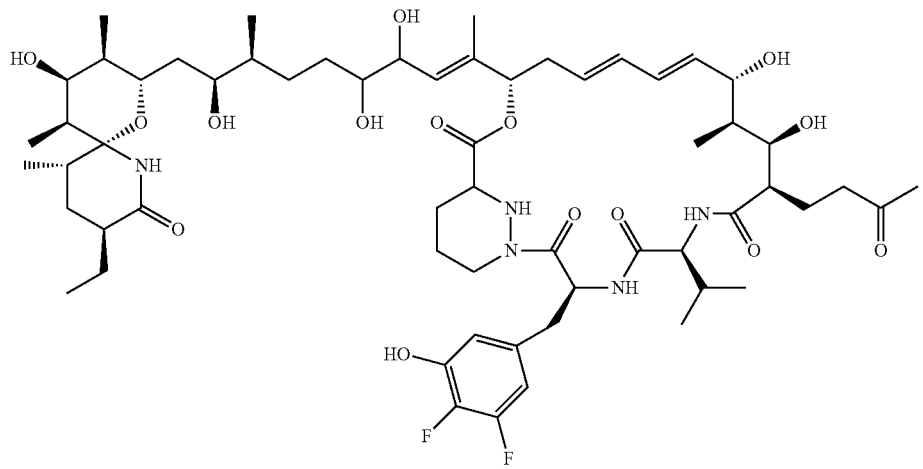

28-2

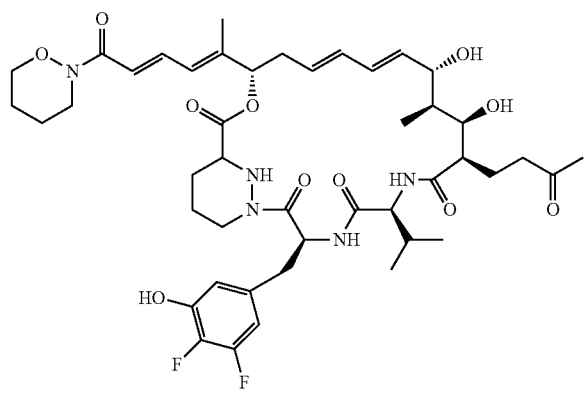

28

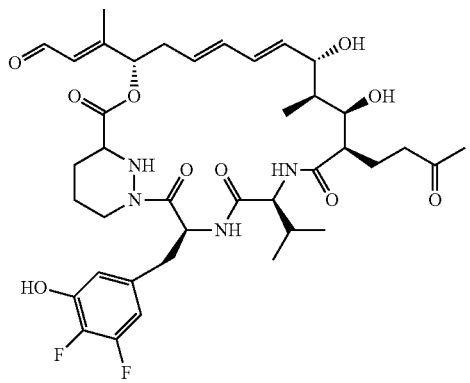

28-3

-continued

To a stirred solution of 15 (349 mg, 0.31 mmol), (DHQ)₂PHAL (14 mg, 0.0186 mmol), osmium tetroxide (0.117 mL, 0.0093 mmol) in tert-butyl alcohol (2.5 wt %, 0.079 mmol/ml), and methanesulfonamide (59 mg, 0.62 mmol) in 15 mL tert-butyl alcohol was added at room temperature, a solution of potassium ferricyanide (128 mg, 0.93 mmol) and potassium carbonate (306 mg, 0.93 mmol) in 15 mL water, resulting in a brown emulsion. After 2 h a solution of sodium sulfite was added, and stirring was continued for 20 min. The resulting mixture was extracted with ethyl acetate (3×50 ml). The combined organic layers were washed with brine, dried over anhydrous sodium sulfate, filtered, and concentrated under reduced pressure, purified by reverse-phase flash chromatography to yield 28-2 as a white solid.

To a stirred solution of 28-2 (170 mg, 0.1466 mmol) in 15 mL of a 2:1 mixture of THF and water was added sodium periodate (62 mg, 0.2931 mmol). The resulting mixture was stirred at room temperature for 3 h, and then saturated aqueous sodium bicarbonate was added. This mixture was extracted with three portions of ethyl acetate. The combined organic layers were washed with one portion of water and two portions of saturated brine, dried over anhydrous sodium sulfate, filtered, and concentrated under reduced pressure. The residue was purified by reverse-phase flash chromatography to yield 28-3 as a white solid.

To a solution of 21 (41 mg, 0.155 mmol) in THF (1.0 mL) was added NaH (2.3 mg, 0.0575 mmol) in anhydrous THF (0.2 mL) at 0° C. with stirring. The solution was then stirred at 20° C. until it became clear. Then 28-3 (30 mg, 0.0387 mmol) was added to the clear solution and the mixture stirred at 20° C. for 2 h. The mixture was quenched with water (10 mL) and extracted with ethyl acetate (3×20 mL). The organic layer was washed with brine and dried over Na₂SO₄, filtered, evaporated. The residue was purified by preparative HPLC to obtained 28 as a white solid.

Example 19

Preparation of Compound 29

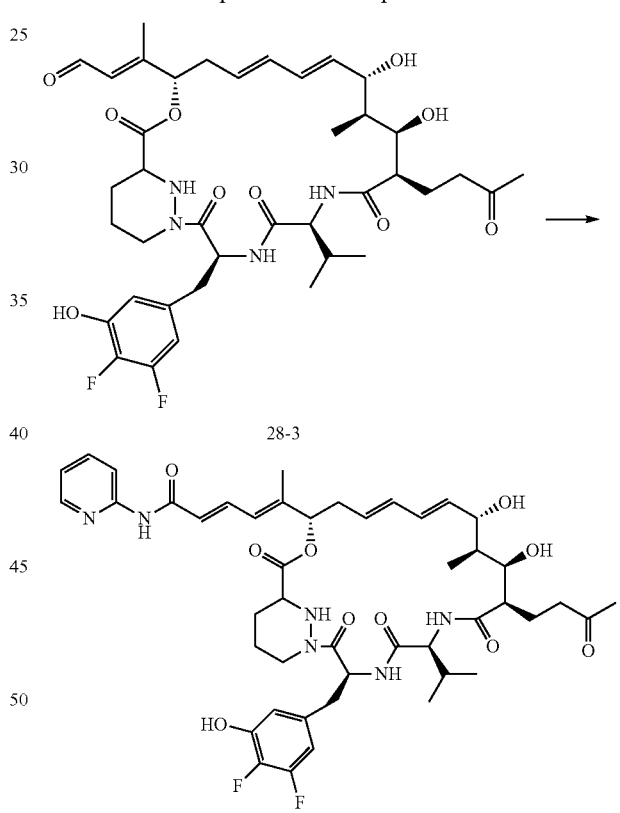

29

To a solution of 22 (42 mg, 0.155 mmol) in THF (1.0 mL) was added NaH (2.3 mg, 0.0575 mmol) in anhydrous THF (0.2 mL) at 0° C. with stirring. The solution was then stirred at 20° C. until it became clear. Then 28-3 (30 mg, 0.0387 mmol) was added to the clear solution and the mixture stirred at 20° C. for 2 h. The mixture was quenched with water (10 mL) and extracted with ethyl acetate (3×20 mL). The organic layer was washed with brine and dried over Na₂SO₄, filtered, evaporated. The residue was purified by preparative HPLC to obtained 29 as a white solid.

Example 20

Preparation of Compound 30

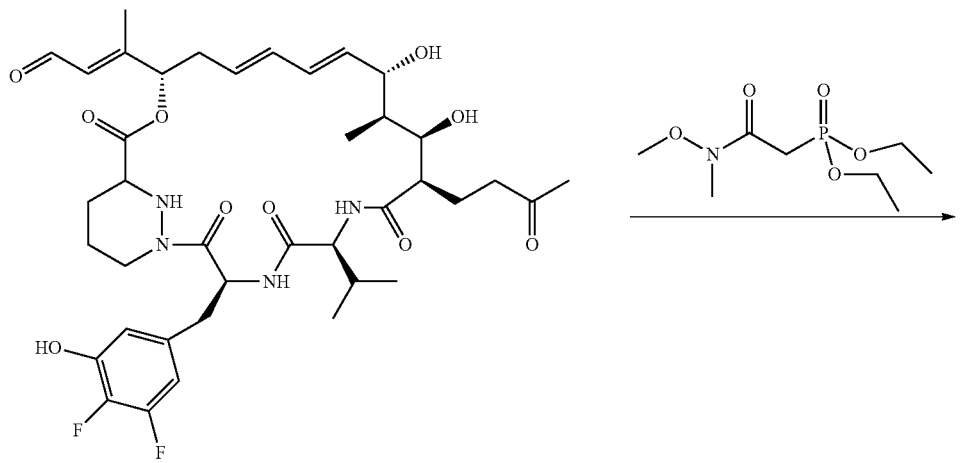

28-3

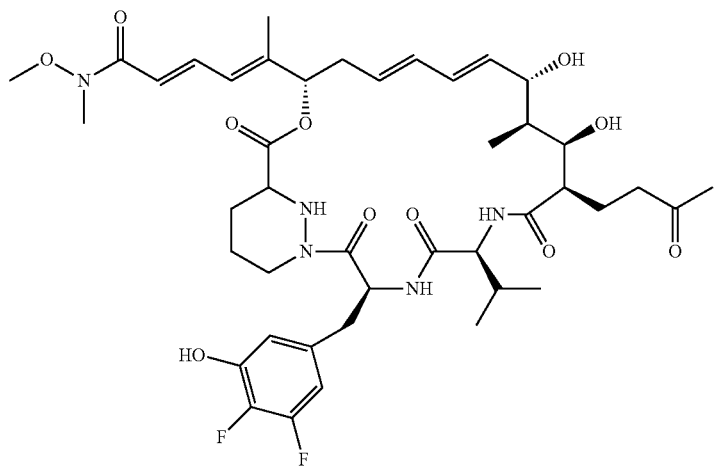

30

To a solution of diethyl (2-(methoxy(methyl)amino)-2-oxoethyl)phosphonate (37 mg, 0.155 mmol) in THF (1.0 mL) was added NaH (2.3 mg, 0.0575 mmol) in anhydrous THF (0.2 mL) at 0° C. with stirring. The solution was then stirred at 20° C. until it became clear. Then 28-3 (30 mg, 0.0387 mmol) was added to the clear solution and the mixture stirred at 20° C. for 2 h. The mixture was quenched with water (10 mL) and extracted with ethyl acetate (3×20 mL). The organic layer was washed with brine and dried over $Na_2SO_4$, filtered, evaporated. The residue was purified by preparative HPLC to obtained 30 as a white solid.

Example 21

Biological Data—In Vivo Oral Bioavailability

To assess the pharmacokinetics of the compounds in an in vivo setting, compounds were dosed po at 10 or 5 mg/kg and iv at 1 mg/kg to groups of CD1 mice. The compounds tested are mentioned above or listed in the table below:

List of Tested Compounds which are Published*
| Compound number | |
|---|---|
| 31 | 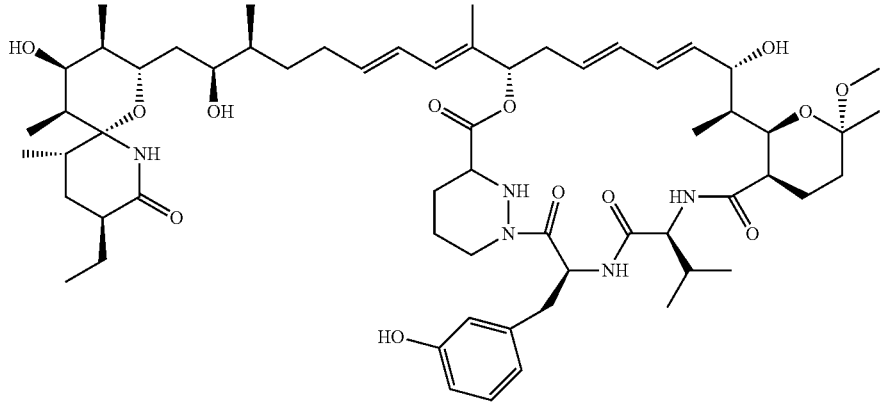 |
| 32 | 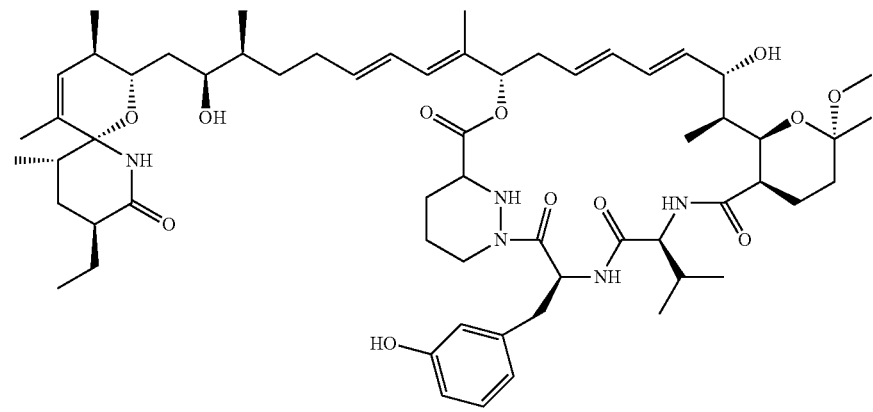 |
| 33 | 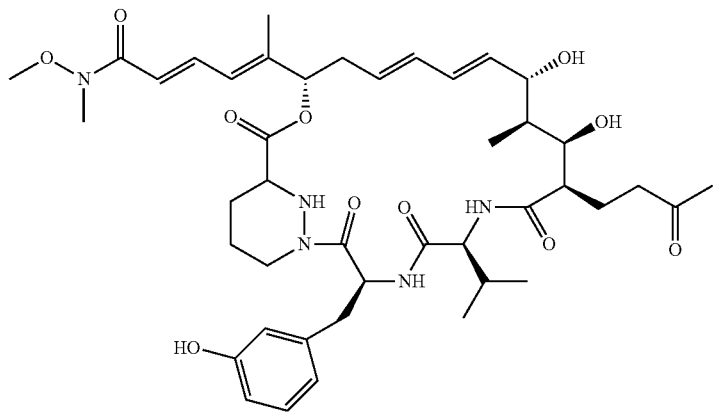 [SMILES: CON(C)C(=O)/C=C/C=C(\C)[C@@H]1C/C=C/C=C/[C@H](O)[C@H](C)[C@@H](O)[C@@H](CCC(C)=O)C(=O)N[C@@H](C(C)C)C(=O)N[C@@H](Cc2cccc(O)c2)C(=O)N2CCCC(N2)C(=O)O1] |

| Compound number | |
|---|---|
| 34 | 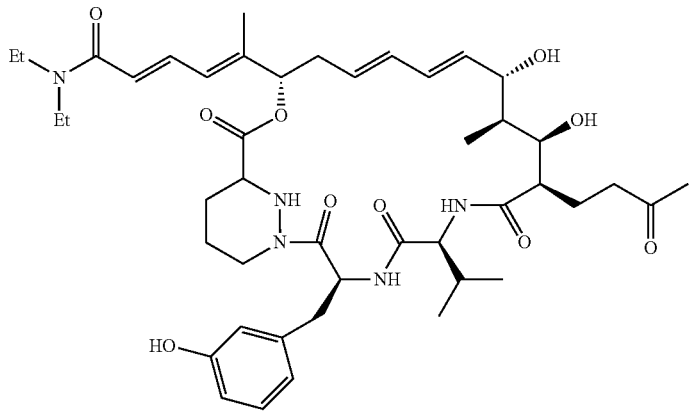 [SMILES: CCN(CC)C(=O)/C=C/C=C(\C)[C@@H]1C/C=C/C=C/[C@H](O)[C@H](C)[C@@H](O)[C@@H](CCC(C)=O)C(=O)N[C@@H](C(C)C)C(=O)N[C@@H](Cc2cccc(O)c2)C(=O)N2CCCC(N2)C(=O)O1] |
| 35 | 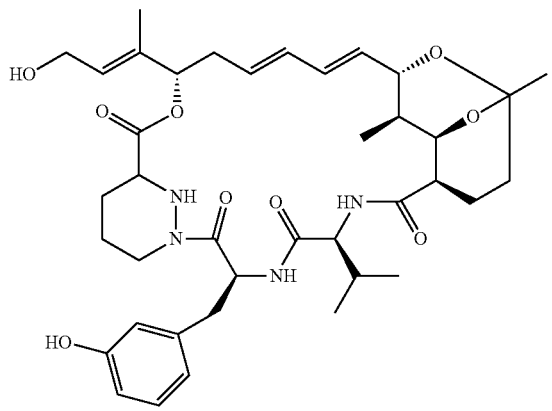 [SMILES: C/C(=C\CO)[C@@H]1C/C=C/C=C/[C@@H]2OC3(C)CC[C@@H](C(=O)N[C@@H](C(C)C)C(=O)N[C@@H](Cc4cccc(O)c4)C(=O)N4CCCC(N4)C(=O)O1)[C@H](O3)[C@H]2C] |
| 36 | 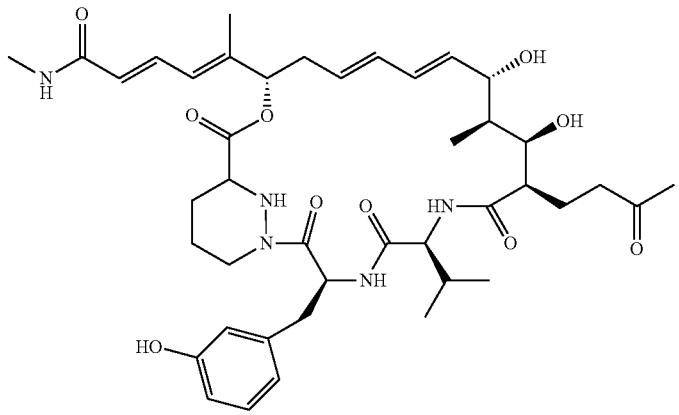 [SMILES: CNC(=O)/C=C/C=C(\C)[C@@H]1C/C=C/C=C/[C@H](O)[C@H](C)[C@@H](O)[C@@H](CCC(C)=O)C(=O)N[C@@H](C(C)C)C(=O)N[C@@H](Cc2cccc(O)c2)C(=O)N2CCCC(N2)C(=O)O1] |

| Compound number | |
|---|---|
| 37 | 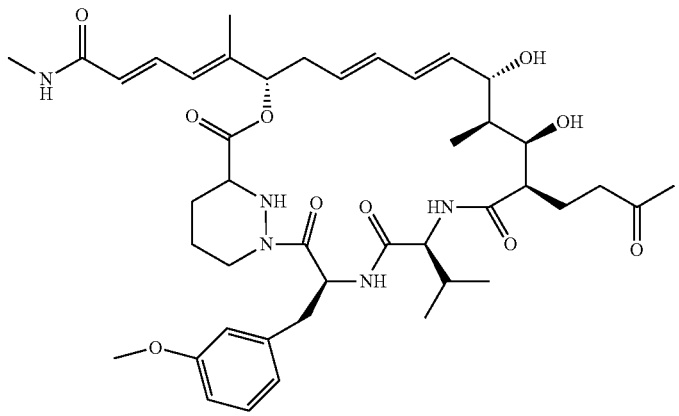 [SMILES: CNC(=O)/C=C/C=C(\C)[C@@H]1C/C=C/C=C/[C@H](O)[C@H](C)[C@@H](O)[C@@H](CCC(C)=O)C(=O)N[C@@H](C(C)C)C(=O)N[C@@H](Cc2cccc(OC)c2)C(=O)N2CCCC(N2)C(=O)O1] |
| 38 | 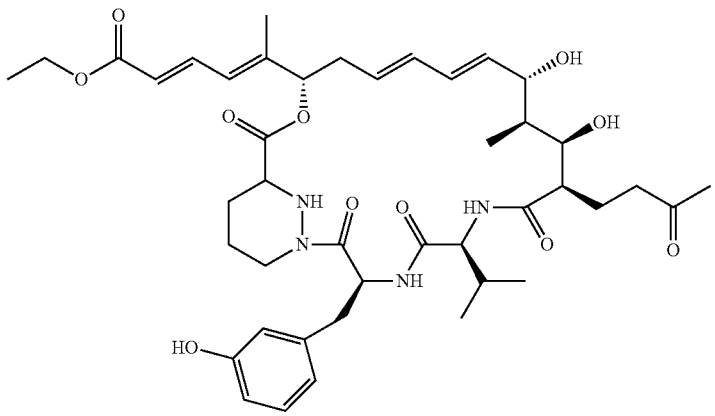 [SMILES: CCCC(=O)/C=C/C=C(\C)[C@@H]1C/C=C/C=C/[C@H](O)[C@H](C)[C@@H](O)[C@@H](CCC(C)=O)C(=O)N[C@@H](C(C)C)C(=O)N[C@@H](Cc2cccc(O)c2)C(=O)N2CCCC(N2)C(=O)O1] |
| 39 | 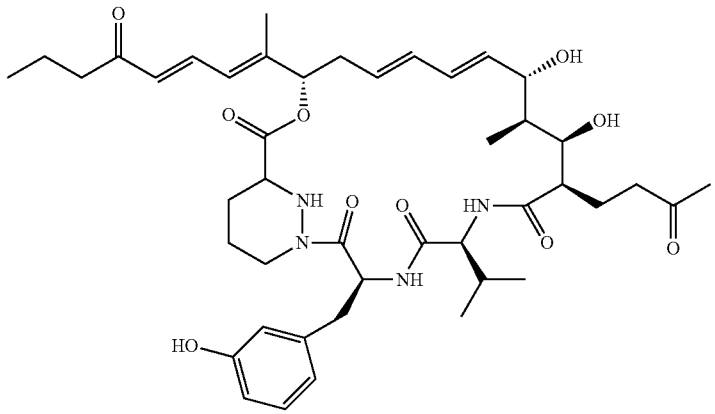 |

| Compound number | |
|---|---|
| 40 | 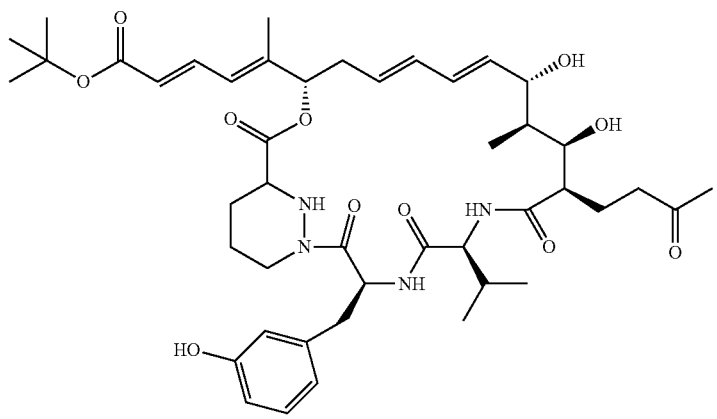 [SMILES: CC(=O)CC[C@H]1C(=O)N[C@@H](C(C)C)C(=O)N[C@@H](Cc2cccc(O)c2)C(=O)N2CCCC(N2)C(=O)O[C@H](/C(C)=C/C=C/C(=O)OC(C)(C)C)C/C=C/C=C/[C@H](O)[C@H](C)[C@H]1O] |
| 41 | 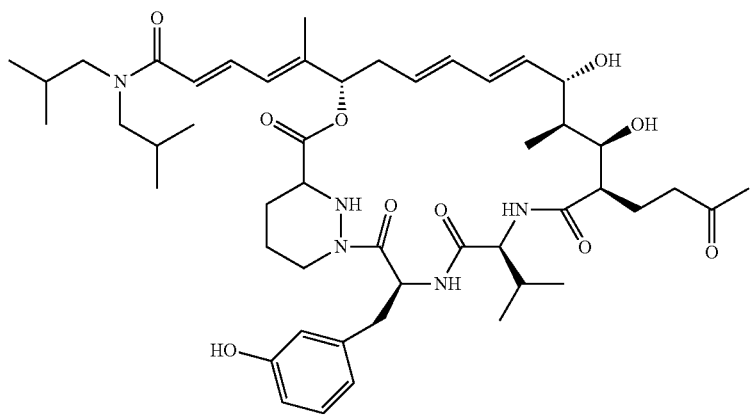 [SMILES: CC(=O)CC[C@H]1C(=O)N[C@@H](C(C)C)C(=O)N[C@@H](Cc2cccc(O)c2)C(=O)N2CCCC(N2)C(=O)O[C@H](/C(C)=C/C=C/C(=O)N(CC(C)C)CC(C)C)C/C=C/C=C/[C@H](O)[C@H](C)[C@H]1O] |
| 42 | 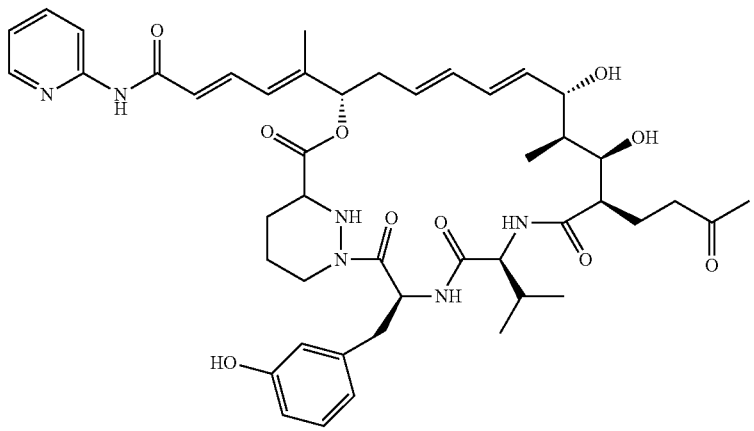 [SMILES: CC(=O)CC[C@H]1C(=O)N[C@@H](C(C)C)C(=O)N[C@@H](Cc2cccc(O)c2)C(=O)N2CCCC(N2)C(=O)O[C@H](/C(C)=C/C=C/C(=O)Nc2ccccn2)C/C=C/C=C/[C@H](O)[C@H](C)[C@H]1O] |

| Compound number | |
|---|---|
| 43 | 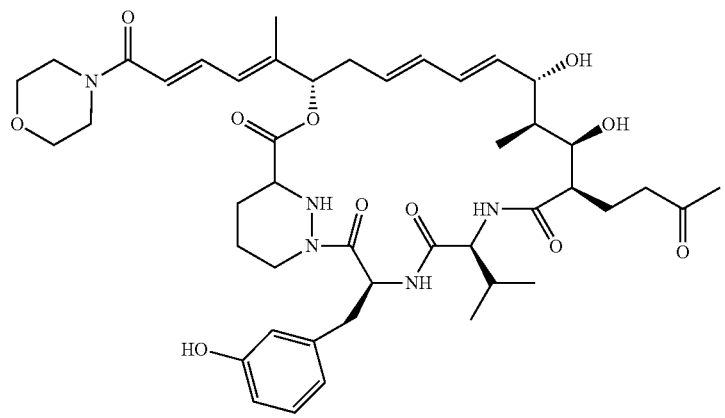 [SMILES: CC(=O)CC[C@H]1C(=O)N[C@@H](C(C)C)C(=O)N[C@@H](Cc2cccc(O)c2)C(=O)N2CCCC(N2)C(=O)O[C@H](/C(C)=C/C=C/C(=O)N2CCOCC2)C/C=C/C=C/[C@H](O)[C@H](C)[C@H]1O] |
| 44 | 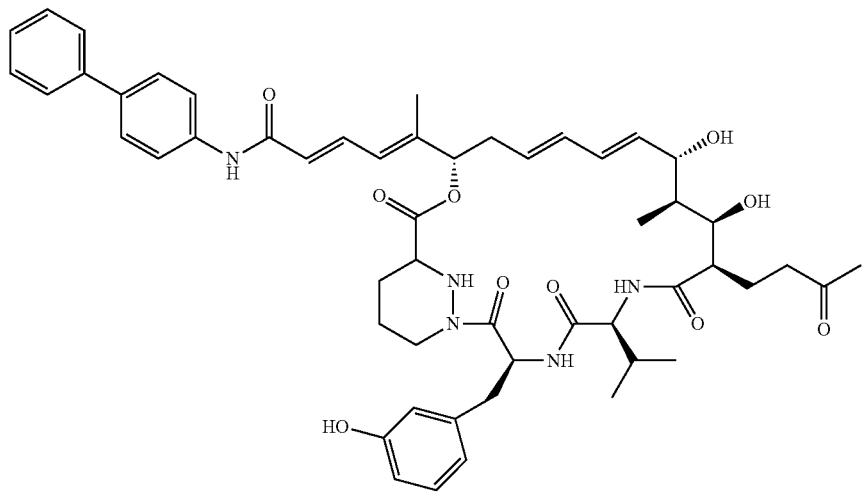 [SMILES: CC(=O)CC[C@H]1C(=O)N[C@@H](C(C)C)C(=O)N[C@@H](Cc2cccc(O)c2)C(=O)N2CCCC(N2)C(=O)O[C@H](/C(C)=C/C=C/C(=O)Nc2ccc(-c3ccccc3)cc2)C/C=C/C=C/[C@H](O)[C@H](C)[C@H]1O] |
| 45 | 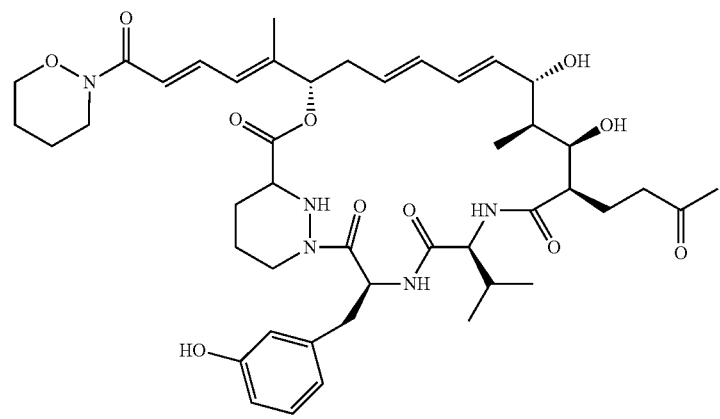 [SMILES: CC(=O)CC[C@H]1C(=O)N[C@@H](C(C)C)C(=O)N[C@@H](Cc2cccc(O)c2)C(=O)N2CCCC(N2)C(=O)O[C@H](/C(C)=C/C=C/C(=O)N2CCCCO2)C/C=C/C=C/[C@H](O)[C@H](C)[C@H]1O] |
*see WO2011/098809, WO2011/098808 and WO2011/098805 for disclosure and preparation methods, these documents are incorporated herein in their entirety.

Pharmacokinetic analysis was carried out as described in the general methods.

| Compound | AUClast after 1 mg/kg i.v. dose | AUClast after 5 mg/kg p.o. dose | AUClast after 10 mg/kg p.o. dose | Oral bioavailability F % |
|---|---|---|---|---|
| Cyclosporine A, 1 | 1010 | | 8793 | 90.8 |
| Sanglifehrin A, 5 | 16473 | | 2839 | 1.4 |
| Sanglifehrin B, 7 | 14067 | | 5693 | 3.9 |
| Sanglifehrin C, 31 | 1257 | | 25 | 0.2 |
| Sanglifehrin D, 32 | 2157 | | 19.8 | 0.03 |
| 33 | 14333 | | 2203 | 1.6 |
| 34 | 14033 | | 800 | 0.1 |
| 35 | 813 | | 11.3 | 0.1 |
| 36 | 4923 | | 17.8 | 0.04 |
| 37 | 1218 | | 4.76 | 0.04 |
| 38 | 5793 | | 3090 | 5.5 |
| 39 | 1660 | | 111 | 0.9 |
| 40 | 4910 | | 3877 | 7.8 |
| 41 | 1943 | | 453 | 2.4 |
| 42 | 11658 | | 919 | 0.7 |
| 43 | 9801 | | 8983 | 9.2 |
| 44 | 2497 | | 0 | 0 |
| 45 | 15100 | | 4837 | 3.2 |
| 23 | 22867 | 2760 | | 2.4 |
| 24 | 45467 | 8223 | | 3.6 |
| 26 | 5503 | 421 | | 1.5 |

As can be seen, sanglifehrins have low oral bioavailability, as shown by a low F % value.

Example 22

Biological Data—In Vitro Stability in Different Matrices

Stability of compounds was analysed in simulated gastric fluid, pH1.2 (SGF) and phosphate buffered saline, pH7.3 (PBS). See FIG. 1 for HPLC traces for PBS and SGF incubations of 24. The retention time of 24 is 11.1-11.3 minutes.

| Compound | SGF $t_{1/2}$ (hrs) | SGF % remaining after 1 hour | SGF + Pepsin, % remaining after 1 hour | SGF + denatured pepsin, % remaining after 1 hour | PBS $t_{1/2}$ (hrs) | PBS % remaining after 1 hour |
|---|---|---|---|---|---|---|
| CsA, 1 | >24 | 100% | — | — | >24 | — |
| SfA, 5 | ~1 | 52% | 41% | 49% | ~3 | 76% |
| 33 | 0.66 | — | 25% | — | >24 | — |
| 45 | <0.33 | 13% | 17% | 15% | >24 | 100% |
| 24 | <0.33 | 18% | 23% | 30% | >24 | 100% |

As can be seen, all of the sanglifehrins are more stable in PBS than in SGF with or without pepsin, whilst the other cyclophilin inhibitor from a different chemical class, cyclosporine A, is stable in all matrices tested. From this experiment it may be concluded that the sanglifehrins are degraded in acidic conditions (modelled on stomach acid) but are stable at neutral or alkaline pH.

Example 23

Biological Data—Generation of Enterically Coated Capsules and Dissolution Studies Approximately 5 mg of 24 was weighed into size '3' gelatin capsules which were then placed into a size '0' gelatin capsule. Coating of half of the capsules was then achieved by individually dipping each capsule into the coating solution (Opadry enteric coat solution 5% w/w, dichloromethane:methanol 40:60 95% w/w) and allowing them air dry at ambient for at least 6 hours or overnight. Capsules were coated by dipping the capsule body into the solution first and then allowed to air dry by placing in holder such that the body was facing upwards and the cap in contact with the holder. Once dried, the capsule cap was then dipped into the coating solution and dried the same way as described above with body in contact with the holder. After both the capsule body and cap were coated, this was treated as 1 coating cycle. After sufficient drying, the weights of the capsules were measured and compared to the initial values. This procedure was repeated several times until the desired weight gain (11 mg) for the capsule was achieved.

Dissolution studies were then conducted in acidic (pH1.0) and pH 6.8 buffer media as follows:

Acid Stage: 750 mL of 0.1M HCl was placed in a 1 L vessel and the apparatus assembled. The medium was allowed to equilibrate to a temperature of 37±0.5° C. One capsule (coated or uncoated) was placed in the apparatus, the vessel covered and the mixture paddle stirred at 50 rpm. An aliquot was taken from the fluid at T=0, after 30 minutes (T=30 min) and after 60 minutes (T=60 min) of operation in 0.1M HCl and proceed immediately as directed under buffer stage. Perform an analysis of the aliquot using a suitable assay method.

Buffer Stage: Immediately on completion of the acid stage, 250 mL of 0.2M solution of Tri-Sodium Phosphate Dodecahydrate (with 2% tween 80) equilibrated to 37±0.5° C. was added. This was adjusted as necessary, with 2N HCl or 2M NaOH to a pH of 6.8±0.05 within 5 minutes. The study was then continued for a further 90 minutes, with the mixture paddle stirred at 75 rpm, with aliquots of the fluid taken at T=0, 15, 30, 45, 60, and 90 min.

Using the methods described above, enterically coated capsules were compared to uncoated capsules, and the aliquots withdrawn analysed by HPLC to determine levels of 24.

FIG. 2 and the table below shows the results of the study. The uncoated capsules dissolved completely after around 5 minutes in the acidic medium while the coated capsules still remained intact after 1 hour. This observation was supported by the HPLC results showing that at 60 minutes, no release of 24 was detected for the coated capsules. As the uncoated capsules had dissolved completely after 5 minutes in the acidic medium allowing 24 to disperse fully in the medium, the release of 24 from these capsules should be much higher at 60 minutes. This low value of release was most likely due to degradation of 24 in the acidic medium. This hypothesis is supported by the percentage release values after 90 minutes in the basic medium showing that only around 12% release of 24 was detected for the uncoated capsules compared to around 63% release for the coated capsules. This suggests that a substantial amount of 24 from the uncoated capsules had degraded in the acidic medium prior to the basic stage. After changing to the basic medium, the coated capsules dissolved completely in 5 minutes allowing 24 to disperse fully in the medium. The release of API increased gradually and at the end of the study (90 min in the basic medium) the percentage of release was around 63%.

| | Enterically coated capsules | | Uncoated capsules | | |
|---|---|---|---|---|---|
| Time (min) | 24 in solution (n = 3) (% of amount dosed) | Stdev | 24 in solution (n = 3) (% of amount dosed) | Stdev | pH |
| 0 | 0.0 | 0.0 | 0.0 | 0.0 | 1.0 |
| 30 | 0.0 | 0.0 | 4.6 | 1.1 | 1.0 |
| 60 | 0.0 | 0.0 | 7.3 | 2.1 | 1.0 |
| 75 | 5.0 | 3.3 | 12.0 | 3.7 | 6.8 |
| 90 | 17.2 | 7.1 | 9.5 | 4.7 | 6.8 |
| 105 | 30.3 | 6.2 | 11.8 | 3.1 | 6.8 |
| 120 | 41.2 | 6.1 | 17.7 | 4.1 | 6.8 |
| 150 | 63.2 | 4.9 | 12.2 | 0.9 | 6.8 |

This data supports the hypothesis that enterically coated capsules increase the amount of sanglifehrin available in the intestinal compartment, and therefore can improve the oral bioavailability and/or reduce the variability of sanglifehrin analogues when dosed to patients.

Example 24

Biological Data—Comparison of In Vivo Pharmacokinetics in Dogs or Human Patients Following Oral Dosing of Enterically and Non-Enterically Coated Tablets 24 is filled into enterically coated and non-enterically tablets or capsules, optionally with excipients to aid intestinal solubility and/or permeability. 2 mg/kg 24 in each form (enterically coated and non-enterically coated) is then dosed to groups of 3 non-naïve beagle dogs or human patients within a regulated clinical trial environment. Blood samples are taken after 0, 0.083, 0.25, 0.5, 1, 2, 4, 8 and 24 hours, and concentration of 24 in whole blood is calculated by LCMS/MS using hydroxymacrocycle as an internal standard. AUClast is then calculated for each tablet. Oral bioavailability is expected to be higher in the group dosed with enterically coated tablets and/or variability between animals/patients is expected to be lower in the group dosed with enterically coated tablets.

REFERENCES

Appel, N., T. Schaller, et al. (2006). "From structure to function: new insights into hepatitis C virus RNA replication." *J Biol Chem* 281(15): 9833-6.

Banteli, R., J. Wagner, et al. (2001). "Synthesis of derivatives of the novel cyclophilin-binding immunosuppressant sanglifehrin A with reduced numbers of polar functions." *Bioorg Med Chem Lett* 11(12): 1609-12.

Chatterji, U., M. Bobardt, et al. (2009). "The isomerase active site of cyclophilin a is critical for HCV replication." *J Biol Chem*.

Colgan, J., M. Asmal, et al. (2000). "Isolation, characterization and targeted disruption of mouse ppia: cyclophilin A is not essential for mammalian cell viability." *Genomics* 68(2): 167-78.

Crabbe, R., G. Vuagniaux, et al. (2009). "An evaluation of the cyclophilin inhibitor Debio 025 and its potential as a treatment for chronic hepatitis C." *Expert Opin Investig Drugs* 18(2): 211-20.

Dolinski, K., S. Muir, et al. (1997). "All cyclophilins and FK506 binding proteins are, individually and collectively, dispensable for viability in Saccharomyces cerevisiae." *Proc Natl Acad Sci USA* 94(24): 13093-8.

E. Lawitz, R. R., T. Nguyen, M. Huang, J. Ke, J. Praestgaard, D. Serra, M. Koziel, T. Evans (2009). "Safety And Antiviral Efficacy Of 14 Days Of The Cyclophilin Inhibitor Nim811 In Combination With Pegylated Interferon .2a In Relapsed Genotype 1 Hcv Infected Patients." *Journal of Hepatology* 50(S1): S379.

Egorin, M. J., T. F. Lagattuta, et al. (2002). "Pharmacokinetics, tissue distribution, and metabolism of 17-(dimethylaminoethylamino)-17-demethoxygeldanamycin (NSC 707545) in CD2F1 mice and Fischer 344 rats." *Cancer Chemother Pharmacol* 49(1): 7-19.

Fehr, T., J. Kallen, et al. (1999). "Sanglifehrins A, B, C and D, novel cyclophilin-binding compounds isolated from Streptomyces sp. A92-308110. II. Structure elucidation, stereochemistry and physico-chemical properties." *J Antibiot (Tokyo)* 52(5): 474-9.

Flisiak, R., A. Horban, et al. (2008). "The cyclophilin inhibitor Debio-025 shows potent anti-hepatitis C effect in patients coinfected with hepatitis C and human immunodeficiency virus." *Hepatology* 47(3): 817-26.

Furniss, B. S., Furniss, A. I., Vogel, A. I., Ed. (1989). *Vogel's Textbook of Practical Organic Chemistry*, Prentice Hall.

Gaither, L. A., Borawski, J., Anderson, L. J., Balabanis, K. A. et al., (2010). "Multiple cyclophilins involved in different cellular pathways mediate HCV replication" *Virology* 397: 43-55

Glavinas, H., Krajcsi, P., Cserepes, J., Sarkadi, B. (2004). "The role of ABC transporters in drug resistance, metabolism and toxicity." *Curr. Drug. Deliv.* 1(1): 27-42.

Gomez, L., H. Thibault, et al. (2007). "Inhibition of mitochondrial permeability transition improves functional recovery and reduces mortality following acute myocardial infarction in mice." *Am J Physiol Heart Circ Physiol* 293(3): H1654-61.

Goto, K., Watashi, K., Inoue, D., Hijikata, M., Shimotohno, K. (2009) "Identification of cellular and viral factors related to anti-hepatitis C virus activity of cyclophilin inhibitor" *Cancer Science* 100(10): 1943-1950

Gregory, M. A., Bobardt, M., et al. (2011) "Preclinical Characterization of Naturally Occurring Polyketide Cyclophilin Inhibitors from the Sanglifehrin Family" *Antimicrob. Agents Chemother.* 55(5)1975-1981

Hanoulle, X., Badillo A, Wieruszeski J M, Verdegem D, Landrieu I, Bartenschlager R, Penin F, Lippens G (2009). "Hepatitis C virus NS5A protein is a substrate for the Peptidyl-Prolyl cis/trans isomerase activity of Cyclophilins A and B." *J Biol Chem*.

Hartel, C., P. Iblher, et al. (2006). "Immunosuppressive activity of the immunophilin-binding drug Sanglifehrin A in human whole blood: potent inhibition of interleukin-6 produced by lymphocytes and monocytes." *Scand J Immunol* 63(1): 26-34.

Herrler, M., H. Bang, et al. (1994). "Cloning and characterization of ppiB, a *Bacillus subtilis* gene which encodes a cyclosporin A-sensitive peptidyl-prolyl cis-trans isomerase." *Mol Microbiol* 11(6): 1073-83.

Hite, M., Turner, S., Federici, C. (2003). "Part 1: Oral delivery of poorly soluble drugs". *Pharmaceutical Manufacturing and Packing Sourcer*. Summer 2003 issue.

Immecke, S. N., Baal., N, et al. (2011). "The Cyclophilin-Binding Agent Sanglifehrin A Is a Dendritic Cell Chemokine and Migration Inhibitor." PLOS one 6(3): e18406

Inoue, K., K. Sekiyama, et al. (2003). "Combined interferon alpha2b and cyclosporin A in the treatment of chronic hepatitis C: controlled trial." *J Gastroenterol* 38(6): 567-72.

Inoue, K., T. Umehara, et al. (2007). "Evaluation of a cyclophilin inhibitor in hepatitis C virus-infected chimeric mice in vivo." *Hepatology* 45(4): 921-8.

Ishii, N., K. Watashi, et al. (2006). "Diverse effects of cyclosporine on hepatitis C virus strain replication." *J Virol* 80(9): 4510-20.

Ke, J., E. L., R. Rozier, T. Marbury, N. Nguyen, D. Serra, K. Dole, J. Praestgaard, M. Huang, T. Evans (2009). "Safety, And Tolerability Of Nim811, A Novel Cyclophilin Inhibitor For Hcv, Following Single And Multiple Ascending Doses In Healthy Volunteers And Hcv-Infected Patients." *Journal of Hepatology* 50(S1): S229.

Jacobson, I., McHutchison, J G, Sulkowski, M. (2007). *Gastroenterol & Hepatol* 3(S34): 1-10.

Kallen, J., R. Sedrani, et al. (2005). "Structure of human cyclophilin A in complex with the novel immunosuppressant sanglifehrin A at 1.6 A resolution." *J Biol Chem* 280(23): 21965-71.

Kawasaki, H., E. S. Mocarski, et al. (2007). "Cyclosporine inhibits mouse cytomegalovirus infection via a cyclophilin-dependent pathway specifically in neural stem/progenitor cells." *J Virol* 81(17): 9013-23.

Konig, J. H., Glaeser, M. Keiser, K. Mandery, U. Klotz and M. F. Fromm (2010), *Drug Metab Dispos,* 39, 1097-1102.

Manns, M. P., G. R. Foster, et al. (2007). "The way forward in HCV treatment—finding the right path." *Nat Rev Drug Discov* 6(12): 991-1000.

Martin Cabrejas, L. M., S. Rohrbach, et al. (1999). "Macrolide Analogues of the Novel Immunosuppressant Sanglifehrin New Application of the Ring-Closing Metathesis Reaction." *Angew Chem Int Ed Engl* 38(16): 2443-2446.

Mathy, J. E., S. Ma, et al. (2008). "Combinations of cyclophilin inhibitor NIM811 with hepatitis C Virus NS3-4A Protease or NS5B polymerase inhibitors enhance antiviral activity and suppress the emergence of resistance." *Antimicrob Agents Chemother* 52(9): 3267-75.

Melnikova, I. (2008). "Hepatitis C therapies." *Nature Rev Drug Disc* 7: 799-800.

Metternich, R., Denni, D., Thai, B, Sedrani, R. (1999). "Toward a Total Synthesis of the Immunosuppressant Sanglifehrin A. Preparation of Two Relay Compounds by Degradation and Their Use in the Reassembly of the Natural Product." *J. Org. Chem.* 64: 9632-9639.

Millay, D. P., M. A. Sargent, et al. (2008). "Genetic and pharmacologic inhibition of mitochondrial-dependent necrosis attenuates muscular dystrophy." *Nat Med* 14(4): 442-7.

Moss, S. et al., "Sangamides, a new class of cyclophilin-inhibiting host-targeted antivirals for treatment of HCV infection." *Med. Chem. Commun., DOI:*10.1039/C1MD00227A Nelson, D. R., Ghalib, R. H., Sulkowski, M., Schiff, E., Rustgi, V., Pockros, P. J., Wang, C., Decosterd Kerhuel, D., and P. Grosgurin, Porchet, H., Crabbe, R. (2009). "Efficacy And Safety Of The Cyclophilin Inhibitor Debio 025 In Combination With Pegylated Interferon Alpha-2a And Ribavirin In Previously Null-Responder Genotype 1 Hcv Patients." *Journal of Hepatology* 50(S1): S40.

Niwa, T., Yamamoto, S, Saito, M, Shiraga, T, Takagi, A. (2007). "Effect of Cyclosporine and Tacrolimus on Cytochrome P450 Activities in Human Liver Microsomes." *Yakugaku Zasshi* 127(1): 209-216.

Paeshuyse, J., A. Kaul, et al. (2006). "The non-immunosuppressive cyclosporin DEBIO-025 is a potent inhibitor of hepatitis C virus replication in vitro." *Hepatology* 43(4): 761-70.

Parfieniuk, A., J. Jaroszewicz, et al. (2007). "Specifically targeted antiviral therapy for hepatitis C virus." *World J Gastroenterol* 13(43): 5673-81.

Pawlotsky, J. M. (2000). "Hepatitis C virus resistance to antiviral therapy." *Hepatology* 32(5): 889-96.

Pawlotsky, J. M. (2005). "Current and future concepts in hepatitis C therapy." *Semin Liver Dis* 25(1): 72-83.

Pawlotsky, J. M. (2006). "Virology of hepatitis B and C viruses and antiviral targets." *J Hepatol* 44(1 Suppl): S10-3.

Pemberton, T. J. and J. E. Kay (2003). "Cyclophilin sensitivity to sanglifehrin A can be correlated to the same specific tryptophan residue as cyclosporin A." *FEBS Lett* 555(2): 335-40.

Pockros, P. (2008). "Emerging Therapies for Chronic Hepatitis C Virus." *Gastroenterol and Hepatology* 4(10): 729-734.

Ptak, R. G., P. A. Gallay, et al. (2008). "Inhibition of human immunodeficiency virus type 1 replication in human cells by Debio-025, a novel cyclophilin binding agent." *Antimicrob Agents Chemother* 52(4): 1302-17.

Qu, X., Jiang, N. et al., (2011). "Cloning, sequencing and characterization of the biosynthetic gene cluster of sanglifehrin A, a potent cyclophilin inhibitor." *Mol. Biosyst.* 7:852-861

Robida, J. M., H. B. Nelson, et al. (2007). "Characterization of hepatitis C virus subgenomic replicon resistance to cyclosporine in vitro." *J Virol* 81(11): 5829-40.

Hopkins, S. D. H., E. Gavis, J. Lalezari, E. Glutzer, B. DiMassimo, P. Rusnak, S. Wring, C. Smitley, Y. and Ribeill (2009). "Safety, plasma pharmacokinetics, and anti-viral activity of SCY-635 in adult patients with chronic hepatitis C virus infection." *Journal of Hepatology* 50(S1): S36.

Sanglier, J. J., V. Quesniaux, et al. (1999). "Sanglifehrins A, B, C and D, novel cyclophilin-binding compounds isolated from *Streptomyces* sp. A92-308110.1. Taxonomy, fermentation, isolation and biological activity." *J Antibiot (Tokyo)* 52(5): 466-73.

Schneider, M. D. (2005). "Cyclophilin D: knocking on death's door." *Sci STKE* 2005(287): pe26.

Sedrani, R., J. Kallen, et al. (2003). "Sanglifehrin-cyclophilin interaction: degradation work, synthetic macrocyclic analogues, X-ray crystal structure, and binding data." *J Am Chem Soc* 125(13): 3849-59.

Seden, K. D. Back and S. Khoo (2010), *J Antimicrob Chemother,* 65, 1079-1085.

Smith, M. B. a. M., J., Ed. (2001). *March's advanced organic chemistry,* John Wiley and Sons Inc., UK.

Steinschulte, C., T. Taner, et al. (2003). "Cutting edge: sanglifehrin A, a novel cyclophilin-binding immunosuppressant blocks bioactive IL-12 production by human dendritic cells." *J Immunol* 171(2): 542-6.

Strader, D. B., T. Wright, et al. (2004). "Diagnosis, management, and treatment of hepatitis C." *Hepatology* 39(4): 1147-71.

Tropschug, M., I. B. Barthelmess, et al. (1989). "Sensitivity to cyclosporin A is mediated by cyclophilin in *Neurospora crassa* and *Saccharomyces cerevisiae.*" *Nature* 342 (6252): 953-5.

Vrolijk, J. M., A. Kaul, et al. (2003). "A replicon-based bioassay for the measurement of interferons in patients with chronic hepatitis C." *J Virol Methods* 110(2): 201-9.

Wring, S. C. Wille, C. Rewerts, R. Randolph, A. Scribner and S. Hopkins (2010), *Journal of Hepatology,* 52, S263

Yang, F., J. M. Robotham, et al. (2008). "Cyclophilin A is an essential cofactor for hepatitis C virus infection and the principal mediator of cyclosporine resistance in vitro." *J Virol* 82(11): 5269-78.

Zenke, G., U. Strittmatter, et al. (2001). "Sanglifehrin A, a novel cyclophilin-binding compound showing immunosuppressive activity with a new mechanism of action." *J Immunol* 166(12): 7165-71.

Zeuzem, S. and E. Herrmann (2002). "Dynamics of hepatitis C virus infection." *Ann Hepatol* 1(2): 56-63.

Zhang, L. H. and J. O. Liu (2001). "Sanglifehrin A, a novel cyclophilin-binding immunosuppressant, inhibits IL-2-dependent T cell proliferation at the G1 phase of the cell cycle." *J Immunol* 166(9): 5611-8.

All references including patent and patent applications referred to in this application are incorporated herein by reference to the fullest extent possible.

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

The invention claimed is:

1. A pharmaceutical dosage form for oral administration comprising a sanglifehrin as active ingredient in which the sanglifehrin active ingredient is protected by provision of a layer of enteric coat, said enteric coat being stable in the acid environment of the stomach, and adapted to release the active ingredient in the higher pH environment of the small intestine, wherein the sanglifehrin is a compound of formula (I) or a pharmaceutically acceptable salt thereof:

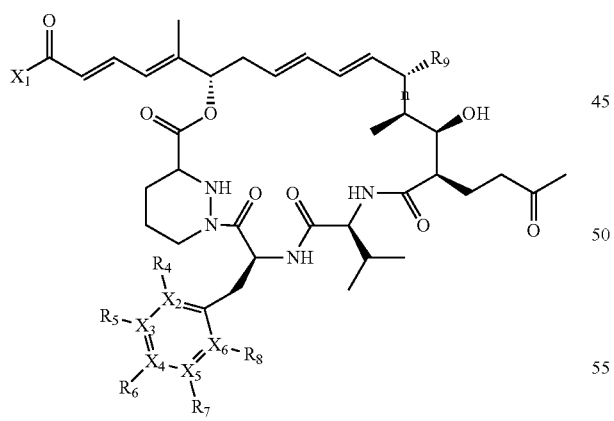

wherein:

the moiety $X_1$ represents $-OR_1$, $-NR_1R_2$ or $R_3$;

$R_1$, $R_2$ and $R_3$ independently represent alkyl, alkenyl, cycloalkyl, cycloalkenyl, alkylcycloalkyl, alkylcycloalkenyl, alkenylcycloalkyl, alkenylcycloalkenyl, aryl, heteroaryl, alkylaryl, alkylheteroaryl, alkenylaryl or alkenylheteroaryl any of which groups may optionally be substituted by monocylic aryl or monocyclic heteroaryl;

and wherein one or more carbon atoms of $R_1$, $R_2$ and $R_3$ not being part of an aryl or heteroaryl group are optionally replaced by a heteroatom selected from O, N and $S(O)_p$ in which p represents 0, 1 or 2 and wherein one or more carbon atoms of $R_1$, $R_2$ and $R_3$ are optionally replaced by carbonyl;

or $R_1$ and $R_2$ are linked such that $NR_1R_2$ represents a saturated or unsaturated heterocyclic ring containing the specified nitrogen atom and wherein one or more carbon atoms of said ring are optionally replaced by a further heteroatom selected from O, N and $S(O)_p$ in which p represents 0, 1 or 2 and wherein one or more carbon atoms of said ring are optionally replaced by carbonyl and which heterocyclic ring may optionally be fused to an aryl or heteroaryl ring;

and wherein one or more carbon atoms of an $R_1$, $R_2$ and $R_3$ group may optionally be substituted by one or more halogen atoms;

or $R_1$ and/or $R_2$ represents hydrogen;

$R_9$ represents H or OH;

n represents a single or double bond, save that when n represents a double bond $R_9$ represents H;

$R_4$, $R_5$, $R_6$, $R_7$ and $R_8$ independently represent H, F, Cl, Br, alkenyl or alkyl wherein one or more carbon atoms of said alkyl group are optionally replaced by a heteroatom selected from O, N and $S(O)_p$ in which p represents 0, 1 or 2 and wherein one or more carbon atoms of said alkyl group are optionally replaced by carbonyl and which alkyl group may optionally be substituted by one or more halogen atoms;

$X_2$, $X_3$, $X_4$, $X_5$ and $X_6$ independently represent C or N, and in the case of any of these groups representing N the attached substituent is absent;

with the proviso that where $R_4$, $R_6$, $R_7$ and $R_8$ all represent H and $X_2$, $X_3$, $X_4$, $X_5$ and $X_6$ all represent C, then $R_5$ cannot represent OH, —Oalkyl or —O(CO)alkyl;

including any tautomer thereof; and including a methanol adduct thereof in which a ketal is formed by the combination of the C-53 keto and the C-15 hydroxyl group and methanol.

2. The pharmaceutical dosage form according to claim 1 wherein the sanglifehrin is compound 24 or a pharmaceutically acceptable salt thereof:

(24)

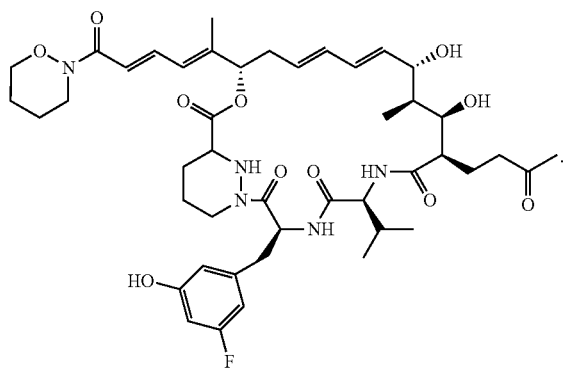

3. The pharmaceutical dosage form according to claim 1 wherein the active ingredient is particulate and the enteric coat is applied to the particles of active ingredient.

4. The pharmaceutical dosage form according to claim 1 wherein the active ingredient is in the form of a granulate, and the enteric coat is applied to the granules of active ingredient.

5. The pharmaceutical dosage form according to claim 1 wherein the active ingredient is coated onto a non-pareil and the enteric coat is applied to the coated non-pareil.

6. The pharmaceutical dosage form according to claim 1 wherein the active ingredient is contained within a capsule, said capsule being provided with an enteric coat.

7. The pharmaceutical dosage form according to claim 1 wherein the active ingredient is contained within a tablet, said tablet being provided with an enteric coat.

* * * * *